(12) United States Patent
Sadelain et al.

(10) Patent No.: US 12,331,129 B2
(45) Date of Patent: Jun. 17, 2025

(54) CHIMERIC RECEPTORS TARGETING ADGRE2 AND/OR CLEC12A AND USES THEREOF

(71) Applicants: MEMORIAL SLOAN-KETTERING CANCER CENTER, New York, NY (US); MILLENNIUM PHARMACEUTICALS, INC., Cambridge, MA (US); SLOAN-KETTERING INSTITUTE FOR CANCER RESEARCH, New York, NY (US); MEMORIAL HOSPITAL FOR CANCER AND ALLIED DISEASES, New York, NY (US)

(72) Inventors: Michel Sadelain, New York, NY (US); Sascha P. Haubner, New York, NY (US); Jorge Mansilla-Soto, Forest Hills, NY (US); Xingyue He, Cambridge, MA (US); Gary Shapiro, Cambridge, MA (US)

(73) Assignees: MEMORIAL SLOAN-KETTERING CANCER CENTER, New York, NY (US); SLOAN-KETTERING INSTITUTE FOR CANCER RESEARCH, New York, NY (US); MEMORIAL HOSPITAL FOR CANCER AND ALLIED DISEASES, New York, NY (US); MILLENNIUM PHARMACEUTICALS, INC., Cambridge, MA (US)

( * ) Notice: Subject to any disclaimer, the term of this patent is extended or adjusted under 35 U.S.C. 154(b) by 35 days.

(21) Appl. No.: 17/728,183

(22) Filed: Apr. 25, 2022

(65) Prior Publication Data
US 2022/0363775 A1 Nov. 17, 2022

Related U.S. Application Data

(60) Provisional application No. 63/287,655, filed on Dec. 9, 2021, provisional application No. 63/179,799, filed on Apr. 26, 2021.

(51) Int. Cl.
*C07K 16/28* (2006.01)
*A61K 38/00* (2006.01)
(Continued)

(52) U.S. Cl.
CPC ...... *C07K 16/2896* (2013.01); *A61K 39/4611* (2023.05); *A61K 39/4631* (2023.05);
(Continued)

(58) Field of Classification Search
CPC ............ C07K 16/2896; C07K 14/7051; C07K 14/70517; C07K 14/70521;
(Continued)

(56) References Cited

U.S. PATENT DOCUMENTS

| 4,956,778 A | 9/1990 | Naito |
| 5,091,513 A | 2/1992 | Huston et al. |

(Continued)

FOREIGN PATENT DOCUMENTS

| CL | 2022003077 A1 | 7/2023 |
| WO | WO 2014/087010 A1 | 6/2014 |

(Continued)

OTHER PUBLICATIONS

Altschul et al., "Basic Local Alignment Search Tool," J Mol. Biol. 215:403-410 (1990).

(Continued)

*Primary Examiner* — Jeffrey Stucker
*Assistant Examiner* — Laura Ann Essex
(74) *Attorney, Agent, or Firm* — Baker Botts L.L.P.

(57) ABSTRACT

The presently disclosed subject matter provides for chimeric receptors that target ADGRE2 and chimeric receptors that (Continued)

target CLEC12A. The presently disclosed subject matter also provides for cells comprising the ADGRE2-targeted chimeric receptors, cells comprising the CLEC12A-targeted chimeric receptors, and cells comprising the ADGRE2-targeted chimeric receptors and the CLEC12A-targeted chimeric receptors. The presently disclosed subject matter further provides uses of such cells for treating tumors, e.g., AML.

66 Claims, 30 Drawing Sheets

Specification includes a Sequence Listing.

(51) Int. Cl.
*A61K 39/00* (2006.01)
*A61P 35/00* (2006.01)
*A61P 35/02* (2006.01)
*C07K 14/705* (2006.01)
*C07K 14/725* (2006.01)

(52) U.S. Cl.
CPC ............... *A61K 39/464402* (2023.05); *A61K 39/464412* (2023.05); *A61K 39/464429* (2023.05); *A61P 35/00* (2018.01); *A61P 35/02* (2018.01); *C07K 14/7051* (2013.01); *C07K 14/70517* (2013.01); *C07K 14/70521* (2013.01); *C07K 14/70578* (2013.01); *C07K 16/2851* (2013.01); *A61K 38/00* (2013.01); *A61K 2039/505* (2013.01); *A61K 2239/29* (2023.05); *A61K 2239/31* (2023.05); *A61K 2239/38* (2023.05); *A61K 2239/48* (2023.05); *C07K 2317/24* (2013.01); *C07K 2317/565* (2013.01); *C07K 2317/622* (2013.01); *C07K 2317/92* (2013.01); *C07K 2319/02* (2013.01); *C07K 2319/03* (2013.01); *C07K 2319/33* (2013.01)

(58) Field of Classification Search
CPC .......... C07K 14/70578; C07K 16/2851; C07K 2317/24; C07K 2317/565; C07K 2317/622; C07K 2317/92; C07K 2319/02; C07K 2319/03; C07K 2319/33; C07K 14/70596; C07K 2317/21; A61K 35/17; A61K 38/00; A61K 2039/505; A61K 2039/5156; A61K 2039/5158; A61K 39/4611; A61K 39/4631; A61K 39/464402; A61K 39/464412; A61K 39/464429; A61K 2239/29; A61K 2239/31; A61K 2239/38; A61K 2239/48; A61P 35/00; A61P 35/02; C12N 5/0636

See application file for complete search history.

(56) References Cited

U.S. PATENT DOCUMENTS

| | | | |
|---|---|---|---|
| 5,132,405 | A | 7/1992 | Huston et al. |
| 5,399,346 | A | 3/1995 | Anderson et al. |
| 11,370,837 | B2* | 6/2022 | Shi .................. G01N 33/53 |
| 11,634,497 | B2* | 4/2023 | Bender ................ A61P 35/00 424/133.1 |
| 2002/0018783 | A1 | 2/2002 | Sadelain et al. |
| 2005/0196754 | A1 | 9/2005 | Drmanac et al. |
| 2013/0142802 | A1* | 6/2013 | Chang ................ C07K 16/2863 435/69.6 |
| 2018/0327506 | A1 | 11/2018 | Karsunky et al. |
| 2020/0165341 | A1 | 5/2020 | Tsurushita et al. |
| 2020/0317777 | A1 | 10/2020 | Sadelain et al. |
| 2020/0345779 | A1 | 11/2020 | Davila |
| 2020/0347139 | A1 | 11/2020 | Rascon et al. |
| 2020/0392230 | A1* | 12/2020 | Tu .......................... A61P 35/00 |
| 2023/0018888 | A1 | 1/2023 | Banerjee et al. |
| 2023/0111279 | A1 | 4/2023 | Yoshihara |

FOREIGN PATENT DOCUMENTS

| | | |
|---|---|---|
| WO | WO 2018/027197 A1 | 2/2018 |
| WO | WO 2019/133969 A2 | 7/2019 |
| WO | WO 2019/139888 A1 | 7/2019 |
| WO | WO 2019/157454 A1 | 8/2019 |
| WO | WO 2020/232447 A1 | 11/2020 |

OTHER PUBLICATIONS

Altschul et al., "Gapped BLAST and PSI-BLAST: a new generation of protein database search programs," Nucleic Acids Res. 25(17):3389-3402 (1997).
Anderson, "Prospects for Human Gene Therapy," Science 226:401-409 (1984).
Baeuerle et al., "Synthetic TRuC receptors engaging the complete T cell receptor for potent anti-tumor response," Nature Communications 10:2087 (2019) 12 pgs.
Bakker et al., "C-Type Lectin-Like Molecule-1: A Novel Myeloid Cell Surface Marker Associated with Acute Myeloid Leukemia," Cancer Research 64:8443-8450 (2004).
Blomer et al., "Highly efficient and sustained gene transfer in adult neurons with a lentivirus vector," Journal of Virology 71:6641-6649 (1997).
Boyden et al., "Vibratory Urticaria Associated with a Missense Variant in *ADGRE2*," N Engl J Med. 374(7):656-663 (2016).
Bregni et al., "Human Peripheral Blood Hematopoietic Progenitors Are Optimal Targets of Retroviral-Mediated Gene Transfer," Blood 80:1418-1422 (1992).
Brigham et al., "Rapid Communication: In vivo Transfection of Murine Lungs with a Functioning Prokaryotic Gene Using a Liposome Vehicle," Am J Med Sci 298:278-281 (1989).
Brocks et al., "A TNF receptor antagonistic scFv, which is not secreted in mammalian cells, is expressed as a soluble mono- and bivalent scFv derivative in insect cells," Immunotechnology 3(3):173-184 (1997).
Cayouette et al., "Adenovirus-Mediated Gene Transfer of Ciliary Neurotrophic Factor Can Prevent Photoreceptor Degeneration in the Retinal Degeneration (rd) Mouse," Human Gene Therapy 8:423-430 (1997).
Cornetta et al., "Gene Transfer into Primates and Prospects for Gene Therapy in Humans," Nucleic Acid Research and Molecular Biology 36:311-322 (1987).
Danos et al., "Safe and efficient generation of recombinant retroviruses with amphotropic and ecotropic host ranges," Proc Natl Acad Sci USA 85:6460-6464 (1988).
Dupont et al., "Artificial Antigen-Presenting Cells Transduced with Telomerase Efficiently Expand Epitope-Specific, Human Leukocyte Antigen-Restricted Cytotoxic T Cells," Cancer Res 65:5417-5427 (2005).
Eglitis et al., "Retroviral Vectors for Introduction of Genes into Mammalian Cells," BioTechniques 6:608-614 (1988).
Felgner et al., Lipofection: A highly efficient, lipid-mediated DNA-transfection procedure, Proc Natl Acad Sci U.S.A. 84:7413-7417 (1987).
Feucht et al., "Calibration of CAR activation potential directs alternative T cell fates and therapeutic potency," Nature Medicine 25:82-88 (2019).
Fife et al., "Inhibition of T cell activation and autoimmune diabetes using a B cell surface-linked CTLA-4 agonist," J Clin Invest 116(8):2252-2261 (2006).
Friedmann, "Progress toward Human Gene Therapy," Science 244:1275-1281 (1989).
Giomarelli et al., "Inhibition of thrombin-induced platelet aggregation using human single-chain Fv antibodies specific for TREM-like transcript-I," Thromb Haemost 97(6):955-963 (2007).

(56) References Cited

OTHER PUBLICATIONS

Haubner et al., "Coexpression profile of leukemic stem cell markers for combinatorial targeted therapy in AML," Leukemia 33:64-74 (2019).
Helsen et al., "The chimeric TAC receptor co-opts the T cell receptor yielding robust anti-tumor activity without toxicity," Nature Communications 9:3049 (2018) 13 pgs.
Ho et al., "Inhibition of Cocaine Binding to the Human Dopamine Transporter by a Single Chain Anti-Idiotypic Antibody: Its Cloning, Expression and Functional Properties," BioChim Biophys Acta 1638(3):257-266 (2003).
Hughes et al., "Retroviral Gene Transfer to Primitive Normal and Leukemic Hematopoietic Cells Using Clinically Applicable Procedures," J Clin Invest 89:1817-1824 (1992).
Huston et al., "Protein engineering of antibody binding sites: Recovery of specific activity in an anti-digoxin single-chain Fv analogue produced in *Escherichia coli*," Proc. Nat. Acad. Sci. USA, 85:5879-5883 (1988).
Johnson, "Gene Therapy for Cystic Fibrosis," Chest 107:77S-83S (1995).
Kabat et al., Sequences of Proteins of Immunological Interest, 4th U.S. Department of Health and Human Services, National Institutes of Health (1987).
Kido et al., "Use of a retroviral vector with an internal opsin promoter to direct gene expression to retinal photoreceptor cells," Current Eye Research 15:833-844 (1996).
Kloss et al., "Combinatorial antigen recognition with balanced signaling promotes selective tumor eradication by engineered T cells," Nature Biotechnology 31(1):71-75 (2013).
Krause et al., "Antigen-dependent CD28 Signaling Selectively Enhances Survival and Proliferation in Genetically Modified Activated Human Primary T Lymphocytes," J. Exp. Med. 188(4):619-626 (1998).
Lahoud et al., "Targeting Antigen to Mouse Dendritic Cells via Clec9A Induces Potent CD4 T Cell Responses Biased toward a Follicular Helper Phenotype," J Immunol 187:842-850 (2011).
Le Gal La Salle et al., "An Adenovirus Vector for Gene Transfer into Neurons and Glia in the Brain," Science 259:988-990 (1993).
Ledbetter et al., "Agonistic Activity of a CD40-Specific Single-Chain Fv Constructed from the Variable Regions of mAb G28-5," Crit Rev Immunol 17(5-6):427-435 (1997).
Lefranc et al., "IMGT unique numbering for immunoglobulin and T cell receptor variable domains and Ig superfamily V-like domains," Dev. Comp. Immunol. 27:55-77 (2003).
Lefranc, The IMGT Unique Numbering for Immunoglobulins, T-Cell Receptors, and Ig-Like Domains The Immunologist 7:132-136 (1999).
Lin et al., "Human EMR2, a Novel EGF-TM7 Molecule on Chromosome 19p13.1, Is Closely Related to CD97," Genomics 67:188-200 (2000).
Lin et al., "Identification and Characterization of a Seven Transmembrane Hormone Receptor Using Differential Display," Genomics 41:301-308 (1997).
Liu et al., "Chimeric STAR receptors using TCR machinery mediate robust responses against solid tumors," Science Translational Medicine 13(586):eabb5191 (2021) 17 pgs.
Marshall et al., "Identification and Characterization of a Novel Human Myeloid Inhibitory C-type Lectin-like Receptor (MICL) That Is Predominantly Expressed on Granulocytes and Monocytes," J Biol Chem 279(15): 14792-14802 (2004).
Miller et al., "Generation of Helper-Free Amphotropic Retroviruses That Transduce a Dominant-Acting, Methotrexate-Resistant Dihydrofolate Reductase Gene," Mol Cell Biol 5:431-437 (1985).
Miller et al., "Improved Retroviral Vectors for Gene Transfer and Expression," Biotechniques 7:980-990 (1989).
Miller et al., "Redesign of retrovirus packaging cell lines to avoid recombination leading to helper virus production," Mol Cell Biol 6:2895-2902 (1986).
Miller, "Retrovirus Packaging Cells," Human Gene Therapy 1:5-14 (1990).
Miyoshi et al., "Stable and efficient gene transfer into the retina using an HIV-based lentiviral vector," Proc. Natl. Acad. Sci. U.S.A. 94:10319-10323 (1997).
Moen, "Directions in Gene Therapy," Blood Cells 17:407-416 (1991).
Moosmayer et al., "A single-chain TNF receptor antagonist is an effective inhibitor of TNF mediated cytotoxicity," Ther Immunol 2:31-40 (1995).
Morgan et al., "Cancer Regression in Patients After Transfer of Genetically Engineered Lymphocytes," Science 314:126-129 (2006).
Morris, "Epitope Mapping of Protein Antigens by Competition ELISA," The Protein Protocols Handbook pp. 595-600 (1996).
Myers et al., "Optimal Alignments in Linear Space," Comput. Appl. Biosci., 4:11-17 (1988).
Naldini et al., "In Vivo Gene Delivery and Stable Transduction of Nondividing Cells by a Lentiviral Vector," Science 272:263-267 (1996).
Needleman et al., "A General Method Applicable to the Search for Similarities in the Amino Acid Sequence of Two Proteins," J Mol. Biol. 48:443-453 (1970).
Neumann et al., "Clec12a Is an Inhibitory Receptor for Uric Acid Crystals that Regulates Inflammation in Response to Cell Death," Immunity 40:389-399 (2014).
Ono et al., "Plasmid DNAs directly injected into mouse brain with lipofectin can be incorporated and expressed by brain cells," Neurosci Lett 117:259-263 (1990).
Panelli et al., "A Tumor-Infiltrating Lymphocyte from a Melanoma Metastasis with Decreased Expression of Melanoma Differentiation Antigens Recognizes MAGE-12," J Immunol 164:4382-4392 (2000).
Panelli et al., "Expansion of Tumor-T Cell Pairs from Fine Needle Aspirates of Melanoma Metastases," J Immunol 164:495-504 (2000).
Papanicolaou et al., "Rapid expansion of cytomegalovirus-specific cytotoxic T lymphocytes by artificial antigen-presenting cells expressing a single HLA allele," Blood 102:2498-2505 (2003).
Perna et al., "Integrating Proteomics and Transcriptomics for Systematic Combinatorial Chimeric Antigen Receptor Therapy of AML," Cancer Cell 32:506-519 (2017).
Peter et al., "Protective effects of an anti-melanocortin-4 receptor scFv derivative in lipopolysaccharide-induced cachexia in rats," J Cachexia Sarcopenia Muscle 4:79-88 (2013).
Peter et al., "scFv Single Chain Antibody Variable Fragment as Inverse Agonist of the β2-Adrenergic Receptor," J Biol Chem 278(38):36740-36747 (2003).
Pyz et al., "Characterisation of murine MICL (CLEC12A) and evidence for an endogenous ligand," Eur J Immunol 38(4):1157-1163 (2008).
Rosenberg et al., "Gene Transfer Into Humans—Immunotherapy of Patients With Advanced Melanoma, Using Tumor-Infiltrating Lymphocytes Modified By Retroviral Gene Transduction," N Engl J Med 323:570-578 (1990).
Sadelain et al., "Targeting Tumours with Genetically Enhanced T Lymphocytes," Nat Rev Cancer 3:35-45 (2003).
Sancho et al., "Signaling by myeloid C-type lectin receptors in immunity and homeostasis" Annu Rev. Immunol 30:491-529 (2012).
Sharp, "Gene Therapy," The Lancet 337:1277-1278 (1991).
Shen et al., "Engineering Peptide Linkers for scFv Immunosensors," Anal. Chem. 80(6):1910-1917 (2008).
Shieh et al., "Transgenic Expression of Single-Chain Anti-CTLA-4 Fv on β Cells Protects Nonobese Diabetic Mice from Autoimmune Diabetes," J Immunol 183(4):2277-2285 (2009).
Straubinger et al., "Liposomes as Carriers for Intracellular Delivery of Nucleic Acids," Methods in Enzymol 101:512-527 (1983).
Tashiro et al., "Treatment of Acute Myeloid Leukemia with T Cells Expressing Chimeric Antigen Receptors Directed to C-type Lectin-like Molecule 1," Molecular Therapy 25:2202-2213 (2017).
Tolstoshev et al., "Gene expression using retroviral vectors," Cur Opin Biotechnol 1:55-61 (1990).
Wahl et al., "Improved Radioimaging and Tumor Localization with Monoclonal F(ab')2," J Nucl Med 24:316-325 (1983).
Wolff et al., "Direct Gene Transfer into Mouse Muscle in Vivo," Science 247:1465-1468 (1990).
Wu et al., "Receptor-mediated Gene Delivery and Expression in Vivo," J Biol Chem 263:14621-14624 (1988).

(56) References Cited

OTHER PUBLICATIONS

Wu et al., "Targeting Genes: Delivery and Persistent Expression of a Foreign Gene Driven by Mammalian Regulatory Elements in Vivo," J Biol Chem 264:16985-16987 (1989).
Xie et al., "Direct demonstration of MuSK involvement in acetylcholine receptor clustering through identification of agonist ScFv," Nat Biotech 15(8):768-771 (1997).
Xu et al., "A novel antibody-TCR (AbTCR) platform combines Fab-based antigen recognition with gamma/delta-TCR signaling to facilitate T-cell cytotoxicity with low cytokine release," Cell Discovery 4:62 (2018) 13 pgs.
Xu et al., "Correction of the enzyme deficiency in hematopoietic cells of Gaucher patients using a clinically acceptable retroviral supernatant transduction protocol," Exp Hemat 22:223-230 (1994).
Yan et al., "Targeting C-type lectin receptors for cancer immunity," Front Immunol 6:408 (2015) 9 pgs.
Zhao et al., "Characteristics of an scFv Antibody Fragment That Binds to Immunoglobulin G of Graves' Disease Patients and Inhibits Autoantibody-Mediated Thyroid-Stimulating Activity," Hybridoma (Larchmt) 27(6):445-451 (2008).
International Search Report and Written Opinion mailed Nov. 15, 2022 in International Application No. PCT/US22/26131.
Yang et al., "Characterization of upregulated adhesion GPCRs in acute myeloid leukemia," Transl Res. 212:26-35 (2019).

\* cited by examiner

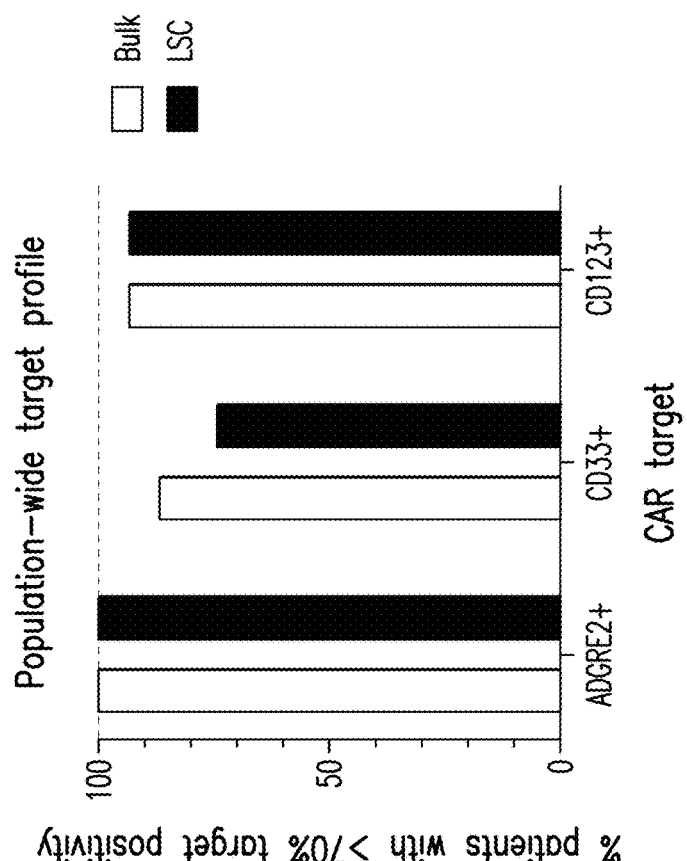
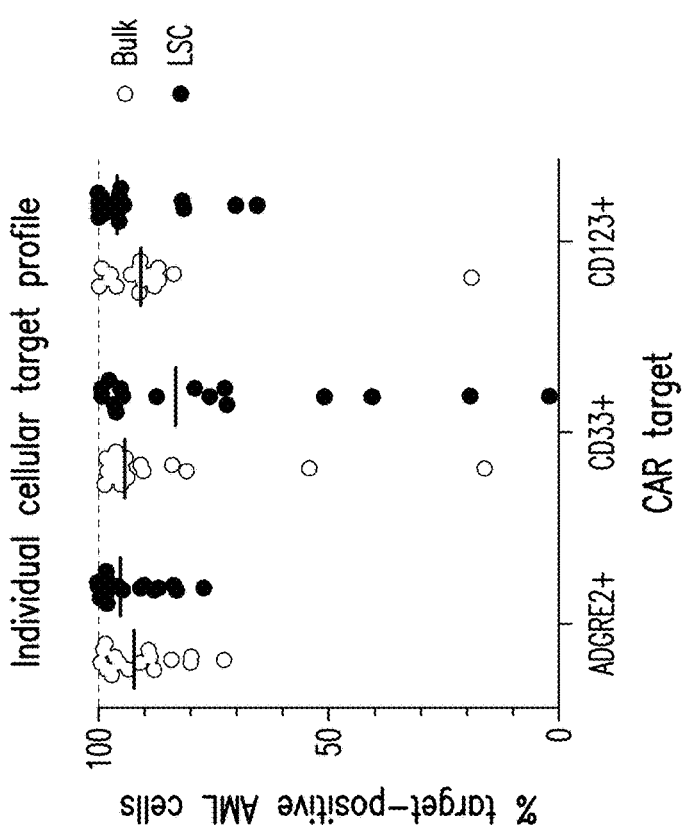
FIGURE 1B
FIGURE 1A

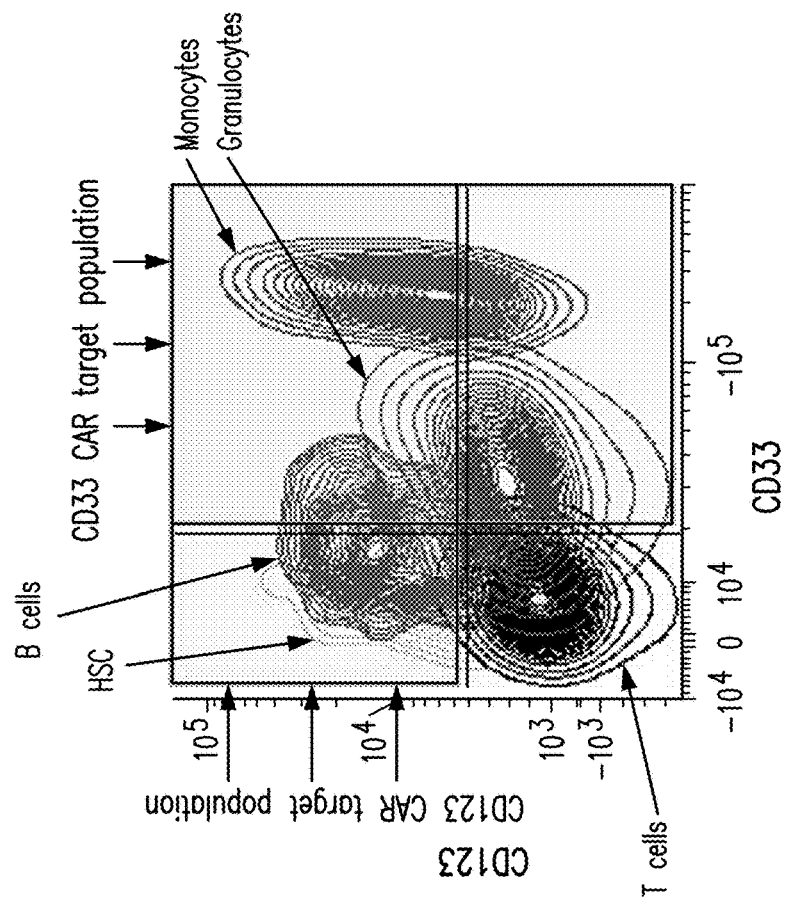
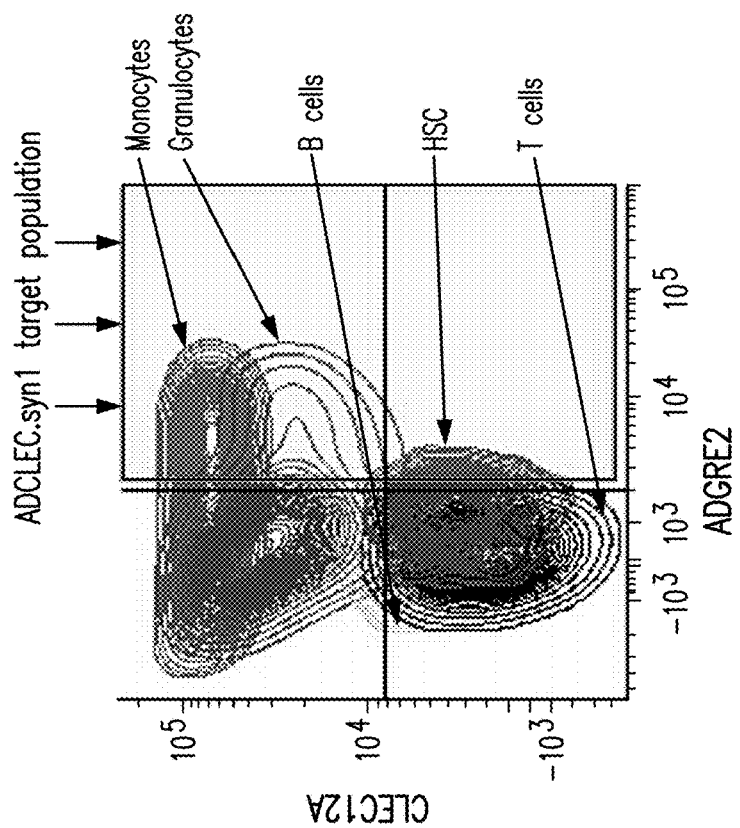
FIGURE 4B
FIGURE 4A

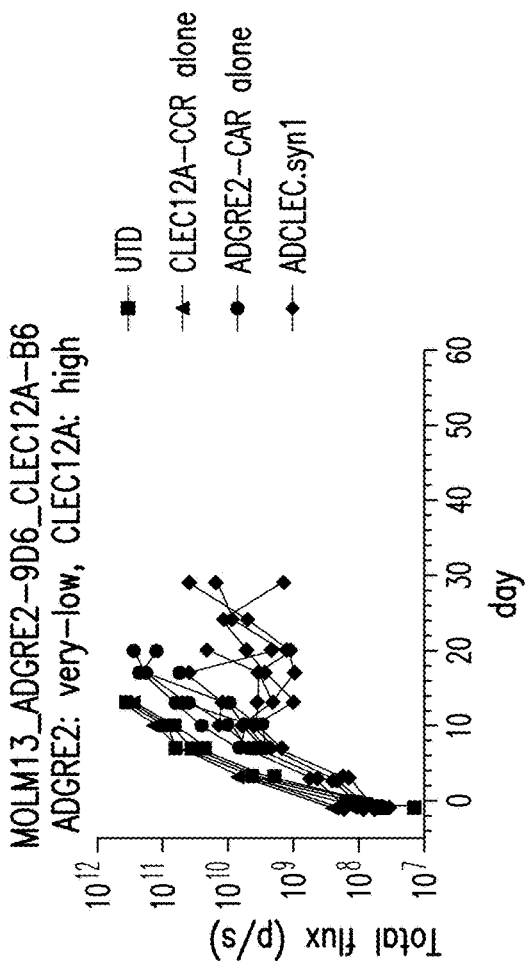
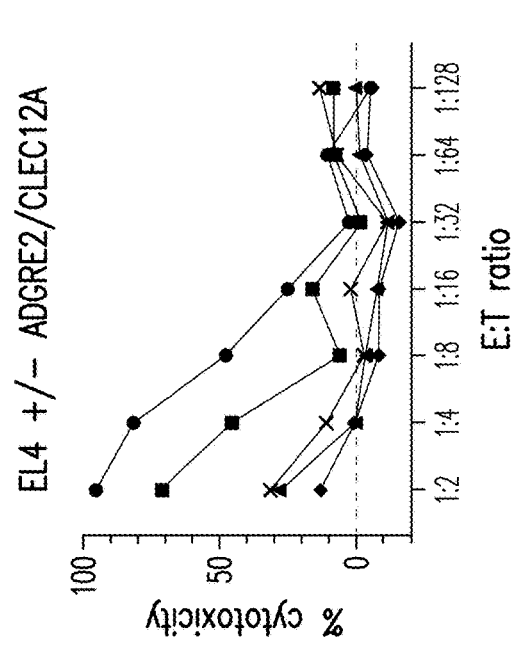
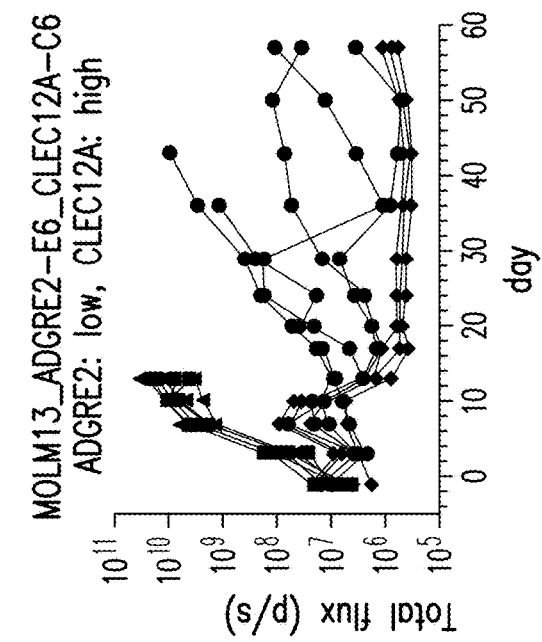
FIGURE 12A
FIGURE 12B
FIGURE 12C

FIGURE 15
CAR T cell manufacturing plan

Selection of CD4+ and CD8+ Cells from Autologous Patient Apheresis Product
Apheresis collection
Selection of CD4+ and CD8+ T cells with Miltenyi beads
↓
Cryopreservation of CD4+/CD8+ cellular product in 10% HSA in Plasmalyte mixed with CS10 at 1:1 (volume: volume) ratio, and determine the % of CD3+ in the cryopreserved cellular product
↓

ADCLEC.syn1 CAR T cell Production

[Day 0] Activation
Thaw CD8+/CD4+ T cells at 37°C
Wash cells with 3 volumes of 1% HSA in Plasmalyte by centrifugation at 300xg for 10 min
↓
Count the cell numbers of washed CD8+/CD4+ T cells
↓
Based on %CD3+ cells, resuspend 100E6 to 300E6 CD3+ cells in complete X-Vivo15 media (X-Vivo15 + 5% human AB serum + 1x Glutamax + 20mM HEPES + 1mM sodium pyruvate + 1x MEM vitamin solution + 1.6 mg/mL N-Acetylcysteine) + 45 mg/mL Gentamicin + 20 IU/mL IL7 + 100 IU/mL IL15)
↓
Activate T cells with Dynabeads® ClinEx Vivo CD3/CD28 using a bead to T cell ratio of 1:1 for approximately 48hr in a 37°C incubator with 5% CO2
↓

[Day 2] Transduction
Transduce the activated T cells with ADCLEC.syn1 vector stocks in PL72/PL240 bag with overwrap pouch/seal. Spin at 1200 rpm for 60 min at RT at 0.5E6 cells/mL
↓

[Day 3]
Transfer the transduced cells to the G-Rex bioreactor and grow the cells in complete X-Vivo15 media w/o gentamicin
↓

[Day 7 and Day 10]
Spike IL7 and IL15 into the medium to maintain 20 IU/mL IL7 + 100 IU/mL IL15
↓

[Day ≤14]
When the target number of cells is reached, wash the cells with 1%HSA in 1x Plasmalyte A using a closed system cell washer & debead using a ClinExVivo magnet
↓

Cryopreservation and Storage of the Final Product
Formulate the final product in Cryostor CS10 cryopresevation buffer (50% CS10 + 5% HSA in Plasmalyte)
↓
Store the final product in approximately 1 mL to 130 mL in CellSeal vial 2mL, Cell Seal vial 5 mL, CryoStor 50, CryoStor 250 bags or equivalent in vapor-phase liquid nitrogen

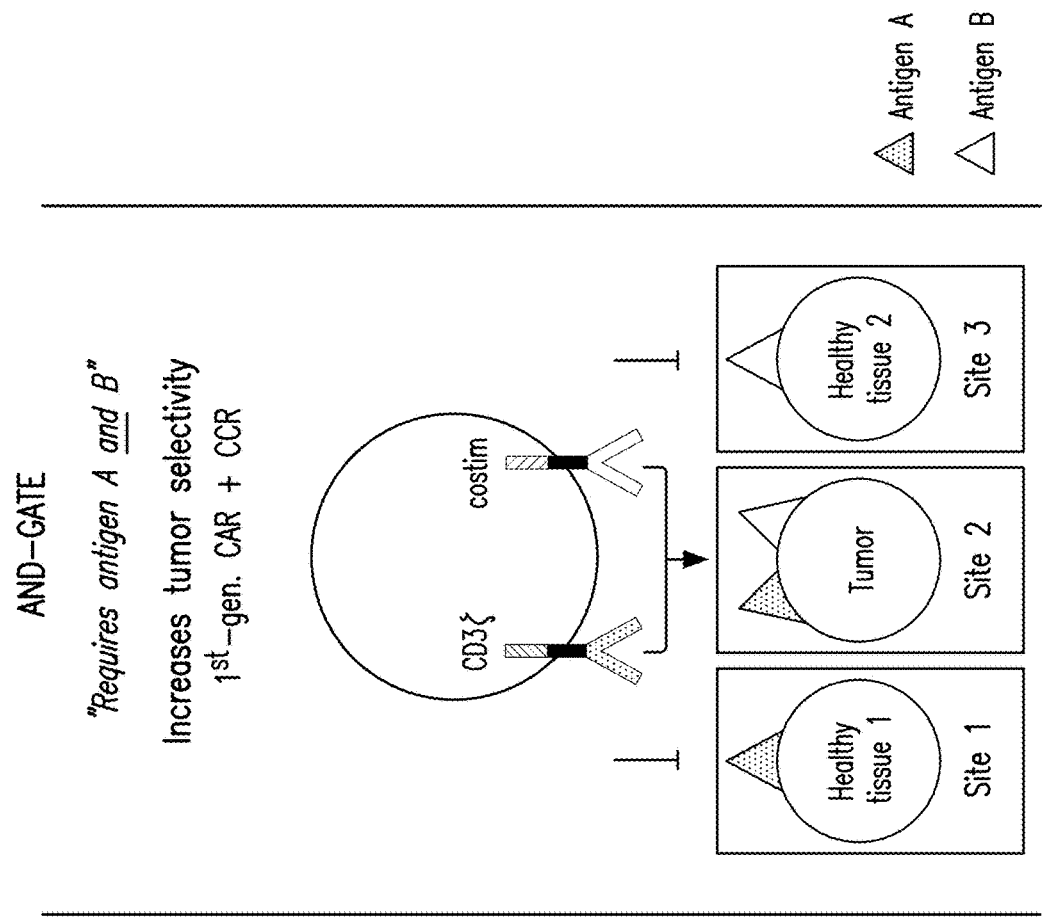
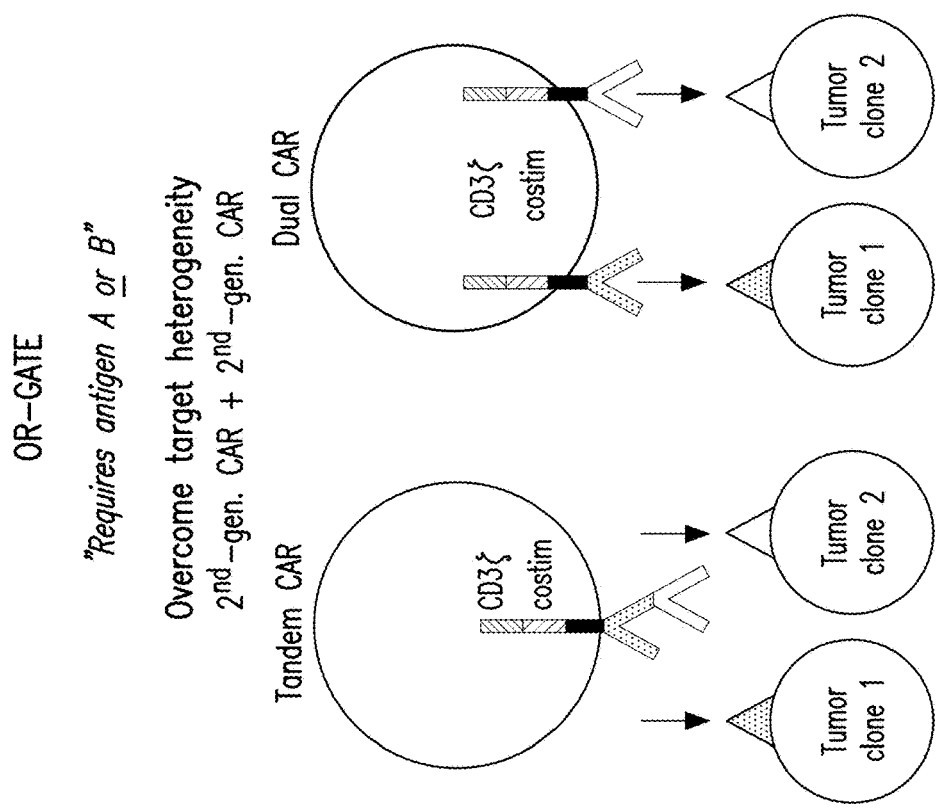
FIGURE 18A

SEQUENCE LISTING

```
<160> NUMBER OF SEQ ID NOS: 151

<210> SEQ ID NO 1
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Gly Gly Gly Ser Gly Gly Gly Gly Ser Gly Gly Gly Ser Gly Gly
1               5                   10                  15

Gly Gly Ser

<210> SEQ ID NO 2
<211> LENGTH: 15
<212> TYPE: PRT
```

<210> SEQ ID NO 2
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gly Gly Gly Gly Ser Gly Gly Gly Gly Ser Gly Gly Gly Gly Ser
1               5                   10                  15

<210> SEQ ID NO 3
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gly Gly Gly Gly Ser Gly Gly Gly Gly Ser Gly Gly Gly Gly Ser Gly
1               5                   10                  15

Gly Gly Ser Gly Gly Gly Gly Ser
            20

<210> SEQ ID NO 4
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Gly Gly Gly Ser Gly Gly Gly Ser Gly Gly Gly Gly Ser Gly
1               5                   10                  15

Gly Gly Gly Ser Gly Gly Gly Ser Gly Gly Gly Gly Ser
            20                  25

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gly Gly Gly Gly Ser
1               5

<210> SEQ ID NO 6
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gly Gly Gly Gly Ser Gly Gly Gly Gly Ser
1               5                   10

<210> SEQ ID NO 7
<211> LENGTH: 235
<212> TYPE: PRT
<213> ORGANISM: Homo sapiens

<400> SEQUENCE: 7

Met Ala Leu Pro Val Thr Ala Leu Leu Leu Pro Ala Leu Leu Leu
1               5                   10                  15

His Ala Ala Arg Pro Ser Gln Phe Arg Val Ser Pro Leu Asp Arg Thr
            20                  25                  30

Trp Asn Leu Gly Glu Thr Val Glu Leu Lys Cys Gln Val Leu Leu Ser
                35                  40                  45

Asn Pro Thr Ser Gly Cys Ser Trp Leu Phe Gln Pro Arg Gly Ala Ala
50                      55                  60

Ala Ser Pro Thr Phe Leu Leu Tyr Leu Ser Gln Asn Lys Pro Lys Ala
65                  70                  75                  80

Ala Glu Gly Leu Asp Thr Gln Arg Phe Ser Gly Lys Arg Leu Gly Asp
                85                  90                  95

Thr Phe Val Leu Thr Leu Ser Asp Phe Arg Arg Glu Asn Glu Gly Tyr
                100                 105                 110

Tyr Phe Cys Ser Ala Leu Ser Asn Ser Ile Met Tyr Phe Ser His Phe
            115                 120                 125

Val Pro Val Phe Leu Pro Ala Lys Pro Thr Thr Thr Pro Ala Pro Arg
130                 135                 140

Pro Pro Thr Pro Ala Pro Thr Ile Ala Ser Gln Pro Leu Ser Leu Arg
145                 150                 155                 160

Pro Glu Ala Cys Arg Pro Ala Ala Gly Gly Ala Val His Thr Arg Gly
                165                 170                 175

Leu Asp Phe Ala Cys Asp Ile Tyr Ile Trp Ala Pro Leu Ala Gly Thr
                180                 185                 190

Cys Gly Val Leu Leu Leu Ser Leu Val Ile Thr Leu Tyr Cys Asn His
            195                 200                 205

Arg Asn Arg Arg Arg Val Cys Lys Cys Pro Arg Pro Val Val Lys Ser
210                 215                 220

Gly Asp Lys Pro Ser Leu Ser Ala Arg Tyr Val
225                 230                 235

<210> SEQ ID NO 8
<211> LENGTH: 213
<212> TYPE: DNA
<213> ORGANISM: Homo sapiens

<400> SEQUENCE: 8
cccaccacga cgccagcgcc gcgaccacca accccggcgc ccacgatcgc gtcgcagccc      60
ctgtccctgc gccagaggc gtgccggcca gcggcggggg gcgcagtgca cacgaggggg     120
ctggacttcg cctgtgatat ctacatctgg gcgcccctgg ccgggacttg tggggtcctt    180
ctcctgtcac tggttatcac cctttactgc aac                                  213

<210> SEQ ID NO 9
<211> LENGTH: 247
<212> TYPE: PRT
<213> ORGANISM: Mus musculus

<400> SEQUENCE: 9

Met Ala Ser Pro Leu Thr Arg Phe Leu Ser Leu Asn Leu Leu Leu Met
1               5                   10                  15

Gly Glu Ser Ile Ile Leu Gly Ser Gly Glu Ala Lys Pro Gln Ala Pro
                20                  25                  30

Glu Leu Arg Ile Phe Pro Lys Lys Met Asp Ala Glu Leu Gly Gln Lys
            35                  40                  45

```
Val Asp Leu Val Cys Glu Val Leu Gly Ser Val Ser Gln Gly Cys Ser
 50                  55                  60

Trp Leu Phe Gln Asn Ser Ser Lys Leu Pro Gln Pro Thr Phe Val
 65                  70                  75                  80

Val Tyr Met Ala Ser Ser His Asn Lys Ile Thr Trp Asp Lys Leu
                 85                  90                  95

Asn Ser Ser Lys Leu Phe Ser Ala Val Arg Asp Thr Asn Asn Lys Tyr
                100                 105                 110

Val Leu Thr Leu Asn Lys Phe Ser Lys Glu Asn Glu Gly Tyr Tyr Phe
                115                 120                 125

Cys Ser Val Ile Ser Asn Ser Val Met Tyr Phe Ser Ser Val Val Pro
130                 135                 140

Val Leu Gln Lys Val Asn Ser Thr Thr Thr Lys Pro Val Leu Arg Thr
145                 150                 155                 160

Pro Ser Pro Val His Pro Thr Gly Thr Ser Gln Pro Gln Arg Pro Glu
                165                 170                 175

Asp Cys Arg Pro Arg Gly Ser Val Lys Gly Thr Gly Leu Asp Phe Ala
                180                 185                 190

Cys Asp Ile Tyr Ile Trp Ala Pro Leu Ala Gly Ile Cys Val Ala Pro
                195                 200                 205

Leu Leu Ser Leu Ile Ile Thr Leu Ile Cys Tyr His Arg Ser Arg Lys
210                 215                 220

Arg Val Cys Lys Cys Pro Arg Pro Leu Val Arg Gln Glu Gly Lys Pro
225                 230                 235                 240

Arg Pro Ser Glu Lys Ile Val
                245

<210> SEQ ID NO 10
<211> LENGTH: 220
<212> TYPE: PRT
<213> ORGANISM: Homo sapiens

<400> SEQUENCE: 10

Met Leu Arg Leu Leu Ala Leu Asn Leu Phe Pro Ser Ile Gln Val
 1               5                  10                  15

Thr Gly Asn Lys Ile Leu Val Lys Gln Ser Pro Met Leu Val Ala Tyr
                 20                  25                  30

Asp Asn Ala Val Asn Leu Ser Cys Lys Tyr Ser Tyr Asn Leu Phe Ser
                 35                  40                  45

Arg Glu Phe Arg Ala Ser Leu His Lys Gly Leu Asp Ser Ala Val Glu
 50                  55                  60

Val Cys Val Val Tyr Gly Asn Tyr Ser Gln Gln Leu Gln Val Tyr Ser
 65                  70                  75                  80

Lys Thr Gly Phe Asn Cys Asp Gly Lys Leu Gly Asn Glu Ser Val Thr
                 85                  90                  95

Phe Tyr Leu Gln Asn Leu Tyr Val Asn Gln Thr Asp Ile Tyr Phe Cys
                100                 105                 110

Lys Ile Glu Val Met Tyr Pro Pro Tyr Leu Asp Asn Glu Lys Ser
                115                 120                 125

Asn Gly Thr Ile Ile His Val Lys Gly Lys His Leu Cys Pro Ser Pro
                130                 135                 140

Leu Phe Pro Gly Pro Ser Lys Pro Phe Trp Val Leu Val Val Val Gly
145                 150                 155                 160

Gly Val Leu Ala Cys Tyr Ser Leu Leu Val Thr Val Ala Phe Ile Ile
                165                 170                 175
```

```
Phe Trp Val Arg Ser Lys Arg Ser Arg Leu Leu His Ser Asp Tyr Met
            180                 185                 190

Asn Met Thr Pro Arg Arg Pro Gly Pro Thr Arg Lys His Tyr Gln Pro
            195                 200                 205

Tyr Ala Pro Pro Arg Asp Phe Ala Ala Tyr Arg Ser
    210                 215                 220

<210> SEQ ID NO 11
<211> LENGTH: 81
<212> TYPE: DNA
<213> ORGANISM: Homo sapiens

<400> SEQUENCE: 11
ttttgggtgc tggtggtggt tggtggagtc ctggcttgct atagcttgct agtaacagtg      60
gcctttatta ttttctgggt g                                               81

<210> SEQ ID NO 12
<211> LENGTH: 218
<212> TYPE: PRT
<213> ORGANISM: Mus musculus

<400> SEQUENCE: 12

Met Thr Leu Arg Leu Leu Phe Leu Ala Leu Asn Phe Phe Ser Val Gln
1               5                   10                  15

Val Thr Glu Asn Lys Ile Leu Val Lys Gln Ser Pro Leu Leu Val Val
            20                  25                  30

Asp Ser Asn Glu Val Ser Leu Ser Cys Arg Tyr Ser Tyr Asn Leu Leu
        35                  40                  45

Ala Lys Glu Phe Arg Ala Ser Leu Tyr Lys Gly Val Asn Ser Asp Val
    50                  55                  60

Glu Val Cys Val Gly Asn Gly Asn Phe Thr Tyr Gln Pro Gln Phe Arg
65                  70                  75                  80

Ser Asn Ala Glu Phe Asn Cys Asp Gly Asp Phe Asp Asn Glu Thr Val
            85                  90                  95

Thr Phe Arg Leu Trp Asn Leu His Val Asn His Thr Asp Ile Tyr Phe
            100                 105                 110

Cys Lys Ile Glu Phe Met Tyr Pro Pro Pro Tyr Leu Asp Asn Glu Arg
        115                 120                 125

Ser Asn Gly Thr Ile Ile His Ile Lys Glu Lys His Leu Cys His Thr
    130                 135                 140

Gln Ser Ser Pro Lys Leu Phe Trp Ala Leu Val Val Val Ala Gly Val
145                 150                 155                 160

Leu Phe Cys Tyr Gly Leu Leu Val Thr Val Ala Leu Cys Val Ile Trp
            165                 170                 175

Thr Asn Ser Arg Arg Asn Arg Leu Leu Gln Ser Asp Tyr Met Asn Met
            180                 185                 190

Thr Pro Arg Arg Pro Gly Leu Thr Arg Lys Pro Tyr Gln Pro Tyr Ala
            195                 200                 205

Pro Ala Arg Asp Phe Ala Ala Tyr Arg Pro
    210                 215

<210> SEQ ID NO 13
<211> LENGTH: 117
<212> TYPE: DNA
<213> ORGANISM: Artificial Sequence
<220> FEATURE:
<223> OTHER INFORMATION: Description of Artificial Sequence: Synthetic
``` polynucleotide

<400> SEQUENCE: 13
attgaagtta tgtatcctcc tccttaccta gacaatgaga agagcaatgg aaccattatc    60
catgtgaaag ggaaacacct ttgtccaagt cccctatttc ccggaccttc taagccc    117

<210> SEQ ID NO 14
<211> LENGTH: 164
<212> TYPE: PRT
<213> ORGANISM: Homo sapiens

<400> SEQUENCE: 14

Met Lys Trp Lys Ala Leu Phe Thr Ala Ala Ile Leu Gln Ala Gln Leu
1               5                   10                  15

Pro Ile Thr Glu Ala Gln Ser Phe Gly Leu Leu Asp Pro Lys Leu Cys
            20                  25                  30

Tyr Leu Leu Asp Gly Ile Leu Phe Ile Tyr Gly Val Ile Leu Thr Ala
        35                  40                  45

Leu Phe Leu Arg Val Lys Phe Ser Arg Ser Ala Asp Ala Pro Ala Tyr
    50                  55                  60

Gln Gln Gly Gln Asn Gln Leu Tyr Asn Glu Leu Asn Leu Gly Arg Arg
65                  70                  75                  80

Glu Glu Tyr Asp Val Leu Asp Lys Arg Arg Gly Arg Asp Pro Glu Met
                85                  90                  95

Gly Gly Lys Pro Gln Arg Arg Lys Asn Pro Gln Glu Gly Leu Tyr Asn
            100                 105                 110

Glu Leu Gln Lys Asp Lys Met Ala Glu Ala Tyr Ser Glu Ile Gly Met
        115                 120                 125

Lys Gly Glu Arg Arg Arg Gly Lys Gly His Asp Gly Leu Tyr Gln Gly
    130                 135                 140

Leu Ser Thr Ala Thr Lys Asp Thr Tyr Asp Ala Leu His Met Gln Ala
145                 150                 155                 160

Leu Pro Pro Arg

<210> SEQ ID NO 15
<211> LENGTH: 22
<212> TYPE: PRT
<213> ORGANISM: Homo sapiens

<400> SEQUENCE: 15

Gln Asn Gln Leu Tyr Asn Glu Leu Asn Leu Gly Arg Arg Glu Glu Tyr
1               5                   10                  15

Asp Val Leu Asp Lys Arg
            20

<210> SEQ ID NO 16
<211> LENGTH: 66
<212> TYPE: DNA
<213> ORGANISM: Homo sapiens

<400> SEQUENCE: 16
cagaaccagc tctataacga gctcaatcta ggacgaagag aggagtacga tgttttggac    60
aagaga    66

<210> SEQ ID NO 17
<211> LENGTH: 22
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 17

Gln Asn Gln Leu Phe Asn Glu Leu Asn Leu Gly Arg Arg Glu Glu Phe
1               5                   10                  15

Asp Val Leu Asp Lys Arg
            20

<210> SEQ ID NO 18
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
cagaaccagc tctttaacga gctcaatcta ggacgaagag aggagttcga tgttttggac     60
aagaga                                                                66

<210> SEQ ID NO 19
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gln Glu Gly Leu Tyr Asn Glu Leu Gln Lys Asp Lys Met Ala Glu Ala
1               5                   10                  15

Tyr Ser Glu Ile Gly Met Lys
            20

<210> SEQ ID NO 20
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
caggaaggcc tgtacaatga actgcagaaa gataagatgg cggaggccta cagtgagatt     60
gggatgaaa                                                             69

<210> SEQ ID NO 21
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Gln Glu Gly Leu Phe Asn Glu Leu Gln Lys Asp Lys Met Ala Glu Ala
1               5                   10                  15

Phe Ser Glu Ile Gly Met Lys
            20

<210> SEQ ID NO 22
<211> LENGTH: 69
```

<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
caggaaggcc tgttcaatga actgcagaaa gataagatgg cggaggcctt cagtgagatt    60
gggatgaaa                                                            69

<210> SEQ ID NO 23
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

His Asp Gly Leu Tyr Gln Gly Leu Ser Thr Ala Thr Lys Asp Thr Tyr
1               5                   10                  15

Asp Ala Leu His Met Gln
            20

<210> SEQ ID NO 24
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
cacgatggcc tttaccaggg tctcagtaca gccaccaagg acacctacga cgcccttcac    60
atgcag                                                               66

<210> SEQ ID NO 25
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

His Asp Gly Leu Phe Gln Gly Leu Ser Thr Ala Thr Lys Asp Thr Phe
1               5                   10                  15

Asp Ala Leu His Met Gln
            20

<210> SEQ ID NO 26
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
cacgatggcc ttttccaggg tctcagtaca gccaccaagg acaccttcga cgcccttcac    60
atgcag                                                               66

<210> SEQ ID NO 27
<211> LENGTH: 112

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Phe Asn Glu Leu Gln Lys
    50                  55                  60

Asp Lys Met Ala Glu Ala Phe Ser Glu Ile Gly Met Lys Gly Glu Arg
65                  70                  75                  80

Arg Arg Gly Lys Gly His Asp Gly Leu Phe Gln Gly Leu Ser Thr Ala
                85                  90                  95

Thr Lys Asp Thr Phe Asp Ala Leu His Met Gln Ala Leu Pro Pro Arg
            100                 105                 110

<210> SEQ ID NO 28
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 28
agagtgaagt tcagcaggag cgcagacgcc cccgcgtacc agcagggcca gaaccagctc      60
tataacgagc tcaatctagg acgaagagag gagtacgatg ttttggacaa gagacgtggc     120
cgggaccctg agatggggggg aaagccgaga aggaagaacc ctcaggaagg cctgttcaat    180
gaactgcaga aagataagat ggcggaggcc ttcagtgaga ttgggatgaa aggcgagcgc     240 cggagggggca aggggcacga tggccttttc cagggtctca gtacagccac caaggacacc    300
ttcgacgccc ttcacatgca ggccctgccc cctcgc                               336

<210> SEQ ID NO 29
<211> LENGTH: 123
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 29
aggagtaaga ggagcaggct cctgcacagt gactacatga acatgactcc ccgccgcccc      60
gggcccaccc gcaagcatta ccagccctat gccccaccac gcgacttcgc agcctatcgc     120
tcc                                                                   123

<210> SEQ ID NO 30
<211> LENGTH: 255
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30
```

Met Gly Asn Ser Cys Tyr Asn Ile Val Ala Thr Leu Leu Leu Val Leu
1               5                   10                  15

Asn Phe Glu Arg Thr Arg Ser Leu Gln Asp Pro Cys Ser Asn Cys Pro
            20                  25                  30

Ala Gly Thr Phe Cys Asp Asn Asn Arg Asn Gln Ile Cys Ser Pro Cys
        35                  40                  45

Pro Pro Asn Ser Phe Ser Ser Ala Gly Gly Gln Arg Thr Cys Asp Ile
50                  55                  60

Cys Arg Gln Cys Lys Gly Val Phe Arg Thr Arg Lys Glu Cys Ser Ser
65                  70                  75                  80

Thr Ser Asn Ala Glu Cys Asp Cys Thr Pro Gly Phe His Cys Leu Gly
                85                  90                  95

Ala Gly Cys Ser Met Cys Glu Gln Asp Cys Lys Gln Gly Gln Glu Leu
            100                 105                 110

Thr Lys Lys Gly Cys Lys Asp Cys Cys Phe Gly Thr Phe Asn Asp Gln
        115                 120                 125

Lys Arg Gly Ile Cys Arg Pro Trp Thr Asn Cys Ser Leu Asp Gly Lys
130                 135                 140

Ser Val Leu Val Asn Gly Thr Lys Glu Arg Asp Val Val Cys Gly Pro
145                 150                 155                 160

Ser Pro Ala Asp Leu Ser Pro Gly Ala Ser Ser Val Thr Pro Pro Ala
                165                 170                 175

Pro Ala Arg Glu Pro Gly His Ser Pro Gln Ile Ile Ser Phe Phe Leu
            180                 185                 190

Ala Leu Thr Ser Thr Ala Leu Leu Phe Leu Leu Phe Phe Leu Thr Leu
        195                 200                 205

Arg Phe Ser Val Val Lys Arg Gly Arg Lys Lys Leu Leu Tyr Ile Phe
210                 215                 220

Lys Gln Pro Phe Met Arg Pro Val Gln Thr Thr Gln Glu Glu Asp Gly
225                 230                 235                 240

Cys Ser Cys Arg Phe Pro Glu Glu Glu Glu Gly Gly Cys Glu Leu
                245                 250                 255

```
<210> SEQ ID NO 31
<211> LENGTH: 126
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 31
aaacggggca gaaagaagct cctgtatata ttcaaacaac catttatgag accagtacaa      60
actactcaag aggaagatgg ctgtagctgc cgatttccag aagaagaaga aggaggatgt     120
gaactg                                                                126

<210> SEQ ID NO 32
<211> LENGTH: 823
<212> TYPE: PRT
<213> ORGANISM: Homo sapiens

<400> SEQUENCE: 32
```

Met Gly Gly Arg Val Phe Leu Val Phe Leu Ala Phe Cys Val Trp Leu
1               5                   10                  15

Thr Leu Pro Gly Ala Glu Thr Gln Asp Ser Arg Gly Cys Ala Arg Trp
            20                  25                  30

```
Cys Pro Gln Asp Ser Ser Cys Val Asn Ala Thr Ala Cys Arg Cys Asn
         35                  40                  45

Pro Gly Phe Ser Ser Phe Ser Glu Ile Ile Thr Thr Pro Met Glu Thr
 50                      55                  60

Cys Asp Asp Ile Asn Glu Cys Ala Thr Leu Ser Lys Val Ser Cys Gly
 65                  70                  75                  80

Lys Phe Ser Asp Cys Trp Asn Thr Glu Gly Ser Tyr Asp Cys Val Cys
                 85                  90                  95

Ser Pro Gly Tyr Glu Pro Val Ser Gly Ala Lys Thr Phe Lys Asn Glu
            100                 105                 110

Ser Glu Asn Thr Cys Gln Asp Val Asp Glu Cys Gln Gln Asn Pro Arg
        115                 120                 125

Leu Cys Lys Ser Tyr Gly Thr Cys Val Asn Thr Leu Gly Ser Tyr Thr
    130                 135                 140

Cys Gln Cys Leu Pro Gly Phe Lys Leu Lys Pro Glu Asp Pro Lys Leu
145                 150                 155                 160

Cys Thr Asp Val Asn Glu Cys Thr Ser Gly Gln Asn Pro Cys His Ser
                165                 170                 175

Ser Thr His Cys Leu Asn Asn Val Gly Ser Tyr Gln Cys Arg Cys Arg
            180                 185                 190

Pro Gly Trp Gln Pro Ile Pro Gly Ser Pro Asn Gly Pro Asn Asn Thr
            195                 200                 205

Val Cys Glu Asp Val Asp Glu Cys Ser Ser Gly Gln His Gln Cys Asp
    210                 215                 220

Ser Ser Thr Val Cys Phe Asn Thr Val Gly Ser Tyr Ser Cys Arg Cys
225                 230                 235                 240

Arg Pro Gly Trp Lys Pro Arg His Gly Ile Pro Asn Asn Gln Lys Asp
            245                 250                 255

Thr Val Cys Glu Asp Met Thr Phe Ser Thr Trp Thr Pro Pro Pro Gly
            260                 265                 270

Val His Ser Gln Thr Leu Ser Arg Phe Phe Asp Lys Val Gln Asp Leu
    275                 280                 285

Gly Arg Asp Tyr Lys Pro Gly Leu Ala Asn Asn Thr Ile Gln Ser Ile
    290                 295                 300

Leu Gln Ala Leu Asp Glu Leu Leu Glu Ala Pro Gly Asp Leu Glu Thr
305                 310                 315                 320

Leu Pro Arg Leu Gln Gln His Cys Val Ala Ser His Leu Leu Asp Gly
                325                 330                 335

Leu Glu Asp Val Leu Arg Gly Leu Ser Lys Asn Leu Ser Asn Gly Leu
            340                 345                 350

Leu Asn Phe Ser Tyr Pro Ala Gly Thr Glu Leu Ser Leu Glu Val Gln
            355                 360                 365

Lys Gln Val Asp Arg Ser Val Thr Leu Arg Gln Asn Gln Ala Val Met
    370                 375                 380

Gln Leu Asp Trp Asn Gln Ala Gln Lys Ser Gly Asp Pro Gly Pro Ser
385                 390                 395                 400

Val Val Gly Leu Val Ser Ile Pro Gly Met Gly Lys Leu Leu Ala Glu
                405                 410                 415

Ala Pro Leu Val Leu Glu Pro Glu Lys Gln Met Leu Leu His Glu Thr
            420                 425                 430

His Gln Gly Leu Leu Gln Asp Gly Ser Pro Ile Leu Leu Ser Asp Val
        435                 440                 445
```

```
Ile Ser Ala Phe Leu Ser Asn Asn Asp Thr Gln Asn Leu Ser Ser Pro
            450                 455                 460

Val Thr Phe Thr Phe Ser His Arg Ser Val Ile Pro Arg Gln Lys Val
465                 470                 475                 480

Leu Cys Val Phe Trp Glu His Gly Gln Asn Gly Cys Gly His Trp Ala
                485                 490                 495

Thr Thr Gly Cys Ser Thr Ile Gly Thr Arg Asp Thr Ser Thr Ile Cys
            500                 505                 510

Arg Cys Thr His Leu Ser Ser Phe Ala Val Leu Met Ala His Tyr Asp
            515                 520                 525

Val Gln Glu Asp Pro Val Leu Thr Val Ile Thr Tyr Met Gly Leu
530                 535                 540

Ser Val Ser Leu Leu Cys Leu Leu Ala Ala Leu Thr Phe Leu Leu
545                 550                 555                 560

Cys Lys Ala Ile Gln Asn Thr Ser Thr Ser Leu His Leu Gln Leu Ser
                565                 570                 575

Leu Cys Leu Phe Leu Ala His Leu Leu Phe Leu Val Ala Ile Asp Gln
                580                 585                 590

Thr Gly His Lys Val Leu Cys Ser Ile Ile Ala Gly Thr Leu His Tyr
            595                 600                 605

Leu Tyr Leu Ala Thr Leu Thr Trp Met Leu Leu Glu Ala Leu Tyr Leu
610                 615                 620

Phe Leu Thr Ala Arg Asn Leu Thr Val Val Asn Tyr Ser Ser Ile Asn
625                 630                 635                 640

Arg Phe Met Lys Lys Leu Met Phe Pro Val Gly Tyr Gly Val Pro Ala
                645                 650                 655

Val Thr Val Ala Ile Ser Ala Ala Ser Arg Pro His Leu Tyr Gly Thr
                660                 665                 670

Pro Ser Arg Cys Trp Leu Gln Pro Glu Lys Gly Phe Ile Trp Gly Phe
            675                 680                 685

Leu Gly Pro Val Cys Ala Ile Phe Ser Val Asn Leu Val Leu Phe Leu
            690                 695                 700

Val Thr Leu Trp Ile Leu Lys Asn Arg Leu Ser Ser Leu Asn Ser Glu
705                 710                 715                 720

Val Ser Thr Leu Arg Asn Thr Arg Met Leu Ala Phe Lys Ala Thr Ala
                725                 730                 735

Gln Leu Phe Ile Leu Gly Cys Thr Trp Cys Leu Gly Ile Leu Gln Val
                740                 745                 750

Gly Pro Ala Ala Arg Val Met Ala Tyr Leu Phe Thr Ile Ile Asn Ser
            755                 760                 765

Leu Gln Gly Val Phe Ile Phe Leu Val Tyr Cys Leu Leu Ser Gln Gln
            770                 775                 780

Val Arg Glu Gln Tyr Gly Lys Trp Ser Lys Gly Ile Arg Lys Leu Lys
785                 790                 795                 800

Thr Glu Ser Glu Met His Thr Leu Ser Ser Ser Ala Lys Ala Asp Thr
                805                 810                 815

Ser Lys Pro Ser Thr Val Asn
            820

<210> SEQ ID NO 33
<211> LENGTH: 8
<212> TYPE: PRT
<213> ORGANISM: Artificial Sequence
<220> FEATURE:
<223> OTHER INFORMATION: Description of Artificial Sequence: Synthetic
```

```
                             peptide

<400> SEQUENCE: 33

Gly Tyr Thr Phe Thr Asn Tyr Trp
1               5

<210> SEQ ID NO 34
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Val Tyr Pro Gly Asp Gly Asp Thr
1               5

<210> SEQ ID NO 35
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Ala Arg Gly Phe Thr Ala Tyr Gly Met Asp Tyr
1               5                   10

<210> SEQ ID NO 36
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Ser Ser Val Ser Tyr
1               5

<210> SEQ ID NO 37
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Asp Thr Ser
1

<210> SEQ ID NO 38
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Gln Gln Trp Ser Ser Asn Pro Leu Thr
1               5

<210> SEQ ID NO 39
```

<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Gln Val Gln Leu Gln Gln Ser Gly Ala Glu Val Ala Lys Pro Gly Ala
1               5                   10                  15

Ser Val Lys Leu Ser Cys Lys Ala Ser Gly Tyr Thr Phe Thr Asn Tyr
            20                  25                  30

Trp Met Gln Trp Ile Lys Gln Ala Pro Gly Gln Gly Leu Glu Trp Ile
        35                  40                  45

Gly Ala Val Tyr Pro Gly Asp Gly Asp Thr Arg His Thr Gln Lys Phe
    50                  55                  60

Lys Gly Lys Ala Thr Leu Thr Ala Asp Lys Ser Ser Thr Ala Tyr
65                  70                  75                  80

Met Glu Val Ser Ser Leu Arg Ser Glu Asp Thr Ala Val Tyr Tyr Cys
                85                  90                  95

Ala Arg Gly Phe Thr Ala Tyr Gly Met Asp Tyr Trp Gly Gln Gly Thr
            100                 105                 110

Thr Val Thr Val Ser Ser
        115

<210> SEQ ID NO 40
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Glu Ile Val Leu Thr Gln Ser Pro Ala Thr Met Ser Ala Ser Pro Gly
1               5                   10                  15

Glu Arg Val Thr Met Ser Cys Ser Ala Ser Ser Ser Val Ser Tyr Met
            20                  25                  30

His Trp Tyr Gln Gln Lys Ser Gly Gln Ser Pro Lys Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Asp Tyr Thr Phe Thr Ile Ser Ser Met Glu Pro Glu
65                  70                  75                  80

Asp Phe Ala Thr Tyr Tyr Cys Gln Gln Trp Ser Ser Asn Pro Leu Thr
                85                  90                  95

Phe Gly Gly Gly Thr Lys Leu Glu Ile Lys
            100                 105

<210> SEQ ID NO 41
<211> LENGTH: 239
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Gln Val Gln Leu Gln Gln Ser Gly Ala Glu Val Ala Lys Pro Gly Ala
1               5                   10                  15

```
Ser Val Lys Leu Ser Cys Lys Ala Ser Gly Tyr Thr Phe Thr Asn Tyr
            20                  25                  30

Trp Met Gln Trp Ile Lys Gln Ala Pro Gly Gln Gly Leu Glu Trp Ile
        35                  40                  45

Gly Ala Val Tyr Pro Gly Asp Gly Asp Thr Arg His Thr Gln Lys Phe
    50                  55                  60

Lys Gly Lys Ala Thr Leu Thr Ala Asp Lys Ser Thr Ser Thr Ala Tyr
65                  70                  75                  80

Met Glu Val Ser Ser Leu Arg Ser Glu Asp Thr Ala Val Tyr Tyr Cys
                85                  90                  95

Ala Arg Gly Phe Thr Ala Tyr Gly Met Asp Tyr Trp Gly Gln Gly Thr
            100                 105                 110

Thr Val Thr Val Ser Ser Gly Gly Gly Gly Ser Gly Gly Gly Gly Ser
        115                 120                 125

Gly Gly Gly Gly Ser Glu Ile Val Leu Thr Gln Ser Pro Ala Thr Met
    130                 135                 140

Ser Ala Ser Pro Gly Glu Arg Val Thr Met Ser Cys Ser Ala Ser Ser
145                 150                 155                 160

Ser Val Ser Tyr Met His Trp Tyr Gln Gln Lys Ser Gly Gln Ser Pro
                165                 170                 175

Lys Arg Trp Ile Tyr Asp Thr Ser Lys Leu Ala Ser Gly Val Pro Ala
            180                 185                 190

Arg Phe Ser Gly Ser Gly Ser Gly Thr Asp Tyr Thr Phe Thr Ile Ser
        195                 200                 205

Ser Met Glu Pro Glu Asp Phe Ala Thr Tyr Tyr Cys Gln Gln Trp Ser
    210                 215                 220

Ser Asn Pro Leu Thr Phe Gly Gly Gly Thr Lys Leu Glu Ile Lys
225                 230                 235

<210> SEQ ID NO 42
<211> LENGTH: 717
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 42
caagttcagc tccagcagag cggcgccgaa gtggcaaagc ctggagcgtc agtcaagctg      60
tcctgcaaag cgagtggcta cgttcacg aactactgga tgcagtggat aaagcaggct      120
cccgggcagg gtctggagtg gattggagcc gtctacccag gggacggcga caccggcac      180 actcaaaagt tcaagggcaa ggccaccctg accgctgaca gagcacaag cacagcgtac      240 atggaggtgt cctctttgag atccgaagat accgctgtgt attattgtgc cggggcttc      300 actgcatacg ggatggatta ctggggacaa ggcactaccg tgactgtcag ctccggggt      360 ggaggctcag gcgggggggg ttcaggaggg ggggatctg aaattgtgct gacacagagc      420
cctgccacaa tgtctgctag ccctggcgag cgcgtgacca tgtcttgtag cgccagcagc      480
agcgtgtcct acatgcattg gtatcaacag aagtccggcc agtctcccaa gcggtggatc      540
tacgatacaa gcaagctggc ctccggcgtg cccgccagat tttctggcag cggctctgga      600
acagattaca ccttcaccat tctagcatg gaacctgagg attttgccac ctactattgc      660
cagcagtggt ccagcaatcc cctgacattt ggaggaggca ccaagctgga aattaag      717

<210> SEQ ID NO 43
```

```
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43
```

Gln Val Gln Leu Gln Gln Ser Gly Ala Glu Val Lys Lys Pro Gly Ala
1               5                   10                  15

Ser Val Lys Leu Ser Cys Lys Ala Ser Gly Tyr Thr Phe Thr Asn Tyr
            20                  25                  30

Trp Met Gln Trp Ile Arg Gln Ala Pro Gly Gln Gly Leu Glu Trp Ile
        35                  40                  45

Gly Ala Val Tyr Pro Gly Asp Gly Asp Thr Arg Tyr Thr Gln Lys Phe
50                  55                  60

Gln Gly Arg Ala Thr Leu Thr Ala Asp Thr Ser Ile Ser Thr Ala Tyr
65                  70                  75                  80

Met Glu Val Ser Arg Leu Arg Ser Asp Asp Thr Ala Val Tyr Tyr Cys
                85                  90                  95

Ala Arg Gly Phe Thr Ala Tyr Gly Met Asp Tyr Trp Gly Gln Gly Thr
            100                 105                 110

Thr Val Thr Val Ser Ser
        115

```
<210> SEQ ID NO 44
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44
```

Glu Ile Val Leu Thr Gln Ser Pro Ala Thr Met Ser Ala Ser Pro Gly
1               5                   10                  15

Glu Arg Val Thr Met Ser Cys Ser Ala Ser Ser Ser Val Ser Tyr Met
            20                  25                  30

His Trp Tyr Gln Gln Lys Ser Gly Leu Ser Pro Lys Arg Trp Ile Tyr
        35                  40                  45

Asp Thr Ser Lys Leu Ala Ser Gly Val Pro Arg Phe Ser Gly Ser
50                  55                  60

Gly Ser Gly Thr Asp Tyr Thr Phe Thr Ile Ser Arg Met Glu Pro Glu
65                  70                  75                  80

Asp Phe Ala Thr Tyr Tyr Cys Gln Gln Trp Ser Ser Asn Pro Leu Thr
                85                  90                  95

Phe Gly Gly Gly Thr Lys Leu Glu Ile Lys
            100                 105

```
<210> SEQ ID NO 45
<211> LENGTH: 239
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45
```

Gln Val Gln Leu Gln Gln Ser Gly Ala Glu Val Lys Lys Pro Gly Ala
1               5                   10                  15

Ser Val Lys Leu Ser Cys Lys Ala Ser Gly Tyr Thr Phe Thr Asn Tyr
                20                  25                  30

Trp Met Gln Trp Ile Arg Gln Ala Pro Gly Gln Gly Leu Glu Trp Ile
            35                  40                  45

Gly Ala Val Tyr Pro Gly Asp Gly Asp Thr Arg Tyr Thr Gln Lys Phe
        50                  55                  60

Gln Gly Arg Ala Thr Leu Thr Ala Asp Thr Ser Ile Ser Thr Ala Tyr
65                  70                  75                  80

Met Glu Val Ser Arg Leu Arg Ser Asp Asp Thr Ala Val Tyr Tyr Cys
                85                  90                  95

Ala Arg Gly Phe Thr Ala Tyr Gly Met Asp Tyr Trp Gly Gln Gly Thr
            100                 105                 110

Thr Val Thr Val Ser Ser Gly Gly Gly Gly Ser Gly Gly Gly Gly Ser
        115                 120                 125

Gly Gly Gly Gly Ser Glu Ile Val Leu Thr Gln Ser Pro Ala Thr Met
    130                 135                 140

Ser Ala Ser Pro Gly Glu Arg Val Thr Met Ser Cys Ser Ala Ser Ser
145                 150                 155                 160

Ser Val Ser Tyr Met His Trp Tyr Gln Gln Lys Ser Gly Leu Ser Pro
                165                 170                 175

Lys Arg Trp Ile Tyr Asp Thr Ser Lys Leu Ala Ser Gly Val Pro Asp
            180                 185                 190

Arg Phe Ser Gly Ser Gly Ser Gly Thr Asp Tyr Thr Phe Thr Ile Ser
        195                 200                 205

Arg Met Glu Pro Glu Asp Phe Ala Thr Tyr Tyr Cys Gln Gln Trp Ser
210                 215                 220

Ser Asn Pro Leu Thr Phe Gly Gly Gly Thr Lys Leu Glu Ile Lys
225                 230                 235

<210> SEQ ID NO 46
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Gln Val Gln Leu Gln Gln Ser Gly Ala Glu Val Lys Lys Pro Gly Ala
1               5                   10                  15

Ser Val Lys Leu Ser Cys Lys Ala Ser Gly Tyr Thr Phe Thr Asn Tyr
                20                  25                  30

Trp Met Gln Trp Val Arg Gln Ala Pro Gly Gln Gly Leu Glu Trp Ile
            35                  40                  45

Gly Ala Val Tyr Pro Gly Asp Gly Asp Thr Arg Tyr Thr Gln Lys Phe
        50                  55                  60

Gln Gly Arg Ala Thr Leu Thr Ala Asp Thr Ser Thr Ser Thr Val Tyr
65                  70                  75                  80

Met Glu Val Ser Ser Leu Arg Ser Glu Asp Thr Ala Val Tyr Tyr Cys
                85                  90                  95

Ala Arg Gly Phe Thr Ala Tyr Gly Met Asp Tyr Trp Gly Gln Gly Thr
            100                 105                 110

Thr Val Thr Val Ser Ser
        115

<210> SEQ ID NO 47

```
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Glu Ile Val Leu Thr Gln Ser Pro Ala Thr Met Ser Ala Ser Pro Gly
1               5                   10                  15

Glu Arg Val Thr Met Ser Cys Ser Ala Ser Ser Ser Val Ser Tyr Met
            20                  25                  30

His Trp Tyr Gln Gln Lys Ser Gly Leu Ser Pro Lys Arg Trp Ile Tyr
        35                  40                  45

Asp Thr Ser Lys Leu Ala Ser Gly Val Pro Asp Arg Phe Ser Gly Ser
    50                  55                  60

Gly Ser Gly Thr Asp Tyr Thr Phe Thr Ile Ser Arg Met Glu Pro Glu
65                  70                  75                  80

Asp Phe Ala Thr Tyr Tyr Cys Gln Gln Trp Ser Ser Asn Pro Leu Thr
                85                  90                  95

Phe Gly Gly Gly Thr Lys Leu Glu Ile Lys
            100                 105

<210> SEQ ID NO 48
<211> LENGTH: 239
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Gln Val Gln Leu Gln Gln Ser Gly Ala Glu Val Lys Lys Pro Gly Ala
1               5                   10                  15

Ser Val Lys Leu Ser Cys Lys Ala Ser Gly Tyr Thr Phe Thr Asn Tyr
            20                  25                  30

Trp Met Gln Trp Val Arg Gln Ala Pro Gly Gln Gly Leu Glu Trp Ile
        35                  40                  45

Gly Ala Val Tyr Pro Gly Asp Gly Asp Thr Arg Tyr Thr Gln Lys Phe
    50                  55                  60

Gln Gly Arg Ala Thr Leu Thr Ala Asp Thr Ser Thr Ser Thr Val Tyr
65                  70                  75                  80

Met Glu Val Ser Ser Leu Arg Ser Glu Asp Thr Ala Val Tyr Tyr Cys
                85                  90                  95

Ala Arg Gly Phe Thr Ala Tyr Gly Met Asp Tyr Trp Gly Gln Gly Thr
            100                 105                 110

Thr Val Thr Val Ser Ser Gly Gly Gly Ser Gly Gly Gly Gly Ser
        115                 120                 125

Gly Gly Gly Gly Ser Glu Ile Val Leu Thr Gln Ser Pro Ala Thr Met
    130                 135                 140

Ser Ala Ser Pro Gly Glu Arg Val Thr Met Ser Cys Ser Ala Ser Ser
145                 150                 155                 160

Ser Val Ser Tyr Met His Trp Tyr Gln Gln Lys Ser Gly Leu Ser Pro
                165                 170                 175

Lys Arg Trp Ile Tyr Asp Thr Ser Lys Leu Ala Ser Gly Val Pro Asp
            180                 185                 190

Arg Phe Ser Gly Ser Gly Ser Gly Thr Asp Tyr Thr Phe Thr Ile Ser
        195                 200                 205
```

Arg Met Glu Pro Glu Asp Phe Ala Thr Tyr Tyr Cys Gln Gln Trp Ser
        210                 215                 220

Ser Asn Pro Leu Thr Phe Gly Gly Gly Thr Lys Leu Glu Ile Lys
225                 230                 235

<210> SEQ ID NO 49
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Gln Val Gln Leu Gln Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Met Gln Trp Val Arg Gln Ala Pro Gly Gln Gly Leu Glu Trp Met
        35                  40                  45

Gly Ala Val Tyr Pro Gly Asp Gly Asp Thr Arg His Thr Gln Lys Phe
    50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Phe Thr Ala Tyr Gly Met Asp Tyr Trp Gly Gln Gly Thr
            100                 105                 110

Leu Val Thr Val Ser Ser
        115

<210> SEQ ID NO 50
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Glu Ile Val Leu Thr Gln Ser Pro Ala Thr Leu Ser Leu Ser Pro Gly
1               5                   10                  15

Glu Arg Ala Thr Leu Ser Cys Ser Ala Ser Ser Ser Val Ser Tyr Met
            20                  25                  30

His Trp Tyr Gln Gln Lys Pro Gly Leu Ala Pro Arg Leu Leu Ile Tyr
        35                  40                  45

Asp Thr Ser Lys Leu Ala Ser Gly Ile Pro Asp Arg Phe Ser Gly Ser
    50                  55                  60

Gly Ser Gly Thr Asp Phe Thr Leu Thr Ile Ser Arg Leu Glu Pro Glu
65                  70                  75                  80

Asp Phe Ala Val Tyr Tyr Cys Gln Gln Trp Ser Ser Asn Pro Leu Thr
                85                  90                  95

Phe Gly Gln Gly Thr Lys Val Glu Ile Lys
            100                 105

<210> SEQ ID NO 51
<211> LENGTH: 242
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 51

Gln Val Gln Leu Gln Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Met Gln Trp Val Arg Gln Ala Pro Gly Gln Gly Leu Glu Trp Met
        35                  40                  45

Gly Ala Val Tyr Pro Gly Asp Gly Asp Thr Arg His Thr Gln Lys Phe
    50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Phe Thr Ala Tyr Gly Met Asp Tyr Trp Gly Gln Gly Thr
            100                 105                 110

Leu Val Thr Val Ser Ser Ala Ser Thr Gly Gly Gly Ser Gly Gly
        115                 120                 125

Gly Gly Ser Gly Gly Gly Ser Glu Ile Val Leu Thr Gln Ser Pro
    130                 135                 140

Ala Thr Leu Ser Leu Ser Pro Gly Glu Arg Ala Thr Leu Ser Cys Ser
145                 150                 155                 160

Ala Ser Ser Val Ser Tyr Met His Trp Tyr Gln Gln Lys Pro Gly
            165                 170                 175

Leu Ala Pro Arg Leu Leu Ile Tyr Asp Thr Ser Lys Leu Ala Ser Gly
        180                 185                 190

Ile Pro Asp Arg Phe Ser Gly Ser Gly Ser Gly Thr Asp Phe Thr Leu
    195                 200                 205

Thr Ile Ser Arg Leu Glu Pro Glu Asp Phe Ala Val Tyr Tyr Cys Gln
        210                 215                 220

Gln Trp Ser Ser Asn Pro Leu Thr Phe Gly Gln Gly Thr Lys Val Glu
225                 230                 235                 240

Ile Lys

<210> SEQ ID NO 52
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Gln Val Gln Leu Gln Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Met Gln Trp Val Arg Gln Ala Pro Gly Gln Gly Leu Glu Trp Ile
        35                  40                  45

Gly Ala Val Tyr Pro Gly Asp Gly Asp Thr Arg His Thr Gln Lys Phe
    50                  55                  60

Lys Gly Arg Val Thr Met Thr Ala Asp Lys Ser Thr Ser Thr Val Tyr
65                  70                  75                  80
```

```
Met Glu Leu Ser Ser Leu Arg Ser Glu Asp Thr Ala Val Tyr Tyr Cys
                85                  90                  95

Ala Arg Gly Phe Thr Ala Tyr Gly Met Asp Tyr Trp Gly Gln Gly Thr
            100                 105                 110

Leu Val Thr Val Ser Ser
        115
```

<210> SEQ ID NO 53
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

```
Gln Ile Val Leu Thr Gln Ser Pro Ala Thr Leu Ser Leu Ser Pro Gly
1               5                   10                  15

Glu Arg Ala Thr Leu Thr Cys Ser Ala Ser Ser Val Ser Tyr Met
            20                  25                  30

His Trp Tyr Gln Gln Lys Pro Gly Leu Ser Pro Lys Arg Trp Ile Tyr
        35                  40                  45

Asp Thr Ser Lys Leu Ala Ser Gly Val Pro Asp Arg Phe Ser Gly Ser
    50                  55                  60

Gly Ser Gly Thr Asp Tyr Thr Phe Thr Ile Arg Arg Leu Glu Pro Glu
65                  70                  75                  80

Asp Phe Ala Thr Tyr Tyr Cys Gln Gln Trp Ser Ser Asn Pro Leu Thr
                85                  90                  95

Phe Gly Gln Gly Thr Lys Val Glu Ile Lys
            100                 105
```

<210> SEQ ID NO 54
<211> LENGTH: 242
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

```
Gln Val Gln Leu Gln Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Met Gln Trp Val Arg Gln Ala Pro Gly Gln Gly Leu Glu Trp Ile
        35                  40                  45

Gly Ala Val Tyr Pro Gly Asp Gly Asp Thr Arg His Thr Gln Lys Phe
    50                  55                  60

Lys Gly Arg Val Thr Met Thr Ala Asp Lys Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Phe Thr Ala Tyr Gly Met Asp Tyr Trp Gly Gln Gly Thr
            100                 105                 110

Leu Val Thr Val Ser Ser Ala Ser Thr Gly Gly Gly Ser Gly Gly
        115                 120                 125

Gly Gly Ser Gly Gly Gly Gly Ser Gln Ile Val Leu Thr Gln Ser Pro
    130                 135                 140
```

```
Ala Thr Leu Ser Leu Ser Pro Gly Glu Arg Ala Thr Leu Thr Cys Ser
145                 150                 155                 160

Ala Ser Ser Ser Val Ser Tyr Met His Trp Tyr Gln Gln Lys Pro Gly
                165                 170                 175

Leu Ser Pro Lys Arg Trp Ile Tyr Asp Thr Ser Lys Leu Ala Ser Gly
            180                 185                 190

Val Pro Asp Arg Phe Ser Gly Ser Gly Ser Gly Thr Asp Tyr Thr Phe
        195                 200                 205

Thr Ile Arg Arg Leu Glu Pro Glu Asp Phe Ala Thr Tyr Tyr Cys Gln
    210                 215                 220

Gln Trp Ser Ser Asn Pro Leu Thr Phe Gly Gln Gly Thr Lys Val Glu
225                 230                 235                 240

Ile Lys

<210> SEQ ID NO 55
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Gln Val Gln Leu Gln Gln Ser Gly Ala Glu Val Lys Lys Pro Gly Ala
1               5                   10                  15

Ser Val Lys Leu Ser Cys Lys Ala Ser Gly Tyr Thr Phe Thr Asn Tyr
            20                  25                  30

Trp Met Gln Trp Ile Arg Gln Ala Pro Gly Gln Gly Leu Glu Trp Ile
        35                  40                  45

Gly Ala Val Tyr Pro Gly Asp Gly Asp Thr Arg Tyr Thr Gln Lys Phe
    50                  55                  60

Gln Gly Arg Ala Thr Leu Thr Ala Asp Thr Ser Thr Ser Thr Ala Tyr
65                  70                  75                  80

Met Glu Val Ser Ser Leu Arg Ser Glu Asp Thr Ala Val Tyr Tyr Cys
                85                  90                  95

Ala Arg Gly Phe Thr Ala Tyr Gly Met Asp Tyr Trp Gly Gln Gly Thr
            100                 105                 110

Thr Val Thr Val Ser Ser
        115

<210> SEQ ID NO 56
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Glu Ile Val Leu Thr Gln Ser Pro Ala Thr Leu Ser Ala Ser Pro Gly
1               5                   10                  15

Glu Arg Val Thr Met Ser Cys Ser Ala Ser Ser Ser Val Ser Tyr Met
            20                  25                  30

His Trp Tyr Gln Gln Lys Pro Gly Leu Ala Pro Arg Arg Trp Ile Tyr
        35                  40                  45

Asp Thr Ser Lys Leu Ala Ser Gly Val Pro Asp Arg Phe Ser Gly Ser
    50                  55                  60

Gly Ser Gly Thr Asp Tyr Thr Phe Thr Ile Ser Arg Met Glu Pro Glu
```

```
                65                  70                  75                  80
Asp Phe Ala Thr Tyr Tyr Cys Gln Gln Trp Ser Ser Asn Pro Leu Thr
                    85                  90                  95

Phe Gly Gly Gly Thr Lys Leu Glu Ile Lys
                    100                 105

<210> SEQ ID NO 57
<211> LENGTH: 239
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Gln Val Gln Leu Gln Gln Ser Gly Ala Glu Val Lys Lys Pro Gly Ala
1               5                   10                  15

Ser Val Lys Leu Ser Cys Lys Ala Ser Gly Tyr Thr Phe Thr Asn Tyr
                20                  25                  30

Trp Met Gln Trp Ile Arg Gln Ala Pro Gly Gln Gly Leu Glu Trp Ile
            35                  40                  45

Gly Ala Val Tyr Pro Gly Asp Gly Asp Thr Arg Tyr Thr Gln Lys Phe
        50                  55                  60

Gln Gly Arg Ala Thr Leu Thr Ala Asp Thr Ser Thr Ser Thr Ala Tyr
65                  70                  75                  80

Met Glu Val Ser Ser Leu Arg Ser Glu Asp Thr Ala Val Tyr Tyr Cys
                85                  90                  95

Ala Arg Gly Phe Thr Ala Tyr Gly Met Asp Tyr Trp Gly Gln Gly Thr
            100                 105                 110

Thr Val Thr Val Ser Ser Gly Gly Gly Ser Gly Gly Gly Gly Ser
        115                 120                 125

Gly Gly Gly Gly Ser Glu Ile Val Leu Thr Gln Ser Pro Ala Thr Leu
    130                 135                 140

Ser Ala Ser Pro Gly Glu Arg Val Thr Met Ser Cys Ser Ala Ser Ser
145                 150                 155                 160

Ser Val Ser Tyr Met His Trp Tyr Gln Gln Lys Pro Gly Leu Ala Pro
                165                 170                 175

Arg Arg Trp Ile Tyr Asp Thr Ser Lys Leu Ala Ser Gly Val Pro Asp
            180                 185                 190

Arg Phe Ser Gly Ser Gly Ser Gly Thr Asp Tyr Thr Phe Thr Ile Ser
        195                 200                 205

Arg Met Glu Pro Glu Asp Phe Ala Thr Tyr Tyr Cys Gln Gln Trp Ser
    210                 215                 220

Ser Asn Pro Leu Thr Phe Gly Gly Gly Thr Lys Leu Glu Ile Lys
225                 230                 235

<210> SEQ ID NO 58
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Met Tyr Arg Met Gln Leu Leu Ser Cys Ile Ala Leu Ser Leu Ala Leu
1               5                   10                  15

Val Thr Asn Ser
```

```
                    20

<210> SEQ ID NO 59
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Met Tyr Ser Met Gln Leu Ala Ser Cys Val Thr Leu Thr Leu Val Leu
1               5                   10                  15

Leu Val Asn Ser
            20

<210> SEQ ID NO 60
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Met Glu Thr Pro Ala Gln Leu Leu Phe Leu Leu Leu Leu Trp Leu Pro
1               5                   10                  15

Asp Thr Thr Gly
            20

<210> SEQ ID NO 61
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Met Glu Thr Asp Thr Leu Leu Leu Trp Val Leu Leu Leu Trp Val Pro
1               5                   10                  15

Gly Ser Thr Gly
            20

<210> SEQ ID NO 62
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Met Ala Leu Pro Val Thr Ala Leu Leu Leu Pro Leu Ala Leu Leu Leu
1               5                   10                  15

His Ala Ala Arg Pro
            20

<210> SEQ ID NO 63
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 63

Met Ala Leu Pro Val Thr Ala Leu Leu Leu Pro Leu Ala Leu Leu Leu
1               5                   10                  15

His Ala

<210> SEQ ID NO 64
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Met Lys Trp Val Thr Phe Ile Ser Leu Leu Phe Ser Ser Ala Tyr Ser
1               5                   10                  15

<210> SEQ ID NO 65
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Met Asp Ser Lys Gly Ser Ser Gln Lys Gly Ser Arg Leu Leu Leu Leu
1               5                   10                  15

Leu Val Val Ser Asn Leu Leu Leu Cys Gln Gly Val Val Ser
            20                  25                  30

<210> SEQ ID NO 66
<211> LENGTH: 462
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Gln Val Gln Leu Gln Gln Ser Gly Ala Glu Val Ala Lys Pro Gly Ala
1               5                   10                  15

Ser Val Lys Leu Ser Cys Lys Ala Ser Gly Tyr Thr Phe Thr Asn Tyr
            20                  25                  30

Trp Met Gln Trp Ile Lys Gln Ala Pro Gly Gln Gly Leu Glu Trp Ile
        35                  40                  45

Gly Ala Val Tyr Pro Gly Asp Gly Asp Thr Arg His Thr Gln Lys Phe
    50                  55                  60

Lys Gly Lys Ala Thr Leu Thr Ala Asp Lys Ser Thr Ser Thr Ala Tyr
65                  70                  75                  80

Met Glu Val Ser Ser Leu Arg Ser Glu Asp Thr Ala Val Tyr Tyr Cys
                85                  90                  95

Ala Arg Gly Phe Thr Ala Tyr Gly Met Asp Tyr Trp Gly Gln Gly Thr
            100                 105                 110

Thr Val Thr Val Ser Ser Gly Gly Gly Ser Gly Gly Gly Gly Ser
        115                 120                 125

Gly Gly Gly Gly Ser Glu Ile Val Leu Thr Gln Ser Pro Ala Thr Met
    130                 135                 140

Ser Ala Ser Pro Gly Glu Arg Val Thr Met Ser Cys Ser Ala Ser Ser
145                 150                 155                 160
```

-continued

```
Ser Val Ser Tyr Met His Trp Tyr Gln Gln Lys Ser Gly Gln Ser Pro
            165                 170                 175

Lys Arg Trp Ile Tyr Asp Thr Ser Lys Leu Ala Ser Gly Val Pro Ala
        180                 185                 190

Arg Phe Ser Gly Ser Gly Ser Gly Thr Asp Tyr Thr Phe Thr Ile Ser
        195                 200                 205

Ser Met Glu Pro Glu Asp Phe Ala Thr Tyr Tyr Cys Gln Gln Trp Ser
    210                 215                 220

Ser Asn Pro Leu Thr Phe Gly Gly Gly Thr Lys Leu Glu Ile Lys Arg
225                 230                 235                 240

Ala Ala Ala Ile Glu Val Met Tyr Pro Pro Tyr Leu Asp Asn Glu
                245                 250                 255

Lys Ser Asn Gly Thr Ile Ile His Val Lys Gly Lys His Leu Cys Pro
            260                 265                 270

Ser Pro Leu Phe Pro Gly Pro Ser Lys Pro Phe Trp Val Leu Val Val
        275                 280                 285

Val Gly Gly Val Leu Ala Cys Tyr Ser Leu Leu Val Thr Val Ala Phe
    290                 295                 300

Ile Ile Phe Trp Val Arg Ser Lys Arg Ser Arg Leu Leu His Ser Asp
305                 310                 315                 320

Tyr Met Asn Met Thr Pro Arg Arg Pro Gly Pro Thr Arg Lys His Tyr
                325                 330                 335

Gln Pro Tyr Ala Pro Pro Arg Asp Phe Ala Ala Tyr Arg Ser Arg Val
            340                 345                 350

Lys Phe Ser Arg Ser Ala Asp Ala Pro Ala Tyr Gln Gln Gly Gln Asn
        355                 360                 365

Gln Leu Tyr Asn Glu Leu Asn Leu Gly Arg Arg Glu Glu Tyr Asp Val
    370                 375                 380

Leu Asp Lys Arg Arg Gly Arg Asp Pro Glu Met Gly Gly Lys Pro Arg
385                 390                 395                 400

Arg Lys Asn Pro Gln Glu Gly Leu Phe Asn Glu Leu Gln Lys Asp Lys
                405                 410                 415

Met Ala Glu Ala Phe Ser Glu Ile Gly Met Lys Gly Glu Arg Arg Arg
            420                 425                 430

Gly Lys Gly His Asp Gly Leu Phe Gln Gly Leu Ser Thr Ala Thr Lys
        435                 440                 445

Asp Thr Phe Asp Ala Leu His Met Gln Ala Leu Pro Pro Arg
    450                 455                 460
```

<210> SEQ ID NO 67
<211> LENGTH: 1386
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 67

```
caagttcagc tccagcagag cggcgccgaa gtggcaaagc tggagcgtc agtcaagctg      60 tcctgcaaag cgagtggcta tacgttcacg aactactgga tgcagtggat aaagcaggct     120
cccgggcagg gtctggagtg gattggagcc gtctacccag gggacggcga cacccggcac     180
actcaaaagt tcaagggcaa ggccacccctg accgctgaca agagcacaag cacagcgtac     240
atggaggtgt cctctttgag atccgaagat accgctgtgt attattgtgc ccggggcttc     300
actgcatacg ggatggatta ctggggacaa ggcactaccg tgactgtcag ctccgggggt     360
```

-continued

```
ggaggctcag gcggggggggg ttcaggaggg gggggatctg aaattgtgct gacacagagc      420
cctgccacaa tgtctgctag ccctggcgag cgcgtgacca tgtcttgtag cgccagcagc      480
agcgtgtcct acatgcattg gtatcaacag aagtccggcc agtctcccaa gcggtggatc      540
tacgatacaa gcaagctggc ctccggcgtg cccgccagat ttctggcag cggctctgga       600 acagattaca ccttcaccat ctctagcatg gaacctgagg attttgccac ctactattgc      660
cagcagtggt ccagcaatcc cctgacattt ggaggaggca ccaagctgga aattaagaga      720
gcggccgcaa ttgaagttat gtatcctcct ccttacctag acaatgagaa gagcaatgga      780
accattatcc atgtgaaagg gaaacacctt tgtccaagtc ccctatttcc cggaccttct      840 aagcccttt gggtgctggt ggtggttggt ggagtcctgg cttgctatag cttgctagta       900
acagtggcct ttattatttt ctgggtgagg agtaagagga gcaggctcct gcacagtgac      960
tacatgaaca tgactccccg ccgccccggg cccacccgca agcattacca gccctatgcc     1020
ccaccacgcg acttcgcagc ctatcgctcc agagtgaagt tcagcaggag cgcagacgcc     1080
cccgcgtacc agcagggcca gaaccagctc tataacgagc tcaatctagg acgaagagag     1140
gagtacgatg ttttgacaa gagacgtggc cgggaccctg agatgggggg aaagccgaga      1200
aggaagaacc ctcaggaagg cctgttcaat gaactgcaga agataagat ggcggaggcc      1260 ttcagtgaga ttgggatgaa aggcgagcgc cggagggggca aggggcacga tggccttttc     1320
cagggtctca gtacagccac caaggacacc ttcgacgccc ttcacatgca ggccctgccc     1380
cctcgc                                                                1386
```

<210> SEQ ID NO 68
<211> LENGTH: 265
<212> TYPE: PRT
<213> ORGANISM: Homo sapiens

<400> SEQUENCE: 68

```
Met Ser Glu Glu Val Thr Tyr Ala Asp Leu Gln Phe Gln Asn Ser Ser
1               5                  10                  15

Glu Met Glu Lys Ile Pro Glu Ile Gly Lys Phe Gly Glu Lys Ala Pro
            20                  25                  30

Pro Ala Pro Ser His Val Trp Arg Pro Ala Ala Leu Phe Leu Thr Leu
        35                  40                  45

Leu Cys Leu Leu Leu Leu Ile Gly Leu Gly Val Leu Ala Ser Met Phe
    50                  55                  60

His Val Thr Leu Lys Ile Glu Met Lys Lys Met Asn Lys Leu Gln Asn
65                  70                  75                  80

Ile Ser Glu Glu Leu Gln Arg Asn Ile Ser Leu Gln Leu Met Ser Asn
                85                  90                  95

Met Asn Ile Ser Asn Lys Ile Arg Asn Leu Ser Thr Thr Leu Gln Thr
            100                 105                 110

Ile Ala Thr Lys Leu Cys Arg Glu Leu Tyr Ser Lys Glu Gln Glu His
        115                 120                 125

Lys Cys Lys Pro Cys Pro Arg Arg Trp Ile Trp His Lys Asp Ser Cys
    130                 135                 140

Tyr Phe Leu Ser Asp Asp Val Gln Thr Trp Gln Glu Ser Lys Met Ala
145                 150                 155                 160

Cys Ala Ala Gln Asn Ala Ser Leu Leu Lys Ile Asn Asn Lys Asn Ala
                165                 170                 175

Leu Glu Phe Ile Lys Ser Gln Ser Arg Ser Tyr Asp Tyr Trp Leu Gly
```

```
                    180                 185                 190
Leu Ser Pro Glu Glu Asp Ser Thr Arg Gly Met Arg Val Asp Asn Ile
            195                 200                 205

Ile Asn Ser Ser Ala Trp Val Ile Arg Asn Ala Pro Asp Leu Asn Asn
            210                 215                 220

Met Tyr Cys Gly Tyr Ile Asn Arg Leu Tyr Val Gln Tyr Tyr His Cys
225                 230                 235                 240

Thr Tyr Lys Lys Arg Met Ile Cys Glu Lys Met Ala Asn Pro Val Gln
                245                 250                 255

Leu Gly Ser Thr Tyr Phe Arg Glu Ala
                260                 265

<210> SEQ ID NO 69
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Gly Gly Ser Ile Ser Ser Ser Thr Tyr Tyr
1               5                   10

<210> SEQ ID NO 70
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Thr His Tyr Arg Gly Ser Thr
1               5

<210> SEQ ID NO 71
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Ala Arg Glu Leu Thr Gly Glu Val Phe Asp Tyr
1               5                   10

<210> SEQ ID NO 72
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Gln Ser Ile Ser Ser Tyr
1               5

<210> SEQ ID NO 73
<211> LENGTH: 3
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 73

Ala Ala Ser
1

<210> SEQ ID NO 74
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Gln Gln Ser Tyr Ser Thr Pro Phe Thr
1               5

<210> SEQ ID NO 75
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Thr Tyr Tyr Trp Gly Trp Ile Arg Gln Pro Pro Arg Lys Gly Leu Glu
        35                  40                  45

Trp Ile Gly Ser Thr His Tyr Arg Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Val Ser Ser Val Thr Ala Ala Asp Thr Ala Val Tyr Tyr
                85                  90                  95

Cys Ala Arg Glu Leu Thr Gly Glu Val Phe Asp Tyr Trp Gly Gln Gly
            100                 105                 110

Thr Leu Val Thr Val Ser Ser
        115

<210> SEQ ID NO 76
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60
```

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Phe
                85                  90                  95

Thr Phe Gly Pro Gly Thr Lys Val Asp Ile Lys
            100                 105

<210> SEQ ID NO 77
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 77
cagctccagc tccaagagtc agggccaggt ctcgtgaaac cgagtgagac cctgtccctg      60
acctgcacag tgagtggtgg atcaatctca agctctacct actattgggg gtggattcgg     120 cagccccta gaaaggggct tgagtggatt ggcagcactc attatcgagg atctacctat      180
tataatcctt ctctgaaaag cagagttacc atctctgtgg atacgtccaa aaatcagttc     240
agtctgaagg tatcatccgt gactgctgcc gacacggccg tgtactattg cgcgagggag     300
ctgacaggtg aggtctttga ctactggggc cagggcacac tcgtgaccgt gtcttct       357

<210> SEQ ID NO 78
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 78
gacatccaga tgacgcagtc cccttccagc ttgtccgcat ctgtgggtga tagggtcacg      60
attacatgta gggctagtca gagtatttct agttacctga attggtacca gcagaaacca     120
ggcaaggcac caaagttgct catctatgcg gcctcctctc tgcaatctgg cgtgccgtcc     180
agatttagtg gatcaggctc cggaaccgat ttcacccta cgatctcctc acttcaaccc     240
gaggatttcg ccacatatta ctgtcaacaa agctattcta caccgttcac cttcggaccg     300
gggacaaaag tggatattaa a                                               321

<210> SEQ ID NO 79
<211> LENGTH: 244
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
                20                  25                  30

Thr Tyr Tyr Trp Gly Trp Ile Arg Gln Pro Pro Arg Lys Gly Leu Glu
            35                  40                  45

Trp Ile Gly Ser Thr His Tyr Arg Gly Ser Thr Tyr Tyr Asn Pro Ser
        50                  55                  60

```
Leu Lys Ser Arg Val Thr Ile Ser Val Asp Thr Ser Lys Asn Gln Phe
 65                  70                  75                  80

Ser Leu Lys Val Ser Ser Val Thr Ala Ala Asp Thr Ala Val Tyr Tyr
                 85                  90                  95

Cys Ala Arg Glu Leu Thr Gly Glu Val Phe Asp Tyr Trp Gly Gln Gly
            100                 105                 110

Thr Leu Val Thr Val Ser Ser Ala Ser Thr Gly Gly Gly Gly Ser Gly
        115                 120                 125

Gly Gly Gly Ser Gly Gly Gly Gly Ser Asp Ile Gln Met Thr Gln Ser
    130                 135                 140

Pro Ser Ser Leu Ser Ala Ser Val Gly Asp Arg Val Thr Ile Thr Cys
145                 150                 155                 160

Arg Ala Ser Gln Ser Ile Ser Ser Tyr Leu Asn Trp Tyr Gln Gln Lys
                165                 170                 175

Pro Gly Lys Ala Pro Lys Leu Leu Ile Tyr Ala Ala Ser Ser Leu Gln
            180                 185                 190

Ser Gly Val Pro Ser Arg Phe Ser Gly Ser Gly Ser Gly Thr Asp Phe
        195                 200                 205

Thr Leu Thr Ile Ser Ser Leu Gln Pro Glu Asp Phe Ala Thr Tyr Tyr
    210                 215                 220

Cys Gln Gln Ser Tyr Ser Thr Pro Phe Thr Phe Gly Pro Gly Thr Lys
225                 230                 235                 240

Val Asp Ile Lys

<210> SEQ ID NO 80
<211> LENGTH: 732
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 80
cagctccagc tccaagagtc agggccaggt ctcgtgaaac cgagtgagac cctgtccctg    60
acctgcacag tgagtggtgg atcaatctca agctctacct actattgggg gtggattcgg   120
cagcccccta gaaaggggct tgagtggatt ggcagcactc attatcgagg atctacctat   180
tataatcctt ctctgaaaag cagagttacc atctctgtgg atacgtccaa aaatcagttc   240
agtctgaagg tatcatccgt gactgctgcc gacacggccg tgtactattg cgcgagggag   300
ctgacaggtg aggtctttga ctactggggc cagggcacac tcgtgaccgt gtcttctgcc   360
tcaacaggag ggggtgggag tggaggcggt ggatcagggg gaggagggag tgacatccag   420
atgacgcagt ccccttccag cttgtccgca tctgtgggtg atagggtcac gattacatgt   480
agggctagtc agagtatttc tagttacctg aattggtacc agcagaaacc aggcaaggca   540
ccaaagttgc tcatctatgc ggcctcctct ctgcaatctg gcgtgccgtc cagatttagt   600
ggatcaggct ccggaaccga tttcacccct acgatctcct cacttcaacc cgaggatttc   660
gccacatatt actgtcaaca aagctattct acaccgttca ccttcggacc ggggacaaaa   720
gtggatatta aa                                                       732

<210> SEQ ID NO 81
<211> LENGTH: 8
<212> TYPE: PRT
<213> ORGANISM: Artificial Sequence
<220> FEATURE:
<223> OTHER INFORMATION: Description of Artificial Sequence: Synthetic
```

```
                         peptide

<400> SEQUENCE: 81

Gly Gly Ser Ile Ser Thr Tyr Tyr
1               5

<210> SEQ ID NO 82
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Ile Tyr Tyr Ser Gly Ser Thr
1               5

<210> SEQ ID NO 83
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Ala Arg Glu Asp Tyr Tyr Gly Ser Gly Ser Pro Phe Asp Tyr
1               5                   10

<210> SEQ ID NO 84
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Gln Gly Ile Arg Tyr Asp
1               5

<210> SEQ ID NO 85
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Leu Gln Asp Tyr Asn Phe Pro Arg Thr
1               5

<210> SEQ ID NO 86
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Thr Tyr
            20                  25                  30
```

```
Tyr Trp Ser Trp Ile Arg Gln Pro Pro Gly Lys Gly Leu Glu Trp Ile
            35                  40                  45

Gly Tyr Ile Tyr Tyr Ser Gly Ser Thr Lys Tyr Asn Pro Ser Leu Lys
    50                  55                  60

Ser Arg Val Thr Ile Ser Val Asp Thr Ser Lys Asn Leu Phe Ser Leu
65                  70                  75                  80

Lys Leu Ser Ser Val Thr Ala Ala Asp Thr Ala Val Tyr Tyr Cys Ala
                85                  90                  95

Arg Glu Asp Tyr Tyr Gly Ser Gly Ser Pro Phe Asp Tyr Trp Gly Gln
                    100                 105                 110

Gly Thr Leu Val Thr Val Ser Ser
            115                 120

<210> SEQ ID NO 87
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Tyr Asp
            20                  25                  30

Leu Gly Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Tyr Asn Phe Pro Arg
                85                  90                  95

Thr Phe Gly Gln Gly Thr Lys Val Glu Ile Lys
            100                 105

<210> SEQ ID NO 88
<211> LENGTH: 245
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Thr Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Lys Tyr Asn Pro Ser Leu Lys
    50                  55                  60

Ser Arg Val Thr Ile Ser Val Asp Thr Ser Lys Asn Leu Phe Ser Leu
65                  70                  75                  80

Lys Leu Ser Ser Val Thr Ala Ala Asp Thr Ala Val Tyr Tyr Cys Ala
                85                  90                  95
```

```
Arg Glu Asp Tyr Tyr Gly Ser Gly Ser Pro Phe Asp Tyr Trp Gly Gln
            100                 105                 110

Gly Thr Leu Val Thr Val Ser Ser Ala Ser Thr Gly Gly Gly Gly Ser
        115                 120                 125

Gly Gly Gly Gly Ser Gly Gly Gly Ser Ala Ile Gln Met Thr Gln
    130                 135                 140

Ser Pro Ser Ser Leu Ser Ala Ser Val Gly Asp Arg Val Thr Ile Thr
145                 150                 155                 160

Cys Arg Ala Ser Gln Gly Ile Arg Tyr Asp Leu Gly Trp Tyr Gln Gln
                165                 170                 175

Lys Pro Gly Lys Ala Pro Lys Leu Leu Ile Tyr Ala Ala Ser Ser Leu
            180                 185                 190

Gln Ser Gly Val Pro Ser Arg Phe Ser Gly Ser Gly Ser Gly Thr Asp
        195                 200                 205

Phe Thr Leu Thr Ile Ser Ser Leu Gln Pro Glu Asp Phe Ala Thr Tyr
    210                 215                 220

Tyr Cys Leu Gln Asp Tyr Asn Phe Pro Arg Thr Phe Gly Gln Gly Thr
225                 230                 235                 240

Lys Val Glu Ile Lys
            245

<210> SEQ ID NO 89
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Gly Phe Thr Phe Ser Ser Tyr Gly
1               5

<210> SEQ ID NO 90
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Ile Ser Tyr Asp Gly Ser Asp Lys
1               5

<210> SEQ ID NO 91
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Ala Arg Asp Lys Gly Tyr Tyr Phe Asp Tyr
1               5                   10

<210> SEQ ID NO 92
<211> LENGTH: 7
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 92

Gln Ser Val Gly Asn Arg Tyr
1               5

<210> SEQ ID NO 93
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Gly Ala Ser
1

<210> SEQ ID NO 94
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Gln Gln Asp Tyr Asn Leu Pro Leu Thr
1               5

<210> SEQ ID NO 95
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asp Lys Tyr Tyr Val Asp Ser Val
    50                  55                  60

Lys Gly Arg Phe Thr Ile Ser Arg Asp Asn Ser Lys Asn Thr Leu Tyr
65                  70                  75                  80

Leu His Met Asn Ser Leu Arg Ala Glu Asp Thr Ala Val Tyr Tyr Cys
                85                  90                  95

Ala Arg Asp Lys Gly Tyr Tyr Phe Asp Tyr Trp Gly Gln Gly Thr Leu
            100                 105                 110

Val Thr Val Ser Ser
        115

<210> SEQ ID NO 96
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 96

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Gly Asn Arg
                20                  25                  30

Tyr Leu Ser Trp Tyr Gln Gln Lys Pro Gly Gln Ala Pro Arg Leu Leu
            35                  40                  45

Ile Tyr Gly Ala Ser Thr Arg Ala Thr Gly Ile Pro Ala Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Val Tyr Tyr Cys Gln Gln Asp Tyr Asn Leu Pro
                85                  90                  95

Leu Thr Phe Gly Gly Gly Thr Lys Val Glu Ile Lys
                100                 105

<210> SEQ ID NO 97
<211> LENGTH: 243
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 97

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Ser Tyr Asp Gly Ser Asp Lys Tyr Tyr Val Asp Ser Val
    50                  55                  60

Lys Gly Arg Phe Thr Ile Ser Arg Asp Asn Ser Lys Asn Thr Leu Tyr
65                  70                  75                  80

Leu His Met Asn Ser Leu Arg Ala Glu Asp Thr Ala Val Tyr Tyr Cys
                85                  90                  95

Ala Arg Asp Lys Gly Tyr Tyr Phe Asp Tyr Trp Gly Gln Gly Thr Leu
                100                 105                 110

Val Thr Val Ser Ser Ala Ser Thr Gly Gly Gly Gly Ser Gly Gly Gly
            115                 120                 125

Gly Ser Gly Gly Gly Gly Ser Glu Ile Val Met Thr Gln Ser Pro Ala
130                 135                 140

Thr Leu Ser Leu Ser Pro Gly Glu Arg Ala Thr Leu Ser Cys Arg Ala
145                 150                 155                 160

Ser Gln Ser Val Gly Asn Arg Tyr Leu Ser Trp Tyr Gln Gln Lys Pro
                165                 170                 175

Gly Gln Ala Pro Arg Leu Leu Ile Tyr Gly Ala Ser Thr Arg Ala Thr
                180                 185                 190

Gly Ile Pro Ala Arg Phe Ser Gly Ser Gly Ser Gly Thr Asp Phe Thr
            195                 200                 205

Leu Thr Ile Ser Ser Leu Gln Pro Glu Asp Phe Ala Val Tyr Tyr Cys
    210                 215                 220

Gln Gln Asp Tyr Asn Leu Pro Leu Thr Phe Gly Gly Gly Thr Lys Val
225                 230                 235                 240
```

Glu Ile Lys

<210> SEQ ID NO 98
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Ala Arg Asp Gly Ser Arg Tyr Phe Asp Tyr
1               5                   10

<210> SEQ ID NO 99
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Gln Ser Val His Ser Lys Tyr
1               5

<210> SEQ ID NO 100
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 100

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asp Lys Tyr Ser Ala Asp Ser Val
    50                  55                  60

Lys Gly Arg Phe Asn Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Ser Arg Tyr Phe Asp Tyr Trp Gly Gln Gly Thr Leu
            100                 105                 110

Val Thr Val Ser Ser
        115

<210> SEQ ID NO 101
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101

Glu Ile Phe Met Thr Gln Ser Pro Ala Thr Leu Ser Leu Ser Pro Gly
1               5                   10                  15

Glu Arg Ala Thr Leu Ser Cys Arg Ala Ser Gln Ser Val His Ser Lys
            20                  25                  30

Tyr Leu Ser Trp Tyr Gln Gln Lys Pro Gly Gln Ala Pro Ser Leu Leu
                35                  40                  45

Ile Tyr Gly Ala Ser Thr Arg Ala Thr Gly Ile Pro Ala Arg Phe Ser
 50                      55                  60

Gly Ser Gly Ser Gly Thr Asp Phe Thr Leu Thr Ile Ser Ser Leu Gln
 65                  70                  75                  80

Pro Glu Asp Phe Ala Val Tyr Tyr Cys Gln Gln Asp Tyr Asn Leu Pro
                 85                  90                  95

Ile Thr Phe Gly Gln Gly Thr Arg Leu Glu Ile Lys
            100                 105

<210> SEQ ID NO 102
<211> LENGTH: 243
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 102

Gln Val Gln Leu Val Glu Ser Gly Gly Gly Val Val Gln Pro Gly Arg
 1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
                35                  40                  45

Ala Val Ile Ser Tyr Asp Gly Ser Asp Lys Tyr Ser Ala Asp Ser Val
 50                      55                  60

Lys Gly Arg Phe Asn Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Gly Ser Arg Tyr Phe Asp Tyr Trp Gly Gln Gly Thr Leu
            100                 105                 110

Val Thr Val Ser Ser Ala Ser Thr Gly Gly Gly Gly Ser Gly Gly Gly
            115                 120                 125

Gly Ser Gly Gly Gly Ser Glu Ile Phe Met Thr Gln Ser Pro Ala
130                 135                 140

Thr Leu Ser Leu Ser Pro Gly Glu Arg Ala Thr Leu Ser Cys Arg Ala
145                 150                 155                 160

Ser Gln Ser Val His Ser Lys Tyr Leu Ser Trp Tyr Gln Gln Lys Pro
                165                 170                 175

Gly Gln Ala Pro Ser Leu Leu Ile Tyr Gly Ala Ser Thr Arg Ala Thr
            180                 185                 190

Gly Ile Pro Ala Arg Phe Ser Gly Ser Gly Ser Gly Thr Asp Phe Thr
        195                 200                 205

Leu Thr Ile Ser Ser Leu Gln Pro Glu Asp Phe Ala Val Tyr Tyr Cys
    210                 215                 220

Gln Gln Asp Tyr Asn Leu Pro Ile Thr Phe Gly Gln Gly Thr Arg Leu
225                 230                 235                 240

Glu Ile Lys

<210> SEQ ID NO 103

```
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Ile Tyr Phe Ser Gly Ser Thr
1               5

<210> SEQ ID NO 104
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Gln Gly Ile Arg Asn Asp
1               5

<210> SEQ ID NO 105
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Leu Gln Asp Tyr Asn Tyr Pro Arg Thr
1               5

<210> SEQ ID NO 106
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 106

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Thr Tyr
            20                  25                  30

Tyr Trp Ser Trp Ile Arg Gln Pro Pro Gly Lys Gly Leu Glu Trp Leu
        35                  40                  45

Gly Tyr Ile Tyr Phe Ser Gly Ser Thr Asn Tyr Asn Pro Ser Leu Lys
    50                  55                  60

Ser Arg Leu Thr Ile Ser Val Ala Ala Ser Lys Ser Gln Phe Ser Leu
65                  70                  75                  80

Lys Leu Ser Ser Val Thr Ala Ala Asp Thr Ala Val Tyr Tyr Cys Ala
                85                  90                  95

Arg Glu Asp Tyr Tyr Gly Ser Gly Ser Pro Phe Asp Tyr Trp Gly Gln
            100                 105                 110

Gly Thr Leu Val Thr Val Ser Ser
        115                 120

<210> SEQ ID NO 107
<211> LENGTH: 107
<212> TYPE: PRT
```

<213> ORGANISM: Artificial Sequence
<220> FEATURE:
<223> OTHER INFORMATION: Description of Artificial Sequence: Synthetic polypeptide

<400> SEQUENCE: 107

```
Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Phe Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Tyr Phe Thr Leu Thr Ile Ser Ser Leu Gln Pro
65                  70                  75                  80

Glu Asp Ser Ala Thr Tyr Tyr Cys Leu Gln Asp Tyr Asn Tyr Pro Arg
                85                  90                  95

Thr Phe Gly Gln Gly Thr Lys Val Glu Ile Lys
            100                 105
```

<210> SEQ ID NO 108
<211> LENGTH: 245
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 108

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Ser Ile Ser Thr Tyr
            20                  25                  30

Tyr Trp Ser Trp Ile Arg Gln Pro Pro Gly Lys Gly Leu Glu Trp Leu
        35                  40                  45

Gly Tyr Ile Tyr Phe Ser Gly Ser Thr Asn Tyr Asn Pro Ser Leu Lys
    50                  55                  60

Ser Arg Leu Thr Ile Ser Val Ala Ala Ser Lys Ser Gln Phe Ser Leu
65                  70                  75                  80

Lys Leu Ser Ser Val Thr Ala Ala Asp Thr Ala Val Tyr Tyr Cys Ala
                85                  90                  95

Arg Glu Asp Tyr Tyr Gly Ser Gly Ser Pro Phe Asp Tyr Trp Gly Gln
                100                 105                 110

Gly Thr Leu Val Thr Val Ser Ser Ala Ser Thr Gly Gly Gly Gly Ser
            115                 120                 125

Gly Gly Gly Gly Ser Gly Gly Gly Ser Ala Ile Gln Met Thr Gln
        130                 135                 140

Ser Pro Ser Ser Leu Ser Ala Ser Val Gly Asp Arg Val Thr Ile Thr
145                 150                 155                 160

Cys Arg Ala Ser Gln Gly Ile Arg Asn Asp Leu Gly Trp Phe Gln Gln
                165                 170                 175

Lys Pro Gly Lys Ala Pro Lys Leu Leu Ile Tyr Ala Ala Ser Ser Leu
                180                 185                 190

Gln Ser Gly Val Pro Ser Arg Phe Ser Gly Ser Gly Ser Gly Thr Tyr
            195                 200                 205

Phe Thr Leu Thr Ile Ser Ser Leu Gln Pro Glu Asp Ser Ala Thr Tyr
```

```
                210                 215                 220
Tyr Cys Leu Gln Asp Tyr Asn Tyr Pro Arg Thr Phe Gly Gln Gly Thr
225                 230                 235                 240

Lys Val Glu Ile Lys
                245

<210> SEQ ID NO 109
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Gly Gly Ser Ile Ser Thr Asp Tyr
1               5

<210> SEQ ID NO 110
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Gln Asp Ile Arg Asn Asp
1               5

<210> SEQ ID NO 111
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 111

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Thr Asp
                20                  25                  30

Tyr Trp Ser Trp Ile Arg Gln Pro Pro Gly Lys Gly Leu Glu Trp Ile
            35                  40                  45

Gly Tyr Ile Tyr Phe Ser Gly Ser Thr Lys Tyr Asn Pro Ser Leu Lys
        50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Glu Asp Tyr Tyr Gly Ser Gly Ser Pro Phe Asp Tyr Trp Gly Gln
            100                 105                 110

Gly Thr Leu Val Thr Val Ser Ser
        115                 120

<210> SEQ ID NO 112
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 112

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Asn Asp
            20                  25                  30

Leu Gly Trp Phe Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Tyr Asn Phe Pro Arg
                85                  90                  95

Thr Phe Gly Gln Gly Thr Lys Val Glu Ile Lys
            100                 105

<210> SEQ ID NO 113
<211> LENGTH: 245
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 113

Gln Val Gln Leu Gln Glu Ser Gly Pro Gly Leu Val Lys Pro Ser Glu
1               5                   10                  15

Thr Leu Ser Leu Thr Cys Thr Val Ser Gly Ser Ile Ser Thr Asp
            20                  25                  30

Tyr Trp Ser Trp Ile Arg Gln Pro Pro Gly Lys Gly Leu Glu Trp Ile
        35                  40                  45

Gly Tyr Ile Tyr Phe Ser Gly Ser Thr Lys Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Glu Asp Tyr Tyr Gly Ser Gly Ser Pro Phe Asp Tyr Trp Gly Gln
                100                 105                 110

Gly Thr Leu Val Thr Val Ser Ser Ala Ser Thr Gly Gly Gly Ser
            115                 120                 125

Gly Gly Gly Gly Ser Gly Gly Gly Ser Ala Ile Gln Met Thr Gln
        130                 135                 140

Ser Pro Ser Ser Leu Ser Ala Ser Val Gly Asp Arg Val Thr Ile Thr
145                 150                 155                 160

Cys Arg Ala Ser Gln Asp Ile Arg Asn Asp Leu Gly Trp Phe Gln Gln
                165                 170                 175

Lys Pro Gly Lys Ala Pro Lys Leu Leu Ile Tyr Ala Ala Ser Ser Leu
            180                 185                 190

Gln Ser Gly Val Pro Ser Arg Phe Ser Gly Ser Gly Ser Gly Thr Asp
        195                 200                 205

Phe Thr Leu Thr Ile Ser Ser Leu Gln Pro Glu Asp Phe Ala Thr Tyr
    210                 215                 220

Tyr Cys Leu Gln Asp Tyr Asn Phe Pro Arg Thr Phe Gly Gln Gly Thr
225                 230                 235                 240

Lys Val Glu Ile Lys
            245

<210> SEQ ID NO 114
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Ala Arg Asp Gly Gln Phe Tyr Phe Asp Tyr
1               5                   10

<210> SEQ ID NO 115
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Gln Ser Val Thr Ser Arg Tyr
1               5

<210> SEQ ID NO 116
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Gln Gln Asp Tyr Asn Leu Pro Leu Thr
1               5

<210> SEQ ID NO 117
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 117

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Glu Gly Leu Glu Trp Val
        35                  40                  45

Thr Val Ile Ser Tyr Asp Gly Ser Asp Lys Tyr Tyr Ala Asp Ser Val
    50                  55                  60

Lys Gly Arg Phe Thr Ile Ser Arg Asp Asn Ser Lys Ser Thr Leu Phe
65                  70                  75                  80

Leu Gln Met Asn Ser Leu Arg Ala Glu Asp Thr Ala Val Tyr Tyr Cys
                85                  90                  95

Ala Arg Asp Gly Gln Phe Tyr Phe Asp Tyr Trp Gly Gln Gly Thr Leu
            100                 105                 110

Val Thr Val Ser Ser

```
                                        115

<210> SEQ ID NO 118
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 118

Glu Ile Val Met Thr Gln Ser Pro Ala Thr Leu Ser Leu Ser Pro Gly
1               5                   10                  15

Glu Ser Ala Thr Leu Ser Cys Arg Ala Ser Gln Ser Val Thr Ser Arg
            20                  25                  30

Tyr Leu Ser Trp Tyr Gln Gln Lys Pro Gly Gln Ala Pro Arg Leu Leu
        35                  40                  45

Met Tyr Gly Ala Ser Thr Arg Pro Thr Gly Ile Pro Ala Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Val Tyr Tyr Cys Gln Gln Asp Tyr Asn Leu Pro
                85                  90                  95

Leu Thr Phe Gly Gly Gly Thr Lys Val Glu Ile Lys
            100                 105

<210> SEQ ID NO 119
<211> LENGTH: 243
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 119

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Glu Gly Leu Glu Trp Val
        35                  40                  45

Thr Val Ile Ser Tyr Asp Gly Ser Asp Lys Tyr Tyr Ala Asp Ser Val
    50                  55                  60

Lys Gly Arg Phe Thr Ile Ser Arg Asp Asn Ser Lys Ser Thr Leu Phe
65                  70                  75                  80

Leu Gln Met Asn Ser Leu Arg Ala Glu Asp Thr Ala Val Tyr Tyr Cys
                85                  90                  95

Ala Arg Asp Gly Gln Phe Tyr Phe Asp Tyr Trp Gly Gln Gly Thr Leu
            100                 105                 110

Val Thr Val Ser Ser Ala Ser Thr Gly Gly Gly Gly Ser Gly Gly Gly
        115                 120                 125

Gly Ser Gly Gly Gly Gly Ser Glu Ile Val Met Thr Gln Ser Pro Ala
    130                 135                 140

Thr Leu Ser Leu Ser Pro Gly Glu Ser Ala Thr Leu Ser Cys Arg Ala
145                 150                 155                 160

Ser Gln Ser Val Thr Ser Arg Tyr Leu Ser Trp Tyr Gln Gln Lys Pro
                165                 170                 175

Gly Gln Ala Pro Arg Leu Leu Met Tyr Gly Ala Ser Thr Arg Pro Thr
```

```
                180                 185                 190
Gly Ile Pro Ala Arg Phe Ser Gly Ser Gly Ser Gly Thr Asp Phe Thr
                    195                 200                 205

Leu Thr Ile Ser Ser Leu Gln Pro Glu Asp Phe Ala Val Tyr Tyr Cys
                    210                 215                 220

Gln Gln Asp Tyr Asn Leu Pro Leu Thr Phe Gly Gly Gly Thr Lys Val
225                 230                 235                 240

Glu Ile Lys

<210> SEQ ID NO 120
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Gly Phe Thr Phe Ser Asn Tyr Gly
1               5

<210> SEQ ID NO 121
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Ile Ser Tyr Asp Gly Ser Asp Lys
1               5

<210> SEQ ID NO 122
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Ala Arg Asp Ser Gly Arg Tyr Phe Phe Asp Tyr
1               5                   10

<210> SEQ ID NO 123
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Gln Ser Val Ser Ser Arg Ser
1               5

<210> SEQ ID NO 124
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124
```

Gly Pro Ser
1

<210> SEQ ID NO 125
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

His Gln Asp Tyr Asn Leu Pro Leu Thr
1               5

<210> SEQ ID NO 126
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 126

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asp Lys Ser Tyr Lys Asp Ser Val
    50                  55                  60

Lys Gly Arg Phe Thr Ile Ala Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Ser Gly Arg Tyr Phe Phe Asp Tyr Trp Gly Gln Gly Thr
            100                 105                 110

Leu Val Thr Val Ser Ser
        115

<210> SEQ ID NO 127
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 127

Glu Ile Ile Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Arg
            20                  25                  30

Ser Leu Ser Trp Tyr Gln His Lys Pro Gly Gln Ala Pro Arg Leu Leu
        35                  40                  45

Ile Tyr Gly Pro Ser Thr Arg Ala Thr Gly Ile Pro Ala Arg Phe Ser
    50                  55                  60

Gly Ser Gly Ser Gly Thr Asp Phe Thr Leu Thr Ile Ser Ser Leu Gln
65                  70                  75                  80

```
Pro Glu Asp Phe Ala Val Tyr Tyr Cys His Gln Asp Tyr Asn Leu Pro
                85                  90                  95

Leu Thr Phe Gly Gly Gly Thr Lys Val Glu Ile Lys
            100                 105

<210> SEQ ID NO 128
<211> LENGTH: 244
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 128

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asp Lys Tyr Tyr Lys Asp Ser Val
    50                  55                  60

Lys Gly Arg Phe Thr Ile Ala Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Ser Gly Arg Tyr Phe Phe Asp Tyr Trp Gly Gln Gly Thr
            100                 105                 110

Leu Val Thr Val Ser Ser Ala Ser Thr Gly Gly Gly Ser Gly Gly
        115                 120                 125

Gly Gly Ser Gly Gly Gly Ser Glu Ile Ile Met Thr Gln Ser Pro
    130                 135                 140

Ala Thr Leu Ser Leu Ser Pro Gly Glu Arg Ala Thr Leu Ser Cys Arg
145                 150                 155                 160

Ala Ser Gln Ser Val Ser Ser Arg Ser Leu Ser Trp Tyr Gln His Lys
                165                 170                 175

Pro Gly Gln Ala Pro Arg Leu Leu Ile Tyr Gly Pro Ser Thr Arg Ala
            180                 185                 190

Thr Gly Ile Pro Ala Arg Phe Ser Gly Ser Gly Ser Gly Thr Asp Phe
        195                 200                 205

Thr Leu Thr Ile Ser Ser Leu Gln Pro Glu Asp Phe Ala Val Tyr Tyr
    210                 215                 220

Cys His Gln Asp Tyr Asn Leu Pro Leu Thr Phe Gly Gly Gly Thr Lys
225                 230                 235                 240

Val Glu Ile Lys

<210> SEQ ID NO 129
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Gly Phe Thr Phe Ser Lys Tyr Gly
1               5
```

```
<210> SEQ ID NO 130
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Ile Trp Tyr Asp Gly Ser Ile Lys
1               5

<210> SEQ ID NO 131
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Ala Arg Gly Ser Leu Trp Phe Gly Glu Phe Tyr Phe Asp Tyr
1               5                   10

<210> SEQ ID NO 132
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Gln Gly Ile Ser Ser Ala
1               5

<210> SEQ ID NO 133
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Asp Ala Ser
1

<210> SEQ ID NO 134
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Gln Gln Phe Asn Asn Tyr Pro Arg Thr
1               5

<210> SEQ ID NO 135
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 135
```

Gln Val Lys Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Lys Tyr
                20                  25                  30

Gly Met His Trp Val Arg Gln Ala Pro Gly Lys Gly Leu Glu Trp Val
            35                  40                  45

Ala Phe Ile Trp Tyr Asp Gly Ser Ile Lys Asn Tyr Ala Asp Ser Val
        50                  55                  60

Lys Gly Arg Phe Thr Thr Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Ser Leu Trp Phe Gly Glu Phe Tyr Phe Asp Tyr Trp Gly
            100                 105                 110

Gln Gly Thr Leu Val Thr Val Ser Ser
            115                 120

<210> SEQ ID NO 136
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 136

Ala Ile Gln Leu Thr Gln Ser Pro Ser Ser Leu Ser Ala Ser Val Gly
1               5                   10                  15

Asp Arg Val Thr Ile Thr Cys Arg Thr Ser Gln Gly Ile Ser Ser Ala
                20                  25                  30

Leu Ala Trp Tyr Gln Gln Lys Pro Gly Lys Thr Pro Lys Leu Leu Ile
            35                  40                  45

Tyr Asp Ala Ser Ser Leu Glu Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Asn Tyr Pro Arg
                85                  90                  95

Thr Phe Gly Gln Gly Thr Lys Val Glu Ile Lys
            100                 105

<210> SEQ ID NO 137
<211> LENGTH: 246
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 137

Gln Val Lys Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Lys Tyr
                20                  25                  30

Gly Met His Trp Val Arg Gln Ala Pro Gly Lys Gly Leu Glu Trp Val
            35                  40                  45

Ala Phe Ile Trp Tyr Asp Gly Ser Ile Lys Asn Tyr Ala Asp Ser Val
        50                  55                  60

```
Lys Gly Arg Phe Thr Thr Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gly Ser Leu Trp Phe Gly Glu Phe Tyr Phe Asp Tyr Trp Gly
            100                 105                 110

Gln Gly Thr Leu Val Thr Val Ser Ser Ala Ser Thr Gly Gly Gly Gly
            115                 120                 125

Ser Gly Gly Gly Gly Ser Gly Gly Gly Ser Ala Ile Gln Leu Thr
130                 135                 140

Gln Ser Pro Ser Ser Leu Ser Ala Ser Val Gly Asp Arg Val Thr Ile
145                 150                 155                 160

Thr Cys Arg Thr Ser Gln Gly Ile Ser Ser Ala Leu Ala Trp Tyr Gln
            165                 170                 175

Gln Lys Pro Gly Lys Thr Pro Lys Leu Leu Ile Tyr Asp Ala Ser Ser
            180                 185                 190

Leu Glu Ser Gly Val Pro Ser Arg Phe Ser Gly Ser Gly Ser Gly Thr
            195                 200                 205

Asp Phe Thr Leu Thr Ile Ser Ser Leu Gln Pro Glu Asp Phe Ala Thr
210                 215                 220

Tyr Tyr Cys Gln Gln Phe Asn Asn Tyr Pro Arg Thr Phe Gly Gln Gly
225                 230                 235                 240

Thr Lys Val Glu Ile Lys
            245

<210> SEQ ID NO 138
<211> LENGTH: 361
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 138

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Thr Tyr Tyr Trp Gly Trp Ile Arg Gln Pro Pro Arg Lys Gly Leu Glu
        35                  40                  45

Trp Ile Gly Ser Thr His Tyr Arg Gly Ser Thr Tyr Tyr Asn Pro Ser
 50                  55                  60

Leu Lys Ser Arg Val Thr Ile Ser Val Asp Thr Ser Lys Asn Gln Phe
 65                  70                  75                  80

Ser Leu Lys Val Ser Ser Val Thr Ala Ala Asp Thr Ala Val Tyr Tyr
                 85                  90                  95

Cys Ala Arg Glu Leu Thr Gly Glu Val Phe Asp Tyr Trp Gly Gln Gly
            100                 105                 110

Thr Leu Val Thr Val Ser Ser Ala Ser Thr Gly Gly Gly Gly Ser Gly
            115                 120                 125

Gly Gly Gly Ser Gly Gly Gly Ser Asp Ile Gln Met Thr Gln Ser
130                 135                 140

Pro Ser Ser Leu Ser Ala Ser Val Gly Asp Arg Val Thr Ile Thr Cys
145                 150                 155                 160

Arg Ala Ser Gln Ser Ile Ser Ser Tyr Leu Asn Trp Tyr Gln Gln Lys
```

```
                165                 170                 175
Pro Gly Lys Ala Pro Lys Leu Leu Ile Tyr Ala Ala Ser Ser Leu Gln
            180                 185                 190
Ser Gly Val Pro Ser Arg Phe Ser Gly Ser Gly Ser Gly Thr Asp Phe
        195                 200                 205
Thr Leu Thr Ile Ser Ser Leu Gln Pro Glu Asp Phe Ala Thr Tyr Tyr
    210                 215                 220
Cys Gln Gln Ser Tyr Ser Thr Pro Phe Thr Phe Gly Pro Gly Thr Lys
225                 230                 235                 240
Val Asp Ile Lys Arg Ala Ala Ala Pro Thr Thr Thr Pro Ala Pro Arg
                245                 250                 255
Pro Pro Thr Pro Ala Pro Thr Ile Ala Ser Gln Pro Leu Ser Leu Arg
            260                 265                 270
Pro Glu Ala Cys Arg Pro Ala Ala Gly Gly Ala Val His Thr Arg Gly
        275                 280                 285
Leu Asp Phe Ala Cys Asp Ile Tyr Ile Trp Ala Pro Leu Ala Gly Thr
    290                 295                 300
Cys Gly Val Leu Leu Leu Ser Leu Val Ile Thr Leu Tyr Cys Asn Lys
305                 310                 315                 320
Arg Gly Arg Lys Lys Leu Leu Tyr Ile Phe Lys Gln Pro Phe Met Arg
                325                 330                 335
Pro Val Gln Thr Thr Gln Glu Glu Asp Gly Cys Ser Cys Arg Phe Pro
            340                 345                 350
Glu Glu Glu Glu Gly Gly Cys Glu Leu
        355                 360

<210> SEQ ID NO 139
<211> LENGTH: 1083
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 139
cagctccagc tccaagagtc agggccaggt ctcgtgaaac cgagtgagac cctgtccctg     60
acctgcacag tgagtggtgg atcaatctca agctctacct actattgggg gtggattcgg    120
cagcccccta gaaggggct tgagtggatt ggcagcactc attatcgagg atctacctat    180
tataatcctt ctctgaaaag cagagttacc atctctgtgg atacgtccaa aaatcagttc    240
agtctgaagg tatcatccgt gactgctgcc gacacggccg tgtactattg cgcgagggag    300
ctgacaggtg aggtctttga ctactggggc cagggcacac tcgtgaccgt gtcttctgcc    360
tcaacaggag ggggtgggag tggaggcggt ggatcagggg gaggagggag tgacatccag    420
atgacgcagt cccctttccag cttgtccgca tctgtgggtg atagggtcac gattacatgt    480
agggctagtc agagtatttc tagttacctg aattggtacc agcagaaacc aggcaaggca    540
ccaaagttgc tcatctatgc ggcctcctct ctgcaatctg gcgtgccgtc cagatttagt    600
ggatcaggct ccggaaccga tttcaccctt acgatctcct cacttcaacc cgaggatttc    660
gccacatatt actgtcaaca aagctattct acaccgttca ccttcggacc ggggacaaaa    720
gtggatatta aacgggcggc cgcccccacc acgacgccag cgccgcgacc accaaccccg    780
gcgcccacga tcgcgtcgca gcccctgtcc ctgcgcccag aggcgtgccg gccagcggcg    840
ggggcgcag tgcacacgag ggggctggac ttcgcctgtg atatctacat ctgggcgccc    900
```

```
ctggccggga cttgtggggt ccttctcctg tcactggtta tcacccttta ctgcaacaaa       960
cggggcagaa agaagctcct gtatatattc aaacaaccat ttatgagacc agtacaaact      1020
actcaagagg aagatggctg tagctgccga tttccagaag aagaagaagg aggatgtgaa      1080
ctg                                                                    1083
```

<210> SEQ ID NO 140
<211> LENGTH: 881
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 140

```
Met Ala Leu Pro Val Thr Ala Leu Leu Leu Pro Leu Ala Leu Leu Leu
1               5                   10                  15

His Ala Gln Val Gln Leu Gln Gln Ser Gly Ala Glu Val Ala Lys Pro
            20                  25                  30

Gly Ala Ser Val Lys Leu Ser Cys Lys Ala Ser Gly Tyr Thr Phe Thr
        35                  40                  45

Asn Tyr Trp Met Gln Trp Ile Lys Gln Ala Pro Gly Gln Gly Leu Glu
    50                  55                  60

Trp Ile Gly Ala Val Tyr Pro Gly Asp Gly Asp Thr Arg His Thr Gln
65                  70                  75                  80

Lys Phe Lys Gly Lys Ala Thr Leu Thr Ala Asp Lys Ser Thr Ser Thr
                85                  90                  95

Ala Tyr Met Glu Val Ser Ser Leu Arg Ser Glu Asp Thr Ala Val Tyr
            100                 105                 110

Tyr Cys Ala Arg Gly Phe Thr Ala Tyr Gly Met Asp Tyr Trp Gly Gln
        115                 120                 125

Gly Thr Thr Val Thr Val Ser Ser Gly Gly Gly Gly Ser Gly Gly Gly
    130                 135                 140

Gly Ser Gly Gly Gly Gly Ser Glu Ile Val Leu Thr Gln Ser Pro Ala
145                 150                 155                 160

Thr Met Ser Ala Ser Pro Gly Glu Arg Val Thr Met Ser Cys Ser Ala
                165                 170                 175

Ser Ser Ser Val Ser Tyr Met His Trp Tyr Gln Gln Lys Ser Gly Gln
            180                 185                 190

Ser Pro Lys Arg Trp Ile Tyr Asp Thr Ser Lys Leu Ala Ser Gly Val
        195                 200                 205

Pro Ala Arg Phe Ser Gly Ser Gly Ser Gly Thr Asp Tyr Thr Phe Thr
    210                 215                 220

Ile Ser Ser Met Glu Pro Glu Asp Phe Ala Thr Tyr Tyr Cys Gln Gln
225                 230                 235                 240

Trp Ser Ser Asn Pro Leu Thr Phe Gly Gly Gly Thr Lys Leu Glu Ile
                245                 250                 255

Lys Arg Ala Ala Ala Ile Glu Val Met Tyr Pro Pro Tyr Leu Asp
            260                 265                 270

Asn Glu Lys Ser Asn Gly Thr Ile Ile His Val Lys Gly Lys His Leu
        275                 280                 285

Cys Pro Ser Pro Leu Phe Pro Gly Pro Ser Lys Pro Phe Trp Val Leu
    290                 295                 300

Val Val Val Gly Gly Val Leu Ala Cys Tyr Ser Leu Leu Val Thr Val
305                 310                 315                 320
```

-continued

```
Ala Phe Ile Ile Phe Trp Val Arg Ser Lys Arg Ser Arg Leu Leu His
                325                 330                 335

Ser Asp Tyr Met Asn Met Thr Pro Arg Arg Pro Gly Pro Thr Arg Lys
            340                 345                 350

His Tyr Gln Pro Tyr Ala Pro Pro Arg Asp Phe Ala Ala Tyr Arg Ser
        355                 360                 365

Arg Val Lys Phe Ser Arg Ser Ala Asp Ala Pro Ala Tyr Gln Gln Gly
    370                 375                 380

Gln Asn Gln Leu Tyr Asn Glu Leu Asn Leu Gly Arg Arg Glu Glu Tyr
385                 390                 395                 400

Asp Val Leu Asp Lys Arg Arg Gly Arg Asp Pro Glu Met Gly Gly Lys
                405                 410                 415

Pro Arg Arg Lys Asn Pro Gln Glu Gly Leu Phe Asn Glu Leu Gln Lys
            420                 425                 430

Asp Lys Met Ala Glu Ala Phe Ser Glu Ile Gly Met Lys Gly Glu Arg
        435                 440                 445

Arg Arg Gly Lys Gly His Asp Gly Leu Phe Gln Gly Leu Ser Thr Ala
    450                 455                 460

Thr Lys Asp Thr Phe Asp Ala Leu His Met Gln Ala Leu Pro Pro Arg
465                 470                 475                 480

Gly Ser Gly Ala Thr Asn Phe Ser Leu Leu Lys Gln Ala Gly Asp Val
                485                 490                 495

Glu Glu Asn Pro Gly Pro Met Ala Leu Pro Val Thr Ala Leu Leu Leu
            500                 505                 510

Pro Leu Ala Leu Leu Leu His Ala Gln Leu Gln Leu Gln Glu Ser Gly
        515                 520                 525

Pro Gly Leu Val Lys Pro Ser Glu Thr Leu Ser Leu Thr Cys Thr Val
    530                 535                 540

Ser Gly Gly Ser Ile Ser Ser Thr Tyr Tyr Trp Gly Trp Ile Arg
545                 550                 555                 560

Gln Pro Pro Arg Lys Gly Leu Glu Trp Ile Gly Ser Thr His Tyr Arg
                565                 570                 575

Gly Ser Thr Tyr Tyr Asn Pro Ser Leu Lys Ser Arg Val Thr Ile Ser
            580                 585                 590

Val Asp Thr Ser Lys Asn Gln Phe Ser Leu Lys Val Ser Ser Val Thr
        595                 600                 605

Ala Ala Asp Thr Ala Val Tyr Tyr Cys Ala Arg Glu Leu Thr Gly Glu
    610                 615                 620

Val Phe Asp Tyr Trp Gly Gln Gly Thr Leu Val Thr Val Ser Ser Ala
625                 630                 635                 640

Ser Thr Gly Gly Gly Gly Ser Gly Gly Gly Gly Ser Gly Gly Gly Gly
                645                 650                 655

Ser Asp Ile Gln Met Thr Gln Ser Pro Ser Ser Leu Ser Ala Ser Val
            660                 665                 670

Gly Asp Arg Val Thr Ile Thr Cys Arg Ala Ser Gln Ser Ile Ser Ser
        675                 680                 685

Tyr Leu Asn Trp Tyr Gln Gln Lys Pro Gly Lys Ala Pro Lys Leu Leu
    690                 695                 700

Ile Tyr Ala Ala Ser Ser Leu Gln Ser Gly Val Pro Ser Arg Phe Ser
705                 710                 715                 720

Gly Ser Gly Ser Gly Thr Asp Phe Thr Leu Thr Ile Ser Ser Leu Gln
                725                 730                 735

Pro Glu Asp Phe Ala Thr Tyr Tyr Cys Gln Gln Ser Tyr Ser Thr Pro
```

```
                    740                 745                 750
Phe Thr Phe Gly Pro Gly Thr Lys Val Asp Ile Lys Arg Ala Ala Ala
            755                 760                 765

Pro Thr Thr Thr Pro Ala Pro Arg Pro Pro Thr Pro Ala Pro Thr Ile
        770                 775                 780

Ala Ser Gln Pro Leu Ser Leu Arg Pro Glu Ala Cys Arg Pro Ala Ala
785                 790                 795                 800

Gly Gly Ala Val His Thr Arg Gly Leu Asp Phe Ala Cys Asp Ile Tyr
                805                 810                 815

Ile Trp Ala Pro Leu Ala Gly Thr Cys Gly Val Leu Leu Leu Ser Leu
            820                 825                 830

Val Ile Thr Leu Tyr Cys Asn Lys Arg Gly Arg Lys Lys Leu Leu Tyr
            835                 840                 845

Ile Phe Lys Gln Pro Phe Met Arg Pro Val Gln Thr Thr Gln Glu Glu
        850                 855                 860

Asp Gly Cys Ser Cys Arg Phe Pro Glu Glu Glu Glu Gly Gly Cys Glu
865                 870                 875                 880

Leu
```

<210> SEQ ID NO 141
<211> LENGTH: 8940
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 141

```
ggattagtcc aatttgttaa agacaggata tcagtggtcc aggctctagt tttgactcaa      60
caatatcacc agctgaagcc tatagagtac gagccataga taaaataaaa gatttattt     120
agtctccaga aaaaggggg aatgaaagac cccacctgta ggtttggcaa gctagcttaa     180
gtaacgccat tttgcaaggc atggaaaaat acataactga aatagagaa gttcagatca     240
aggtcaggaa cagatggaac agctgaatat gggccaaaca ggatatctgt ggtaagcagt     300
tcctgccccg gctcagggcc aagaacagat ggaacagctg aatatgggcc aaacaggata     360
tctgtggtaa gcagttcctg ccccggctca gggccaagaa cagatggtcc ccagatgcgg     420
tccagccctc agcagtttct agagaaccat cagatgtttc agggtgccc caaggacctg     480
aaatgaccct gtgccttatt tgaactaacc aatcagttcg cttctcgctt ctgttcgcgc     540
gcttctgctc cccgagctca ataaaagagc ccacaacccc tcactcgggg cgccagtcct     600
ccgattgact gagtcgcccg ggtacccgtg tatccaataa accctcttgc agttgcatcc     660
gacttgtggt ctcgctgttc cttgggaggg tctcctctga gtgattgact acccgtcagc     720
gggggtcttt cacatgcagc atgtatcaaa attaatttgg ttttttttct taagtattta     780
cattaaatgg ccatagtact taagttaca ttggcttcct tgaaataaac atggagtatt     840
cagaatgtgt cataaatatt tctaatttta agatagtatc tccattggct ttctactttt     900
tcttttattt ttttttgtcc tctgtcttcc atttgttgtt gttgttgttt gtttgtttgt     960
ttgttggttg gttggttaat ttttttttaa agatcctaca ctatagttca agctagacta    1020
ttagctactc tgtaacccag ggtgaccttg aagtcatggg tagcctgctg tttagccttt    1080
cccacatcta agattacagg tatgagctat cattttggt atattgattg attgattgat    1140
tgatgtgtgt gtgtgtgatt gtgtttgtgt gtgtgattgt gtatatgtgt gtatggttgt    1200
```

-continued

```
gtgtgattgt gtgtatgtat gtttgtgtgt gattgtgtgt gtgtgattgt gcatgtgtgt    1260
gtgtgtgatt gtgtttatgt gtatgattgt gtgtgtgtgt gtgtgtgtgt gtgtgtgtgt    1320
gtgtgtgtgt gtgttgtgta tatatattta tggtagtgag aggcaacgct ccggctcagg    1380
tgtcaggttg gttttttgaga cagagtcttt cacttagctt ggaattcact ggccgtcgtt   1440
ttacaacgtc gtgactggga aaccctggc gttacccaac ttaatcgcct tgcagcacat    1500
cccccttttcg ccagctggcg taatagcgaa gaggcccgca ccgatcgccc ttcccaacag   1560
ttgcgcagcc tgaatggcga atggcgcctg atgcggtatt ttctccttac gcatctgtgc    1620
ggtatttcac accgcatatg gtgcactctc agtacaatct gctctgatgc cgcatagtta   1680
agccagcccc gacacccgcc aacacccgct gacgcgccct gacgggcttg tctgctcccg    1740
gcatccgctt acagacaagc tgtgaccgtc tccgggagct gcatgtgtca gaggttttca    1800
ccgtcatcac cgaaacgcgc gagacgaaag gcctcgtga tacgcctatt tttataggtt     1860
aatgtcatga taataatggt ttcttagacg tcaggtggca cttttcgggg aaatgtgcgc    1920
ggaacccta tttgtttatt ttttttaaata cattcaaata tgtatccgct catgagacaa    1980
taaccctgat aaatgcttca ataatattga aaaggaaga gtatgagcca tattcaacgg    2040
gaaacgtcga ggccgcgatt aaattccaac atggatgctg atttatatgg gtataaatgg   2100
gctcgcgata atgtcgggca atcaggtgcg acaatctatc gcttgtatgg gaagcccgat    2160
gcgccagagt tgtttctgaa acatggcaaa ggtagcgttg ccaatgatgt tacagatgag    2220
atggtcagac taaactggct gacggaattt atgcctcttc cgaccatcaa gcattttatc    2280
cgtactcctg atgatgcatg gttactcacc actgcgatcc ccggaaaaac agcattccag    2340
gtattagaag aatatcctga ttcaggtgaa aatattgttg atgcgctggc agtgttcctg    2400
cgccggttgc attcgattcc tgtttgtaat tgtccttttta acagcgatcg cgtatttcgt    2460
ctcgctcagg cgcaatcacg aatgaataac ggtttggttg atgcgagtga ttttgatgac    2520
gagcgtaatg gctggcctgt tgaacaagtc tggaaagaaa tgcataaact tttgccattc    2580
tcaccggatt cagtcgtcac tcatggtgat ttctcacttg ataaccttat ttttgacgag    2640
gggaaattaa taggttgtat tgatgttgga cgagtcggaa tcgcagaccg ataccaggat    2700
cttgccatcc tatggaactg cctcggtgag ttttctcctt cattacagaa acggcttttt    2760
caaaaatatg gtattgataa tcctgatatg aataaattgc agtttcattt gatgctcgat    2820
gagttttctc aactgtcaga ccaagtttac tcatatatac tttagattga tttaaaactt    2880
catttttaat ttaaaaggat ctaggtgaag atccttttg ataatctcat gaccaaaatc     2940
ccttaacgtg agttttcgtt ccactgagcg tcagaccccg tagaaaagat caaaggatct    3000
tcttgagatc ctttttttct gcgcgtaatc tgctgcttgc aaacaaaaaa accaccgcta   3060
ccagcggtgg tttgtttgcc ggatcaagag ctaccaactc ttttttccgaa ggtaactggc    3120
ttcagcagag cgcagatacc aaatactgtt cttctagtgt agccgtagtt aggccaccac    3180
ttcaagaact ctgtagcacc gcctacatac ctcgctctgc taatcctgtt accagtggct    3240
gctgccagtg gcgataagtc gtgtcttacc gggttggact caagacgata gttaccggat    3300
aaggcgcagc ggtcgggctg aacggggggt tcgtgcacac agcccagctt ggagcgaacg    3360
acctacaccg aactgagata cctacagcgt gagctatgag aaagcgccac gcttcccgaa    3420
gggagaaagg cggacaggta tccggtaagc ggcagggtcg gaacaggaga gcgcacgagg    3480
gagcttccag ggggaaacgc ctggtatctt tatagtcctg tcgggtttcg ccacctctga    3540
cttgagcgtc gatttttgtg atgctcgtca gggggggcgga gcctatggaa aaacgccagc    3600
```

```
aacgcggcct ttttacggtt cctggccttt tgctggcctt ttgctcacat gttctttcct    3660
gcgttatccc ctgattctgt ggataaccgt attaccgcct tgagtgagc tgataccgct     3720
cgccgcagcc gaacgaccga gcgcagcgag tcagtgagcg aggaagcgga agagcgccca    3780
atacgcaaac cgcctctccc cgcgcgttgg ccgattcatt aatgcagctg gcacgacagg    3840
tttcccgact ggaaagcggg cagtgagcgc aacgcaatta atgtgagtta gctcactcat    3900
taggcacccc aggctttaca ctttatgctt ccggctcgta tgttgtgtgg aattgtgagc    3960
ggataacaat ttcacacagg aaacagctat gaccatgatt acgccaagct tgctcttag    4020
gagtttccta atacatccca aactcaaata tataaagcat ttgacttgtt ctatgcccta    4080
gggggcgggg ggaagctaag ccagctttt ttaacattta aaatgttaat tccatttaa     4140
atgcacagat gttttatt cataagggtt tcaatgtgca tgaatgctgc aatattcctg     4200
ttaccaaagc tagtataaat aaaaatagat aaacgtggaa attacttaga gtttctgtca    4260
ttaacgtttc cttcctcagt tgacaacata atgcgctgc tgagaagcca gtttgcatct    4320
gtcaggatca atttcccatt atgccagtca tattaattac tagtcaatta gttgattttt    4380
attttgaca tatacatgtg aaagacccca cctgtaggtt tggcaagcta gcttaagtaa     4440
cgccattttg caaggcatgg aaaaatacat aactgagaat agaaaagttc agatcaaggt    4500
caggaacaga tggaacagct gaatatgggc caaacaggat atctgtggta agcagttcct    4560
gccccggctc agggccaaga acagatggaa cagctgaata tgggccaaac aggatatctg    4620
tggtaagcag ttcctgcccc ggctcagggc caagaacaga tggtcccag atgcggtcca    4680
gccctcagca gtttctagag aaccatcaga tgtttccagg gtgccccaag acctgaaat    4740
gaccctgtgc cttatttgaa ctaaccaatc agttcgcttc tcgcttctgt tcgcgcgctt    4800
ctgctccccg agctcaataa aagagcccac aaccctcac tcggcgcgcc agtcctccga    4860
ttgactgagt cgcccgggta cccgtgtatc caataaaccc tcttgcagtt gcatccgact    4920
tgtggtctcg ctgttccttg ggagggtctc ctctgagtga ttgactaccc gtcagcgggg    4980
gtctttcatt tggggggctcg tccgggatcg ggagacccct gcccaggggac caccgaccca    5040
ccaccgggag gtaagctggc cagcaactta tctgtgtctg tccgattgtc tagtgtctat    5100
gactgatttt atgcgcctgc gtcggtacta gttagctaac tagctctgta tctggcggac    5160
ccgtggtgga actgacgagt tcggaacacc cggccgcaac cctgggagac gtcccaggga    5220
cttcgggggc cgttttgtg gcccgacctg agtcctaaaa tcccgatcgt ttaggactct    5280
ttggtgcacc cccttagag gagggatatg tggttctggt aggagacgag aacctaaaac    5340
agttcccgcc tccgtctgaa tttttgcttt cggtttggga ccgaagccgc gccgcgcgtc    5400
ttgtctgctg cagcatcgtt ctgtgttgtc tctgtctgac tgtgtttctg tatttgtctg    5460
aaaatatggg cccgggctag actgttacca ctcccttaag tttgacctta ggtcactgga    5520
aagatgtcga gcggatcgct cacaaccagt cggtagatgt caagaagaga cgttgggtta    5580
ccttctgctc tgcagaatgg ccaacctta acgtcggatg gccgcgagac ggcacctta     5640
accgagacct catcacccag gttaagatca aggtctttc acctggcccg catggacacc    5700
cagaccaggt cccctacatc gtgacctggg aagccttggc ttttgacccc ctcccctggg    5760
tcaagccctt tgtacaccct aagcctccgc ctcctcttcc tccatccgcc ccgtctctcc    5820
cccttgaacc tcctcgttcg acccgcctc gatcctcct ttatccagcc ctcactcctt     5880
ctctaggcgc cccatatgg ccatatgaga tcttatatgg ggcaccccg cccttgtaa      5940
```

-continued

```
acttccctga ccctgacatg acaagagtta ctaacagccc ctctctccaa gctcacttac     6000
aggctctcta cttagtccag cacgaagtct ggagacctct ggcggcagcc taccaagaac     6060
aactggaccg accggtggta cctcaccctt accgagtcgg cgacacagtg tgggtccgcc     6120
gacaccagac taagaaccta gaacctcgct ggaaaggacc ttacacagtc ctgctgacca     6180
cccccaccgc cctcaaagta gacggcatcg cagcttggat acacgccgcc cacgtgaagg     6240
ctgccgaccc cggggtggga ccatcctcta gactgccatg gctctcccag tgactgccct     6300
actgcttccc ctagcgcttc tcctgcatgc acaagttcag ctccagcaga gcggcgccga     6360
agtggcaaag cctggagcgt cagtcaagct gtcctgcaaa gcgagtggct atacgttcac     6420
gaactactgg atgcagtgga taaagcaggc tcccgggcag ggtctggagt ggattggagc     6480
cgtctaccca ggggacggcg acacccggca cactcaaaag ttcaagggca aggccaccct     6540
gaccgctgac aagagcacaa gcacagcgta catggaggtg tcctctttga gatccgaaga     6600
taccgctgtg tattattgtg cccgggggctt cactgcatac gggatggatt actggggaca     6660
aggcactacc gtgactgtca gctccggggg tggaggctca ggcgggggggg gttcaggagg     6720 gggggatct gaaattgtgc tgacacagag ccctgccaca atgtctgcta gccctggcga     6780
gcgcgtgacc atgtcttgta gcgccagcag cagcgtgtcc tacatgcatt ggtatcaaca     6840
gaagtccggc cagtctccca gcggtggat ctacgataca agcaagctgg cctccggcgt     6900 gccc gccaga ttttctggca gcggctctgg aacagattac accttcacca tctctagcat     6960
ggaacctgag gattttgcca cctactattg ccagcagtgg tccagcaatc ccctgacatt     7020
tggaggaggc accaagctgg aaattaagag agcggccgca attgaagtta tgtatcctcc     7080
tccttaccta gacaatgaga agagcaatgg aaccattatc catgtgaaag ggaaacacct     7140
ttgtccaagt cccctatttc ccggaccttc taagcccttt tgggtgctgg tggtggttgg     7200
tggagtcctg gcttgctata gcttgctagt aacagtggcc tttattattt tctgggtgag     7260
gagtaagagg agcaggctcc tgcacagtga ctacatgaac atgactcccc gccgccccgg     7320
gcccacccgc aagcattacc agccctatgc cccaccacgc gacttcgcag cctatcgctc     7380
cagagtgaag ttcagcagga gcgcagacgc ccccgcgtac cagcagggcc agaaccagct     7440
ctataacgag ctcaatctag gacgaagaga ggagtacgat gttttggaca gagacgtgg     7500 ccgggaccct gagatggggg gaaagccgag aaggaagaac cctcaggaag gcctgttcaa     7560
tgaactgcag aaagataaga tggcggaggc cttcagtgag attgggatga aggcgagcg     7620 ccggagggggc aaggggcacg atggcctttt ccagggtctc agtacagcca ccaaggacac     7680
cttcgacgcc cttcacatgc aggccctgcc ccctcgcgga agcggagcta ctaacttcag     7740
cctgctgaag caggctggag acgtggagga gaaccctgga cccatggccc tgcccgtcac     7800
cgctttgctt ctgccactgg ccttgctgct ccacgctcag ctccagctcc aagagtcagg     7860
gccaggtctc gtgaaaccga gtgagaccct gtccctgacc tgcacagtga gtggtggatc     7920
aatctcaagc tctacctact attggggtg gattcggcag cccccttagaa aggggcttga     7980 gtggattggc agcactcatt atcgaggatc tacctattat aatccttctc tgaaaagcag     8040
agttaccatc tctgtggata cgtccaaaaa tcagttcagt ctgaaggtat catccgtgac     8100
tgctgccgac acggccgtgt actattgcgc gagggagctg acaggtgagg tctttgacta     8160
ctggggccag ggcacactcg tgaccgtgtc ttctgcctca acaggagggg gtgggagtgg     8220 aggcggttgga tcagggggag gagggagtga catccagatg acgcagtccc cttccagctt     8280
gtccgcatct gtgggtgata gggtcacgat tacatgtagg gctagtcaga gtatttctag     8340
```

-continued

```
ttacctgaat tggtaccagc agaaaccagg caaggcacca agttgctca tctatgcggc    8400 ctcctctctg caatctggcg tgccgtccag atttagtgga tcaggctccg gaaccgattt    8460 caccccttacg atctcctcac ttcaaccccga ggatttcgcc acatattact gtcaacaaag    8520
ctattctaca ccgttcacct tcggaccggg gacaaaagtg gatattaaac gggcggccgc    8580
ccccaccacg acgccagcgc cgcgaccacc aaccccggcg cccacgatcg cgtcgcagcc    8640
cctgtccctg cgcccagagg cgtgccggcc agcggcgggg ggcgcagtgc acacgagggg    8700
gctggacttc gcctgtgata tctacatctg ggcgcccctg gccgggactt gtggggtcct    8760
tctcctgtca ctggttatca ccctttactg caacaaacgg ggcagaaaga agctcctgta    8820
tatattcaaa caaccattta tgagaccagt acaaactact caagaggaag atggctgtag    8880
ctgccgattt ccagaagaag aagaaggagg atgtgaactg taacagccac tcgaggatcc    8940
```

<210> SEQ ID NO 142
<211> LENGTH: 22
<212> TYPE: PRT
<213> ORGANISM: Artificial Sequence
<220> FEATURE:
<223> OTHER INFORMATION: Description of Artificial Sequence: Synthetic peptide

<400> SEQUENCE: 142

Gly Ser Gly Ala Thr Asn Phe Ser Leu Leu Lys Gln Ala Gly Asp Val
1               5                   10                  15

Glu Glu Asn Pro Gly Pro
            20

<210> SEQ ID NO 143
<211> LENGTH: 66
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 143

```
ggaagcggag ctactaactt cagcctgctg aagcaggctg agacgtgga ggagaaccct    60 ggaccc                                                              66
```

<210> SEQ ID NO 144
<211> LENGTH: 354
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 144

```
caagttcagc tccagcagag cggcgccgaa gtggcaaagc ctggagcgtc agtcaagctg    60
tcctgcaaag cgagtggcta tacgttcacg aactactgga tgcagtggat aaagcaggct    120
cccgggcagg gtctggagtg gattggagcc gtctacccag ggacggcga cacccggcac    180 actcaaaagt tcaagggcaa ggccacccctg accgctgaca gagcacaag cacagcgtac    240 atggaggtgt cctctttgag atccgaagat accgctgtgt attattgtgc ccggggcttc    300
actgcatacg gatggatta ctggggacaa ggcactaccg tgactgtcag ctcc          354
```

<210> SEQ ID NO 145
<211> LENGTH: 318

<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 145
gaaattgtgc tgacacagag ccctgccaca atgtctgcta gccctggcga gcgcgtgacc    60
atgtcttgta gcgccagcag cagcgtgtcc tacatgcatt ggtatcaaca gaagtccggc   120
cagtctccca gcggtggat ctacgataca agcaagctgg cctccggcgt gcccgccaga    180 tttctggca gcggctctgg aacagattac accttcacca tctctagcat ggaacctgag    240
gattttgcca cctactattg ccagcagtgg tccagcaatc ccctgacatt tggaggaggc    300
accaagctgg aaattaag                                                  318

<210> SEQ ID NO 146
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 146

Gln Val Gln Leu Val Gln Ser Gly Ala Glu Val Ala Lys Pro Gly Ala
1               5                   10                  15

Ser Val Lys Leu Ser Cys Lys Ala Ser Gly Tyr Thr Phe Thr Asn Tyr
                20                  25                  30

Trp Met Gln Trp Ile Lys Gln Ala Pro Gly Gln Gly Leu Glu Trp Ile
            35                  40                  45

Gly Ala Val Tyr Pro Gly Asp Gly Asp Thr Arg His Thr Gln Lys Phe
        50                  55                  60

Lys Gly Lys Ala Thr Leu Thr Ala Asp Lys Ser Thr Ser Thr Ala Tyr
65                  70                  75                  80

Met Glu Val Ser Ser Leu Arg Ser Glu Asp Thr Ala Val Tyr Tyr Cys
                85                  90                  95

Ala Arg Gly Phe Thr Ala Tyr Gly Met Asp Tyr Trp Gly Gln Gly Thr
            100                 105                 110

Thr Val Thr Val Ser Ser
        115

<210> SEQ ID NO 147
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 147

Glu Ile Val Leu Thr Gln Ser Pro Ala Thr Met Ser Ala Ser Pro Gly
1               5                   10                  15

Glu Arg Val Thr Met Ser Cys Ser Ala Ser Ser Ser Val Ser Tyr Met
                20                  25                  30

His Trp Tyr Gln Gln Lys Ser Gly Gln Ser Pro Lys Arg Trp Ile Tyr
            35                  40                  45

Asp Thr Ser Lys Leu Ala Ser Gly Val Pro Ala Arg Phe Ser Gly Ser
        50                  55                  60

Gly Ser Gly Thr Asp Tyr Thr Phe Thr Ile Ser Ser Met Glu Pro Glu

```
                65                  70                  75                  80
Asp Phe Ala Thr Tyr Tyr Cys Gln Gln Trp Ser Ser Asn Pro Leu Thr
                    85                  90                  95

Phe Gly Gly Gly Thr Lys Leu Glu Ile Lys
                100                 105

<210> SEQ ID NO 148
<211> LENGTH: 239
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 148

Gln Val Gln Leu Val Gln Ser Gly Ala Glu Val Ala Lys Pro Gly Ala
1               5                   10                  15

Ser Val Lys Leu Ser Cys Lys Ala Ser Gly Tyr Thr Phe Thr Asn Tyr
                20                  25                  30

Trp Met Gln Trp Ile Lys Gln Ala Pro Gly Gln Gly Leu Glu Trp Ile
            35                  40                  45

Gly Ala Val Tyr Pro Gly Asp Gly Asp Thr Arg His Thr Gln Lys Phe
    50                  55                  60

Lys Gly Lys Ala Thr Leu Thr Ala Asp Lys Ser Thr Ser Thr Ala Tyr
65                  70                  75                  80

Met Glu Val Ser Ser Leu Arg Ser Glu Asp Thr Ala Val Tyr Tyr Cys
                85                  90                  95

Ala Arg Gly Phe Thr Ala Tyr Gly Met Asp Tyr Trp Gly Gln Gly Thr
            100                 105                 110

Thr Val Thr Val Ser Ser Gly Gly Gly Ser Gly Gly Gly Gly Ser
        115                 120                 125

Gly Gly Gly Gly Ser Glu Ile Val Leu Thr Gln Ser Pro Ala Thr Met
    130                 135                 140

Ser Ala Ser Pro Gly Glu Arg Val Thr Met Ser Cys Ser Ala Ser Ser
145                 150                 155                 160

Ser Val Ser Tyr Met His Trp Tyr Gln Gln Lys Ser Gly Gln Ser Pro
                165                 170                 175

Lys Arg Trp Ile Tyr Asp Thr Ser Lys Leu Ala Ser Gly Val Pro Ala
            180                 185                 190

Arg Phe Ser Gly Ser Gly Ser Gly Thr Asp Tyr Thr Phe Thr Ile Ser
        195                 200                 205

Ser Met Glu Pro Glu Asp Phe Ala Thr Tyr Tyr Cys Gln Gln Trp Ser
    210                 215                 220

Ser Asn Pro Leu Thr Phe Gly Gly Gly Thr Lys Leu Glu Ile Lys
225                 230                 235

<210> SEQ ID NO 149
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Ala Ser Thr Gly Gly Gly Ser Gly Gly Gly Gly Ser Gly Gly Gly
1               5                   10                  15

Gly Ser
```

```
<210> SEQ ID NO 150
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Arg Ala Ala Ala
1

<210> SEQ ID NO 151
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Gln Gln Asp Tyr Asn Leu Pro Ile Thr
1               5
```

CHIMERIC RECEPTORS TARGETING ADGRE2 AND/OR CLEC12A AND USES THEREOF

CROSS-REFERENCE TO RELATED APPLICATIONS

This application claims priority to U.S. Provisional Patent Application Ser. No. 63/179,799, filed Apr. 26, 2021, and U.S. Provisional Patent Application Ser. No. 63/287,655, filed Dec. 9, 2021, the contents of each of which are incorporated by reference in their entirety, and to each of which priority is claimed.

SEQUENCE LISTING

The specification further incorporates by reference the Sequence Listing submitted herewith via EFS on Apr. 25, 2022. Pursuant to 37 C.F.R. § 1.52(e)(5), the Sequence Listing text file, identified as 087108_0109_SL.txt, is 150,763 bytes in size and was created on Apr. 25, 2022. The Sequence Listing, electronically filed herewith, does not extend beyond the scope of the specification and thus does not contain new matter.

1. INTRODUCTION

The presently disclosed subject matter provides methods and compositions for immunotherapies. It relates to chimeric receptors that target ADGRE2, and chimeric receptors that target CLEC12A, cells comprising such chimeric receptors, and methods of using such cells for treatments, e.g., for treating acute myeloid leukemia (AML).

2. BACKGROUND OF THE INVENTION

Cell-based immunotherapy is a therapy with curative potential for the treatment of cancer. T cells and other immune cells may be modified to target tumor antigens through the introduction of genetic material coding for artificial or synthetic receptors for antigen, termed Chimeric Antigen Receptors (CARs), specific to selected antigens. Targeted T cell therapy using CARs has shown recent clinical success in treating hematologic malignancies.

Relapsed and refractory acute myeloid leukemia (R/R AML) has a very poor prognosis. The only curative option is allogeneic hematopoietic stem cell transplantation, which is often associated with treatment failure and significant therapy-related toxicity and mortality. Novel therapeutic approaches are therefore direly needed for R/R AML. Over the past few years, autologous T cells genetically modified to express a chimeric antigen receptor (CAR) targeting CD19 have revolutionized the treatment and improved the outcomes of patients with R/R B-cell hematologic malignancies, leading to the approval by the FDA of three CD19 CARs (tisagenlecleucel, axicabtagene ciloleucel, and brexucabtagene autoleucel) for R/R acute lymphoblastic leukemia and/or certain B-cell non-Hodgkin lymphomas. In the case of AML, the clinical investigation of CAR T cell therapy is still in an early phase, and clinical results mainly with CD33 and CD123 CAR T cells suggest challenges both in terms of safety and efficacy, which are due to abundant expression of CD33 and CD123 in normal hematopoiesis and phenotypic heterogeneity in AML tumor cells. Accordingly, there are needs for a novel combinatorial CAR format for R/R AML that has the potential to provide improved safety and efficacy relative to alternative CAR therapies currently under clinical investigation.

3. SUMMARY OF THE INVENTION

The presently disclosed subject matter provides chimeric receptors that target ADGRE2, and chimeric receptors that target CLEC12A, cells comprising such chimeric receptors, and methods of using such cells for treatments, e.g., for treating acute myeloid leukemia (AML).

In one aspect, the presently disclosed subject matter provides chimeric receptors that target ADGRE2. In certain embodiments, the ADGRE2-targeted chimeric receptor comprises an extracellular antigen-binding domain that binds to ADGRE2, a transmembrane domain, and an intracellular domain. In certain embodiments, the extracellular antigen-binding domain comprises: a) a heavy chain variable region comprising a CDR1 comprising the amino acid sequence set forth in SEQ ID NO: 33 or a conservative modification thereof, a CDR2 comprising the amino acid sequence set forth in SEQ ID NO: 34 or a conservative modification thereof, and a CDR3 comprising the amino acid sequence set forth in SEQ ID NO: 35 or a conservative modification thereof; and/or b) a light chain variable region comprising a CDR1 comprising the amino acid sequence set forth in SEQ ID NO: 36 or a conservative modification thereof, a CDR2 comprising the amino acid sequence set forth in SEQ ID NO: 37 or a conservative modification thereof, and a CDR3 comprising the amino acid sequence set forth in SEQ ID NO: 38 or a conservative modification thereof.

In certain embodiments, the extracellular antigen-binding domain comprises a single-chain variable fragment (scFv), a Fab, or a F(ab)$_2$. In certain embodiments, the extracellular antigen-binding domain comprises an scFv. In certain embodiments, the scFv is a humanized scFv.

In certain embodiments, the heavy chain variable region comprises a CDR1 comprising the amino acid sequence set forth in SEQ ID NO: 33, a CDR2 comprising the amino acid sequence set forth in SEQ ID NO: 34, and a CDR3 comprising the amino acid sequence set forth in SEQ ID NO: 35. In certain embodiments, the light chain variable region comprises a CDR1 comprising the amino acid sequence set forth in SEQ ID NO: 36, a CDR2 comprising the amino acid sequence set forth in SEQ ID NO: 37, and a CDR3 comprising the amino acid sequence set forth in SEQ ID NO: 38. In certain embodiments, the heavy chain variable region comprises a CDR1 comprising the amino acid sequence set forth in SEQ ID NO: 33, a CDR2 comprising the amino acid sequence set forth in SEQ ID NO: 34, and a CDR3 comprising the amino acid sequence set forth in SEQ ID NO: 35; and the light chain variable region comprises a CDR1 comprising the amino acid sequence set forth in SEQ ID NO: 36, a CDR2 comprising the amino acid sequence set forth in SEQ ID NO: 37, and a CDR3 comprising the amino acid sequence set forth in SEQ ID NO: 38.

In certain embodiments, the heavy chain variable region comprises an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% identical or homologous to the amino acid sequence set forth in SEQ ID NO: 39, SEQ ID NO:43, SEQ ID NO:46, SEQ ID NO:49, SEQ ID NO: 52, SEQ ID NO: 55, or SEQ ID NO: 146. In certain embodiments, the heavy chain variable region comprises the amino acid sequence set forth in SEQ ID NO: 39, SEQ ID NO:43, SEQ ID NO:46, or SEQ ID NO:49. In certain embodiments, the heavy chain variable region comprises the amino acid sequence set forth in SEQ ID NO: 39.

In certain embodiments, the light chain variable region comprises an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% identical or homologous to the amino acid sequence set forth in SEQ ID NO: 40, SEQ ID NO: 44, SEQ ID NO: 47, SEQ ID NO: 50, SEQ ID NO: 53, SEQ ID NO: 56, or SEQ ID NO: 147. In certain embodiments, the light chain variable region comprises the amino acid sequence set forth in SEQ ID NO: 40, SEQ ID NO: 44, SEQ ID NO: 47, or SEQ ID NO: 50. In certain embodiments, the light chain variable region comprises the amino acid sequence set forth in SEQ ID NO: 40.

In certain embodiments, the heavy chain variable region comprises an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% identical or homologous to the amino acid sequence set forth in SEQ ID NO: 39, SEQ ID NO:43, SEQ ID NO:46, SEQ ID NO:49, SEQ ID NO: 52, or SEQ ID NO: 55; and the light chain variable region comprises an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% identical or homologous to the amino acid sequence set forth in SEQ ID NO: 40, SEQ ID NO: 44, SEQ ID NO: 47, SEQ ID NO: 50, SEQ ID NO: 53, or SEQ ID NO: 56. In certain embodiments, the heavy chain variable region comprises the amino acid sequence set forth in SEQ ID NO: 39, SEQ ID NO:43, SEQ ID NO:46, or SEQ ID NO:49; and the light chain variable region comprises the amino acid sequence set forth in SEQ ID NO: 40, SEQ ID NO: 44, SEQ ID NO: 47, or SEQ ID NO: 50.

In certain embodiments,
a) the heavy chain variable region comprises the amino acid sequence set forth in SEQ ID NO: 39; and the light chain variable region comprises the amino acid sequence set forth in SEQ ID NO: 40;
b) the heavy chain variable region comprises the amino acid sequence set forth in SEQ ID NO: 43; and the light chain variable region comprises the amino acid sequence set forth in SEQ ID NO: 44;
c) the heavy chain variable region comprises the amino acid sequence set forth in SEQ ID NO: 46; and the light chain variable region comprises the amino acid sequence set forth in SEQ ID NO: 47;
d) the heavy chain variable region comprises the amino acid sequence set forth in SEQ ID NO: 49; and the light chain variable region comprises the amino acid sequence set forth in SEQ ID NO: 50;
e) the heavy chain variable region comprises the amino acid sequence set forth in SEQ ID NO: 52; and the light chain variable region comprises the amino acid sequence set forth in SEQ ID NO: 53;
f) the heavy chain variable region comprises the amino acid sequence set forth in SEQ ID NO: 55; and the light chain variable region comprises the amino acid sequence set forth in SEQ ID NO: 56; or
g) the heavy chain variable region comprises the amino acid sequence set forth in SEQ ID NO: 146; and the light chain variable region comprises the amino acid sequence set forth in SEQ ID NO: 147.

In certain embodiments,
a) the heavy chain variable region comprises the amino acid sequence set forth in SEQ ID NO: 39; and the light chain variable region comprises the amino acid sequence set forth in SEQ ID NO: 40;
b) the heavy chain variable region comprises the amino acid sequence set forth in SEQ ID NO: 43; and the light chain variable region comprises the amino acid sequence set forth in SEQ ID NO: 44;
c) the heavy chain variable region comprises the amino acid sequence set forth in SEQ ID NO: 46; and the light chain variable region comprises the amino acid sequence set forth in SEQ ID NO: 47; or
d) the heavy chain variable region comprises the amino acid sequence set forth in SEQ ID NO: 49; and the light chain variable region comprises the amino acid sequence set forth in SEQ ID NO: 50.

In certain embodiments, the heavy chain variable region comprises the amino acid sequence set forth in SEQ ID NO: 39; and the light chain variable region comprises the amino acid sequence set forth in SEQ ID NO: 40.

In certain embodiments, the extracellular antigen-binding domain comprises a linker between the heavy chain variable region and the light chain variable region. In certain embodiments, the linker consists of the amino acid sequence set forth in SEQ ID NO: 1, SEQ ID NO: 2, SEQ ID NO: 3, SEQ ID NO: 4, SEQ ID NO: 5, SEQ ID NO: 6, or SEQ ID NO: 149.

In certain embodiments, the heavy chain variable region and the light chain variable region are positioned from the N- to the C-terminus: $V_H$-$V_L$. In certain embodiments, the extracellular antigen-binding domain comprises or is an scFv, which comprises or consists of the amino acid sequence set forth in SEQ ID NO: 41, SEQ ID NO: 45, SEQ ID NO: 48, SEQ ID NO: 51, SEQ ID NO: 54, SEQ ID NO: 57, SEQ ID NO: 148. In certain embodiments, the extracellular antigen-binding domain comprises or is an scFv, which comprises or consists of the amino acid sequence set forth in SEQ ID NO: 41, SEQ ID NO: 45, SEQ ID NO: 48, or SEQ ID NO: 51. In certain embodiments, the extracellular antigen-binding domain comprises or is an scFv, which comprises or consists of the amino acid sequence set forth in SEQ ID NO: 41.

In certain embodiments, the extracellular antigen-binding domain binds to ADGRE2 with a dissociation constant ($K_D$) of less than about $10^{-8}$ M, less than about $10^{-9}$ M, less than about $10^{-10}$ M, less than about $10^{-11}$ M, less than about $10^{-12}$ M, or less than about $10^{-13}$ M. In certain embodiments, the extracellular antigen-binding domain binds to ADGRE2 with an EC50 of between about 1 and about 100 nM. In certain embodiments, the EC50 is between about 10 and about 95 nM. In certain embodiments, the EC50 is between about 25 and about 75 nM.

In certain embodiments, the transmembrane domain comprises a CD8 polypeptide, a CD28 polypeptide, a CD3ζ polypeptide, a CD4 polypeptide, a 4-1BB polypeptide, an OX40 polypeptide, an ICOS polypeptide, a CTLA-4 polypeptide, a PD-1 polypeptide, a LAG-3 polypeptide, a 2B4 polypeptide, or a BTLA polypeptide. In certain embodiments, the transmembrane domain comprises a CD28 polypeptide.

In certain embodiments, the intracellular domain comprises a CD3ζ polypeptide. In certain embodiments, the CD3ζ polypeptide is a modified CD3ζ polypeptide. In certain embodiments, the modified CD3ζ polypeptide comprises a native ITAM1, an ITAM2 variant consisting of two loss-of-function mutations, and an ITAM3 variant consisting of two loss-of-function mutations. In certain embodiments, the native ITAM1 consists of the amino acid sequence set forth in SEQ ID NO: 15. In certain embodiments, the ITAM2 variant consists of the amino acid sequence set forth in SEQ ID NO: 21. In certain embodiments, the ITAM3 variant consists of the amino acid sequence set forth in SEQ ID NO: 25. In certain embodiments, the modified CD3ζ polypeptide comprises or consists of the amino acid sequence set forth in SEQ ID NO: 27.

In certain embodiments, the intracellular domain further comprises at least one co-stimulatory signaling region. In certain embodiments, the at least one co-stimulatory signaling region comprises a CD28 polypeptide, a 4-1BB polypeptide, an OX40 polypeptide, an ICOS polypeptide, a DAP-10 polypeptide, or a combination thereof. In certain embodiments, the at least one co-stimulatory signaling region comprises a CD28 polypeptide.

In certain embodiments, the ADGRE2-targeted chimeric receptor is a chimeric antigen receptor (CAR), a chimeric co-stimulating receptor (CCR), or a TCR like fusion molecule. In certain embodiments, the ADGRE2-targeted chimeric receptor is a CAR.

In one aspect, the presently disclosed subject matter provides chimeric receptors that target CLEC12A. In certain embodiments, the CLEC12A-targeted chimeric receptor comprises an extracellular antigen-binding domain that binds to CLEC12A, a transmembrane domain, and an intracellular domain. In certain embodiments, the extracellular antigen-binding domain comprises a heavy chain variable region comprising:

i) a CDR1 comprising the amino acid sequence set forth in SEQ ID NO: 69 or a conservative modification thereof, a CDR2 comprising the amino acid sequence set forth in SEQ ID NO: 70 or a conservative modification thereof, and a CDR3 comprising the amino acid sequence set forth in SEQ ID NO: 71 or a conservative modification thereof;
  ii) a CDR1 comprising the amino acid sequence set forth in SEQ ID NO: 81 or a conservative modification thereof, a CDR2 comprising the amino acid sequence set forth in SEQ ID NO: 82 or a conservative modification thereof, and a CDR3 comprising the amino acid sequence set forth in SEQ ID NO: 83 or a conservative modification thereof;
  iii) a CDR1 comprising the amino acid sequence set forth in SEQ ID NO: 89 or a conservative modification thereof, a CDR2 comprising the amino acid sequence set forth in SEQ ID NO: 90 or a conservative modification thereof, and a CDR3 comprising the amino acid sequence set forth in SEQ ID NO: 91 or a conservative modification thereof;
  iv) a CDR1 comprising the amino acid sequence set forth in SEQ ID NO: 89 or a conservative modification thereof, a CDR2 comprising the amino acid sequence set forth in SEQ ID NO: 90 or a conservative modification thereof, and a CDR3 comprising the amino acid sequence set forth in SEQ ID NO: 98 or a conservative modification thereof;
  v) a CDR1 comprising the amino acid sequence set forth in SEQ ID NO: 81 or a conservative modification thereof, a CDR2 comprising the amino acid sequence set forth in SEQ ID NO: 103 or a conservative modification thereof, and a CDR3 comprising the amino acid sequence set forth in SEQ ID NO: 83 or a conservative modification thereof;
  vi) a CDR1 comprising the amino acid sequence set forth in SEQ ID NO: 109 or a conservative modification thereof, a CDR2 comprising the amino acid sequence set forth in SEQ ID NO: 103 or a conservative modification thereof, and a CDR3 comprising the amino acid sequence set forth in SEQ ID NO: 83 or a conservative modification thereof;
  vii) a CDR1 comprising the amino acid sequence set forth in SEQ ID NO: 89 or a conservative modification thereof, a CDR2 comprising the amino acid sequence set forth in SEQ ID NO: 90 or a conservative modification thereof, and a CDR3 comprising the amino acid sequence set forth in SEQ ID NO: 114 or a conservative modification thereof;
  viii) a CDR1 comprising the amino acid sequence set forth in SEQ ID NO: 120 or a conservative modification thereof, a CDR2 comprising the amino acid sequence set forth in SEQ ID NO: 121 or a conservative modification thereof, and a CDR3 comprising the amino acid sequence set forth in SEQ ID NO: 122 or a conservative modification thereof; or
  ix) a CDR1 comprising the amino acid sequence set forth in SEQ ID NO: 129 or a conservative modification thereof, a CDR2 comprising the amino acid sequence set forth in SEQ ID NO: 130 or a conservative modification thereof, and a CDR3 comprising the amino acid sequence set forth in SEQ ID NO: 131 or a conservative modification thereof; and/or a light chain variable region comprising:

i) a CDR1 comprising the amino acid sequence set forth in SEQ ID NO: 72 or a conservative modification thereof, a CDR2 comprising the amino acid sequence set forth in SEQ ID NO: 73 or a conservative modification thereof, and a CDR3 comprising the amino acid sequence set forth in SEQ ID NO: 74 or a conservative modification thereof;
  ii) a CDR1 comprising the amino acid sequence set forth in SEQ ID NO: 84 or a conservative modification thereof, a CDR2 comprising the amino acid sequence set forth in SEQ ID NO: 73 or a conservative modification thereof, and a CDR3 comprising the amino acid sequence set forth in SEQ ID NO: 85 or a conservative modification thereof;
  iii) a CDR1 comprising the amino acid sequence set forth in SEQ ID NO: 92 or a conservative modification thereof, a CDR2 comprising the amino acid sequence set forth in SEQ ID NO: 93 or a conservative modification thereof, and a CDR3 comprising the amino acid sequence set forth in SEQ ID NO: 94 or a conservative modification thereof;
  iv) a CDR1 comprising the amino acid sequence set forth in SEQ ID NO: 99 or a conservative modification thereof, a CDR2 comprising the amino acid sequence set forth in SEQ ID NO: 93 or a conservative modification thereof, and a CDR3 comprising the amino acid sequence set forth in SEQ ID NO: 151 or a conservative modification thereof;
  v) a CDR1 comprising the amino acid sequence set forth in SEQ ID NO: 104 or a conservative modification thereof, a CDR2 comprising the amino acid sequence set forth in SEQ ID NO: 73 or a conservative modification thereof, and a CDR3 comprising the amino acid sequence set forth in SEQ ID NO: 105 or a conservative modification thereof;

vi) a CDR1 comprising the amino acid sequence set forth in SEQ ID NO: 110 or a conservative modification thereof, a CDR2 comprising the amino acid sequence set forth in SEQ ID NO: 73 or a conservative modification thereof, and a CDR3 comprising the amino acid sequence set forth in SEQ ID NO: 85 or a conservative modification thereof;

vii) a CDR1 comprising the amino acid sequence set forth in SEQ ID NO: 115 or a conservative modification thereof, a CDR2 comprising the amino acid sequence set forth in SEQ ID NO: 93 or a conservative modification thereof, and a CDR3 comprising the amino acid sequence set forth in SEQ ID NO: 116 or a conservative modification thereof;

viii) a CDR1 comprising the amino acid sequence set forth in SEQ ID NO: 123 or a conservative modification thereof, a CDR2 comprising the amino acid sequence set forth in SEQ ID NO: 124 or a conservative modification thereof, and a CDR3 comprising the amino acid sequence set forth in SEQ ID NO: 125 or a conservative modification thereof; or ix) a CDR1 comprising the amino acid sequence set forth in SEQ ID NO: 132 or a conservative modification thereof, a CDR2 comprising the amino acid sequence set forth in SEQ ID NO: 133 or a conservative modification thereof, and a CDR3 comprising the amino acid sequence set forth in SEQ ID NO: 134 or a conservative modification thereof.

In certain embodiments, the extracellular antigen-binding domain comprises a single-chain variable fragment (scFv), a Fab, or a F(ab)$_2$. In certain embodiments, the extracellular antigen-binding domain comprises an scFv. In certain embodiments, the scFv is a human scFv.

In certain embodiments, the heavy chain variable region comprises:

a) a CDR1 comprising the amino acid sequence set forth in SEQ ID NO: 69, a CDR2 comprising the amino acid sequence set forth in SEQ ID NO: 70, and a CDR3 comprising the amino acid sequence set forth in SEQ ID NO: 71;

b) a CDR1 comprising the amino acid sequence set forth in SEQ ID NO: 81, a CDR2 comprising the amino acid sequence set forth in SEQ ID NO: 82, and a CDR3 comprising the amino acid sequence set forth in SEQ ID NO: 83;

c) a CDR1 comprising the amino acid sequence set forth in SEQ ID NO: 89, a CDR2 comprising the amino acid sequence set forth in SEQ ID NO: 90, and a CDR3 comprising the amino acid sequence set forth in SEQ ID NO: 91;

d) a CDR1 comprising the amino acid sequence set forth in SEQ ID NO: 89, a CDR2 comprising the amino acid sequence set forth in SEQ ID NO: 90, and a CDR3 comprising the amino acid sequence set forth in SEQ ID NO: 98;

e) a CDR1 comprising the amino acid sequence set forth in SEQ ID NO: 81, a CDR2 comprising the amino acid sequence set forth in SEQ ID NO: 103, and a CDR3 comprising the amino acid sequence set forth in SEQ ID NO: 83;

f) a CDR1 comprising the amino acid sequence set forth in SEQ ID NO: 109, a CDR2 comprising the amino acid sequence set forth in SEQ ID NO: 103, and a CDR3 comprising the amino acid sequence set forth in SEQ ID NO: 83;

g) a CDR1 comprising the amino acid sequence set forth in SEQ ID NO: 89, a CDR2 comprising the amino acid sequence set forth in SEQ ID NO: 90, and a CDR3 comprising the amino acid sequence set forth in SEQ ID NO: 114;

h) a CDR1 comprising the amino acid sequence set forth in SEQ ID NO: 120, a CDR2 comprising the amino acid sequence set forth in SEQ ID NO: 121, and a CDR3 comprising the amino acid sequence set forth in SEQ ID NO: 122; or i) a CDR1 comprising the amino acid sequence set forth in SEQ ID NO: 129, a CDR2 comprising the amino acid sequence set forth in SEQ ID NO: 130, and a CDR3 comprising the amino acid sequence set forth in SEQ ID NO: 131.

In certain embodiments, the heavy chain variable region comprises:

a) a CDR1 comprising the amino acid sequence set forth in SEQ ID NO: 69, a CDR2 comprising the amino acid sequence set forth in SEQ ID NO: 70, and a CDR3 comprising the amino acid sequence set forth in SEQ ID NO: 71;

b) a CDR1 comprising the amino acid sequence set forth in SEQ ID NO: 81, a CDR2 comprising the amino acid sequence set forth in SEQ ID NO: 82, and a CDR3 comprising the amino acid sequence set forth in SEQ ID NO: 83;

c) a CDR1 comprising the amino acid sequence set forth in SEQ ID NO: 89, a CDR2 comprising the amino acid sequence set forth in SEQ ID NO: 90, and a CDR3 comprising the amino acid sequence set forth in SEQ ID NO: 91; or d) a CDR1 comprising the amino acid sequence set forth in SEQ ID NO: 89, a CDR2 comprising the amino acid sequence set forth in SEQ ID NO: 90, and a CDR3 comprising the amino acid sequence set forth in SEQ ID NO: 98.

In certain embodiments, the heavy chain variable region comprises a CDR1 comprising the amino acid sequence set forth in SEQ ID NO: 69, a CDR2 comprising the amino acid sequence set forth in SEQ ID NO: 70, and a CDR3 comprising the amino acid sequence set forth in SEQ ID NO: 71.

In certain embodiments, the light chain variable region comprises:

a) a CDR1 comprising the amino acid sequence set forth in SEQ ID NO: 72, a CDR2 comprising the amino acid sequence set forth in SEQ ID NO: 73, and a CDR3 comprising the amino acid sequence set forth in SEQ ID NO: 74;

b) a CDR1 comprising the amino acid sequence set forth in SEQ ID NO: 84, a CDR2 comprising the amino acid sequence set forth in SEQ ID NO: 73, and a CDR3 comprising the amino acid sequence set forth in SEQ ID NO: 85;

c) a CDR1 comprising the amino acid sequence set forth in SEQ ID NO: 92, a CDR2 comprising the amino acid sequence set forth in SEQ ID NO: 93, and a CDR3 comprising the amino acid sequence set forth in SEQ ID NO: 94;

d) a CDR1 comprising the amino acid sequence set forth in SEQ ID NO: 99, a CDR2 comprising the amino acid sequence set forth in SEQ ID NO: 93, and a CDR3 comprising the amino acid sequence set forth in SEQ ID NO: 151;

e) a CDR1 comprising the amino acid sequence set forth in SEQ ID NO: 104, a CDR2 comprising the amino acid sequence set forth in SEQ ID NO: 73, and a CDR3 comprising the amino acid sequence set forth in SEQ ID NO: 105;

f) a CDR1 comprising the amino acid sequence set forth in SEQ ID NO: 110, a CDR2 comprising the amino acid sequence set forth in SEQ ID NO: 73, and a CDR3 comprising the amino acid sequence set forth in SEQ ID NO: 85;

g) a CDR1 comprising the amino acid sequence set forth in SEQ ID NO: 115, a CDR2 comprising the amino acid sequence set forth in SEQ ID NO: 93, and a CDR3 comprising the amino acid sequence set forth in SEQ ID NO: 116;

h) a CDR1 comprising the amino acid sequence set forth in SEQ ID NO: 123, a CDR2 comprising the amino acid sequence set forth in SEQ ID NO: 124, and a CDR3 comprising the amino acid sequence set forth in SEQ ID NO: 125; or i) a CDR1 comprising the amino acid sequence set forth in SEQ ID NO: 132, a CDR2 comprising the amino acid sequence set forth in SEQ ID NO: 133, and a CDR3 comprising the amino acid sequence set forth in SEQ ID NO: 134.

In certain embodiments, the light chain variable region comprises:

a) a CDR1 comprising the amino acid sequence set forth in SEQ ID NO: 72, a CDR2 comprising the amino acid sequence set forth in SEQ ID NO: 73, and a CDR3 comprising the amino acid sequence set forth in SEQ ID NO: 74;

b) a CDR1 comprising the amino acid sequence set forth in SEQ ID NO: 84, a CDR2 comprising the amino acid sequence set forth in SEQ ID NO: 73, and a CDR3 comprising the amino acid sequence set forth in SEQ ID NO: 85;

c) a CDR1 comprising the amino acid sequence set forth in SEQ ID NO: 92, a CDR2 comprising the amino acid sequence set forth in SEQ ID NO: 93, and a CDR3 comprising the amino acid sequence set forth in SEQ ID NO: 94; or d) a CDR1 comprising the amino acid sequence set forth in SEQ ID NO: 99, a CDR2 comprising the amino acid sequence set forth in SEQ ID NO: 93, and a CDR3 comprising the amino acid sequence set forth in SEQ ID NO: 151.

In certain embodiments, the light chain variable region comprises a CDR1 comprising the amino acid sequence set forth in SEQ ID NO: 72, a CDR2 comprising the amino acid sequence set forth in SEQ ID NO: 73, and a CDR3 comprising the amino acid sequence set forth in SEQ ID NO: 74.

In certain embodiments, the chimeric receptor comprises:

a) the heavy chain variable region comprises a CDR1 comprising the amino acid sequence set forth in SEQ ID NO: 69, a CDR2 comprising the amino acid sequence set forth in SEQ ID NO: 70, and a CDR3 comprising the amino acid sequence set forth in SEQ ID NO: 71; and the light chain variable region comprises a CDR1 comprising the amino acid sequence set forth in SEQ ID NO: 72, a CDR2 comprising the amino acid sequence set forth in SEQ ID NO: 73, and a CDR3 comprising the amino acid sequence set forth in SEQ ID NO: 74;

b) the heavy chain variable region comprises a CDR1 comprising the amino acid sequence set forth in SEQ ID NO: 81, a CDR2 comprising the amino acid sequence set forth in SEQ ID NO: 82, and a CDR3 comprising the amino acid sequence set forth in SEQ ID NO: 83; and the light chain variable region comprises a CDR1 comprising the amino acid sequence set forth in SEQ ID NO: 84, a CDR2 comprising the amino acid sequence set forth in SEQ ID NO: 73, and a CDR3 comprising the amino acid sequence set forth in SEQ ID NO: 85;

c) the heavy chain variable region comprises a CDR1 comprising the amino acid sequence set forth in SEQ ID NO: 89, a CDR2 comprising the amino acid sequence set forth in SEQ ID NO: 90, and a CDR3 comprising the amino acid sequence set forth in SEQ ID NO: 91; and the light chain variable region comprises a CDR1 comprising the amino acid sequence set forth in SEQ ID NO: 92, a CDR2 comprising the amino acid sequence set forth in SEQ ID NO: 93, and a CDR3 comprising the amino acid sequence set forth in SEQ ID NO: 94;

d) the heavy chain variable region comprises a CDR1 comprising the amino acid sequence set forth in SEQ ID NO: 89, a CDR2 comprising the amino acid sequence set forth in SEQ ID NO: 90, and a CDR3 comprising the amino acid sequence set forth in SEQ ID NO: 98; and the light chain variable region comprises a CDR1 comprising the amino acid sequence set forth in SEQ ID NO: 99, a CDR2 comprising the amino acid sequence set forth in SEQ ID NO: 93, and a CDR3 comprising the amino acid sequence set forth in SEQ ID NO: 151;

e) the heavy chain variable region comprises a CDR1 comprising the amino acid sequence set forth in SEQ ID NO: 81, a CDR2 comprising the amino acid sequence set forth in SEQ ID NO: 103, and a CDR3 comprising the amino acid sequence set forth in SEQ ID NO: 83; and the light chain variable region comprises a CDR1 comprising the amino acid sequence set forth in SEQ ID NO: 104, a CDR2 comprising the amino acid sequence set forth in SEQ ID NO: 73, and a CDR3 comprising the amino acid sequence set forth in SEQ ID NO: 105;

f) the heavy chain variable region comprises a CDR1 comprising the amino acid sequence set forth in SEQ ID NO: 109, a CDR2 comprising the amino acid sequence set forth in SEQ ID NO: 103, and a CDR3 comprising the amino acid sequence set forth in SEQ ID NO: 83; and the light chain variable region comprises a CDR1 comprising the amino acid sequence set forth in SEQ ID NO: 110, a CDR2 comprising the amino acid sequence set forth in SEQ ID NO: 73, and a CDR3 comprising the amino acid sequence set forth in SEQ ID NO: 85;

g) the heavy chain variable region comprises a CDR1 comprising the amino acid sequence set forth in SEQ ID NO: 89, a CDR2 comprising the amino acid sequence set forth in SEQ ID NO: 90, and a CDR3 comprising the amino acid sequence set forth in SEQ ID NO: 114; and the light chain variable region comprises a CDR1 comprising the amino acid sequence set forth in SEQ ID NO: 115, a CDR2 comprising the amino acid sequence set forth in SEQ ID NO: 93, and a CDR3 comprising the amino acid sequence set forth in SEQ ID NO: 116;

h) the heavy chain variable region comprises a CDR1 comprising the amino acid sequence set forth in SEQ ID NO: 120, a CDR2 comprising the amino acid sequence set forth in SEQ ID NO: 121, and a CDR3 comprising the amino acid sequence set forth in SEQ ID NO: 122; and the light chain variable region comprises a CDR1 comprising the amino acid sequence set forth in SEQ ID NO: 123, a CDR2 comprising the amino acid sequence set forth in SEQ ID NO: 124, and a CDR3 comprising the amino acid sequence set forth in SEQ ID NO: 125; or i) the heavy chain variable region comprises a CDR1 comprising the amino acid sequence set forth in SEQ ID NO: 129, a CDR2 comprising the amino acid sequence set forth in SEQ ID NO: 130, and a CDR3 comprising the amino acid sequence set forth in SEQ ID NO: 131; and the light chain variable region comprises a CDR1 comprising the amino acid sequence set forth in SEQ ID NO: 132, a CDR2 comprising the amino acid sequence set forth in SEQ ID NO: 133, and a CDR3 comprising the amino acid sequence set forth in SEQ ID NO: 134.

In certain embodiments, a) the heavy chain variable region comprises a CDR1 comprising the amino acid sequence set forth in SEQ ID NO: 69, a CDR2 comprising the amino acid sequence set forth in SEQ ID NO: 70, and a CDR3 comprising the amino acid sequence set forth in SEQ ID NO: 71; and the light chain variable region comprises a CDR1 comprising the amino acid sequence set forth in SEQ ID NO: 72, a CDR2 comprising the amino acid sequence set forth in SEQ ID NO: 73, and a CDR3 comprising the amino acid sequence set forth in SEQ ID NO: 74;

b) the heavy chain variable region comprises a CDR1 comprising the amino acid sequence set forth in SEQ ID NO: 81, a CDR2 comprising the amino acid sequence set forth in SEQ ID NO: 82, and a CDR3 comprising the amino acid sequence set forth in SEQ ID NO: 83; and the light chain variable region comprises a CDR1 comprising the amino acid sequence set forth in SEQ ID NO: 84, a CDR2 comprising the amino acid sequence set forth in SEQ ID NO: 73, and a CDR3 comprising the amino acid sequence set forth in SEQ ID NO: 85;

c) the heavy chain variable region comprises a CDR1 comprising the amino acid sequence set forth in SEQ ID NO: 89, a CDR2 comprising the amino acid sequence set forth in SEQ ID NO: 90, and a CDR3 comprising the amino acid sequence set forth in SEQ ID NO: 91; and the light chain variable region comprises a CDR1 comprising the amino acid sequence set forth in SEQ ID NO: 92, a CDR2 comprising the amino acid sequence set forth in SEQ ID NO: 93, and a CDR3 comprising the amino acid sequence set forth in SEQ ID NO: 94; or d) the heavy chain variable region comprises a CDR1 comprising the amino acid sequence set forth in SEQ ID NO: 89, a CDR2 comprising the amino acid sequence set forth in SEQ ID NO: 90, and a CDR3 comprising the amino acid sequence set forth in SEQ ID NO: 98; and the light chain variable region comprises a CDR1 comprising the amino acid sequence set forth in SEQ ID NO: 99, a CDR2 comprising the amino acid sequence set forth in SEQ ID NO: 93, and a CDR3 comprising the amino acid sequence set forth in SEQ ID NO: 151.

In certain embodiments, the heavy chain variable region comprises a CDR1 comprising the amino acid sequence set forth in SEQ ID NO: 69, a CDR2 comprising the amino acid sequence set forth in SEQ ID NO: 70, and a CDR3 comprising the amino acid sequence set forth in SEQ ID NO: 71; and the light chain variable region comprises a CDR1 comprising the amino acid sequence set forth in SEQ ID NO: 72, a CDR2 comprising the amino acid sequence set forth in SEQ ID NO: 73, and a CDR3 comprising the amino acid sequence set forth in SEQ ID NO: 74.

In certain embodiments, the heavy chain variable region comprises an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% identical or homologous to the amino acid sequence set forth in SEQ ID NO: 75, SEQ ID NO: 86, SEQ ID NO: 95, SEQ ID NO: 100, SEQ ID NO: 106, SEQ ID NO: 111, SEQ ID NO: 117, SEQ ID NO: 126, or SEQ ID NO: 135. In certain embodiments, the heavy chain variable region comprises the amino acid sequence set forth in SEQ ID NO: 75, SEQ ID NO: 86, SEQ ID NO: 95, SEQ ID NO: 100, SEQ ID NO: 106, SEQ ID NO: 111, SEQ ID NO: 117, SEQ ID NO: 126, or SEQ ID NO: 135. In certain embodiments, the heavy chain variable region comprises the amino acid sequence set forth in SEQ ID NO: 75, SEQ ID NO: 86, SEQ ID NO: 95, or SEQ ID NO: 100. In certain embodiments, the heavy chain variable region comprises the amino acid sequence set forth in SEQ ID NO: 75.

In certain embodiments, the light chain variable region comprises an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% identical or homologous to the amino acid sequence set forth in SEQ ID NO: 76, SEQ ID NO: 87, SEQ ID NO: 96, SEQ ID NO: 101, SEQ ID NO: 107, SEQ ID NO: 112, SEQ ID NO: 118, SEQ ID NO: 127, or SEQ ID NO: 136. In certain embodiments, the light chain variable region comprises the amino acid sequence set forth in SEQ ID NO: 76, SEQ ID NO: 87, SEQ ID NO: 96, SEQ ID NO: 101, SEQ ID NO: 107, SEQ ID NO: 112, SEQ ID NO: 118, SEQ ID NO: 127, or SEQ ID NO: 136. In certain embodiments, the light chain variable region comprises the amino acid sequence set forth in SEQ ID NO: 76, SEQ ID NO: 87, SEQ ID NO: 96, or SEQ ID NO: 101. In certain embodiments, the light chain variable region comprises the amino acid sequence set forth in SEQ ID NO: 76.

In certain embodiments, a) the heavy chain variable region comprises the amino acid sequence set forth in SEQ ID NO: 75; and the light chain variable region comprises the amino acid sequence set forth in SEQ ID NO: 76;

b) the heavy chain variable region comprises the amino acid sequence set forth in SEQ ID NO: 86; and the light chain variable region comprises the amino acid sequence set forth in SEQ ID NO: 87;

c) the heavy chain variable region comprises the amino acid sequence set forth in SEQ ID NO: 95; and the light chain variable region comprises the amino acid sequence set forth in SEQ ID NO: 96;

d) the heavy chain variable region comprises the amino acid sequence set forth in SEQ ID NO: 100; and the light chain variable region comprises the amino acid sequence set forth in SEQ ID NO: 101;

e) the heavy chain variable region comprises the amino acid sequence set forth in SEQ ID NO: 106; and the light chain variable region comprises the amino acid sequence set forth in SEQ ID NO: 107;

f) the heavy chain variable region comprises the amino acid sequence set forth in SEQ ID NO: 111; and the light chain variable region comprises the amino acid sequence set forth in SEQ ID NO: 112;

g) the heavy chain variable region comprises the amino acid sequence set forth in SEQ ID NO: 117; and the light chain variable region comprises the amino acid sequence set forth in SEQ ID NO: 118;

h) the heavy chain variable region comprises the amino acid sequence set forth in SEQ ID NO: 126; and the light chain variable region comprises the amino acid sequence set forth in SEQ ID NO: 127; or i) the heavy chain variable region comprises the amino acid sequence set forth in SEQ ID NO: 135; and the light chain variable region comprises the amino acid sequence set forth in SEQ ID NO: 136.

In certain embodiments, the chimeric receptor comprises:

a) the heavy chain variable region comprises the amino acid sequence set forth in SEQ ID NO: 75; and the light chain variable region comprises the amino acid sequence set forth in SEQ ID NO: 76;

b) the heavy chain variable region comprises the amino acid sequence set forth in SEQ ID NO: 86; and the light chain variable region comprises the amino acid sequence set forth in SEQ ID NO: 87;

c) the heavy chain variable region comprises the amino acid sequence set forth in SEQ ID NO: 95; and the light chain variable region comprises the amino acid sequence set forth in SEQ ID NO: 96; or d) the heavy chain variable region comprises the amino acid sequence set forth in SEQ ID NO: 100; and the light chain variable region comprises the amino acid sequence set forth in SEQ ID NO: 101.

In certain embodiments, the heavy chain variable region comprises the amino acid sequence set forth in SEQ ID NO: 75; and the light chain variable region comprises the amino acid sequence set forth in SEQ ID NO: 76.

In certain embodiments, the extracellular antigen-binding domain comprises a linker between the heavy chain variable region and the light chain variable region. In certain embodiments, the linker consists of the amino acid sequence set forth in SEQ ID NO: 1, SEQ ID NO: 2, SEQ ID NO: 3, SEQ ID NO: 4, SEQ ID NO: 5, SEQ ID NO: 6, or SEQ ID NO: 149.

In certain embodiments, the heavy chain variable region and the light chain variable region are positioned from the N- to the C-terminus: $V_H$-$V_L$. In certain embodiments, the extracellular antigen-binding domain comprises or is an scFv, which comprises or consists of the amino acid sequence set forth in SEQ ID NO: 79, SEQ ID NO: 88, SEQ ID NO: 97, SEQ ID NO: 102, SEQ ID NO: 108, SEQ ID NO: 113, SEQ ID NO: 119, SEQ ID NO: 128, or SEQ ID NO: 137. In certain embodiments, the extracellular antigen-binding domain comprises or is an scFv, which comprises or consists of the amino acid sequence set forth in SEQ ID NO: 79, SEQ ID NO: 88, SEQ ID NO: 97, or SEQ ID NO: 102. In certain embodiments, the extracellular antigen-binding domain comprises or is an scFv, which comprises or consists of the amino acid sequence set forth in SEQ ID NO: 79.

In certain embodiments, the extracellular antigen-binding domain comprises binds to CLEC12A with a disassociation constant ($K_D$) of less than about $10^{-8}$ M, less than about $10^{-9}$ M, less than about $10^{-10}$ M, less than about $10^{-11}$ M, less than about $10^{-12}$ M, or less than about $10^{-13}$ M. In certain embodiments, the $K_D$ is about 0.1 pM or below. In certain embodiments, the $K_D$ is between about 0.05 pM and about 0.5 pM. In certain embodiments, the $K_D$ is between about 0.1 nM and about 5.0 nM. In certain embodiments, the $K_D$ is between about 0.3 nM and about 3.5 nM. In certain embodiments, the extracellular antigen-binding domain binds to CLEC12A with an EC50 of between about 1 nM and about 100 nM.

In certain embodiments, the transmembrane domain comprises a CD8 polypeptide, a CD28 polypeptide, a CD3ζ polypeptide, a CD4 polypeptide, a 4-1BB polypeptide, an OX40 polypeptide, an ICOS polypeptide, a CTLA-4 polypeptide, a PD-1 polypeptide, a LAG-3 polypeptide, a 2B4 polypeptide, or a BTLA polypeptide. In certain embodiments, the transmembrane domain comprises a CD8 polypeptide.

In certain embodiments, the CLEC12A-targeted chimeric receptor is a chimeric antigen receptor (CAR), a chimeric co-stimulating receptor (CCR), or a TCR like fusion molecule. In certain embodiments, the CLEC12A-targeted chimeric receptor is a chimeric co-stimulating receptor (CCR).

In certain embodiments, the intracellular domain does not comprise a CD3ζ polypeptide. In certain embodiments, the intracellular domain comprises at least one co-stimulatory signaling region. In certain embodiments, the at least one co-stimulatory signaling region comprises a CD28 polypeptide, a 4-1BB polypeptide, an OX40 polypeptide, an ICOS polypeptide, a DAP-10 polypeptide, or a combination thereof. In certain embodiments, the at least one co-stimulatory signaling region comprises a 4-1BB polypeptide.

In certain embodiments, the chimeric receptor is expressed from a vector. In certain embodiments, the vector is a viral vector. In certain embodiments, the viral vector is a retroviral vector.

The presently disclosed subject matter further provides cells comprising the chimeric receptor disclosed herein. In certain embodiments, the cell comprises an ADGRE2-targeted chimeric receptor disclosed herein. In certain embodiments, the cell comprises a CLEC12A-targeted chimeric receptor disclosed herein. In certain embodiments, the cell comprises a) an ADGRE2-targeted chimeric receptor disclosed herein, and b) a CLEC12A-targeted chimeric receptor disclosed herein. In certain embodiments, the ADGRE2-targeted chimeric receptor is a chimeric antigen receptor (CAR) and the CLEC12A-targeted chimeric receptor is a a chimeric co-stimulating receptor (CCR).

In certain embodiments, the CAR comprises an extracellular antigen-binding domain that binds to ADGRE2 and comprises:

a) a heavy chain variable region comprising a CDR1 comprising the amino acid sequence set forth in SEQ ID NO: 33 or a conservative modification thereof, a CDR2 comprising the amino acid sequence set forth in SEQ ID NO: 34 or a conservative modification thereof, and a CDR3 comprising the amino acid sequence set forth in SEQ ID NO: 35 or a conservative modification thereof; and/or b) a light chain variable region comprising a CDR1 comprising the amino acid sequence set forth in SEQ ID NO: 36 or a conservative modification thereof, a CDR2 comprising the amino acid sequence set forth in SEQ ID NO: 37 or a conservative modification thereof, and a CDR3 comprising the amino acid sequence set forth in SEQ ID NO: 38 or a conservative modification thereof.

In certain embodiments, the heavy chain variable region comprises a CDR1 comprising the amino acid sequence set forth in SEQ ID NO: 33, a CDR2 comprising the amino acid sequence set forth in SEQ ID NO: 34, and a CDR3 comprising the amino acid sequence set forth in SEQ ID NO: 35; and the light chain variable region comprises a CDR1 comprising the amino acid sequence set forth in SEQ ID NO: 36, a CDR2 comprising the amino acid sequence set forth in SEQ ID NO: 37, and a CDR3 comprising the amino acid sequence set forth in SEQ ID NO: 38.

In certain embodiments,
a) the heavy chain variable region comprises an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% identical or homologous to the amino acid sequence set forth in SEQ ID NO: 39; and/or
b) the light chain variable region comprises an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% identical or homologous to the amino acid sequence set forth in SEQ ID NO: 40.

In certain embodiments, the heavy chain variable region comprises the amino acid sequence set forth in SEQ ID NO: 39; and the light chain variable region comprises the amino acid sequence set forth in SEQ ID NO: 40.

In certain embodiments, the CCR comprises an extracellular antigen-binding domain that binds to CLEC12A and comprises:
a) a heavy chain variable region comprising a CDR1 comprising the amino acid sequence set forth in SEQ ID NO: 69 or a conservative modification thereof, a CDR2 comprising the amino acid sequence set forth in SEQ ID NO: 70 or a conservative modification thereof, and a CDR3 comprising the amino acid sequence set forth in SEQ ID NO: 71 or a conservative modification thereof; and/or
b) a light chain variable region comprising a CDR1 comprising the amino acid sequence set forth in SEQ ID NO: 72 or a conservative modification thereof, a CDR2 comprising the amino acid sequence set forth in SEQ ID NO: 73 or a conservative modification thereof, and a CDR3 comprising the amino acid sequence set forth in SEQ ID NO: 74 or a conservative modification thereof.

In certain embodiments, the heavy chain variable region comprises a CDR1 comprising the amino acid sequence set forth in SEQ ID NO: 69, a CDR2 comprising the amino acid sequence set forth in SEQ ID NO: 70, and a CDR3 comprising the amino acid sequence set forth in SEQ ID NO: 71; and the light chain variable region comprises a CDR1 comprising the amino acid sequence set forth in SEQ ID NO: 72, a CDR2 comprising the amino acid sequence set forth in SEQ ID NO: 73, and a CDR3 comprising the amino acid sequence set forth in SEQ ID NO: 74.

In certain embodiments,
a) the heavy chain variable region comprises an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% identical or homologous to the amino acid sequence set forth in SEQ ID NO: 75; and/or
b) the light chain variable region comprises an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% identical or homologous to the amino acid sequence set forth in SEQ ID NO: 76.

In certain embodiments, the heavy chain variable region comprises the amino acid sequence set forth in SEQ ID NO: 75; and the light chain variable region comprises the amino acid sequence set forth in SEQ ID NO: 76.

In certain embodiments, the cell is transduced with the ADGRE2-targeted chimeric receptor and/or the CLEC12A-targeted chimeric receptor. In certain embodiments, the ADGRE2-targeted chimeric receptor and/or the CLEC12A-targeted chimeric receptor is constitutively expressed on the surface of the cell. In certain embodiments, the cell is an immunoresponsive cell. In certain embodiments, the cell is a cell of the lymphoid lineage or a cell of the myeloid lineage. In certain embodiments, the cell is selected from the group consisting of a T cell, a Natural Killer (NK) cell, a stem cell from which a lymphoid cell may be differentiated, and a stem cell from which a myeloid cell may be differentiated. In certain embodiments, the cell is a T cell. In certain embodiments, the T cell is selected from the group consisting of helper T cells, cytotoxic T cells, memory T cells, regulatory T cells, tumor-infiltrating lymphocyte (TIL), Natural Killer T cells, mucosal associated invariant T cells, and T6 T cells. In certain embodiments, the cell is a Natural Killer (NK) cell. In certain embodiments, the NK cell is derived from a stem cell. In certain embodiments, the stem cell is a pluripotent stem cell. In certain embodiments, the pluripotent stem cell is an embryoid stem cell or an induced pluripotent stem cell.

Furthermore, the presently disclosed subject matter provides nucleic acid molecules encoding the chimeric receptors disclosed herein. In certain embodiments, the nucleic acid molecule encodes an ADGRE2-targeted chimeric receptor disclosed herein. In certain embodiments, the nucleic acid molecule encodes a CLEC12A-targeted chimeric receptor disclosed herein.

In certain embodiments, the nucleic acid molecule further comprises a promoter that is operably linked to the chimeric receptor. In certain embodiments, the promoter is endogenous or exogenous. In certain embodiments, the exogenous promoter is selected from the group consisting of an elongation factor (EF)-1 promoter, a cytomegalovirus immediate-early promoter (CMV) promoter, a simian virus 40 early promoter (SV40) promoter, a phosphoglycerate kinase (PGK) promoter, a metallothionein promoter, and Ubiquitin C promoter. In certain embodiments, the promoter is an inducible promoter. In certain embodiments, the inducible promoter is selected from the group consisting of a NFAT transcriptional response element (TRE) promoter, a CD69 promoter, a CD25 promoter, an IL-2 promoter, a 4-1BB promoter, a PD1 promoter, and a LAG3 promoter. In certain embodiments, the promoter is an endogenous promoter. In certain embodiments, the endogenous promoter is selected from a TCR alpha promoter, a TCR beta promoter, and a beta 2-microglobulin promoter.

The presently disclosed subject matter also provides a nucleic acid composition comprising a first nucleic acid molecule encoding an ADGRE2-targeted chimeric receptor disclosed herein, and a second nucleic acid molecule encoding a CLEC12A-targeted chimeric receptor disclosed herein.

The presently disclosed subject matter also provides vectors comprising the nucleic acid molecule disclosed herein or the nucleic acid composition disclosed herein. In certain embodiments, the vector is a viral vector. In certain embodiments, the vector is a retroviral vector.

The presently disclosed subject matter further provides cells expressing the nucleic acid molecule disclosed herein or the nucleic acid composition disclosed herein. In certain embodiments, the cell is a T cell.

The presently disclosed subject matter provides compositions comprising the cell disclosed herein. In certain embodiments, the composition is a pharmaceutical composition further comprising a pharmaceutically acceptable carrier. In certain embodiments, the composition comprises between about $25 \times 10^6$ and about $150 \times 10^6$ cells. In certain embodiments, the composition comprises between about $25 \times 10^6$ and about $50 \times 10^6$ cells. In certain embodiments, the composition comprises about $2.5 \times 10^6$ cells.

The presently disclosed subject matter further provides various methods of using the presently disclosed cells. The presently disclosed subject matter provides methods of reducing tumor burden in a subject. In certain embodiments, the method comprises administering to the subject the cells or the composition disclosed herein. In certain embodiments, the method reduces the number of tumor cells, reduces tumor size, and/or eradicates the tumor in the subject.

The presently disclosed subject matter provides methods of increasing or lengthening survival of a subject having a tumor. In certain embodiments, the methods comprise administering to the subject the cells or the composition disclosed herein.

The presently disclosed subject matter provides methods of treating and/or preventing a tumor in a subject. In certain embodiments, the methods comprise administering to the subject the cells or the composition disclosed herein.

In certain embodiments, the tumor expresses ADGRE2 and/or CLEC12A. In certain embodiments, the tumor is cancer. In certain embodiments, the tumor is blood cancer. In certain embodiments, the tumor is selected from the group consisting of multiple myeloma, leukemia, lymphomas, and myeloid malignancies. In certain embodiments, the leukemia is selected from the group consisting of acute myeloid leukemia (AML), chronic myeloid leukemia (CML), acute lymphocytic leukemia (ALL), chronic lymphocytic leukemia (CLL), acute promyelocytic leukemia (APL), mixed-phenotype acute leukemia (MLL), hairy cell leukemia, and B cell prolymphocytic leukemia. In certain embodiments, the leukemia is acute myeloid leukemia (AML). In certain embodiments, the AML is relapsed/refractory acute myeloid leukemia (R/R AML). In certain embodiments, the myeloid malignancies are selected from the group consisting of myelodysplastic syndromes (MDS), myeloproliferative neoplasms (MPN), myeloid/lymphoid neoplasms (e.g., myeloid/lymphoid neoplasms with eosinophilia and rearrangement of Platelet Derived Growth Factor Receptor Alpha (PDGFRA), Platelet Derived Growth Factor Receptor Beta (PDGFRB), or Fibroblast Growth Factor Receptor 1 (FGFR1), or with PCM1-JAK2), acute myeloid leukemia (AML), blastic plasmacytoid dendritic cell neoplasm, B-lymphoblastic leukemia/lymphoma, and T-lymphoblastic leukemia/lymphoma. In certain embodiments, the myeloid malignancies comprise myelodysplastic syndromes (MDS). In certain embodiments, the subject is a human subject.

Furthermore, the presently disclosed subject matter provides methods for producing cells comprising the chimeric receptors disclosed herein. In certain embodiments, the method comprises introducing into the cell a nucleic acid molecule that encodes the chimeric receptor disclosed herein.

Furthermore, the presently disclosed subject matter provides methods for producing a cell comprising an ADGRE2-targeted chimeric receptor disclosed herein, and a CLEC12A-targeted chimeric receptor disclosed herein. In certain embodiments, the method comprises introducing into the cell a nucleic acid molecule that encodes the ADGRE2-targeted chimeric receptor and a nucleic acid molecule that encodes the CLEC12A-targeted chimeric receptor disclosed herein.

4. BRIEF DESCRIPTION OF THE FIGURES

The following Detailed Description, given by way of example, but not intended to limit the invention to specific embodiments described, may be understood in conjunction with the accompanying drawings.

FIGS. 1A and 1B illustrate target antigen expression profiles of ADGRE2, CD33, and CD123 evaluated via flow cytometry of fresh AML patient samples (peripheral blood or bone marrow); n=16 r/r adult AML patients with the morphological disease. Target expression was compared between bulk AML cells ($CD45_{dim}/SSC_{low}$ gate) and leukemic stem cells [LSC; Lin−CD34+CD38−(CD45RA+) within bulk AML cell gate]. Gates for target-positivity were set based on the same-sample negative control population (T or B cells). FIG. 1A shows the percentage of target-positive AML cells within the bulk or LSC population of an individual patient sample represented by each dot. In the majority of evaluated AML patients >90% of AML cells were positive for ADGRE2, both for bulk and LSC. FIG. 1B shows the percentage of evaluated AML patient population with >70% target-positive AML cells. All evaluated AML patients had >70% ADGRE2-positive AML cells, both for bulk and LSC.

FIG. 2 illustrates a schematic of CAR, CCR, and CAR+ CCR.

FIG. 3 depicts the rationale for ADCLEC.syn1 approach for improved anti-leukemic efficacy compared to CD33 and CD123-CAR. ADGRE2-CAR alone provides some anti-leukemic activity but may be limited due to ADGRE2-low escape mechanisms. CLEC12A-CCR alone does not mediate any cell lysis. ADCLEC.syn1 combines a low-affinity ADGRE2-CAR with a high-affinity CLEC12A-CCR, thereby increasing AML-directed avidity and reducing the risk of ADGRE2-low AML escape. In addition, CLEC12A-CCR-dependent trans-co-stimulation via 4-1BB further enhances T cell functionality. In comparison, single-targeting CD33-CAR or CD123-CAR approaches could be limited in efficacy due to antigen-low escape and phenotypic heterogeneity (see target profiles in FIG. 1).

FIGS. 4A-4C illustrate protein expression profiles of ADGRE2, CLEC12A (CD371), CD33, and CD123 in normal hematopoiesis and non-hematopoietic tissues, showing largely non-overlapping expression profile of ADGRE2 and CLEC12A. FIGS. 4A and 4B show flow cytometric co-expression profiles of ADGRE2/CLEC12A vs CD33/CD123 on representative adult normal donor bone marrow cell populations (gating: monocytes—$CD45_{hi}/SSC_{med}/CD14+$, granulocytes—$CD45_{dim}/SSC_{hi}$, HSC—$CD45_{dim}/SSC_{low}/CD34+/CD38−/CD45RA−/CD90+$, T cells—$CD45_{hi}/SSC_{low}/CD3+$, B cells—$CD45_{hi}/SSC_{low}/CD19+$). FIG. 4C shows a heatmap depicting the summary of immunohistochemistry co-staining for ADGRE2 and CLEC12A in formalin-fixed paraffin-embedded normal human tissues. Staining intensity refers to cellular positivity, excluding fluids with a high probability for unspecific staining. ADGRE2/CLEC12A had expected co-expression on myeloid cells in immune-related tissues (mostly monocytic lineage), but no or restricted overlapping expression was found in other evaluated tissues.

FIG. 5 depicts the rationale for ADCLEC.syn1 approach for improved safety profile compared to CD33- and CD123-CAR. ADGRE2-CAR with optimized affinity and fine-turned CD3ζ-signaling strength alone spares cells with low or very-low levels of ADGRE2 (HSC or granulocytes, respectively). High-affinity CLEC12A-CCR alone does not mediate any cell lysis. ADCLEC.syn1 combines a low-affinity ADGRE2-CAR with a high-affinity CLEC12A-CCR. Normal hematopoietic cells have a largely non-overlapping expression profile of ADGRE2 and CLEC12A, and CLEC12A is negative on HSC. Therefore, the addition of a CLEC12A-CCR does not increase the risk of HSC toxicity.

FIG. 6 illustrates the ADGRE2 scFv binder selection scheme.

FIGS. 7A-7C illustrate in vitro 18 h CAR cytotoxicity assay in the context of different ADGRE2 target expression levels. A favorable profile for leading humanized ADGRE2 scFvs, with maximum cytotoxicity at high ADGRE2 levels and minimal cytotoxicity at very-low ADGRE2 levels was observed. Different humanized ADGRE2 scFv candidates and the original 2A1 scFv were tested in SFG-retroviral 28z1XX CAR vector backbone; for each ADGRE2 scFv, 2 signal peptides were studied, one containing our established CD8a signal peptide and the other containing an alternative IgHV1-4 signal peptide. Shown in colored lines are 6 scFvs with cytotoxicity features. The remaining scFv candidates (not included in the legend) are shown in grey. CAR T cells were cocultured for 18 h with MOLM13 AML cell lines expressing different levels of ADGRE2: high (WT, FIG. 7A), low (clone 1E8, FIG. 7B), and very-low (clone 9D6, FIG. 7C). Cytotoxicity was measured based on the Luciferase signal released from MOLM13 cells.

FIG. 8 illustrates in vivo antitumor CAR efficacy of six (6) humanized ADGRE2 scFvs in the context of different ADGRE2 target expression levels. In vivo antitumor CAR efficacy model showing a favorable profile for leading humanized ADGRE2 scFvs, with potent efficacy at high ADGRE2 levels, reduced cytotoxicity at low ADGRE2 levels, and absent cytotoxicity at very-low ADGRE2 levels. Six different humanized ADGRE2 scFv candidates and the original 2A1 scFv were tested in the SFG-based retroviral 28z1XX CAR backbone. In vivo MOLM13 AML cell line xenograft experiment with 6-8 week-old NSG mice. On day −5, mice were injected via tail-vein with the indicated MOLM13 cell line clone (dose: 1E6 cells per mouse). On day −1, AML engraftment was confirmed via ffLuc-based in vivo bioluminescence imaging. On day 0, mice were injected via tail-vein with CAR T cells (dose: 3E5 CAR-positive cells per mouse). Subsequently, the AML burden was quantified via bioluminescence imaging and is represented via total flux (p/s).

FIG. 9 illustrates CLEC12A scFv binder selection scheme.

FIGS. 10A and 10B illustrate in vitro CAR cytotoxicity of CLEC12A scFvs in TRAC CAR-28z1XX format in the context of AML cell lines U937 and MOLM13. In vitro 18 h CAR cytotoxicity assay showing a favorable profile for leading CLEC12A scFvs, with potent efficacy at high and low CLEC12A levels. Different CLEC12A scFv candidates were tested in TRAC-AAV 28z1XX CAR backbone. Shown in colored lines are the nine (9) scFv with the highest efficacy in the context of different CLEC12A levels. FIG. 10A shows cytotoxicity with CLEC12A-high cell line U937. FIG. 10B shows cytotoxicity with CLEC12A-low cell line MOLM13. The remaining scFv candidates are shown in grey. T cells were cocultured for 18 h with AML cell lines. Cytotoxicity was measured based on Luciferase signal from AML cell lines.

FIG. 11 illustrates in vivo antitumor CAR efficacy model showing high efficacy for leading CLEC12A scFvs. Nine (9) different CLEC12A scFv candidates were tested in the TRAC-AAV 28z1XX CAR backbone. In vivo U937 AML cell line xenograft experiment with 6-8 week-old NSG mice. On day −4, mice were injected via tail-vein with the indicated U937 cell line clone (dose: 1E6 cells per mouse). On day −1, AML engraftment was confirmed via ffLuc-based in vivo bioluminescence imaging. On day 0, mice were injected via tail-vein with CAR T cells (dose: 4E5 CAR-positive cells per mouse). Subsequently, the AML burden was quantified via bioluminescence imaging and is represented via total flux (p/s).

FIGS. 12A-12C illustrate in vitro and in vivo CAR efficacy assays validating the ADCLEC.syn1 concept (as outlined as a schematic in FIG. 3). FIG. 12A shows in vitro 18 h CAR cytotoxicity assay. ADCLEC.syn1-transduced T cells were cocultured with EL4 murine lymphoma cell line expressing no target (ADGRE2−/CLEC12A−) or overexpressing either CAR target alone (ADGRE2+/CLEC12A−), CCR target alone (ADGRE2−/CLEC12A+), or both CAR and CCR target (ADGRE2+/CLEC12A+). CD19-targeting 1928z1XX CAR construct was used as a negative control. % Cytotoxicity indicates target-specific killing efficacy at a given effector:target (E:T) ratio. FIGS. 12B and 12C show in vivo MOLM13 AML cell line xenograft experiment with 6-8 week-old NSG mice. On day −5, mice were injected via tail-vein with the indicated MOLM13 cell line clone (dose: 1×10$^6$ cells per mouse). On day −1, AML engraftment was confirmed via ffLuc-based in vivo bioluminescence imaging. On day 0, mice were injected via tail-vein with CAR T cells (dose: 5×10$^5$ CAR-positive cells per mouse). Subsequently, the AML burden was quantified via bioluminescence imaging and is represented via total flux (p/s).

FIG. 15 illustrates a representative ADCLEC.syn1 CAR T cell manufacturing plan.

Figure 18A:
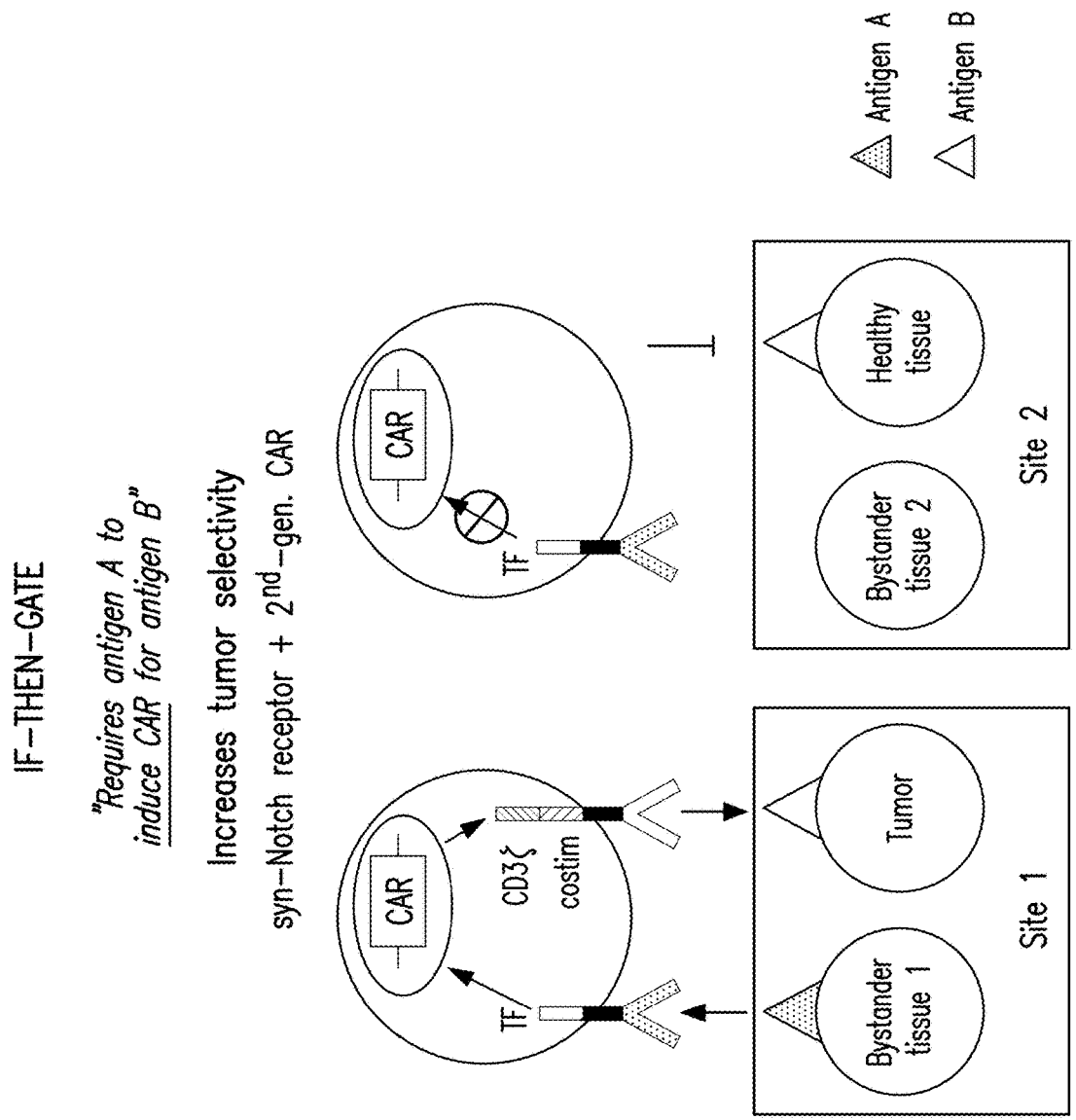
Figure 18B:
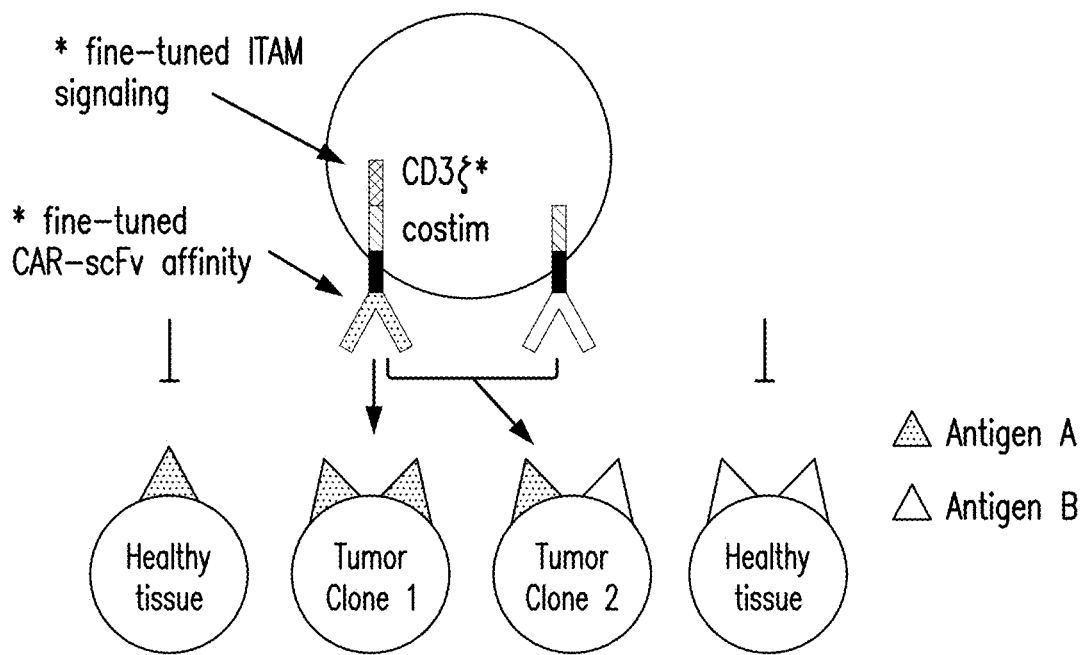

FIGS. 18A and 18B illustrate combinatorial gating strategies. FIG. 18A shows previously described combinatorial CAR gating strategies. FIG. 18B shows the "IF-BETTER" gating strategy.

Figure 19A:
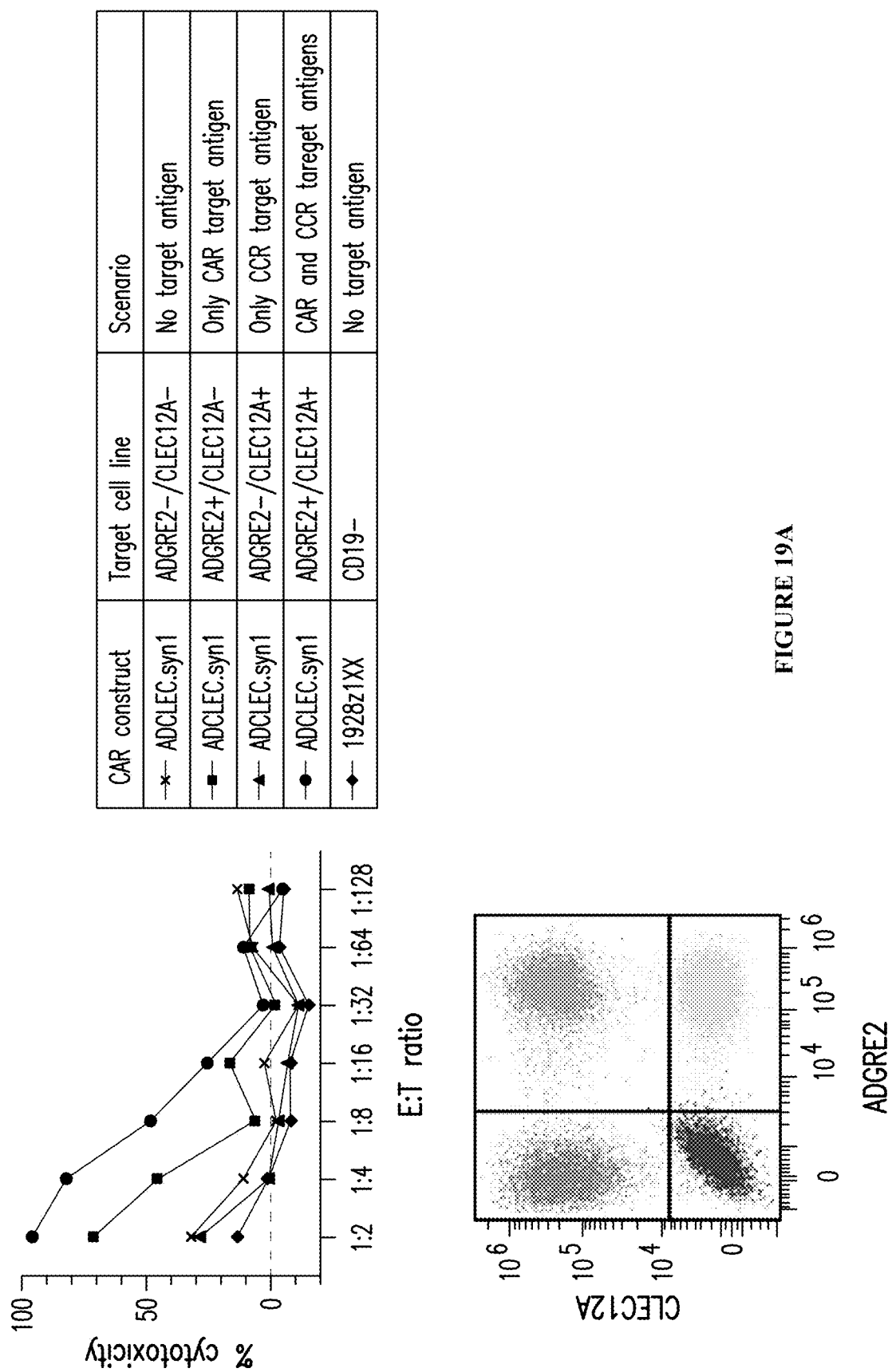
Figure 19B:
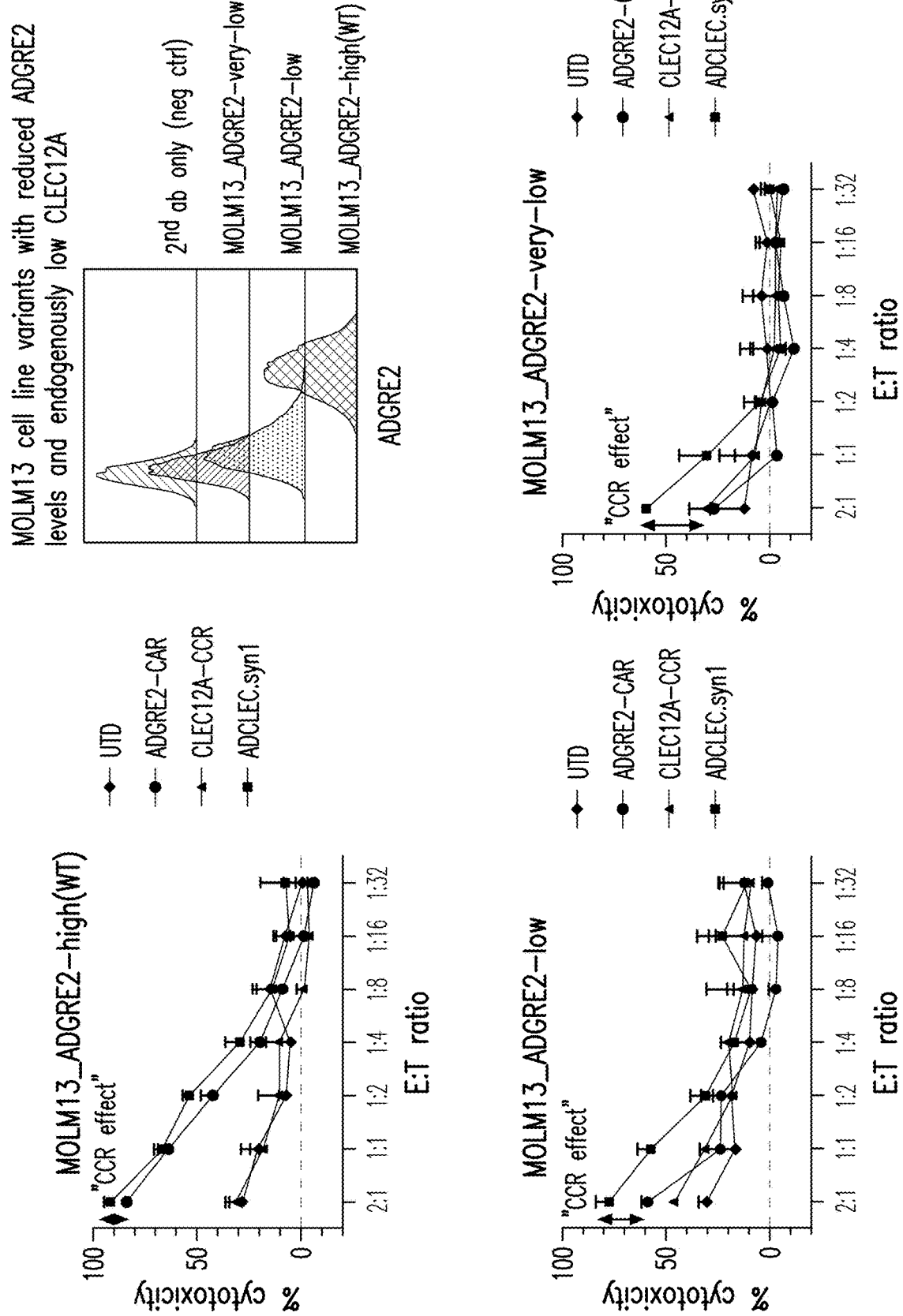

FIGS. 19A and 19B illustrate in vitro CAR efficacy assays validating the "IF-BETTER" gating strategy in the context of ADGRE2/CLEC12A co-targeting via ADCLEC.syn1. FIG. 19A shows cytotoxicity induced by ADCLEC.syn1-transduced T cells and cocultured with EL4 murine lymphoma cell line expressing no target (ADGRE2−/CLEC12A−) or overexpressing either CAR target alone (ADGRE2+/CLEC12A−), CCR target alone (ADGRE2−/CLEC12A+), or both CAR and CCR target (ADGRE2+/

CLEC12A+). 1928z1XX CAR was used as a negative control. FIG. 19B shows cytotoxicity induced by untransduced, ADGRE2-CAR-, CLEC12A-CCR-, or ADCLEC.syn1-transduced T cells cocultured with MOLM13 target cells that were modified to express different ADGRE2 levels (i.e., ADGRE2-high(WT), ADGRE2-low, and ADGRE2-very-low).

Figure 20:
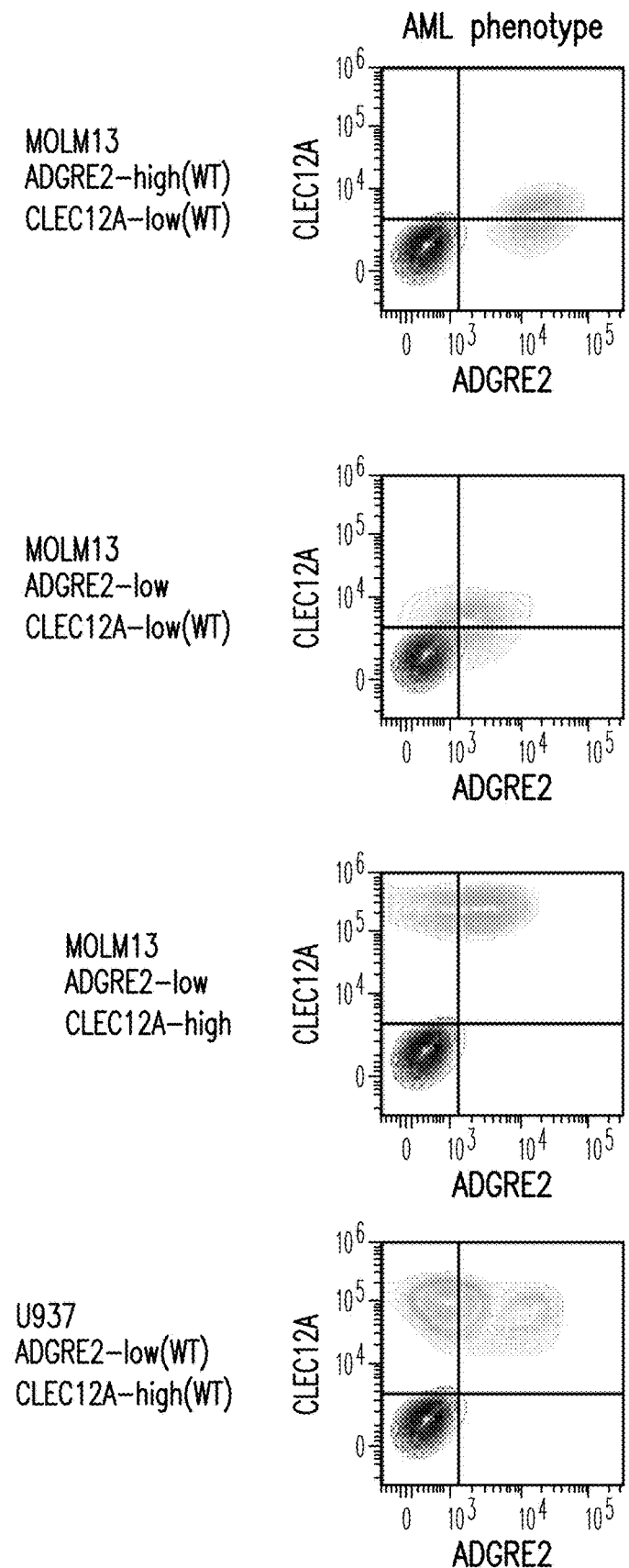
Figure 20:
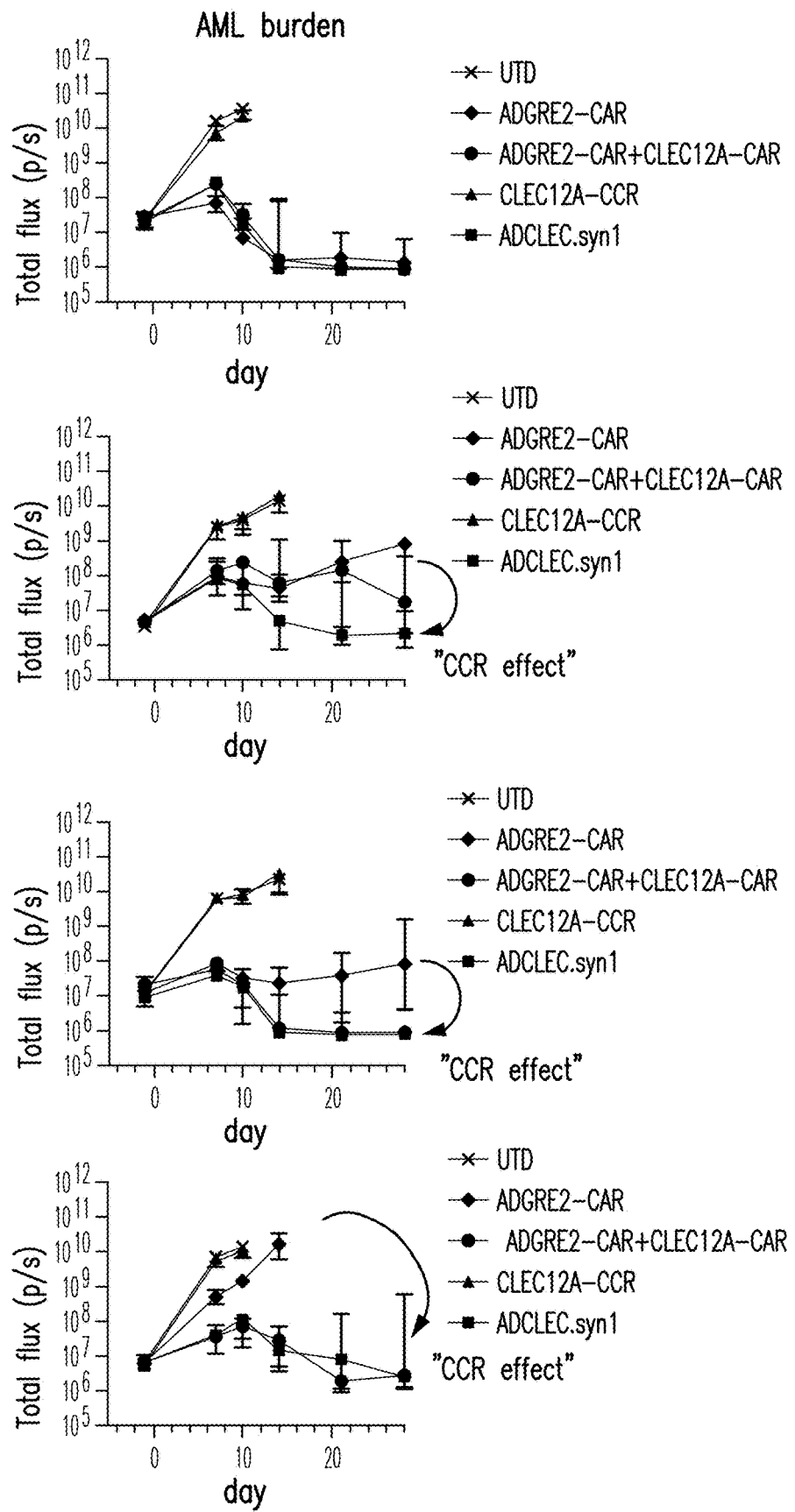
Figure 20:
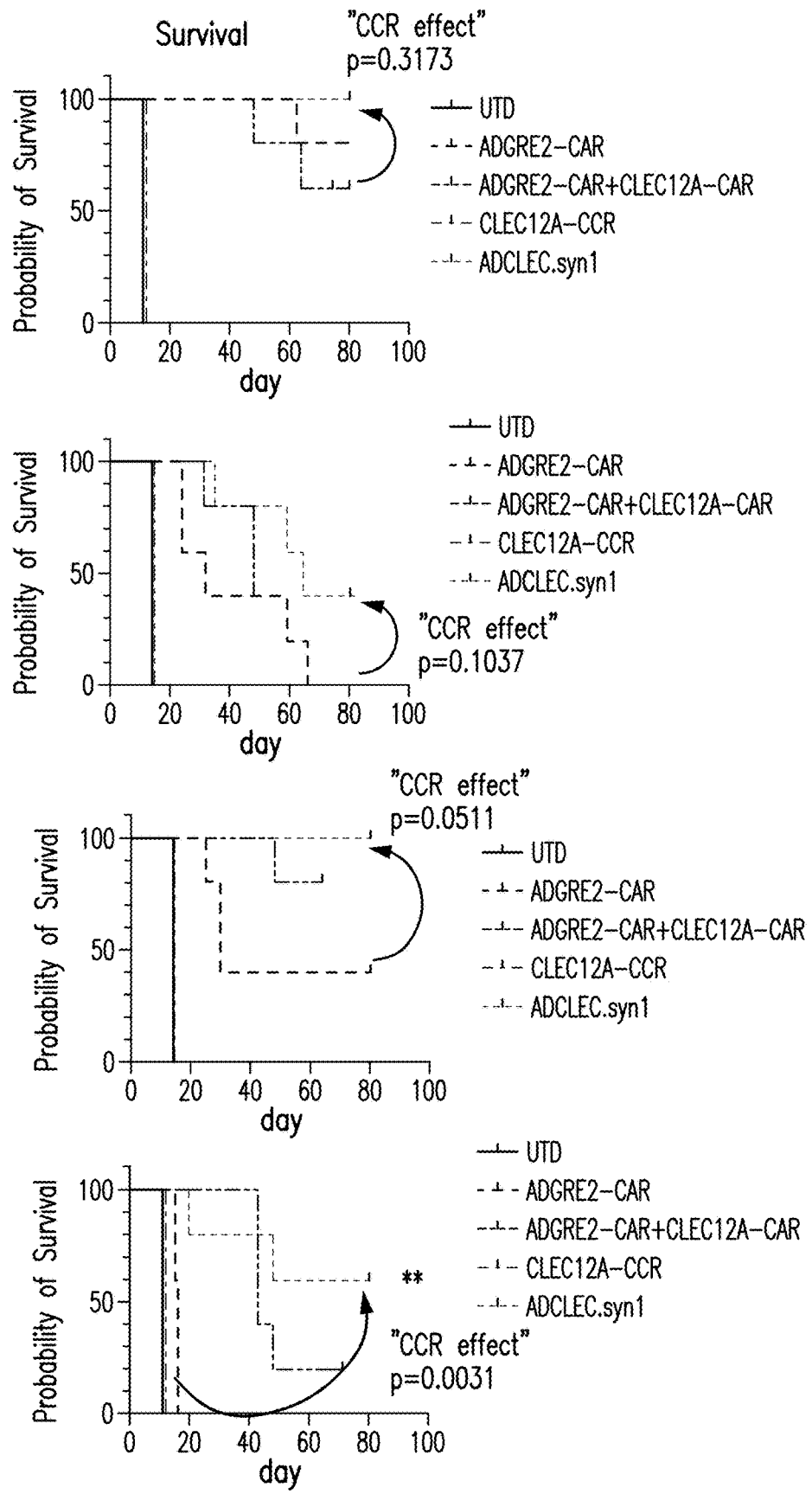

FIG. 20 illustrates in vivo validation of the "IF-BETTER" gating strategy using ADCLEC.syn1 T cells. Tumor growth and survival were determined in NSG AML xenograft models receiving an injection of untransduced, ADGRE2-CAR-, ADGRE2-CAR+CLEC12A-CAR-, CLEC12A-CCR-, or ADCLEC.syn1-transduced T cells.

Figure 21:
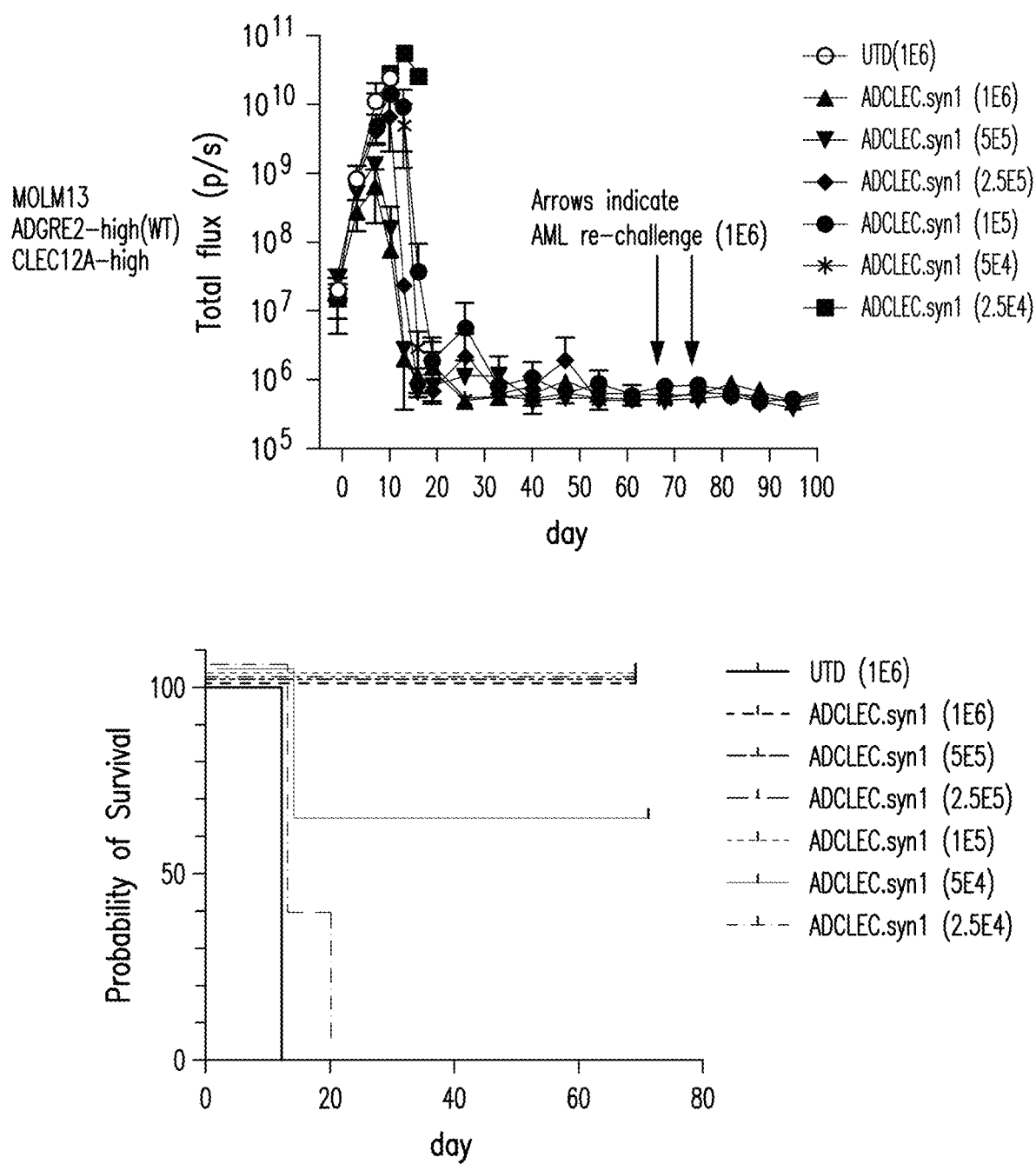

FIG. 21 illustrates in vivo stress test of ADCLEC.syn1 via T cell dose-titration and AML re-challenge. Tumor growth and survival were determined in NSG AML xenograft models receiving an injection of ADCLEC.syn1-transduced T cells at different doses.

5. DETAILED DESCRIPTION OF THE INVENTION

The presently disclosed subject matter provides chimeric receptors that target ADGRE2, and chimeric receptors that target CLEC12A. The presently disclosed subject matter further provides cells comprising the presently disclosed ADGRE2-targeted chimeric receptor, cells comprising the presently disclosed CLEC12A-targeted chimeric receptor, and cells comprising the presently disclosed ADGRE2-targeted chimeric receptor, and the presently disclosed CLEC12A-targeted chimeric receptor. The cells can be immunoresponsive cells, e.g., genetically modified immunoresponsive cells (e.g., T cells or NK cells). The presently disclosed subject matter also provides methods of using such cells for treatments, e.g., for treating and/or preventing a tumor associated with ADGRE2 and/or CLEC12A (e.g., AML).

Non-limiting embodiments of the presently disclosed subject matter are described by the present specification and Examples.

For purposes of clarity of disclosure and not by way of limitation, the detailed description is divided into the following subsections:

5.1. Definitions;
5.2. Chimeric Receptors;
5.3. Extracellular antigen-binding domains of ADGRE2-Targeted Chimeric Receptors;
5.4. Exemplified ADGRE2-Targeted Chimeric Receptors;
5.5. Extracellular antigen-binding domains of CLEC12A-Targeted Chimeric Receptors;
5.6. Exemplified CLEC12A-Targeted Chimeric Receptors;
5.7. Cells;
5.8. Nucleic Acid Molecules, Vector and Genetic Modifications;
5.9. Formulations and Administration; and
5.10. Methods of Treatment.

5.1. Definitions

Unless defined otherwise, all technical and scientific terms used herein have the meaning commonly understood by a person skilled in the art to which the presently disclosed subject matter belongs. The following references provide one of skill with a general definition of many of the terms used in the presently disclosed subject matter: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

As used herein, the term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value.

By "immunoresponsive cell" is meant a cell that functions in an immune response or a progenitor, or progeny thereof. In certain embodiments, the immunoresponsive cell is a cell of lymphoid lineage. Non-limiting examples of cells of lymphoid lineage include T cells, Natural Killer (NK) cells, B cells, and stem cells from which lymphoid cells may be differentiated. In certain embodiments, the immunoresponsive cell is a cell of myeloid lineage.

By "activates an immunoresponsive cell" is meant induction of signal transduction or changes in protein expression in the cell resulting in initiation of an immune response. For example, when CD3 Chains cluster in response to ligand binding and immunoreceptor tyrosine-based inhibition motifs (ITAMs) a signal transduction cascade is produced. In certain embodiments, when an endogenous TCR or an exogenous CAR binds to an antigen, a formation of an immunological synapse occurs that includes clustering of many molecules near the bound receptor (e.g. CD4 or CD8, CD3γ/δ/ε/ζ, etc.). This clustering of membrane bound signaling molecules allows for ITAM motifs contained within the CD3 chains to become phosphorylated. This phosphorylation in turn initiates a T cell activation pathway ultimately activating transcription factors, such as NF-κB and AP-1. These transcription factors induce global gene expression of the T cell to increase IL-2 production for proliferation and expression of master regulator T cell proteins in order to initiate a T cell mediated immune response.

By "stimulates an immunoresponsive cell" is meant a signal that results in a robust and sustained immune response. In various embodiments, this occurs after immune cell (e.g., T-cell) activation or concomitantly mediated through receptors including, but not limited to, CD28, CD137 (4-1BB), OX40, CD40 and ICOS. Receiving multiple stimulatory signals can be important to mount a robust and long-term T cell mediated immune response. T cells can quickly become inhibited and unresponsive to antigen. While the effects of these co-stimulatory signals may vary, they generally result in increased gene expression in order to generate long lived, proliferative, and anti-apoptotic T cells that robustly respond to antigen for complete and sustained eradication.

As used herein, the term "antibody" means not only intact antibody molecules, but also fragments of antibody molecules that retain immunogen-binding ability. Such fragments are also well known in the art and are regularly employed both in vitro and in vivo. Accordingly, as used herein, the term "antibody" means not only intact immunoglobulin molecules but also the well-known active fragments F(ab')₂, and Fab. F(ab')₂, and Fab fragments that lack the Fc fragment of intact antibody, clear more rapidly from the circulation, and may have less non-specific tissue binding of an intact antibody (Wahl et al., *Nucl Med* (1983); 24:316-325). As used herein, include whole native antibodies, bispecific antibodies; chimeric antibodies; Fab, Fab', single chain V region fragments (scFv), fusion polypeptides, and unconventional antibodies. In certain embodiments, an antibody is a glycoprotein comprising at least two heavy (H) chains and two light (L) chains inter-connected by disulfide bonds. Each heavy chain is comprised of a heavy chain variable region (abbreviated herein as $V_H$) and a heavy chain constant ($C_H$) region. The heavy chain constant region is comprised of three domains, CH1, CH2 and CH3. Each light chain is comprised of a light chain variable region (abbreviated herein as $V_L$) and a light chain constant $C_L$ region. The light chain constant region is comprised of one domain, $C_L$. The $V_H$ and $V_L$ regions can be further sub-divided into regions of hypervariability, termed complementarity determining regions (CDR), interspersed with regions that are more conserved, termed framework regions (FR). Each $V_H$ and $V_L$ is composed of three CDRs and four FRs arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

As used herein, "CDRs" are defined as the complementarity determining region amino acid sequences of an antibody which are the hypervariable regions of immunoglobulin heavy and light chains. See, e.g., Kabat et al., Sequences of Proteins of Immunological Interest, 4th U. S. Department of Health and Human Services, National Institutes of Health (1987), or IMGT numbering system (Lefranc, *The Immunologist* (1999); 7:132-136; Lefranc et al., *Dev. Comp. Immunol.* (2003); 27:55-77). Generally, antibodies comprise three heavy chain and three light chain CDRs or CDR regions in the variable region. CDRs provide the majority of contact residues for the binding of the antibody to the antigen or epitope. In certain embodiments, the CDRs regions are delineated using the IMGT numbering system.

As used herein, the term "single-chain variable fragment" or "scFv" is a fusion protein of the variable regions of the heavy ($V_H$) and light chains ($V_L$) of an immunoglobulin (e.g., mouse or human) covalently linked to form a $V_H$::$V_L$ heterodimer. The heavy ($V_H$) and light chains ($V_L$) are either joined directly or joined by a peptide-encoding linker (e.g., 10, 15, 20, 25 amino acids), which connects the N-terminus of the $V_H$ with the C-terminus of the $V_L$, or the C-terminus of the $V_H$ with the N-terminus of the $V_L$. The linker is usually rich in glycine for flexibility, as well as serine or threonine for solubility. The linker can link the heavy chain variable region and the light chain variable region of the extracellular antigen-binding domain. Non-limiting examples of linkers are disclosed in Shen et al., Anal. Chem. 80(6):1910-1917 (2008) and WO 2014/087010, the contents of which are hereby incorporated by reference in their entireties. In certain embodiments, the linker is a G4S linker.

In certain embodiments, the linker comprises or consists of the amino acid sequence set forth in SEQ ID NO: 1, which is provided below:

GGGGSGGGGSGGGSGGGGS [SEQ ID NO: 1]

In certain embodiments, the linker comprise or consists of the amino acid sequence set forth in SEQ ID NO: 2, which is provided below:

GGGGSGGGGSGGGGS [SEQ ID NO: 2]

In certain embodiments, the linker comprises or consists of the amino acid sequence set forth in SEQ ID NO: 3, which is provided below:

GGGGSGGGGSGGGGSGGGSGGGGS [SEQ ID NO: 3]

In certain embodiments, the linker comprises or consists of the amino acid sequence set forth in SEQ ID NO: 4, which is provided below:

GGGGSGGGGSGGGGSGGGGSGGGSGGGGS [SEQ ID NO: 4]

In certain embodiments, the linker comprises or consists of the amino acid sequence set forth in SEQ ID NO: 5, which is provided below:

GGGGS [SEQ ID NO: 5]

In certain embodiments, the linker comprises or consists of the amino acid sequence set forth in SEQ ID NO: 6, which is provided below:

GGGGSGGGS [SEQ ID NO: 6]

In certain embodiments, the linker comprises the first three amino acids of the heavy chain constant region. In certain embodiments, the linker comprises or consists of the amino acid sequence set forth in SEQ ID NO: 149, which is provided below:

ASTGGGGSGGGSGGGGS [SEQ ID NO: 149]

Despite removal of the constant regions and the introduction of a linker, scFv proteins retain the specificity of the original immunoglobulin. Single chain Fv polypeptide antibodies can be expressed from a nucleic acid comprising $V_H$- and $V_L$-encoding sequences as described by Huston, et al. *Proc. Nat. Acad. Sci. USA,* (1988); 85:5879-5883; U.S. Pat. Nos. 5,091,513, 5,132,405 and 4,956,778; and U.S. Patent Publication Nos. 20050196754 and 20050196754. Antagonistic scFvs having inhibitory activity have been described (see, e.g., Zhao et al., *Hybridoma (Larchmt)* (2008); 27(6): 445-51; Peter et al., *J Cachexia Sarcopenia Muscle* (2012); August 12; Shieh et al., *J Imunol* (2009); 183(4):2277-85; Giomarelli et al., *Thromb Haemost* (2007); 97(6):955-63; Fife eta., *J Clin Invst* (2006); 116(8):2252-61; Brocks et al., *Immunotechnology* 1997 3(3):173-84; Moosmayer et al., *Ther Immunol* 1995 2(10:31-40). Agonistic scFvs having stimulatory activity have been described (Peter et al., *J Biol Chem* (2003); 25278(38):36740-7; Xie et al., *Nat Biotech*

1997 15(8):768-71; Ledbetter et al., *Crit Rev Immunol* (1997); 17(5-6):427-55; Ho et al., *BioChim Biophys Acta* (2003); 1638(3):257-66).

The term "chimeric antigen receptor" or "CAR" as used herein refers to a molecule comprising an extracellular antigen-binding domain that is fused to an intracellular signaling domain that is capable of activating or stimulating an immunoresponsive cell. In certain embodiments, the CAR also comprises a transmembrane domain. In certain embodiments, the extracellular antigen-binding domain of a CAR comprises an scFv. The scFv can be derived from fusing the variable heavy and light regions of an antibody. Alternatively or additionally, the scFv may be derived from Fab's (instead of from an antibody, e.g., obtained from Fab libraries). In certain embodiments, the scFv is fused to the transmembrane domain and then to the intracellular signaling domain.

The term "chimeric co-stimulating receptor" or "CCR" refers to a chimeric receptor that binds to an antigen and provides co-stimulatory signals, but does not alone provide an activation signal. CCR is described in Krause, et al., *J. Exp. Med.* (1998); 188(4):619-626, and US20020018783, the contents of which are incorporated by reference in their entireties. CCRs mimic co-stimulatory signals, but unlike, CARs, do not alone provide an activation signal, e.g., CCRs lack a CD3ζ polypeptide.

By "substantially identical" or "substantially homologous" is meant a polypeptide or nucleic acid molecule exhibiting at least about 50% homologous or identical to a reference amino acid sequence (for example, any of the amino acid sequences described herein) or a reference nucleic acid sequence (for example, any of the nucleic acid sequences described herein). In certain embodiments, such a sequence is at least about 60%, at least about 65%, at least about 70%, at least about 75%, at least about 80%, at least about 85%, at least about 90%, at least about 95%, at least about 99%, or at least about 100% homologous or identical to the sequence of the amino acid or nucleic acid used for comparison.

Sequence identity can be measured by using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/ PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between e-3 and e-100 indicating a closely related sequence.

As used herein, the percent homology between two amino acid sequences is equivalent to the percent identity between the two sequences. The percent identity between the two sequences is a function of the number of identical positions shared by the sequences (i.e., % homology=#of identical positions/total #of positions×100), taking into account the number of gaps, and the length of each gap, which need to be introduced for optimal alignment of the two sequences. The comparison of sequences and determination of percent identity between two sequences can be accomplished using a mathematical algorithm.

The percent homology between two amino acid sequences can be determined using the algorithm of E. Meyers and W. Miller (*Comput. Appl. Biosci.,* 4:11-17 (1988)) which has been incorporated into the ALIGN program (version 2.0), using a PAM120 weight residue table, a gap length penalty of 12 and a gap penalty of 4. In addition, the percent homology between two amino acid sequences can be determined using the Needleman and Wunsch (*J. Mol. Biol.* 48:444-453 (1970)) algorithm which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6.

Additionally or alternatively, the amino acids sequences of the presently disclosed subject matter can further be used as a "query sequence" to perform a search against public databases to, for example, identify related sequences. Such searches can be performed using the XBLAST program (version 2.0) of Altschul, et al. (1990) *J. Mol. Biol.* 215: 403-10. BLAST protein searches can be performed with the XBLAST program, score=50, wordlength=3 to obtain amino acid sequences homologous to the specified sequences (e.g., heavy and light chain variable region sequences of scFv m903, m904, m905, m906, and m900) disclosed herein. To obtain gapped alignments for comparison purposes, Gapped BLAST can be utilized as described in Altschul et al., (1997) *Nucleic Acids Res.* 25(17):3389-3402. When utilizing BLAST and Gapped BLAST programs, the default parameters of the respective programs (e.g., XBLAST and NBLAST) can be used. An "effective amount" is an amount sufficient to affect a beneficial or desired clinical result upon treatment. An effective amount can be administered to a subject in one or more doses. In certain embodiments, an effective amount can be an amount that is sufficient to palliate, ameliorate, stabilize, reverse or slow the progression of the disease, or otherwise reduce the pathological consequences of the disease. The effective amount can be determined by a physician on a case-by-case basis and is within the skill of one in the art. Several factors are typically taken into account when determining an appropriate dosage to achieve an effective amount. These factors include age, sex and weight of the subject, the condition being treated, the severity of the condition and the form and effective concentration of the cells administered.

As used herein, the term "endogenous" refers to a nucleic acid molecule or polypeptide that is normally expressed in a cell or tissue.

As used herein, the term "exogenous" refers to a nucleic acid molecule or polypeptide that is not endogenously present in a cell. The term "exogenous" would therefore encompass any recombinant nucleic acid molecule or polypeptide expressed in a cell, such as foreign, heterologous, and over-expressed nucleic acid molecules and polypeptides. By "exogenous" nucleic acid is meant a nucleic acid not present in a native wild-type cell; for example, an exogenous nucleic acid may vary from an endogenous counterpart by sequence, by position/location, or both. For clarity, an exogenous nucleic acid may have the same or different sequence relative to its native endogenous counterpart; it may be introduced by genetic engineering into the cell itself or a progenitor thereof, and may optionally be linked to alternative control sequences, such as a non-native promoter or secretory sequence.

By a "heterologous nucleic acid molecule or polypeptide" is meant a nucleic acid molecule (e.g., a cDNA, DNA or RNA molecule) or polypeptide that is not normally present in a cell or sample obtained from a cell. This nucleic acid may be from another organism, or it may be, for example, an mRNA molecule that is not normally expressed in a cell or sample.

By "modulate" is meant positively or negatively alter. Exemplary modulations include a about 1%, about 2%, about 5%, about 10%, about 25%, about 50%, about 75%, or about 100% change.

By "increase" is meant to alter positively by at least about 5%. An alteration may be by about 5%, about 10%, about 25%, about 30%, about 50%, about 75%, about 100% or more.

By "reduce" is meant to alter negatively by at least about 5%. An alteration may be by about 5%, about 10%, about 25%, about 30%, about 50%, about 75%, or even by about 100%.

The terms "isolated," "purified," or "biologically pure" refer to material that is free to varying degrees from components which normally accompany it as found in its native state. "Isolate" denotes a degree of separation from original source or surroundings. "Purify" denotes a degree of separation that is higher than isolation. A "purified" or "biologically pure" protein is sufficiently free of other materials such that any impurities do not materially affect the biological properties of the protein or cause other adverse consequences. That is, a nucleic acid or peptide is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high-performance liquid chromatography. The term "purified" can denote that a nucleic acid or protein gives rise to essentially one band in an electrophoretic gel. For a protein that can be subjected to modifications, for example, phosphorylation or glycosylation, different modifications may give rise to different isolated proteins, which can be separately purified.

By "isolated cell" is meant a cell that is separated from the molecular and/or cellular components that naturally accompany the cell.

The term "antigen-binding domain" as used herein refers to a domain capable of specifically binding a particular antigenic determinant or set of antigenic determinants present on a cell.

By "receptor" is meant a polypeptide, or portion thereof, present on a cell membrane that selectively binds one or more ligand.

By "signal sequence" or "leader sequence" is meant a peptide sequence (e.g., 5, 10, 15, 20, 25 or 30 amino acids) present at the N-terminus of newly synthesized proteins that directs their entry to the secretory pathway The terms "comprises", "comprising", and are intended to have the broad meaning ascribed to them in U.S. Patent Law and can mean "includes", "including" and the like.

As used herein, "treatment" refers to clinical intervention in an attempt to alter the disease course of the individual or cell being treated, and can be performed either for prophylaxis or during the course of clinical pathology. Therapeutic effects of treatment include, without limitation, preventing occurrence or recurrence of disease, alleviation of symptoms, diminishment of any direct or indirect pathological consequences of the disease, preventing metastases, decreasing the rate of disease progression, amelioration or palliation of the disease state, and remission or improved prognosis. By preventing progression of a disease or disorder, a treatment can prevent deterioration due to a disorder in an affected or diagnosed subject or a subject suspected of having the disorder, but also a treatment may prevent the onset of the disorder or a symptom of the disorder in a subject at risk for the disorder or suspected of having the disorder.

An "individual" or "subject" herein is a vertebrate, such as a human or non-human animal, for example, a mammal. Mammals include, but are not limited to, humans, primates, farm animals, sport animals, rodents and pets. Non-limiting examples of non-human animal subjects include rodents such as mice, rats, hamsters, and guinea pigs; rabbits; dogs; cats; sheep; pigs; goats; cattle; horses; and non-human primates such as apes and monkeys.

As used herein, the term "a conservative sequence modification" refers to an amino acid modification that does not significantly affect or alter the binding characteristics of the presently disclosed chimeric receptors comprising the amino acid sequence. Conservative modifications can include amino acid substitutions, additions and deletions. Modifications can be introduced into the extracellular antigen-binding domain of the presently disclosed chimeric receptors by standard techniques known in the art, such as site-directed mutagenesis and PCR-mediated mutagenesis. Amino acids can be classified into groups according to their physicochemical properties such as charge and polarity. Conservative amino acid substitutions are ones in which the amino acid residue is replaced with an amino acid within the same group. For example, amino acids can be classified by charge: positively-charged amino acids include lysine, arginine, histidine, negatively-charged amino acids include aspartic acid, glutamic acid, neutral charge amino acids include alanine, asparagine, cysteine, glutamine, glycine, isoleucine, leucine, methionine, phenylalanine, proline, serine, threonine, tryptophan, tyrosine, and valine. In addition, amino acids can be classified by polarity: polar amino acids include arginine (basic polar), asparagine, aspartic acid (acidic polar), glutamic acid (acidic polar), glutamine, histidine (basic polar), lysine (basic polar), serine, threonine, and tyrosine; non-polar amino acids include alanine, cysteine, glycine, isoleucine, leucine, methionine, phenylalanine, proline, tryptophan, and valine. Thus, one or more amino acid residues within a CDR region can be replaced with other amino acid residues from the same group and the altered antibody can be tested for retained function (i.e., the functions set forth in (c) through (1) above) using the functional assays described herein. In certain embodiments, no more than one, no more than two, no more than three, no more than four, no more than five residues within a specified sequence or a CDR region are altered.

Other aspects of the presently disclosed subject matter are described in the following disclosure and are within the ambit of the presently disclosed subject matter.

5.2. Chimeric Receptors

In certain embodiments, the presently disclosed chimeric receptor comprises an extracellular antigen-binding domain that binds to ADGRE2 or CLEC12A. The extracellular antigen-binding domain can be an antigen-binding fragment of an antibody, an antigen-binding fragment of a heavy chain variable region ($V_H$) of an antibody, an antigen-binding fragment of a light chain variable region ($V_L$) of an antibody, a single chain variable fragment (scFv), a Fab, or F(ab)$_2$. In certain embodiments, the extracellular antigen-binding fragment is a single chain variable fragment (scFv). In certain embodiments, the scFv is a human scFv. In certain embodiments, the scFv is a humanized scFv. In certain embodiments, the scFv is a murine scFv. In certain embodiments, the Fab is crosslinked.

In certain embodiments, the presently disclosed chimeric receptor is a chimeric antigen receptor (CAR). In certain embodiments, the presently disclosed chimeric receptor is a chimeric co-stimulating receptor (CCR). In certain embodiments, the chimeric receptor is a TCR like fusion molecule.

5.2.1. Chimeric Antigen Receptor (CAR)

In certain embodiments, the chimeric receptor is a CAR. CARs are engineered receptors, which graft or confer a specificity of interest onto an immune effector cell. CARs can be used to graft the specificity of a monoclonal antibody onto a T cell; with transfer of their coding sequence facilitated by retroviral vectors.

There are three generations of CARs. "First generation" CARs are typically composed of an extracellular antigen-binding domain (e.g., an scFv), which is fused to a transmembrane domain, which is fused to cytoplasmic/intracellular signaling domain. "First generation" CARs can provide de novo antigen recognition and cause activation of both CD4+ and CD8+ T cells through their CD3ζ chain signaling domain in a single fusion molecule, independent of HLA-mediated antigen presentation. "Second generation" CARs add intracellular signaling domains from various co-stimulatory molecules (e.g., CD28, 4-1BB, ICOS, OX40) to the cytoplasmic tail of the CAR to provide additional signals to the T cell. "Second generation" CARs comprise those that provide both co-stimulation (e.g., CD28 or 4-1BB) and activation (CD3ζ). "Third generation" CARs comprise those that provide multiple co-stimulation (e.g., CD28 and 4-1BB) and activation (CD3ζ). In certain embodiments, the chimeric receptor is a second generation CAR. In certain embodiments, the chimeric receptor is a CAR that comprises an intracellular domain of a co-stimulatory molecule or a fragment thereof.

5.2.1.1. Extracellular Antigen-Binding Domain of a CAR

In certain embodiments, the extracellular antigen-binding domain is a single chain variable fragment (scFv). In certain embodiments, the scFv is a human scFv. In certain embodiments, the scFv is a humanized scFv. In certain embodiments, the scFv is a murine scFv. In certain embodiments, the scFv is identified by screening scFv phage library with an antigen-Fc fusion protein.

In certain embodiments, the extracellular antigen-binding domain is a Fab. In certain embodiments, the Fab is crosslinked. In certain embodiments, the extracellular antigen-binding domain is a F(ab)$_2$. Any of the foregoing molecules may be comprised in a fusion protein with a heterologous sequence to form the extracellular antigen-binding domain.

Binding of the extracellular antigen-binding domain of a chimeric receptor, e.g., a CAR, can be confirmed by, for example, enzyme-linked immunosorbent assay (ELISA), radioimmunoassay (RIA), FACS analysis, bioassay (e.g., growth inhibition), or Western Blot assay. Each of these assays generally detect the presence of protein-antibody complexes of particular interest by employing a labeled reagent (e.g., an antibody, or an scFv) specific for the complex of interest. For example, the scFv can be radioactively labeled and used in a radioimmunoassay (RIA) (see, for example, Weintraub, B., Principles of Radioimmunoassay, Seventh Training Course on Radioligand Assay Techniques, The Endocrine Society, March, 1986, which is incorporated by reference herein). The radioactive isotope can be detected by such means as the use of a γ counter or a scintillation counter or by autoradiography. In certain embodiments, the extracellular antigen-binding domain of the CAR is labeled with a fluorescent marker. Non-limiting examples of fluorescent markers include green fluorescent protein (GFP), blue fluorescent protein (e.g., EBFP, EBFP2, Azurite, and mKalama1), cyan fluorescent protein (e.g., ECFP, Cerulean, and CyPet), and yellow fluorescent protein (e.g., YFP, Citrine, Venus, and YPet).

5.2.1.2. Transmembrane Domain of a CAR

In certain embodiments, the transmembrane domain of the CAR comprises a hydrophobic alpha helix that spans at least a portion of the membrane. Different transmembrane domains result in different receptor stability. After antigen recognition, receptors cluster and a signal are transmitted to the cell. In accordance with the presently disclosed subject matter, the transmembrane domain of the CAR can comprise a native or modified transmembrane domain of CD8 or a fragment thereof, a native or modified transmembrane domain of CD28 or a fragment thereof, a native or modified transmembrane domain of CD3ζ or a fragment thereof, a native or modified transmembrane domain of CD4 or a fragment thereof, a native or modified transmembrane domain of 4-1BB or a fragment thereof, a native or modified transmembrane domain of OX40 or a fragment thereof, a native or modified transmembrane domain of ICOS or a fragment thereof, a native or modified transmembrane domain of CD84 or a fragment thereof, a native or modified transmembrane domain of CD166 or a fragment thereof, a native or modified transmembrane domain of CD8a or a fragment thereof, a native or modified transmembrane domain of CD8b or a fragment thereof, a native or modified transmembrane domain of ICAM-1 or a fragment thereof, a native or modified transmembrane domain of CTLA-4 or a fragment thereof, a native or modified transmembrane domain of CD27 or a fragment thereof, a native or modified transmembrane domain of CD40 or a fragment thereof, NKGD2 or a fragment thereof, or a combination thereof.

In certain embodiments, the transmembrane domain of the CAR comprises a CD8 polypeptide (e.g., a transmembrane domain of CD8 or a fragment thereof).

In certain embodiments, the transmembrane domain of the CAR comprises a CD8 polypeptide (e.g., a transmembrane domain of CD8 or a fragment thereof). In certain embodiments, the transmembrane domain of the CAR comprises a CD8 polypeptide (e.g., a transmembrane domain of human CD8 or a fragment thereof). In certain embodiments, the CD8 polypeptide comprises or consists of an amino acid sequence that is at least about 85%, about 90%, about 95%, about 96%, about 97%, about 98%, about 99% or about 100% homologous or identical to the amino acid sequence having a NCBI Reference No: NP_001139345.1 (SEQ ID NO: 7) or a fragment thereof, and/or may optionally comprise up to one or up to two or up to three conservative amino acid substitutions. In certain embodiments, the CD8 polypeptide comprises or consists of an amino acid sequence that is a consecutive portion of SEQ ID NO: 7, which is at least about 20, or at least about 30, or at least about 40, or at least about 50, at least about 60, at least about 70, and up to about 235 amino acids in length. In certain embodiments, the CD8 polypeptide comprises or consists of amino acids 1 to 235, 1 to 50, 50 to 100, 100 to 150, 150 to 200, 137 to 207, or 200 to 235 of SEQ ID NO: 7. In certain embodiments, the transmembrane domain of the CAR comprises a CD8 polypeptide comprising or consisting of amino acids 137 to 207 of SEQ ID NO: 7. SEQ ID NO: 7 is provided below.

[SEQ ID NO: 7]
MALPVTALLLPLALLLHAARPSQFRVSPLDRTWNLGETVELKCQVLLSNPT

SGCSWLFQPRGAAASPTFLLYLSQNKPKAAEGLDTQRFSGKRLGDTFVLTL

SDFRRENEGYYFCSALSNSIMYFSHFVPVFLPAKPTTTPAPRPPTPAPTIA

SQPLSLRPEACRPAAGGAVHTRGLDFACDIYIWAPLAGTCGVLLLSLVITL

YCNHRNRRRVCKCPRPVVKSGDKPSLSARYV

An exemplary nucleotide sequence encoding amino acids 137 to 207 of SEQ ID NO: 7 is set forth in SEQ ID NO: 8, which is provided below.

[SEQ ID NO: 8]
Cccaccacgacgccagcgccgcgaccaccaaccccggcgccacgatcgcg tcgcagcccctgtccctgcgcccagaggcgtgccggccagcggcgggggc gcagtgcacacgaggggctggacttcgcctgtgatatctacatctgggcg cccctggccgggacttgtggggtccttctcctgtcactggttatcacccttt tactgcaac In certain embodiments, the transmembrane domain of the CAR comprises a CD8 polypeptide (e.g., a transmembrane domain of mouse CD8 or a fragment thereof). In certain embodiments, the CD8 polypeptide comprises or consists of an amino acid sequence that is at least about 85%, about 90%, about 95%, about 96%, about 97%, about 98%, about 99% or about 100% homologous or identical to the amino acid sequence having a NCBI Reference No: AAA92533.1 (SEQ ID NO: 9) or a fragment thereof, and/or may optionally comprise up to one or up to two or up to three conservative amino acid substitutions. In certain embodiments, the CD8 polypeptide comprises or consists of an amino acid sequence that is a consecutive portion of SEQ ID NO: 9, which is at least about 20, or at least about 30, or at least about 40, or at least about 50, or at least about 60, or at least about 70, or at least about 100, or at least about 200, and up to about 247 amino acids in length. In certain embodiments, the CD8 polypeptide comprises or consists of amino acids 1 to 247, 1 to 50, 50 to 100, 100 to 150, 150 to 200, 151 to 219, or 200 to 247 of SEQ ID NO: 9. In certain embodiments, the transmembrane domain of the CAR comprises a CD8 polypeptide comprising or consisting of amino acids 151 to 219 of SEQ ID NO: 9. SEQ ID NO: 9 is provided below.

[SEQ ID NO: 9]
| 1 | MASPLTRFLS | LNLLLMGESI | ILGSGEAKPQ | APELRIFPKK | MDAELGQKVD | LVCEVLGSVS |
| 61 | QGCSWLFQNS | SSKLPQPTFV | VYMASSHNKI | TWDEKLNSSK | LFSAVRDTNN | KYVLTLNKFS |
| 121 | KENEGYYFCS | VISNSVMYFS | SVVPVLQKVN | STTTKPVLRT | PSPVHPTGTS | QPQRPEDCRP |
| 181 | RGSVKGTGLD | FACDIYIWAP | LAGICVAPLL | SLIITLICYH | RSRKRVCKCP | RPLVRQEGKP |
| 241 | RPSEKIV | | | | | |

In certain embodiments, the transmembrane domain of a presently disclosed CAR comprises a CD28 polypeptide (e.g., a transmembrane domain of CD28 or a fragment thereof).

In certain embodiments, the transmembrane domain of the CAR comprises a CD28 polypeptide (e.g., a transmembrane domain of human CD28 or a fragment thereof). In certain embodiments, the CD28 polypeptide comprises or consists of an amino acid sequence that is at least about 85%, about 90%, about 95%, about 96%, about 97%, about 98%, about 99% or 100% homologous or identical to the amino acid sequence having a NCBI Reference No: NP_006130 (SEQ ID NO: 10) or a fragment thereof, and/or may optionally comprise up to one or up to two or up to three conservative amino acid substitutions. In certain embodiments, the CD28 polypeptide comprises or consists of an amino acid sequence that is a consecutive portion of SEQ ID NO: 10, which is at least about 20, or at least about 30, or at least about 40, or at least about 50, and up to about 220 amino acids in length. In certain embodiments, the CD28 polypeptide comprises or consists of amino acids 1 to 220, 1 to 50, 50 to 100, 100 to 150, 150 to 200, 153 to 179, or 200 to 220 of SEQ ID NO: 9. In certain embodiments, the transmembrane domain of the CAR comprises a CD28 polypeptide comprising or consisting of amino acids 153 to 179 of SEQ ID NO: 10. SEQ ID NO: 10 is provided below:

[SEQ ID NO: 10]
| 1 | MLRLLLALNL | FPSIQVTGNK | ILVKQSPMLV | AYDNAVNLSC | KYSYNLFSRE | FRASLHKGLD |
| 61 | SAVEVCVVYG | NYSQQLQVYS | KTGFNCDGKL | GNESVTFYLQ | NLYVNQTDIY | FCKIEVMYPP |
| 121 | PYLDNEKSNG | TIIHVKGKHL | CPSPLFPGPS | KPFWVLVVVG | GVLACYSLLV | TVAFIIFWVR |
| 181 | SKRSRLLHSD | YMNMTPRRPG | PTRKHYQPYA | PPRDFAAYRS | | |

An exemplary nucleotide sequence encoding amino acid 153 to 179 of SEQ ID NO: 10 is set forth in SEQ ID NO: 11, which is provided below.

[SEQ ID NO: 11]
ttttgggtgctggtggtggttggtggagtcctggcttgctatagcttgcta gtaacagtggcctttattattttctgggtg In certain embodiments, the transmembrane domain of the CAR comprises a CD28 polypeptide (e.g., a transmembrane domain of mouse CD28 or a fragment thereof). In certain embodiments, the CD28 polypeptide comprises or consists of an amino acid sequence that is at least about 85%, about 90%, about 95%, about 96%, about 97%, about 98%, about 99% or 100% homologous or identical to the amino acid sequence having a NCBI Reference No: NP_031668.3 (SEQ ID NO: 12) or a fragment thereof, and/or may optionally comprise up to one or up to two or up to three conservative amino acid substitutions. In certain embodiments, the CD28 polypeptide comprises or consists of an amino acid sequence that is a consecutive portion of SEQ ID NO: 12, which is at least about 20, or at least about 30, or at least about 40, or at least about 50, and up to about 218 amino acids in length. In certain embodiments, the CD28 polypeptide comprises or consists of amino acids 1 to 220, 1 to 50, 50 to 100, 100 to 150, 150 to 200, 151 to 177, or 200 to 218 of SEQ ID NO: 12. In certain embodiments, the transmembrane domain of the CAR comprises a CD28 polypeptide comprising or consisting of amino acids 151 to 177 of SEQ ID NO: 12. SEQ ID NO: 12 is provided below:

CD28 polypeptide comprising or consisting of amino acids 114 to 152 of SEQ ID NO: 10.

An exemplary nucleotide sequence encoding amino acid 114 to 152 of SEQ ID NO: 10 is set forth in SEQ ID NO: 13, which is provided below.

[SEQ ID NO: 13]
attgaagttatgtatcctcctccttacctagacaatgagaagagcaatgga
accattatccatgtgaaagggaaacacctttgtccaagtcccctatttccc
ggaccttctaagccc 5.2.1.3. Intracellular Signaling Domain of a CAR In certain embodiments, the CAR comprises an intracellular signaling domain. In certain embodiments, the intrac-

[SEQ ID NO: 12]
```
  1    MTLRLLFLAL NFFSVQVTEN KILVKQSPLL VVDSNEVSLS CRYSYNLLAK EFRASLYKGV
 61    NSDVEVCVGN GNFTYQPQFR SNAEFNCDGD FDNETVTFRL WNLHVNHTDI YFCKIEFMYP
121    PPYLDNERSN GTIIHIKEKH LCHTQSSPKL FWALVVVAGV LFCYGLLVTV ALCVIWTNSR
181    RNRLLQSDYM NMTPRRPGLT RKPYQPYAPA RDFAAYRP
```

In certain embodiments, the CAR further comprises a spacer region that links the extracellular antigen-binding domain to the transmembrane domain. The spacer region can be flexible enough to allow the antigen binding domain to orient in different directions to facilitate antigen recognition while preserving the activating activity of the CAR.

In certain embodiments, the hinge/spacer region of the CAR comprises a native or modified hinge region of CD8 or a fragment thereof, a native or modified hinge region of CD28 or a fragment thereof, a native or modified hinge region of CD3ζ or a fragment thereof, a native or modified hinge region of CD40 or a fragment thereof, a native or modified hinge region of 4-1BB or a fragment thereof, a native or modified hinge region of OX40 or a fragment thereof, a native or modified hinge region of CD84 or a fragment thereof, a native or modified hinge region of CD166 or a fragment thereof, a native or modified hinge region of CD8a or a fragment thereof, a native or modified hinge region of CD8b or a fragment thereof, a native or modified hinge region of ICOS or a fragment thereof, a native or modified hinge region of ICAM-1 or a fragment thereof, a native or modified hinge region of CTLA-4 or a fragment thereof, a native or modified hinge region of CD27 or a fragment thereof, a native or modified hinge region of CD40 or a fragment thereof, a native or modified hinge region of NKGD2 or a fragment thereof, a synthetic polypeptide (not based on a protein associated with the immune response), or a combination thereof. The hinge/spacer region can be the hinge region from IgG1, or the $CH_2CH_3$ region of immunoglobulin and portions of CD3, a portion of a CD28 polypeptide (e.g., a portion of SEQ ID NO: 10 or 12), a portion of a CD8 polypeptide (e.g., a portion of SEQ ID NO: 7 or 9), a variation of any of the foregoing which is at least about 80%, at least about 85%, at least about 90%, at least about 95%, or at least about 100% homologous or identical thereto, or a synthetic spacer sequence.

In certain embodiments, the hinge/spacer region of the CAR comprises a CD28 polypeptide. In certain embodiments, the hinge/spacer region of the CAR comprises a ellular signaling domain of the CAR comprises a CD3ζ polypeptide. CD3ζ can activate or stimulate a cell (e.g., a cell of the lymphoid lineage, e.g., a T cell). Wild type ("native") CD3ζ comprises three functional immunoreceptor tyrosine-based activation motifs (ITAMs), three functional basic-rich stretch (BRS) regions (BRS1, BRS2 and BRS3). CD3ζ transmits an activation signal to the cell (e.g., a cell of the lymphoid lineage, e.g., a T cell) after antigen is bound. The intracellular signaling domain of the CD3ζ-chain is the primary transmitter of signals from endogenous TCRs.

In certain embodiments, the intracellular signaling domain of the CAR comprises a native CD3ζ. In certain embodiments, the native CD3ζ polypeptide comprises or consists of an amino acid sequence that is at least about 85%, about 90%, about 95%, about 96%, about 97%, about 98%, about 99% or about 100% homologous or identical to the amino acid sequence having a NCBI Reference No: NP_932170 (SEQ ID NO: 14) or a fragment thereof, and/or may optionally comprise up to one or up to two or up to three conservative amino acid substitutions. In certain embodiments, the native CD3ζ polypeptide comprises or consists of an amino acid sequence that is a consecutive portion of SEQ ID NO: 14, which is at least about 20, or at least about 30, or at least about 40, or at least about 50, at least about 100, at least about 110, and up to about 164 amino acids in length. In certain embodiments, the native CD3ζ polypeptide comprises or consists of amino acids 1 to 164, 1 to 50, 50 to 100, 52 to 164, 100 to 150, or 150 to 164 of SEQ ID NO: 14. In certain embodiments, the intracellular signaling domain of the CAR comprises a CD3ζ polypeptide comprising or consisting of amino acids 52 to 164 of SEQ ID NO: 14. SEQ ID NO: 14 is provided below:

[SEQ ID NO: 14]
```
  1   MKWKALFTAA ILQAQLPITE AQSFGLLDPK LCYLLDGILF
      IYGVILTALF LRVKFSRSAD
```

```
 61  APAYQQGQNQ  LYNELNLGRR  EEYDVLDKRR  GRDPEMGGKP
     QRRKNPQEGL  YNELQKDKMA

121  EAYSEIGMKG  ERRRGKGHDG  LYQGLSTATK  DTYDALHMQA
     LPPR
```

In certain embodiments, the intracellular signaling domain of the CAR comprises a modified CD3ζ polypeptide. In certain embodiments, the modified CD3ζ polypeptide comprises one, two or three ITAMs. In certain embodiments, the modified CD3ζ polypeptide comprises a native ITAM1. In certain embodiments, the native ITAM1 comprises or consists of the amino acid sequence set forth in SEQ ID NO: 15.

[SEQ ID NO: 15]
QNQLYNELNLGRREEYDVLDKR

An exemplary nucleotide sequence encoding the amino acid sequence of SEQ ID NO: 15 is set forth in SEQ ID NO: 16, which is provided below.

[SEQ ID NO: 16]
Cagaaccagctctataacgagctcaatctaggacgaagagaggagtacgat gttttggacaagaga In certain embodiments, the modified CD3ζ polypeptide comprises an ITAM1 variant comprising one or more loss-of-function mutations. In certain embodiments, the ITAM1 variant comprises or consists of two loss-of-function mutations. In certain embodiments, each of the one or more (e.g., two) loss of function mutations comprises a mutation of a tyrosine residue in ITAM1. In certain embodiments, the ITAM1 variant consists of two loss-of-function mutations. In certain embodiments, the ITAM1 variant comprises or consists of the amino acid sequence set forth in SEQ ID NO: 17, which is provided below.

[SEQ ID NO: 17]
QNQLFNELNLGRREEFDVLDKR

An exemplary nucleotide sequence encoding the amino acid sequence of SEQ ID NO: 17 is set forth in SEQ ID NO: 18, which is provided below.

[SEQ ID NO: 18]
CAGAACCAGCTCTTTAACGAGCTCAATCTAGGACGAAGAGAGGAGTTCGAT

GTTTTGGACAAGAGA

In certain embodiments, the modified CD3ζ polypeptide comprises a native ITAM2. In certain embodiments, the native ITAM2 comprises or consists of the amino acid sequence set forth in SEQ ID NO: 19, which is provided below.

[SEQ ID NO: 19]
QEGLYNELQKDKMAEAYSEIGMK

An exemplary nucleotide sequence encoding the amino acid sequence of SEQ ID NO: 19 is set forth in SEQ ID NO: 20, which is provided below.

[SEQ ID NO: 20]
CAGGAAGGCCTGTACAATGAACTGCAGAAAGATAAGATGGCGGAGGCCTAC

AGTGAGATTGGGATGAAA

In certain embodiments, the modified CD3ζ polypeptide comprises an ITAM2 variant. In certain embodiments, the ITAM2 variant comprises or consists of one or more loss-of-function mutations. In certain embodiments, the ITAM2 variant comprises or consists of two loss-of-function mutations. In certain embodiments, each of the one or more (e.g., two) the loss of function mutations comprises a mutation of a tyrosine residue in ITAM2. In certain embodiments, the ITAM2 variant consists of two loss-of-function mutations. In certain embodiments, the ITAM2 variant comprises or consists of the amino acid sequence set forth in SEQ ID NO: 21, which is provided below.

[SEQ ID NO: 21]
QEGLFNELQKDKMAEAFSEIGMK

An exemplary nucleotide sequence encoding the amino acid sequence of SEQ ID NO: 21 is set forth in SEQ ID NO: 22, which is provided below.

[SEQ ID NO: 22]
Caggaaggcctgttcaatgaactgcagaaagataagatggcggaggccttc agtgagattgggatgaaa In certain embodiments, the modified CD3ζ polypeptide comprises a native ITAM3. In certain embodiments, the native ITAM3 comprises or consists of the amino acid sequence set forth in SEQ ID NO: 23, which is provided below.

[SEQ ID NO: 23]
HDGLYQGLSTATKDTYDALHMQ

An exemplary nucleotide sequence encoding the amino acid sequence of SEQ ID NO: 23 is set forth in SEQ ID NO: 24, which is provided below.

[SEQ ID NO: 24]
CACGATGGCCTTTACCAGGGTCTCAGTACAGCCACCAAGGACACCTACGAC

GCCCTTCACATGCAG

In certain embodiments, the modified CD3ζ polypeptide comprises an ITAM3 variant. In certain embodiments, the ITAM3 variant comprises or consists of two loss-of-function mutations. In certain embodiments, each of the one or more (e.g., two) the loss of function mutations comprises a mutation of a tyrosine residue in ITAM3. In certain embodiments, the ITAM3 variant comprises or consists of two loss-of-function mutations. In certain embodiments, the ITAM3 variant comprises or consists of the amino acid sequence set forth in SEQ ID NO: 25, which is provided below.

[SEQ ID NO: 25]
HDGLFQGLSTATKDTFDALHMQ

An exemplary nucleotide sequence encoding the amino acid sequence of SEQ ID NO: 25 is set forth in SEQ ID NO: 26, which is provided below.

[SEQ ID NO: 26]
Cacgatggccttttccagggtctcagtacagccaccaaggacaccttcgac gcccttcacatgcag Various modified CD3ζ polypeptides and CARs comprising modified CD3ζ polypeptides are disclosed in International Patent Application Publication No. WO2019/133969, which is incorporated by reference hereby in its entirety.

In certain embodiments, the intracellular signaling domain of the CAR comprises a modified CD3ζ polypeptide comprising a native ITAM1, an ITAM2 variant comprising or consisting of one or more (e.g., two) loss-of-function mutations, and an ITAM3 variant comprising or consisting of one or more (e.g., two) loss-of-function mutations. In certain embodiments, the intracellular signaling domain of the CAR comprises a modified CD3ζ polypeptide comprising a native ITAM1, an ITAM2 variant consisting of two loss-of-function mutations, and an ITAM3 variant consisting of two loss-of-function mutations. In certain embodiments, the intracellular signaling domain of the CAR comprises a modified CD3ζ polypeptide comprising a native ITAM1 consisting of the amino acid sequence set forth in SEQ ID NO: 15, an ITAM2 variant consisting of the amino acid sequence set forth in SEQ ID NO: 21, and an ITAM3 variant consisting of the amino acid sequence set forth in SEQ ID NO: 25. In certain embodiments, the modified CD3ζ polypeptide is designated as "1XX". In certain embodiments, the modified CD3ζ polypeptide comprises or consists of the amino acid sequence set forth in SEQ ID NO: 27. SEQ ID NO: 27 is provided below.

[SEQ ID NO: 27]
RVKFSRSADA PAYQQGQNQL YNELNLGRRE EYDVLDKRRG

RDPEMGGKPR RKNPQEGLFN ELQKDKMAEA FSEIGMKGER

RRGKGHDGLF QGLSTATKDT FDALHMQALP PR

In certain embodiments, the intracellular signaling domain of the CAR comprises a modified CD3ζ polypeptide comprising or consisting of an amino acid sequence that is at least about 80%, at least about 85%, at least about 90%, at least about 95%, at least about 96%, at least about 97%, at least about 98%, or at least about 99%, at least about 100% identical to SEQ ID NO: 27 or a fragment thereof, and/or may optionally comprise up to one or up to two or up to three conservative amino acid substitutions.

An exemplary nucleotide sequence encoding the amino acid sequence of SEQ ID NO: 27 is set forth in SEQ ID NO: 28, which is provided below.

[SEQ ID NO: 28]
agagtgaagttcagcaggagcgcagacgccccgcgtaccagcagggcca gaaccagctctataacgagctcaatctaggacgaagagaggagtacgatg ttttggacaagagacgtggccgggaccctgagatgggggaaagccgaga aggaagaaccctcaggaaggcctgttcaatgaactgcagaaagataagat ggcggaggccttcagtgagattgggatgaaaggcgagcgccggaggggca aggggcacgatggccttttccagggtctcagtacagccaccaaggacacc ttcgacgcccttcacatgcaggccctgccccctcgc In certain embodiments, the CAR is a second-generation CAR. In certain embodiments, the intracellular signaling domain of the CAR further comprises at least a co-stimulatory signaling region. In certain embodiments, the co-stimulatory signaling region comprises an intracellular domain of at least one co-stimulatory molecule or a fragment thereof.

As used herein, a "co-stimulatory molecule" refers to a cell surface molecule other than antigen receptor or its ligand that can provide an efficient response of lymphocytes to an antigen. In certain embodiments, a co-stimulatory molecule can provide optimal lymphocyte activation. Non-limiting examples of co-stimulatory molecules include CD28, 4-1BB, OX40, ICOS, DAP-10, CD27, CD40, and NKGD2. The co-stimulatory molecule can bind to a co-stimulatory ligand, which is a protein expressed on cell surface that upon binding to its receptor produces a co-stimulatory response, i.e., an intracellular response that effects the stimulation provided when an chimeric receptor (e.g., a chimeric antigen receptor (CAR)) binds to its target antigen. As one example, a 4-1BB ligand (i.e., 4-1BBL) may bind to 4-1BB for providing an intracellular signal that in combination with a CAR signal induces an effector cell function of the CAR+ T cell.

In certain embodiments, the intracellular signaling domain of the CAR comprises a co-stimulatory signaling region that comprises a CD28 polypeptide, e.g., an intracellular domain of CD28 or a fragment thereof. In certain embodiments, the CD28 polypeptide comprises or consists of an amino acid sequence that is at least about 80%, at least about 85%, at least about 90%, at least about 95%, at least about 96%, at least about 97%, at least about 98%, or at least about 99%, at least about 100% homologous or identical to the amino acid sequence set forth in SEQ ID NO: 10 or a fragment thereof, and/or may optionally comprise up to one or up to two or up to three conservative amino acid substitutions. In certain embodiments, the CD28 polypeptide comprises or consists of an amino acid sequence that is a consecutive portion of SEQ ID NO: 10, which is at least about 20, or at least about 30, or at least about 40, or at least about 50, and up to about 220 amino acids in length. In certain embodiments, the CD28 polypeptide comprises or consists of amino acids 1 to 220, 1 to 50, 50 to 100, 100 to 150, 114 to 220, 150 to 200, 180 to 220, or 200 to 220 of SEQ ID NO: 10. In certain embodiments, the intracellular signaling domain of the CAR comprises a co-stimulatory signaling region that comprises a CD28 polypeptide comprising or consisting of amino acids 180 to 220 of SEQ ID NO: 10.

An exemplary nucleic acid sequence encoding amino acids 180 to 220 of SEQ ID NO: 10 is set forth in SEQ ID NO: 29, which is provided below.

[SEQ ID NO: 29]
Aggagtaagaggagcaggctcctgcacagtgactacatgaacatgactcc ccgccgccccgggcccacccgcaagcattaccagccctatgccccaccac gcgacttcgcagcctatcgctcc In certain embodiments, the CD28 polypeptide comprises or consists of an amino acid sequence that is at least about 80%, at least about 85%, at least about 90%, at least about 95%, at least about 96%, at least about 97%, at least about 98%, or at least about 99%, at least about 100% homologous or identical to the amino acid sequence set forth in SEQ ID NO: 12 or a fragment thereof, and/or may optionally comprise up to one or up to two or up to three conservative amino acid substitutions. In certain embodiments, the CD28 polypeptide comprises or consists of an amino acid sequence that is a consecutive portion of SEQ ID NO: 12, which is at least about 20, or at least about 30, or at least about 40, or at least about 50, and up to 218 amino acids in length. In certain embodiments, the CD28 polypeptide comprises or consists of amino acids 1 to 218, 1 to 50, 50 to 100, 100 to 150, 150 to 218, 178 to 218, or 200 to 218 of SEQ ID NO: 12. In certain embodiments, the co-stimulatory signaling region of a presently disclosed CAR comprises a CD28 polypeptide that comprises or consists of the amino acids 178 to 218 of SEQ ID NO: 12.

In certain embodiments, the intracellular signaling domain of the CAR comprises a co-stimulatory signaling region that comprises a 4-1BB polypeptide, e.g., an intracellular domain of 4-1BB or a fragment thereof (e.g., an intracellular domain of human 4-1BB or a fragment thereof). The 4-1BB polypeptide can comprise or consists of an amino acid sequence that is at least about 80%, at least about 85%, at least about 90%, at least about 95%, at least about 96%, at least about 97%, at least about 98%, or at least about 99%, at least about 100% homologous or identical to the amino acid sequence having a NCBI Ref. No.: NP_001552 (SEQ ID NO: 30) or a fragment thereof, and/or may optionally comprise up to one or up to two or up to three conservative amino acid substitutions. In certain embodiments, the 4-1BB polypeptide comprises or consists of an amino acid sequence that is a consecutive portion of SEQ ID NO: 30, which is at least about 20, or at least about 30, or at least about 40, or at least about 50, or at least about 100, or at least about 150, or at least about 150, and up to about 255 amino acids in length. In certain embodiments, the 4-1BB polypeptide comprises or consists of amino acids 1 to 255, 1 to 50, 50 to 100, 100 to 150, 150 to 200, 200 to 255, or 214 to 255 of SEQ ID NO: 30. In certain embodiments, the intracellular signaling domain of the CAR comprises a co-stimulatory signaling region that comprises a 4-1BB polypeptide comprising or consisting of amino acids 214 to 255 of SEQ ID NO: 30. SEQ ID NO: 30 is provided below.

```
                                                [SEQ ID NO: 30]
  1  MGNSCYNIVA  TLLLVLNFER  TRSLQDPCSN  CPAGTFCDNN

RNQICSPCPP  NSFSSAGGQR

61  TCDICRQCKG  VFRTRKECSS  TSNAECDCTP  GFHCLGAGCS

MCEQDCKQGQ  ELTKKGCKDC

121  CFGTFNDQKR  GICRPWTNCS  LDGKSVLVNG  TKERDVVCGP

SPADLSPGAS  SVTPPAPARE

181  PGHSPQIISF  FLALTSTALL  FLLFFLTLRF  SVVKRGRKKL

LYIFKQPFMR  PVQTTQEEDG

241  CSCRFPEEEE  GGCEL
```

An exemplary nucleic acid sequence encoding amino acids 214 to 255 of SEQ ID NO: 30 is set forth in SEQ ID NO: 31, which is provided below.

```
                                                [SEQ ID NO: 31]
aaacggggcagaaagaagctcctgtatatattcaaacaaccatttatgag accagtacaaactactcaagaggaagatggctgtagctgccgatttccag aagaagaagaaggaggatgtgaactg
```

In certain embodiments, the intracellular signaling domain of the CAR comprises a co-stimulatory signaling region that comprises intracellular domains of two or more co-stimulatory molecules or portions thereof, e.g., an intracellular domain of CD28 or a fragment thereof and an intracellular domain of 4-1BB or a fragment thereof, or an intracellular domain of CD28 or a fragment thereof and an intracellular domain of OX40 or a fragment thereof.

5.2.2. Chimeric Co-Stimulatory Receptor (CCR)

In certain embodiments, the chimeric receptor is a CCR. The presently disclosed CCR binds to an antigen (e.g., ADGRE2 or CLEC12A) and provides co-stimulatory signals, but does not alone provide an activation signal. In certain embodiments, the CCR does not comprise a CD3ζ polypeptide. CCRs provide co-stimulation, e.g., a CD28-like signal, in the absence of the natural co-stimulatory ligand on the antigen-presenting cell. A combinatorial antigen recognition, i.e., use of a CCR in combination with a CAR, can augment T-cell reactivity against the dual-antigen expressing T cells, thereby improving selective tumor targeting. Kloss et al., describe a strategy that integrates combinatorial antigen recognition, split signaling, and, critically, balanced strength of T-cell activation and co-stimulation to generate T cells that eliminate target cells that express a combination of antigens while sparing cells that express each antigen individually (Kloss et al., Nature Biotechnology (2013); 31(1): 71-75, the content of which is incorporated by reference in its entirety). With this approach, T-cell activation requires CAR-mediated recognition of one antigen, whereas co-stimulation is independently mediated by a CCR specific for a second antigen. To achieve tumor selectivity, the combinatorial antigen recognition approach diminishes the efficiency of T-cell activation to a level where it is ineffective without rescue provided by simultaneous CCR recognition of the second antigen.

In certain embodiments, the CCR comprises an extracellular antigen-binding domain that binds to an antigen (e.g., ADGRE2 or CLEC12A), a transmembrane domain, and a co-stimulatory signaling region that comprises an intracellular domain of at least one co-stimulatory molecule or a fragment thereof. In certain embodiments, the CCR does not alone deliver an activation signal to an immunoresponsive cell. Non-limiting examples of co-stimulatory molecules include CD28, 4-1BB, OX40, ICOS, DAP-10, CD27, CD40, and NKGD2. In certain embodiments, the co-stimulatory signaling region of the CCR comprises an intracellular domain of a co-stimulatory signaling molecule or a fragment thereof. In certain embodiments, the one co-stimulatory signaling molecule is CD28. In certain embodiments, the one co-stimulatory signaling molecule is 4-1BB. In certain embodiments, the co-stimulatory signaling region of the CCR comprises an intracellular domain of a first co-stimulatory signaling molecule or a fragment thereof and an intracellular domain of a second co-stimulatory signaling molecule or a fragment thereof. In certain embodiments, the first and second co-stimulatory signaling molecules are CD28 and 4-1BB.

Similar to a CAR, the extracellular antigen-binding domain of the CCR can be an scFv, a Fab, a F(ab)$_2$, or a fusion protein with a heterologous sequence to form the extracellular antigen-binding domain of the CCR.

5.2.3. TCR Like Fusion Molecules

In certain embodiments, the chimeric receptor is a TCR like fusion molecule. Non-limiting examples of TCR fusion molecules include HLA-Independent TCR-based Chimeric Antigen Receptor (also known as "HIT-CAR", e.g., those disclosed in International Patent Application No. PCT/US19/017525, which is incorporated by reference in its entirety), T cell receptor fusion constructs (TRuCs) (e.g., those disclosed in Baeuerle et al., "Synthetic TRuC receptors engaging the complete T cell receptor for potent anti-tumor response," *Nature Communications* volume 10, Article number: 2087 (2019), which is incorporated by reference in its entirety), synthetic T cell receptor and antigen receptor (STAR) (e.g., those disclosed in Liu et al. Science Translational Medicine (2021); 13(586):eabb5191, which is incorporated by reference in its entirety), antibody-T-cell receptor (AbTCR) (e.g., those disclosed in Xu et al. Cell Discovery (2018) 4:62, which is incorporated by reference in its entirety), and T cell antigen coupler (TAC) (e.g., those disclosed in Helsen et al. Nature Communications (2018); 9:3049, which is incorporated by reference in its entirety).

In certain embodiments, the TCR like fusion molecule comprises an antigen binding chain that comprises an extracellular antigen-binding domain and a constant domain, wherein the TCR like fusion molecule binds to an antigen in an HLA-independent manner. In certain embodiments, the constant domain comprises a T cell receptor constant region selected from the group consisting of a native or modified TRAC polypeptide, a native or modified TRBC polypeptide, a native or modified TRDC polypeptide, a native or modified TRGC polypeptide and any variants or functional fragments thereof. In certain embodiments, the constant domain comprises a native or modified TRAC polypeptide. In certain embodiments, the constant domain comprises a native or modified TRBC polypeptide. In certain embodiments, the constant domain is capable of forming a homodimer or a heterodimer with another constant domain. In certain embodiments, the antigen binding chain is capable of associating with a CD3ζ polypeptide. In certain embodiments, the antigen binding chain, upon binding to an antigen (e.g., ADGRE2 or CLEC12A), is capable of activating the CD3ζ polypeptide associated to the antigen binding chain. In certain embodiments, the activation of the CD3ζ polypeptide is capable of activating an immunoresponsive cell. In certain embodiments, the TCR like fusion molecule is capable of integrating with a CD3 complex and providing HLA-independent antigen recognition. In certain embodiments, the TCR like fusion molecule replaces an endogenous TCR in a CD3/TCR complex. In certain embodiments, the extracellular antigen-binding domain of the TCR like fusion molecule is capable of dimerizing with another extracellular antigen-binding domain. In certain embodiments, the extracellular antigen-binding domain of the TCR like fusion molecule comprises a ligand for a cell-surface receptor, a receptor for a cell surface ligand, an antigen binding portion of an antibody or a fragment thereof or an antigen binding portion of a TCR. In certain embodiments, the extracellular antigen-binding domain of the TCR like fusion molecule comprises one or two immunoglobulin variable region(s). In certain embodiments, the extracellular antigen-binding domain of the TCR like fusion molecule comprises a heavy chain variable region ($V_H$) of an antibody. In certain embodiments, the extracellular antigen-binding domain of the TCR like fusion molecule comprises a light chain variable region ($V_L$) of an antibody. In certain embodiments, the extracellular antigen-binding domain of the TCR like fusion molecule is capable of dimerizing with another extracellular antigen-binding domain. In certain embodiments, the extracellular antigen-binding domain of the TCR like fusion molecule comprises a $V_H$ of an antibody, wherein the $V_H$ is capable of dimerizing with another extracellular antigen-binding domain comprising a $V_L$ of the antibody and form a fragment variable (Fv). In certain embodiments, the extracellular antigen-binding domain of the TCR like fusion molecule comprises a $V_L$ of an antibody, wherein the $V_L$ is capable of dimerizing with another extracellular antigen-binding domain comprising a $V_H$ of the antibody and form a fragment variable (Fv).

5.3. Extracellular Antigen-binding Domain of ADGRE2-Targeted Chimeric Receptors

In certain embodiments, the presently disclosed chimeric receptor targets ADGRE2. In certain embodiments, the presently disclosed chimeric receptor comprises an extracellular antigen-binding domain that binds to ADGRE2.

Adhesion G Protein-Coupled Receptor E2 (ADGRE2), also known as EMR2, CD312, VBU or CD97, is a member of the adhesion GPCR family. It is expressed by monocytes/macrophages, dendritic cells and all types of granulocytes. ADGRE2 is a cell surface receptor that binds to the chondroitin sulfate moiety of glycosaminoglycan chains and promotes cell attachment. It promotes granulocyte chemotaxis, degranulation and adhesion. In macrophages, ADGRE2 promotes the release of inflammatory cytokines, including IL8 and TNF. Signals probably through G-proteins.

In certain embodiments, the presently disclosed chimeric receptor targets human ADGRE2. In certain embodiments, the presently disclosed chimeric receptor comprises an extracellular antigen-binding domain that binds to human ADGRE2. In certain embodiments, the human ADGRE2 comprises or consists of the amino acid sequence with a Uniprot Reference No: Q9UHX3-1 (SEQ ID NO: 32), or a fragment thereof. SEQ ID NO: 32 is provided below:

```
                                              [SEQ ID NO: 32]
MGGRVFLVFL AFCVWLTLPG AETQDSRGCA RWCPQDSSCV

NATACRCNPG ESSESEIITT PMETCDDINE CATLSKVSCG

KFSDCWNTEG SYDCVCSPGY EPVSGAKTFK NESENTCQDV

DECQQNPRLC KSYGTCVNTL GSYTCQCLPG FKLKPEDPKL

CTDVNECTSG QNPCHSSTHC LNNVGSYQCR CRPGWQPIPG

SPNGPNNTVC EDVDECSSGQ HQCDSSTVCF NTVGSYSCRC

RPGWKPRHGI PNNQKDTVCE DMTFSTWTPP PGVHSQTLSR

FFDKVQDLGR DYKPGLANNT IQSILQALDE LLEAPGDLET

LPRLQQHCVA SHLLDGLEDV LRGLSKNLSN GLLNFSYPAG

TELSLEVQKQ VDRSVTLRQN QAVMQLDWNQ AQKSGDPGPS

VVGLVSIPGM GKLLAEAPLV LEPEKQMLLH ETHQGLLQDG

SPILLSDVIS AFLSNNDTQN LSSPVTFTFS HRSVIPRQKV

LCVFWEHGQN GCGHWATTGC STIGTRDTST ICRCTHLSSF

AVLMAHYDVQ EEDPVLTVIT YMGLSVSLLC LLLAALTELL

CKAIQNTSTS LHLQLSLCLF LAHLLFLVAI DQTGHKVLCS

IIAGTLHYLY LATLTWMLLE ALYLFLTARN LTVVNYSSIN

RFMKKLMFPV GYGVPAVTVA ISAASRPHLY GTPSRCWLQP
```

-continued

```
EKGFIWGFLG PVCAIFSVNL VLFLVTLWIL KNRLSSLNSE

VSTLRNTRML AFKATAQLFI LGCTWCLGIL QVGPAARVMA

YLFTIINSLQ GVFIFLVYCL LSQQVREQYG KWSKGIRKLK

TESEMHTLSS SAKADTSKPS TVN
```

Human ADGRE2 comprises an EGF-like 1 domain, an EGF-like 2 domain, an EGF-like 3 domain, an EGF-like 4 domain, an EGF-like 5 domain, and a GPS domain. In certain embodiments, the EGF-like 1 domain comprises or consists of amino acids 25 to 66 of SEQ ID NO: 32. In certain embodiments, the EGF-like 2 domain comprises or consists of amino acids 67 to 118 of SEQ ID NO: 32. In certain embodiments, the EGF-like 3 domain comprises or consists of amino acids 119 to 162 of SEQ ID NO: 32. In certain embodiments, the EGF-like 4 domain comprises or consists of amino acids163 to 211 of SEQ ID NO: 32. In certain embodiments, the EGF-like 5 domain comprises or consists of amino acids 212 to 260 of SEQ ID NO: 32. In certain embodiments, the GPS domain comprises or consists of amino acids 479 to 529 of SEQ ID NO: 32.

In certain embodiments, the presently disclosed chimeric receptor targets an ADGRE2 polypeptide comprising or consisting of an amino acid sequence that is at least about 80%, at least about 85%, at least about 90%, at least about 95%, at least about 96%, at least about 97%, at least about 98%, or at least about 99%, at least about 100% identical to the amino acid sequence set forth in SEQ ID NO: 32 or a fragment thereof.

In certain embodiments, the extracellular antigen-binding domain of a presently disclosed ADGRE2-targeted chimeric receptor binds to the stalk region of ADGRE2. In certain embodiments, the extracellular antigen-binding domain of a presently disclosed ADGRE2-targeted chimeric receptor binds to the GPS domain of ADGRE2. In certain embodiments, the extracellular antigen-binding domain of a presently disclosed ADGRE2-targeted chimeric receptor binds to the EGF-like 5 domain of ADGRE2.

In certain embodiments, the ADGRE2-targeted chimeric receptor is a chimeric antigen receptor (CAR). In certain embodiments, the ADGRE2-targeted CAR has the structure disclosed in Section 5.2.1. In certain embodiments, the ADGRE2-targeted CAR comprises an extracellular antigen-binding domain that binds to ADGRE2, a transmembrane domain, and an intracellular signaling domain.

In certain embodiments, the ADGRE2-targeted chimeric receptor is a Chimeric Co-Stimulatory Receptor (CCR). In certain embodiments, the ADGRE2-targeted CCR has the structure disclosed in Section 5.2.2. In certain embodiments, the ADGRE2-targeted CCR comprises an extracellular antigen-binding domain that binds to ADGRE2, a transmembrane domain, and an intracellular signaling domain that does not provide an activation signal to an immunoresponsive cell, e.g., the intracellular signaling domain does not comprise a CD3ζ polypeptide.

In certain embodiments, the ADGRE2-targeted chimeric receptor is a TCR like Fusion Molecules. In certain embodiments, the ADGRE2-targeted TCR like Fusion Molecules has the structure disclosed in Section 5.2.3.

In certain embodiments, the extracellular antigen-binding domain of the ADGRE2-targeted chimeric receptor (e.g., an ADGRE2-targeted scFv) binds to ADGRE2 (e.g., human ADGRE2) with a dissociation constant ($K_D$) of at least about $1 \times 10^{-6}$ M, at least about $1 \times 10^{-7}$ M, at least about $1 \times 10^{-8}$ M, at least about $1 \times 10^{-9}$ M, or at least about $1 \times 10^{-10}$ M. In certain embodiments, the extracellular antigen-binding domain of the ADGRE2-targeted chimeric receptor (e.g., an ADGRE2-targeted scFv) binds to ADGRE2 (e.g., human ADGRE2) with a dissociation constant ($K_D$) of at least about $2 \times 10^{-8}$ M. In certain embodiments, the extracellular antigen-binding domain of the ADGRE2-targeted chimeric receptor (e.g., an ADGRE2-targeted scFv) to ADGRE2 (e.g., human ADGRE2) with a dissociation constant ($K_D$) of between about $2 \times 10^{-8}$ M and about $8 \times 10^{-9}$ M.

In certain embodiments, the extracellular antigen-binding domain of the ADGRE2-targeted chimeric receptor (e.g., an ADGRE2-targeted scFv) binds to ADGRE2 (e.g., human ADGRE2) with a dissociation constant ($K_D$) between about 1 nM and about 50 nM, between about 5 nM and about 30 nM, between about 5 nM and about 25 nM, or between about 8 nM and about 20 nM. In certain embodiments, the extracellular antigen-binding domain of the ADGRE2-targeted chimeric receptor (e.g., an ADGRE2-targeted scFv) binds to ADGRE2 (e.g., human ADGRE2) with a dissociation constant ($K_D$) of at least about 50 nM, at least about 40 nM, at least about 35 nM, at least about 30 nM, at least about 25 nM, at least about 20 nM, at least about 19 nM, at least about 18 nM, at least about 17 nM, at least about 16 nM, at least about 15 nM, at least about 14 nM, at least about 13 nM, at least about 12 nM, at least about 11 nM, at least about 10 nM, at least about 9 nM, at least about 8 nM, at least about 7 nM, at least about 6 nM, or at least about 5 nM.

In certain embodiments, the extracellular antigen-binding domain of the ADGRE2-targeted chimeric receptor (e.g., an ADGRE2-targeted scFv) comprises a $V_H$ CDR1 comprising the amino acid sequence set forth in SEQ ID NO: 33 or a conservative modification thereof, a $V_H$ CDR2 comprising the amino acid sequence set forth in SEQ ID NO: 34 or a conservative modification thereof, and a $V_H$ CDR3 comprising the amino acid sequence set forth in SEQ ID NO: 35 or a conservative modification thereof. SEQ ID NOs: 33-35 are provided in Table 1.

In certain embodiments, the extracellular antigen-binding domain of the ADGRE2-targeted chimeric receptor (e.g., an ADGRE2-targeted scFv) comprises a $V_L$ CDR1 comprising the amino acid sequence set forth in SEQ ID NO: 36 or a conservative modification thereof, a $V_L$ CDR2 comprising the amino acid sequence set forth in SEQ ID NO: 37 or a conservative modification thereof, and a $V_L$ CDR3 comprising the amino acid sequence set forth in SEQ ID NO: 38 or a conservative modification thereof. SEQ ID NOs: 36-38 are provided in Table 1.

In certain embodiments, the extracellular antigen-binding domain of the ADGRE2-targeted chimeric receptor (e.g., an ADGRE2-targeted scFv) comprises a $V_H$ CDR1 comprising the amino acid sequence set forth in SEQ ID NO: 33 or a conservative modification thereof, a $V_H$ CDR2 comprising the amino acid sequence set forth in SEQ ID NO: 34 or a conservative modification thereof, a $V_H$ CDR3 comprising the amino acid sequence set forth in SEQ ID NO: 35 or a conservative modification thereof, a $V_L$ CDR1 comprising the amino acid sequence set forth in SEQ ID NO: 36 or a conservative modification thereof, a $V_L$ CDR2 comprising the amino acid sequence set forth in SEQ ID NO: 37 or a conservative modification, and a $V_L$ CDR3 comprising the amino acid sequence set forth in SEQ ID NO: 38 or a conservative modification thereof.

In certain embodiments, the extracellular antigen-binding domain of the ADGRE2-targeted chimeric receptor (e.g., an ADGRE2-targeted scFv) comprises a $V_H$ CDR1 comprising the amino acid sequence set forth in SEQ ID NO: 33, a $V_H$ CDR2 comprising the amino acid sequence set forth in SEQ ID NO: 34, a V$_H$ CDR3 comprising the amino acid sequence set forth in SEQ ID NO: 35, a V$_L$ CDR1 comprising the amino acid sequence set forth in SEQ ID NO: 36, a V$_L$ CDR2 comprising the amino acid sequence set forth in SEQ ID NO: 37, and a V$_L$ CDR3 comprising the amino acid sequence set forth in SEQ ID NO: 38.

In certain embodiments, the extracellular antigen-binding domain of the ADGRE2-targeted chimeric receptor (e.g., an ADGRE2-targeted scFv) comprises a V$_H$ comprising an amino acid sequence that is at least about 80% (e.g., at least about 85%, at least about 90%, or at least about 95%) homologous or identical to the amino acid sequence set forth in SEQ ID NO: 39. For example, the extracellular antigen-binding domain of the ADGRE2-targeted chimeric receptor (e.g., an ADGRE2-targeted scFv) comprises a V$_H$ comprising an amino acid sequence that is about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100% homologous or identical to SEQ ID NO: 39. In certain embodiments, the extracellular antigen-binding domain of the ADGRE2-targeted chimeric receptor (e.g., an ADGRE2-targeted scFv) comprises a V$_H$ comprising the amino acid sequence set forth in SEQ ID NO: 39. SEQ ID NO: 39 is provided in Table 1 below.

In certain embodiments, the extracellular antigen-binding domain of the ADGRE2-targeted chimeric receptor (e.g., an ADGRE2-targeted scFv) comprises a V$_L$ comprising an amino acid sequence that is at least about 80% (e.g., at least about 85%, at least about 90%, or at least about 95%) homologous or identical to the amino acid sequence set forth in SEQ ID NO: 40. For example, the extracellular antigen-binding domain of the ADGRE2-targeted chimeric receptor (e.g., an ADGRE2-targeted scFv) comprises a V$_L$ comprising an amino acid sequence that is about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100% homologous or identical to SEQ ID NO: 40. In certain embodiments, the extracellular antigen-binding domain of the ADGRE2-targeted chimeric receptor (e.g., an ADGRE2-targeted scFv) comprises a V$_L$ comprising the amino acid sequence set forth in SEQ ID NO: 40. SEQ ID NO: 40 is provided in Table 1 below.

In certain embodiments, the extracellular antigen-binding domain of the ADGRE2-targeted chimeric receptor (e.g., an ADGRE2-targeted scFv) comprises a V$_H$ comprising the amino acid sequence set forth in SEQ ID NO: 39, and a V$_L$ comprising the amino acid sequence set forth in SEQ ID NO: 40. In certain embodiments, the V$_H$ and V$_L$ are linked via a linker. In certain embodiments, the linker comprises the amino acid sequence set forth in SEQ ID NO: 2. In certain embodiments, the linker comprises the amino acid sequence set forth in SEQ ID NO: 149.

In certain embodiments, the variable regions within the extracellular antigen-binding domain of the ADGRE2-targeted chimeric receptor have to be linked one after another such that at the N-terminus of the extracellular antigen-binding domain, a heavy chain variable region (V$_H$) is positioned. In certain embodiments, if the extracellular antigen-binding domain of the ADGRE2-targeted chimeric receptor is an scFv, the variable regions are positioned from the N- to the C-terminus: V$_H$-V$_L$. In certain embodiments, the ADGRE2-targeted scFv comprises or consists of the amino acid sequence set forth in SEQ ID NO: 41. In certain embodiments, the ADGRE2-targeted scFv is designated as "ADGRE2-A". An exemplary nucleotide sequence encoding the amino acid sequence of SEQ ID NO: 41 is set forth in SEQ ID NO: 42. SEQ ID NOs: 41 and 42 are provided in Table 1. The CDRs provided in Table 1 are identified according to the IMGT numbering system.

TABLE 1

| (ADGRE2-A) | | | |
|---|---|---|---|
| | CDRs | | |
| | 1 | 2 | 3 |
| V$_H$ | GYTFTNYW [SEQ ID NO: 33] | VYPGDGDT [SEQ ID NO: 34] | ARGFTAYGMDY [SEQ ID NO: 35] |
| V$_L$ | SSVSY [SEQ ID NO: 36] | DTS [SEQ ID NO: 37] | QQWSSNPLT [SEQ ID NO: 38] |
| Full V$_H$ | QVQLQQSGAEVAKPGASVKLSCKASGYTFTNYWMQWIKQAPGQGLEWIGAVYPGDGDTR HTQKFKGKATLTADKSTSTAYMEVSSLRSEDTAVYYCARGFTAYGMDYWGQGTTVTVSS [SEQ ID NO: 39] | | |
| Full V$_L$ | EIVLTQSPATMSASPGERVTMSCSASSSVSYMHWYQQKSGQSPKRWIYDTSKLASGVPA RFSGSGSGTDYTFTISSMEPEDFATYYCQQWSSNPLTFGGGTKLEIK [SEQ ID NO: 40] | | |
| DNA Full V$_H$ | caagttcagctccagcagagcggcgccgaagtggcaaagcctggagcgtcagtcaagct gtcctgcaaagcgagtggctatacgttcacgaactactggatgcagtggataaagcagg ctcccgggcagggtctggagtggattggagccgtctacccaggggacggcgacaccgg cacactcaaaagttcaagggcaaggccaccctgaccgctgacaagagcacaagcacagc gtacatggaggtgtcctctttgagatccgaagataccgctgtgtattattgtgcccggg gcttcactgcatacgggatggattactggggacaaggcactaccgtgactgtcagctcc [SEQ ID NO: 144] | | |
| DNA Full V$_L$ | gaaattgtgctgacacagagccctgccacaatgtctgctagccctggcgagcgcgtgac catgtcttgtagcgccagcagcagcgtgtcctacatgcattggtatcaacagaagtccg gccagtctcccaagcggtggatctacgatacaagcaagctggcctccggcgtgcccgcc agatttctggcagcggctctggaacagattacaccttcaccatctctagcatggaacc | | |

TABLE 1-continued

(ADGRE2-A)

CDRs

| 1 | 2 | 3 |
|---|---|---|

| | |
|---|---|
| | tgaggattttgccacctactattgccagcagtggtccagcaatcccctgacatttggag<br>gaggcaccaagctggaaattaag [SEQ ID NO: 145] |
| $V_H$-$V_L$ scFv | QVQLQQSGAEVAKPGASVKLSCKASGYTFTNYWMQWIKQAPGQGLEWIGAVYPGDGDTR<br>HTQKFKGKATLTADKSTSTAYMEVSSLRSEDTAVYYCARGFTAYGMDYWGQGTTVTVSS<br>GGGGSGGGGSGGGGSEIVLTQSPATMSASPGERVTMSCSASSSVSYMHWYQQKSGQSPK<br>RWIYDTSKLASGVPARFSGSGSGTDYTFTISSMEPEDFATYYCQQWSSNPLTFGGGTKL<br>EIK [SEQ ID NO: 41] |
| DNA for $V_H$-$V_L$ scFv | caagttcagctccagcagagcggcgccgaagtggcaaagcctggagcgtcagtcaagct<br>gtcctgcaaagcgagtggctatacgttcacgaactactggatgcagtggataaagcagg<br>ctcccgggcagggtctggagtggattggagccgtctacccaggggacggcgacacccgg<br>cacactcaaaagttcaagggcaaggccaccctgaccgctgacaagagcacaagcacagc<br>gtacatggaggtgtcctctttgagatccgaagataccgctgtgtattattgtgcccggg<br>gcttcactgcatacgggatggattactggggacaaggcactaccgtgactgtcagctcc<br>ggggtggaggctcaggcggggggttcaggagggggggatctgaaattgtgctgac<br>acagagccctgccacaatgtctgctagccctggcgagcgcgtgaccatgtcttgtagcg<br>ccagcagcagcgtgtcctacatgcattggtatcaacagaagtccggccagtctcccaag<br>cggtggatctacgatacaagcaagctggcctccggcgtgcccgccagattttctggcag<br>cggctctggaacagattacaccttcaccatctctagcatggaacctgaggattttgcca<br>cctactattgccagcagtggtccagcaatcccctgacatttggaggaggcaccaagctg<br>gaaattaag [SEQ ID NO: 42] |

In certain embodiments, the extracellular antigen-binding domain of the ADGRE2-targeted chimeric receptor (e.g., an ADGRE2-targeted scFv) comprises a $V_H$ CDR1 comprising the amino acid sequence set forth in SEQ ID NO: 33 or a conservative modification thereof, a $V_H$ CDR2 comprising the amino acid sequence set forth in SEQ ID NO: 34 or a conservative modification thereof, and a $V_H$ CDR3 comprising the amino acid sequence set forth in SEQ ID NO: 35 or a conservative modification thereof. SEQ ID NOs: 33-35 are provided in Tables 1 and 2.

In certain embodiments, the extracellular antigen-binding domain of the ADGRE2-targeted chimeric receptor (e.g., an ADGRE2-targeted scFv) comprises a $V_L$ CDR1 comprising the amino acid sequence set forth in SEQ ID NO: 36 or a conservative modification thereof, a $V_L$ CDR2 comprising the amino acid sequence set forth in SEQ ID NO: 37 or a conservative modification thereof, and a $V_L$ CDR3 comprising the amino acid sequence set forth in SEQ ID NO: 38 or a conservative modification thereof. SEQ ID NOs: 36-38 are provided in Tables 1 and 2.

In certain embodiments, the extracellular antigen-binding domain of the ADGRE2-targeted chimeric receptor (e.g., an ADGRE2-targeted scFv) comprises a $V_H$ CDR1 comprising the amino acid sequence set forth in SEQ ID NO: 33 or a conservative modification thereof, a $V_H$ CDR2 comprising the amino acid sequence set forth in SEQ ID NO: 34 or a conservative modification thereof, a $V_H$ CDR3 comprising the amino acid sequence set forth in SEQ ID NO: 35 or a conservative modification thereof, a $V_L$ CDR1 comprising the amino acid sequence set forth in SEQ ID NO: 36 or a conservative modification thereof, a $V_L$ CDR2 comprising the amino acid sequence set forth in SEQ ID NO: 37 or a conservative modification thereof, and a $V_L$ CDR3 comprising the amino acid sequence set forth in SEQ ID NO: 38 or a conservative modification thereof.

In certain embodiments, the extracellular antigen-binding domain of the ADGRE2-targeted chimeric receptor (e.g., an ADGRE2-targeted scFv) comprises a $V_H$ CDR1 comprising the amino acid sequence set forth in SEQ ID NO: 33, a $V_H$ CDR2 comprising the amino acid sequence set forth in SEQ ID NO: 34, a $V_H$ CDR3 comprising the amino acid sequence set forth in SEQ ID NO: 35, a $V_L$ CDR1 comprising the amino acid sequence set forth in SEQ ID NO: 36, a $V_L$ CDR2 comprising the amino acid sequence set forth in SEQ ID NO: 37, and a $V_L$ CDR3 comprising the amino acid sequence set forth in SEQ ID NO: 38.

In certain embodiments, the extracellular antigen-binding domain of the ADGRE2-targeted chimeric receptor (e.g., an ADGRE2-targeted scFv) comprises a $V_H$ comprising an amino acid sequence that is at least about 80% (e.g., at least about 85%, at least about 90%, or at least about 95%) homologous or identical to the amino acid sequence set forth in SEQ ID NO: 43. For example, the extracellular antigen-binding domain of the ADGRE2-targeted chimeric receptor (e.g., an ADGRE2-targeted scFv) comprises a $V_H$ comprising an amino acid sequence that is about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100% homologous or identical to the amino acid sequence set forth in SEQ ID NO: 43. In certain embodiments, the extracellular antigen-binding domain of the ADGRE2-targeted chimeric receptor comprises a $V_H$ comprising the amino acid sequence set forth in SEQ ID NO: 43. SEQ ID NO: 43 is provided in Table 2 below.

In certain embodiments, the extracellular antigen-binding domain of the ADGRE2-targeted chimeric receptor (e.g., an ADGRE2-targeted scFv) comprises a $V_L$ comprising an amino acid sequence that is at least about 80% (e.g., at least about 85%, at least about 90%, or at least about 95%) homologous or identical to the amino acid sequence set forth in SEQ ID NO: 44. For example, the extracellular antigen-binding domain of the chimeric receptor (e.g., an scFv) comprises a $V_L$ comprising an amino acid sequence that is about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100% homologous or identical to the amino acid sequence set forth in SEQ ID NO: 44. In certain embodiments, the extracellular antigen-binding domain of the ADGRE2-targeted chimeric receptor comprises a V$_L$ comprising the amino acid sequence set forth in SEQ ID NO: 44. SEQ ID NO: 44 is provided in Table 2 below.

In certain embodiments, the extracellular antigen-binding domain of the ADGRE2-targeted chimeric receptor (e.g., an ADGRE2-targeted scFv) comprises a V$_H$ comprising the amino acid sequence set forth in SEQ ID NO: 43, and a V$_L$ comprising the amino acid sequence set forth in SEQ ID NO: 44. In certain embodiments, the V$_H$ and V$_L$ are linked via a linker. In certain embodiments, the linker comprises the amino acid sequence set forth in SEQ ID NO: 2. In certain embodiments, the linker comprises the amino acid sequence set forth in SEQ ID NO: 149.

In certain embodiments, the variable regions within the extracellular antigen-binding domain of the ADGRE2-targeted chimeric receptor have to be linked one after another such that at the N-terminus of the extracellular antigen-binding domain, a heavy chain variable region (V$_H$) is positioned. In certain embodiments, if the extracellular antigen-binding domain of the ADGRE2-targeted chimeric receptor is an scFv, the variable regions are positioned from the N- to the C-terminus: V$_H$-V$_L$. In certain embodiments, the ADGRE2-targeted scFv comprises or consists of the amino acid sequence set forth in SEQ ID NO: 45, which is provided in Table 2. In certain embodiments, the ADGRE2-targeted scFv is designated as "ADGRE2-B". The CDRs provided in Table 2 are identified according to the IMGT numbering system.

the amino acid sequence set forth in SEQ ID NO: 36 or a conservative modification thereof, a V$_L$ CDR2 comprising the amino acid sequence set forth in SEQ ID NO: 37 or a conservative modification thereof, and a V$_L$ CDR3 comprising the amino acid sequence set forth in SEQ ID NO: 38 or a conservative modification thereof. SEQ ID NOs: 36-38 are provided in Tables 1-3.

In certain embodiments, the extracellular antigen-binding domain of the ADGRE2-targeted chimeric receptor (e.g., an ADGRE2-targeted scFv) comprises a V$_H$ CDR1 comprising the amino acid sequence set forth in SEQ ID NO: 33 or a conservative modification thereof, a V$_H$ CDR2 comprising the amino acid sequence set forth in SEQ ID NO: 34 or a conservative modification thereof, a V$_H$ CDR3 comprising the amino acid sequence set forth in SEQ ID NO: 35 or a conservative modification thereof, a V$_L$ CDR1 comprising the amino acid sequence set forth in SEQ ID NO: 36 or a conservative modification thereof, a V$_L$ CDR2 comprising the amino acid sequence set forth in SEQ ID NO: 37 or a conservative modification thereof, and a V$_L$ CDR3 comprising the amino acid sequence set forth in SEQ ID NO: 38 or a conservative modification thereof.

In certain embodiments, the extracellular antigen-binding domain of the ADGRE2-targeted chimeric receptor (e.g., an ADGRE2-targeted scFv) comprises a V$_H$ CDR1 comprising the amino acid sequence set forth in SEQ ID NO: 33, a V$_H$ CDR2 comprising the amino acid sequence set forth in SEQ ID NO: 34, a V$_H$ CDR3 comprising the amino acid sequence set forth in SEQ ID NO: 35, a V$_L$ CDR1 comprising the amino acid sequence set forth in SEQ ID NO: 36, a V$_L$

TABLE 2

| (ADGRE2-B) | | | |
|---|---|---|---|
| | CDRs | | |
| | 1 | 2 | 3 |
| V$_H$ | GYTFTNYW [SEQ ID NO: 33] | VYPGDGDT [SEQ ID NO: 34] | ARGFTAYGMDY [SEQ ID NO: 35] |
| V$_L$ | SSVSY [SEQ ID NO: 36] | DTS [SEQ ID NO: 37] | QQWSSNPLT [SEQ ID NO: 38] |
| Full V$_H$ | QVQLQQSGAEVKKPGASVKLSCKASGYTFTNYWMQWIRQAPGQGLEWIGAVYPGDGDTRYT QKFQGRATLTADTSISTAYMEVSRLRSDDTAVYYCARGFTAYGMDYWGQGTTVTVSS [SEQ ID NO: 43] | | |
| Full V$_L$ | EIVLTQSPATMSASPGERVTMSCSASSSVSYMHWYQQKSGLSPKRWIYDTSKLASGVPDRF SGSGSGTDYTFTISRMEPEDFATYYCQQWSSNPLTFGGGTKLEIK [SEQ ID NO: 44] | | |
| V$_H$-V$_L$ scFv | QVQLQQSGAEVKKPGASVKLSCKASGYTFTNYWMQWIRQAPGQGLEWIGAVYPGDGDTRYT QKFQGRATLTADTSISTAYMEVSRLRSDDTAVYYCARGFTAYGMDYWGQGTTVTVSSGGGG SGGGGSGGGGSEIVLTQSPATMSASPGERVTMSCSASSSVSYMHWYQQKSGLSPKRWIYDT SKLASGVPDRFSGSGSGTDYTFTISRMEPEDFATYYCQQWSSNPLTFGGGTKLEIK [SEQ ID NO: 45] | | |

In certain embodiments, the extracellular antigen-binding domain of the ADGRE2-targeted chimeric receptor (e.g., an ADGRE2-targeted scFv) comprises a V$_H$ CDR1 comprising the amino acid sequence set forth in SEQ ID NO: 33 or a conservative modification thereof, a V$_H$ CDR2 comprising the amino acid sequence set forth in SEQ ID NO: 345 or a conservative modification thereof, and a V$_H$ CDR3 comprising the amino acid sequence set forth in SEQ ID NO: 35 or a conservative modification thereof. SEQ ID NOS: 33-35 are provided in Tables 1-3.

In certain embodiments, the extracellular antigen-binding domain of the ADGRE2-targeted chimeric receptor (e.g., an ADGRE2-targeted scFv) comprises a V$_L$ CDR1 comprising CDR2 comprising the amino acid sequence set forth in SEQ ID NO: 37, and a V$_L$ CDR3 comprising the amino acid sequence set forth in SEQ ID NO: 38.

In certain embodiments, the extracellular antigen-binding domain of the ADGRE2-targeted chimeric receptor (e.g., an ADGRE2-targeted scFv) comprises a V$_H$ comprising an amino acid sequence that is at least about 80% (e.g., at least about 85%, at least about 90%, or at least about 95%) homologous or identical to the amino acid sequence set forth in SEQ ID NO: 46. For example, the extracellular antigen-binding domain of the chimeric receptor (e.g., an scFv) comprises a V$_H$ comprising an amino acid sequence that is about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100% homologous or identical to the amino acid sequence set forth in SEQ ID NO: 46. In certain embodiments, the extracellular antigen-binding domain of the ADGRE2-targeted chimeric receptor comprises a $V_H$ comprising the amino acid sequence set forth in SEQ ID NO: 46. SEQ ID NO: 46 is provided in Table 3 below.

In certain embodiments, the extracellular antigen-binding domain of the ADGRE2-targeted chimeric receptor (e.g., an ADGRE2-targeted scFv) comprises a $V_L$ comprising an amino acid sequence that is at least about 80% (e.g., at least about 85%, at least about 90%, or at least about 95%) homologous or identical to the amino acid sequence set forth in SEQ ID NO: 47. For example, the extracellular antigen-binding domain of the ADGRE2-targeted chimeric receptor (e.g., an ADGRE2-targeted scFv) comprises a $V_L$ comprising an amino acid sequence that is about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100% homologous or identical to the amino acid sequence set forth in SEQ ID NO: 47. In certain embodiments, the extracellular antigen-binding domain of the ADGRE2-targeted chimeric receptor comprises a $V_L$ Comprising the amino acid sequence set forth in SEQ ID NO: 47. SEQ ID NO: 47 is provided in Table 3 below.

In certain embodiments, the extracellular antigen-binding domain of the ADGRE2-targeted chimeric receptor (e.g., an ADGRE2-targeted scFv) comprises a $V_H$ comprising the amino acid sequence set forth in SEQ ID NO: 46, and a $V_L$ comprising the amino acid sequence set forth in SEQ ID NO: 47. In certain embodiments, the $V_H$ and $V_L$ are linked via a linker. In certain embodiments, the linker comprises the amino acid sequence set forth in SEQ ID NO: 2. In certain embodiments, the linker comprises the amino acid sequence set forth in SEQ ID NO: 149.

In certain embodiments, the variable regions within the extracellular antigen-binding domain of the ADGRE2-targeted chimeric receptor have to be linked one after another such that at the N-terminus of the extracellular antigen-binding domain, a heavy chain variable region ($V_H$) is positioned. In certain embodiments, if the extracellular antigen-binding domain of the ADGRE2-targeted chimeric receptor is an scFv, the variable regions are positioned from the N- to the C-terminus: $V_H$-$V_L$. In certain embodiments, the ADGRE2-targeted scFv comprises or consists of the amino acid sequence set forth in SEQ ID NO: 48, which is provided in Table 3. In certain embodiments, the ADGRE2-targeted scFv is designated as "ADGRE2-C". The CDRs provided in Table 3 are identified according to the IMGT numbering system.

TABLE 3

(ADGRE2-C)

| | CDRs | | |
|---|---|---|---|
| | 1 | 2 | 3 |
| $V_H$ | GYTFTNYW [SEQ ID NO: 33] | VYPGDGDT [SEQ ID NO: 34] | ARGFTAYGMDY [SEQ ID NO: 35] |
| $V_L$ | SSVSY [SEQ ID NO: 36] | DTS [SEQ ID NO: 37] | QQWSSNPLT [SEQ ID NO: 38] |
| Full $V_H$ | QVQLQQSGAEVKKPGASVKLSCKASGYTFTNYWMQWVRQAPGQGLEWIGAVYPGDGDTRYT QKFQGRATLTADTSTSTVYMEVSSLRSEDTAVYYCARGFTAYGMDYWGQGTTVTVSS [SEQ ID NO: 46] | | |
| Full $V_L$ | EIVLTQSPATMSASPGERVTMSCSASSSVSYMHWYQQKSGLSPKRWIYDTSKLASGVPDRF SGSGSGTDYTFTISRMEPEDFATYYCQQWSSNPLTFGGGTKLEIK [SEQ ID NO: 47] | | |
| $V_H$-$V_L$ scFv | QVQLQQSGAEVKKPGASVKLSCKASGYTFTNYWMQWVRQAPGQGLEWIGAVYPGDGDTRYT QKFQGRATLTADTSTSTVYMEVSSLRSEDTAVYYCARGFTAYGMDYWGQGTTVTVSS GGGGSGGGGSGGGGSEIVLTQSPATMSASPGERVTMSCSASSSVSYMHWYQQKSGLSPKRW IYDTSKLASGVPDRFSGSGSGTDYTFTISRMEPEDFATYYCQQWSSNPLTFGGGTKLEIK [SEQ ID NO: 48] | | |

In certain embodiments, the extracellular antigen-binding domain of the ADGRE2-targeted chimeric receptor (e.g., an ADGRE2-targeted scFv) comprises a $V_H$ CDR1 comprising the amino acid sequence set forth in SEQ ID NO: 33 or a conservative modification thereof, a $V_H$ CDR2 comprising the amino acid sequence set forth in SEQ ID NO: 34 or a conservative modification thereof, and a $V_H$ CDR3 comprising the amino acid sequence set forth in SEQ ID NO: 35 or a conservative modification thereof. SEQ ID NOS: 33-35 are provided in Tables 1-4.

In certain embodiments, the extracellular antigen-binding domain of the ADGRE2-targeted chimeric receptor (e.g., an ADGRE2-targeted scFv) comprises a $V_L$ CDR1 comprising the amino acid sequence set forth in SEQ ID NO: 36 or a conservative modification thereof, a $V_L$ CDR2 comprising the amino acid sequence set forth in SEQ ID NO: 37 or a conservative modification thereof, and a $V_L$ CDR3 comprising the amino acid sequence set forth in SEQ ID NO: 38 or a conservative modification thereof. SEQ ID NOs: 36-38 are provided in Tables 1-4.

In certain embodiments, the extracellular antigen-binding domain of the ADGRE2-targeted chimeric receptor (e.g., an ADGRE2-targeted scFv) comprises a $V_H$ CDR1 comprising the amino acid sequence set forth in SEQ ID NO: 33 or a conservative modification thereof, a $V_H$ CDR2 comprising the amino acid sequence set forth in SEQ ID NO: 34 or a conservative modification thereof, a $V_H$ CDR3 comprising the amino acid sequence set forth in SEQ ID NO: 35 or a conservative modification thereof, a $V_L$ CDR1 comprising the amino acid sequence set forth in SEQ ID NO: 36 or a conservative modification thereof, a $V_L$ CDR2 comprising the amino acid sequence set forth in SEQ ID NO: 37 or a conservative modification thereof, and a $V_L$ CDR3 comprising the amino acid sequence set forth in SEQ ID NO: 38 or a conservative modification thereof.

In certain embodiments, the extracellular antigen-binding domain of the ADGRE2-targeted chimeric receptor (e.g., an ADGRE2-targeted scFv) comprises a $V_H$ CDR1 comprising the amino acid sequence set forth in SEQ ID NO: 33, a $V_H$ CDR2 comprising the amino acid sequence set forth in SEQ ID NO: 34, a $V_H$ CDR3 comprising the amino acid sequence set forth in SEQ ID NO: 35, a $V_L$ CDR1 comprising the amino acid sequence set forth in SEQ ID NO: 36, a $V_L$ CDR2 comprising the amino acid sequence set forth in SEQ ID NO: 37, and a $V_L$ CDR3 comprising the amino acid sequence set forth in SEQ ID NO: 38.

In certain embodiments, the extracellular antigen-binding domain of the ADGRE2-targeted chimeric receptor (e.g., an ADGRE2-targeted scFv) comprises a $V_H$ comprising an amino acid sequence that is at least about 80% (e.g., at least about 85%, at least about 90%, or at least about 95%) homologous or identical to the amino acid sequence set forth in SEQ ID NO: 49. For example, the extracellular antigen-binding domain of the ADGRE2-targeted chimeric receptor (e.g., an ADGRE2-targeted scFv) comprises a $V_H$ comprising an amino acid sequence that is about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100% homologous or identical to the amino acid sequence set forth in SEQ ID NO: 49. In certain embodiments, the extracellular antigen-binding domain of ADGRE2-targeted chimeric receptor comprises a $V_H$ comprising the amino acid sequence set forth in SEQ ID NO: 49. SEQ ID NO: 49 is provided in Table 4 below.

In certain embodiments, the extracellular antigen-binding domain of the ADGRE2-targeted chimeric receptor (e.g., an ADGRE2-targeted scFv) comprises a $V_L$ comprising an amino acid sequence that is at least about 80% (e.g., at least about 85%, at least about 90%, or at least about 95%) homologous or identical to the amino acid sequence set forth in SEQ ID NO: 50. For example, the extracellular antigen-binding domain of the ADGRE2-targeted chimeric receptor (e.g., an ADGRE2-targeted scFv) comprises a $V_L$ comprising an amino acid sequence that is about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100% homologous or identical to the amino acid sequence set forth in SEQ ID NO: 50. In certain embodiments, the extracellular antigen-binding domain of the ADGRE2-targeted chimeric receptor comprises a $V_L$ Comprising the amino acid sequence set forth in SEQ ID NO: 50. SEQ ID NO: 50 is provided in Table 4 below.

In certain embodiments, the extracellular antigen-binding domain of the ADGRE2-targeted chimeric receptor (e.g., an ADGRE2-targeted scFv) comprises a $V_H$ comprising the amino acid sequence set forth in SEQ ID NO: 49, and a $V_L$ comprising the amino acid sequence set forth in SEQ ID NO: 50. In certain embodiments, the $V_H$ and $V_L$ are linked via a linker. In certain embodiments, the linker comprises the amino acid sequence set forth in SEQ ID NO: 149. In certain embodiments, the linker comprises the amino acid sequence set forth in SEQ ID NO: 2.

In certain embodiments, the variable regions within the extracellular antigen-binding domain of the ADGRE2-targeted chimeric receptor have to be linked one after another such that at the N-terminus of the extracellular antigen-binding domain, a heavy chain variable region ($V_H$) is positioned. In certain embodiments, if the extracellular antigen-binding domain of the ADGRE2-targeted chimeric receptor is an scFv, the variable regions are positioned from the N- to the C-terminus: $V_H$—$V_L$. In certain embodiments, the ADGRE2-targeted scFv comprises or consists of the amino acid sequence set forth in SEQ ID NO: 51, which is provided in Table 4. In certain embodiments, the ADGRE2-targeted scFv is designated as "ADGRE2-D". The CDRs provided in Table 4 are identified according to the IMGT numbering system.

TABLE 4

(ADGRE2-D)

| | CDRs | | |
|---|---|---|---|
| | 1 | 2 | 3 |
| $V_H$ | GYTFTNYW [SEQ ID NO: 33] | VYPGDGDT [SEQ ID NO: 34] | ARGFTAYGMDY [SEQ ID NO: 35] |
| $V_L$ | SSVSY [SEQ ID NO: 36] | DTS [SEQ ID NO: 37] | QQWSSNPLT [SEQ ID NO: 38] |
| Full $V_H$ | QVQLQQSGAEVKKPGASVKVSCKASGYTFTNYWMQWVRQAPGQGLEWMGAVYPGDGDTRHT QKFKGRVTMTRDTSTSTVYMELSSLRSEDTAVYYCARGFTAYGMDYWGQGTLVTVSS [SEQ ID NO: 49] | | |
| Full $V_L$ | EIVLTQSPATLSLSPGERATLSCSASSSVSYMHWYQQKPGLAPRLLIYDTSKLASGIPDRF SGSGSGTDFTLTISRLEPEDFAVYYCQQWSSNPLTFGQGTKVEIK [SEQ ID NO: 50] | | |
| $V_H$-$V_L$ scFv | QVQLQQSGAEVKKPGASVKVSCKASGYTFTNYWMQWVRQAPGQGLEWMGAVYPGDGDTRHT QKFKGRVTMTRDTSTSTVYMELSSLRSEDTAVYYCARGFTAYGMDYWGQGTLVTVSSASTG GGGSGGGGSGGGGSEIVLTQSPATLSLSPGERATLSCSASSSVSYMHWYQQKPGLAPRLLI YDTSKLASGIPDRFSGSGSGTDFTLTISRLEPEDFAVYYCQQWSSNPLTFGQGTKVEIK [SEQ ID NO: 51] | | | amino acid sequence that is at least about 80% (e.g., at least about 85%, at least about 90%, or at least about 95%)

In certain embodiments, the extracellular antigen-binding domain of the ADGRE2-targeted chimeric receptor (e.g., an ADGRE2-targeted scFv) comprises a $V_H$ CDR1 comprising the amino acid sequence set forth in SEQ ID NO: 33 or a conservative modification thereof, a $V_H$ CDR2 comprising the amino acid sequence set forth in SEQ ID NO: 34 or a conservative modification thereof, and a $V_H$ CDR3 comprising the amino acid sequence set forth in SEQ ID NO: 35 or a conservative modification thereof. SEQ ID NOS: 34-36 are provided in Tables 1-5.

In certain embodiments, the extracellular antigen-binding domain of the ADGRE2-targeted chimeric receptor (e.g., an ADGRE2-targeted scFv) comprises a $V_L$ CDR1 comprising the amino acid sequence set forth in SEQ ID NO: 36 or a conservative modification thereof, a $V_L$ CDR2 comprising the amino acid sequence set forth in SEQ ID NO: 37 or a conservative modification thereof, and a $V_L$ CDR3 comprising the amino acid sequence set forth in SEQ ID NO: 38 or a conservative modification thereof. SEQ ID NOs: 36-38 are provided in Tables 1-5.

In certain embodiments, the extracellular antigen-binding domain of the ADGRE2-targeted chimeric receptor (e.g., an ADGRE2-targeted scFv) comprises a $V_H$ CDR1 comprising the amino acid sequence set forth in SEQ ID NO: 33 or a conservative modification thereof, a $V_H$ CDR2 comprising the amino acid sequence set forth in SEQ ID NO: 34 or a conservative modification thereof, a $V_H$ CDR3 comprising the amino acid sequence set forth in SEQ ID NO: 5 or a conservative modification thereof, a $V_L$ CDR1 comprising the amino acid sequence set forth in SEQ ID NO: 36 or a conservative modification thereof, a $V_L$ CDR2 comprising the amino acid sequence set forth in SEQ ID NO: 37 or a conservative modification thereof, and a $V_L$ CDR3 comprising the amino acid sequence set forth in SEQ ID NO: 38 or a conservative modification thereof.

In certain embodiments, the extracellular antigen-binding domain of the ADGRE2-targeted chimeric receptor (e.g., an ADGRE2-targeted scFv) comprises a $V_H$ CDR1 comprising the amino acid sequence set forth in SEQ ID NO: 33, a $V_H$ CDR2 comprising the amino acid sequence set forth in SEQ ID NO: 34, a $V_H$ CDR3 comprising the amino acid sequence set forth in SEQ ID NO: 35, a $V_L$ CDR1 comprising the amino acid sequence set forth in SEQ ID NO: 36, a $V_L$ CDR2 comprising the amino acid sequence set forth in SEQ ID NO: 37, and a $V_L$ CDR3 comprising the amino acid sequence set forth in SEQ ID NO: 38.

In certain embodiments, the extracellular antigen-binding domain of the ADGRE2-targeted chimeric receptor (e.g., an ADGRE2-targeted scFv) comprises a $V_H$ comprising an amino acid sequence that is at least about 80% (e.g., at least about 85%, at least about 90%, or at least about 95%) homologous or identical to the amino acid sequence set forth in SEQ ID NO: 52. For example, the extracellular antigen-binding domain of the ADGRE2-targeted chimeric receptor (e.g., an ADGRE2-targeted scFv) comprises a $V_H$ comprising an amino acid sequence that is about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100% homologous or identical to the amino acid sequence set forth in SEQ ID NO: 52. In certain embodiments, the extracellular antigen-binding domain of the ADGRE2-targeted chimeric receptor comprises a $V_H$ comprising the amino acid sequence set forth in SEQ ID NO: 52. SEQ ID NO: 52 is provided in Table 5 below.

In certain embodiments, the extracellular antigen-binding domain of the ADGRE2-targeted chimeric receptor (e.g., an ADGRE2-targeted scFv) comprises a $V_L$ comprising an amino acid sequence that is at least about 80% (e.g., at least about 85%, at least about 90%, or at least about 95%) homologous or identical to the amino acid sequence set forth in SEQ ID NO: 53. For example, the extracellular antigen-binding domain of the ADGRE2-targeted chimeric receptor (e.g., an ADGRE2-targeted scFv) comprises a $V_L$ comprising an amino acid sequence that is about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100% homologous or identical to the amino acid sequence set forth in SEQ ID NO: 53. In certain embodiments, the extracellular antigen-binding domain of the ADGRE2-targeted chimeric receptor comprises a $V_L$ Comprising the amino acid sequence set forth in SEQ ID NO: 53. SEQ ID NO: 53 is provided in Table 5 below.

In certain embodiments, the extracellular antigen-binding domain of the ADGRE2-targeted chimeric receptor (e.g., an ADGRE2-targeted scFv) comprises a $V_H$ comprising the amino acid sequence set forth in SEQ ID NO: 52, and a $V_L$ comprising the amino acid sequence set forth in SEQ ID NO: 53. In certain embodiments, the $V_H$ and $V_L$ are linked via a linker. In certain embodiments, the linker comprises the amino acid sequence set forth in SEQ ID NO: 149. In certain embodiments, the linker comprises the amino acid sequence set forth in SEQ ID NO: 2.

In certain embodiments, the variable regions within the extracellular antigen-binding domain of the ADGRE2-targeted chimeric receptor have to be linked one after another such that at the N-terminus of the extracellular antigen-binding domain, a heavy chain variable region ($V_H$) is positioned. In certain embodiments, if the extracellular antigen-binding domain of the ADGRE2-targeted chimeric receptor is an scFv, the variable regions are positioned from the N- to the C-terminus: $V_H$-$V_L$. In certain embodiments, the ADGRE2-targeted scFv comprises or consists of the amino acid sequence set forth in SEQ ID NO: 54, which is provided in Table 5. In certain embodiments, the ADGRE2-targeted scFv is designated as "ADGRE2-E". The CDRs provided in Table 5 are identified according to the IMGT numbering system.

TABLE 5

| (ADGRE2-E) | | | |
|---|---|---|---|
| | CDRs | | |
| | 1 | 2 | 3 |
| $V_H$ | GYTFTNYW [SEQ ID NO: 33] | VYPGDGDT [SEQ ID NO: 34] | ARGFTAYGMDY [SEQ ID NO: 35] |
| $V_L$ | SSVSY [SEQ ID NO: 36] | DTS [SEQ ID NO: 37] | QQWSSNPLT [SEQ ID NO: 38] |

TABLE 5-continued (ADGRE2-E)

| | CDRs | | |
|---|---|---|---|
| | 1 | 2 | 3 |

Full V$_H$  QVQLQQSGAEVKKPGASVKVSCKASGYTFTNYWMQWVRQAPGQGLEWIGAVYPGDGDTRHT
QKFKGRVTMTADKSTSTVYMELSSLRSEDTAVYYCARGFTAYGMDYWGQGTLVTVSS
[SEQ ID NO: 52]

Full V$_L$  QIVLTQSPATLSLSPGERATLTCSASSSVSYMHWYQQKPGLSPKRWIYDTSKLASGVPDRF
SGSGSGTDYTFTIRRLEPEDFATYYCQQWSSNPLTFGQGTKVEIK [SEQ ID NO: 53]

V$_H$-V$_L$  QVQLQQSGAEVKKPGASVKVSCKASGYTFTNYWMQWVRQAPGQGLEWIGAVYPGDGDTRHT
scFv  QKFKGRVTMTADKSTSTVYMELSSLRSEDTAVYYCARGFTAYGMDYWGQGTLVTVSSASTG
GGGSGGGSGGGGSQIVLTQSPATLSLSPGERATLTCSASSSVSYMHWYQQKPGLSPKRWI
YDTSKLASGVPDRFSGSGSGTDYTFTIRRLEPEDFATYYCQQWSSNPLTFGQGTKVEIK
[SEQ ID NO: 54]

In certain embodiments, the extracellular antigen-binding domain of the ADGRE2-targeted chimeric receptor (e.g., an ADGRE2-targeted scFv) comprises a V$_H$ CDR1 comprising the amino acid sequence set forth in SEQ ID NO: 33 or a conservative modification thereof, a V$_H$ CDR2 comprising the amino acid sequence set forth in SEQ ID NO: 34 or a conservative modification thereof, and a V$_H$ CDR3 comprising the amino acid sequence set forth in SEQ ID NO: 35 or a conservative modification thereof. SEQ ID NOS: 33-35 are provided in Tables 1-6.

In certain embodiments, the extracellular antigen-binding domain of the ADGRE2-targeted chimeric receptor (e.g., an ADGRE2-targeted scFv) comprises a V$_L$ CDR1 comprising the amino acid sequence set forth in SEQ ID NO: 36 or a conservative modification thereof, a V$_L$ CDR2 comprising the amino acid sequence set forth in SEQ ID NO: 37 or a conservative modification thereof, and a V$_L$ CDR3 comprising the amino acid sequence set forth in SEQ ID NO: 38 or a conservative modification thereof. SEQ ID NOs: 36-38 are provided in Tables 1-6.

In certain embodiments, the extracellular antigen-binding domain of the ADGRE2-targeted chimeric receptor (e.g., an ADGRE2-targeted scFv) comprises a V$_H$ CDR1 comprising the amino acid sequence set forth in SEQ ID NO: 33 or a conservative modification thereof, a V$_H$ CDR2 comprising the amino acid sequence set forth in SEQ ID NO: 34 or a conservative modification thereof, a V$_H$ CDR3 comprising the amino acid sequence set forth in SEQ ID NO: 35 or a conservative modification thereof, a V$_L$ CDR1 comprising the amino acid sequence set forth in SEQ ID NO: 36 or a conservative modification thereof, a V$_L$ CDR2 comprising the amino acid sequence set forth in SEQ ID NO: 37 or a conservative modification thereof, and a V$_L$ CDR3 comprising the amino acid sequence set forth in SEQ ID NO: 38 or a conservative modification thereof.

In certain embodiments, the extracellular antigen-binding domain of the ADGRE2-targeted chimeric receptor (e.g., an ADGRE2-targeted scFv) comprises a V$_H$ CDR1 comprising the amino acid sequence set forth in SEQ ID NO: 33, a V$_H$ CDR2 comprising the amino acid sequence set forth in SEQ ID NO: 34, a V$_H$ CDR3 comprising the amino acid sequence set forth in SEQ ID NO: 35, a V$_L$ CDR1 comprising the amino acid sequence set forth in SEQ ID NO: 36, a V$_L$ CDR2 comprising the amino acid sequence set forth in SEQ ID NO: 37, and a V$_L$ CDR3 comprising the amino acid sequence set forth in SEQ ID NO: 38.

In certain embodiments, the extracellular antigen-binding domain of the ADGRE2-targeted chimeric receptor (e.g., an ADGRE2-targeted scFv) comprises a V$_H$ comprising an amino acid sequence that is at least about 80% (e.g., at least about 85%, at least about 90%, or at least about 95%) homologous or identical to the amino acid sequence set forth in SEQ ID NO: 55. For example, the extracellular antigen-binding domain of the ADGRE2-targeted chimeric receptor (e.g., an ADGRE2-targeted scFv) comprises a V$_H$ comprising an amino acid sequence that is about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100% homologous or identical to the amino acid sequence set forth in SEQ ID NO: 55. In certain embodiments, the extracellular antigen-binding domain of the ADGRE2-targeted chimeric receptor comprises a V$_H$ comprising the amino acid sequence set forth in SEQ ID NO: 55. SEQ ID NO: 55 is provided in Table 6 below.

In certain embodiments, the extracellular antigen-binding domain of the ADGRE2-targeted chimeric receptor (e.g., an ADGRE2-targeted scFv) comprises a V$_L$ comprising an amino acid sequence that is at least about 80% (e.g., at least about 85%, at least about 90%, or at least about 95%) homologous or identical to the amino acid sequence set forth in SEQ ID NO: 56. For example, the extracellular antigen-binding domain of the ADGRE2-targeted chimeric receptor (e.g., an ADGRE2-targeted scFv) comprises a V$_L$ comprising an amino acid sequence that is about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100% homologous or identical to the amino acid sequence set forth in SEQ ID NO: 56. In certain embodiments, the extracellular antigen-binding domain of the ADGRE2-targeted chimeric receptor comprises a V$_L$ Comprising the amino acid sequence set forth in SEQ ID NO: 56. SEQ ID NO: 56 is provided in Table 6 below.

In certain embodiments, the extracellular antigen-binding domain of the ADGRE2-targeted chimeric receptor (e.g., an ADGRE2-targeted scFv) comprises a V$_H$ comprising the amino acid sequence set forth in SEQ ID NO: 55, and a V$_L$ comprising the amino acid sequence set forth in SEQ ID NO: 56. In certain embodiments, the V$_H$ and V$_L$ are linked via a linker. In certain embodiments, the linker comprises the amino acid sequence set forth in SEQ ID NO: 2. In certain embodiments, the linker comprises the amino acid sequence set forth in SEQ ID NO: 149.

In certain embodiments, the variable regions within the extracellular antigen-binding domain of the ADGRE2-targeted chimeric receptor have to be linked one after another such that at the N-terminus of the extracellular antigen-binding domain, a heavy chain variable region ($V_H$) is positioned. In certain embodiments, if the extracellular antigen-binding domain of the ADGRE2-targeted chimeric receptor is an scFv, the variable regions are positioned from the N- to the C-terminus: $V_H$-$V_L$. In certain embodiments, the ADGRE2-targeted scFv comprises or consists of the amino acid sequence set forth in in SEQ ID NO: 57, which is provided in Table 6. In certain embodiments, the ADGRE2-targeted scFv is designated as "ADGRE2-F". The CDRs provided in Table 6 are identified according to the IMGT numbering system.

TABLE 6

(ADGRE2-F)

| | CDRs | | |
|---|---|---|---|
| | 1 | 2 | 3 |
| $V_H$ | GYTFTNYW [SEQ ID NO: 33] | VYPGDGDT [SEQ ID NO: 34] | ARGFTAYGMDY [SEQ ID NO: 35] |
| $V_L$ | SSVSY [SEQ ID NO: 36] | DTS [SEQ ID NO: 37] | QQWSSNPLT [SEQ ID NO: 38] |
| Full $V_H$ | QVQLQQSGAEVKKPGASVKLSCKASGYTFTNYWMQWIRQAPGQGLEWIGAVYPGDGDTRYTQ KFQGRATLTADTSTSTAYMEVSSLRSEDTAVYYCARGFTAYGMDYWGQGTTVTVSS [SEQ ID NO: 55] | | |
| Full $V_L$ | EIVLTQSPATLSASPGERVTMSCSASSSVSYMHWYQQKPGLAPRRWIYDTSKLASGVPDRFS GSGSGTDYTFTISRMEPEDFATYYCQQWSSNPLTFGGGTKLEIK [SEQ ID NO: 56] | | |
| $V_H$-$V_L$ scFv | QVQLQQSGAEVKKPGASVKLSCKASGYTFTNYWMQWIRQAPGQGLEWIGAVYPGDGDTRYTQ KFQGRATLTADTSTSTAYMEVSSLRSEDTAVYYCARGFTAYGMDYWGQGTTVTVSSGGGGSG GGGSGGGGSEIVLTQSPATLSASPGERVTMSCSASSSVSYMHWYQQKPGLAPRRWIYDTSKL ASGVPDRFSGSGSGTDYTFTISRMEPEDFATYYCQQWSSNPLTFGGGTKLEIK [SEQ ID NO: 57] | | |

In certain embodiments, the extracellular antigen-binding domain of the ADGRE2-targeted chimeric receptor (e.g., an ADGRE2-targeted scFv) comprises a $V_H$ CDR1 comprising the amino acid sequence set forth in SEQ ID NO: 33 or a conservative modification thereof, a $V_H$ CDR2 comprising the amino acid sequence set forth in SEQ ID NO: 34 or a conservative modification thereof, and a $V_H$ CDR3 comprising the amino acid sequence set forth in SEQ ID NO: 35 or a conservative modification thereof. SEQ ID NOS: 33-35 are provided in Tables 1-7.

In certain embodiments, the extracellular antigen-binding domain of the ADGRE2-targeted chimeric receptor (e.g., an ADGRE2-targeted scFv) comprises a $V_L$ CDR1 comprising the amino acid sequence set forth in SEQ ID NO: 36 or a conservative modification thereof, a $V_L$ CDR2 comprising the amino acid sequence set forth in SEQ ID NO: 37 or a conservative modification thereof, and a $V_L$ CDR3 comprising the amino acid sequence set forth in SEQ ID NO: 38 or a conservative modification thereof. SEQ ID NOs: 36-38 are provided in Tables 1-7.

In certain embodiments, the extracellular antigen-binding domain of the ADGRE2-targeted chimeric receptor (e.g., an ADGRE2-targeted scFv) comprises a $V_H$ CDR1 comprising the amino acid sequence set forth in SEQ ID NO: 33 or a conservative modification thereof, a $V_H$ CDR2 comprising the amino acid sequence set forth in SEQ ID NO: 34 or a conservative modification thereof, a $V_H$ CDR3 comprising the amino acid sequence set forth in SEQ ID NO: 35 or a conservative modification thereof, a $V_L$ CDR1 comprising the amino acid sequence set forth in SEQ ID NO: 36 or a conservative modification thereof, a $V_L$ CDR2 comprising the amino acid sequence set forth in SEQ ID NO: 37 or a conservative modification thereof, and a $V_L$ CDR3 comprising the amino acid sequence set forth in SEQ ID NO: 38 or a conservative modification thereof.

In certain embodiments, the extracellular antigen-binding domain of the ADGRE2-targeted chimeric receptor (e.g., an ADGRE2-targeted scFv) comprises a $V_H$ CDR1 comprising the amino acid sequence set forth in SEQ ID NO: 33, a $V_H$ CDR2 comprising the amino acid sequence set forth in SEQ ID NO: 34, a $V_H$ CDR3 comprising the amino acid sequence set forth in SEQ ID NO: 35, a $V_L$ CDR1 comprising the amino acid sequence set forth in SEQ ID NO: 36, a $V_L$ CDR2 comprising the amino acid sequence set forth in SEQ ID NO: 37, and a $V_L$ CDR3 comprising the amino acid sequence set forth in SEQ ID NO: 38.

In certain embodiments, the extracellular antigen-binding domain of the ADGRE2-targeted chimeric receptor (e.g., an ADGRE2-targeted scFv) comprises a $V_H$ comprising an amino acid sequence that is at least about 80% (e.g., at least about 85%, at least about 90%, or at least about 95%) homologous or identical to the amino acid sequence set forth in SEQ ID NO: 146. For example, the extracellular antigen-binding domain of the ADGRE2-targeted chimeric receptor (e.g., an ADGRE2-targeted scFv) comprises a $V_H$ comprising an amino acid sequence that is about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100% homologous or identical to the amino acid sequence set forth in SEQ ID NO: 146. In certain embodiments, the extracellular antigen-binding domain of the ADGRE2-targeted chimeric receptor comprises a $V_H$ comprising the amino acid sequence set forth in SEQ ID NO: 146. SEQ ID NO: 146 is provided in Table 7 below.

In certain embodiments, the extracellular antigen-binding domain of the ADGRE2-targeted chimeric receptor (e.g., an ADGRE2-targeted scFv) comprises a $V_L$ comprising an amino acid sequence that is at least about 80% (e.g., at least about 85%, at least about 90%, or at least about 95%) homologous or identical to the amino acid sequence set forth in SEQ ID NO: 147. For example, the extracellular antigen-binding domain of the ADGRE2-targeted chimeric receptor (e.g., an ADGRE2-targeted scFv) comprises a $V_L$ comprising an amino acid sequence that is about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100% homologous or identical to the amino acid sequence set forth in SEQ ID NO: 147. In certain embodiments, the extracellular antigen-binding domain of the ADGRE2-targeted chimeric receptor comprises a $V_L$ Comprising the amino acid sequence set forth in SEQ ID NO: 147. SEQ ID NO: 147 is provided in Table 7 below.

In certain embodiments, the extracellular antigen-binding domain of the ADGRE2-targeted chimeric receptor (e.g., an ADGRE2-targeted scFv) comprises a $V_H$ comprising the amino acid sequence set forth in SEQ ID NO: 146, and a $V_L$ comprising the amino acid sequence set forth in SEQ ID NO: 147. In certain embodiments, the $V_H$ and $V_L$ are linked via a linker. In certain embodiments, the linker comprises the amino acid sequence set forth in SEQ ID NO: 2. In certain embodiments, the linker comprises the amino acid sequence set forth in SEQ ID NO: 149.

In certain embodiments, the variable regions within the extracellular antigen-binding domain of the ADGRE2-targeted chimeric receptor have to be linked one after another such that at the N-terminus of the extracellular antigen-binding domain, a heavy chain variable region ($V_H$) is positioned. In certain embodiments, if the extracellular antigen-binding domain of the ADGRE2-targeted chimeric receptor is an scFv, the variable regions are positioned from the N- to the C-terminus: $V_H$-$V_L$. In certain embodiments, the ADGRE2-targeted scFv comprises or consists of the amino acid sequence set forth in in SEQ ID NO: 148, which is provided in Table 7. In certain embodiments, the ADGRE2-targeted scFv is designated as "ADGRE2-G". The CDRs provided in Table 7 are identified according to the IMGT numbering system.

The $V_H$ and/or $V_L$ amino acid sequences comprising or consisting of at least about 80%, at least about 80%, at least about 85%, at least about 90%, or at least about 95% (e.g., about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99%) homology or identity to a specific sequence (e.g., SEQ ID NO: 39, SEQ ID NO: 40, SEQ ID NO: 43, SEQ ID NO: 44, SEQ ID NO: 46, SEQ ID NO: 47, SEQ ID NO: 49, SEQ ID NO: 50, SEQ ID NO: 52, SEQ ID NO: 53, SEQ ID NO: 55, SEQ ID NO: 56, SEQ ID NO: 146, or SEQ ID NO: 147) may contain substitutions (e.g., conservative substitutions), insertions, or deletions relative to the specified sequence(s), but retain the ability to bind to a target antigen (e.g., ADGRE2). In certain embodiments, a total of 1 to 10 amino acids are substituted, inserted and/or deleted in a specific sequence (e.g., SEQ ID NO: 39, SEQ ID NO: 40, SEQ ID NO: 43, SEQ ID NO: 44, SEQ ID NO: 46, SEQ ID NO: 47, SEQ ID NO: 49, SEQ ID NO: 50, SEQ ID NO: 52, SEQ ID NO: 53, SEQ ID NO: 55, SEQ ID NO: 56, SEQ ID NO: 146, or SEQ ID NO: 147). In certain embodiments, substitutions, insertions, or deletions occur in regions outside the CDRs (e.g., in the FRs) of the extracellular antigen-binding domain. In certain embodiments, the extracellular antigen-binding domain comprises $V_H$ and/or $V_L$ sequence selected from SEQ ID NO: 39, SEQ ID NO: 40, SEQ ID NO: 43, SEQ ID NO: 44, SEQ ID NO: 46, SEQ ID NO: 47, SEQ ID NO: 49, SEQ ID NO: 50, SEQ ID NO: 52, SEQ ID NO: 53, SEQ ID NO: 55, SEQ ID NO: 56, SEQ ID NO: 146, or SEQ ID NO: 147, including post-translational modifications of that sequence (SEQ ID NO: 39, SEQ ID NO: 40, SEQ ID NO: 43, SEQ ID NO: 44, SEQ ID NO: 46, SEQ ID NO: 47, SEQ ID NO: 49, SEQ ID NO: 50, SEQ ID NO: 52, SEQ ID NO: 53, SEQ ID NO: 55, SEQ ID NO: 56, SEQ ID NO: 146, or SEQ ID NO: 147).

In certain embodiments, the extracellular antigen-binding domain of a presently disclosed ADGRE2-targeted chimeric receptor cross-competes for binding to ADGRE2 with a reference antibody or an antigen-binding portion thereof comprising the a $V_H$ CDR1 comprising the amino acid sequence set forth in SEQ ID NO: 33, a $V_H$ CDR2 comprising the amino acid sequence set forth in SEQ ID NO: 34; a $V_H$ CDR3 comprising the amino acid sequence set forth in

TABLE 7

(ADGRE2-G)

| | CDRs | | |
|---|---|---|---|
| | 1 | 2 | 3 |
| $V_H$ | GYTFTNYW [SEQ ID NO: 33] | VYPGDGDT [SEQ ID NO: 34] | ARGFTAYGMDY [SEQ ID NO: 35] |
| $V_L$ | SSVSY [SEQ ID NO: 36] | DTS [SEQ ID NO: 37] | QQWSSNPLT [SEQ ID NO: 38] |
| Full $V_H$ | QVQLVQSGAEVAKPGASVKLSCKASGYTFTNYWMQWIKQAPGQGLEWIGAVYPGDGDTRHTQ KFKGKATLTADKSTSTAYMEVSSLRSEDTAVYYCARGFTAYGMDYWGQGTTVTVSS [SEQ ID NO: 146] | | |
| Full $V_L$ | EIVLTQSPATMSASPGERVTMSCSASSSVSYMHWYQQKSGQSPKRWIYDTSKLASGVPARFS GSGSGTDYTFTISSMEPEDFATYYCQQWSSNPLTFGGGTKLEIK [SEQ ID NO: 147] | | |
| $V_H$-$V_L$ scFv | QVQLVQSGAEVAKPGASVKLSCKASGYTFTNYWMQWIKQAPGQGLEWIGAVYPGDGDTRHTQ KFKGKATLTADKSTSTAYMEVSSLRSEDTAVYYCARGFTAYGMDYWGQGTTVTVSSGGGGSG GGGSGGGGSEIVLTQSPATMSASPGERVTMSCSASSSVSYMHWYQQKSGQSPKRWIYDTSKL ASGVPARFSGSGSGTDYTFTISSMEPEDFATYYCQQWSSNPLTFGGGTKLEIK [SEQ ID NO: 148] | | |

SEQ ID NO: 35; a V$_L$ CDR1 comprising the amino acid sequence set forth in SEQ ID NO: 36; a V$_L$ CDR2 comprising the amino acid sequence set forth in SEQ ID NO: 37; and a V$_L$ CDR3 comprising the amino acid sequence set forth in SEQ ID NO: 38. In certain embodiments, the extracellular antigen-binding domain of a presently disclosed ADGRE2-targeted chimeric receptor cross-competes for binding to ADGRE2 with a reference antibody or an antigen-binding portion thereof comprising the V$_H$ and V$_L$ sequences of, for example, any one of the presently disclosed scFvs (e.g., ADGRE2-A, ADGRE2-B, ADGRE2-C, ADGRE2-D, ADGRE2-E, ADGRE2-F, and ADGRE2-G).

In certain embodiments, the extracellular antigen-binding domain of a presently disclosed ADGRE2-targeted chimeric receptor binds to the same or substantially the same epitope region on ADGRE2 with a reference antibody or an antigen-binding portion thereof comprising the a V$_H$ CDR1 comprising the amino acid sequence set forth in SEQ ID NO: 33, a V$_H$ CDR2 comprising the amino acid sequence set forth in SEQ ID NO: 34; a V$_H$ CDR3 comprising the amino acid sequence set forth in SEQ ID NO: 35; a V$_L$ CDR1 comprising the amino acid sequence set forth in SEQ ID NO: 36; a V$_L$ CDR2 comprising the amino acid sequence set forth in SEQ ID NO: 37; and a V$_L$ CDR3 comprising the amino acid sequence set forth in SEQ ID NO: 38. In certain embodiments, the extracellular antigen-binding domain of a presently disclosed ADGRE2-targeted chimeric receptor binds to the same or substantially the same epitope region on ADGRE2 with a reference antibody or an antigen-binding portion thereof comprising the V$_H$ and V$_L$ sequences of, for example, any one of the presently disclosed scFvs (e.g., ADGRE2-A, ADGRE2-B, ADGRE2-C, ADGRE2-D, ADGRE2-E, ADGRE2-F, and ADGRE2-G).

Extracellular antigen-binding domains of the presently disclosed ADGRE2-targeted chimeric receptors that cross-compete or compete with the reference antibody or antigen-binding portions thereof for binding to ADGRE2 can be identified by using routine methods known in the art, including, but not limited to, ELISAs, radioimmunoassay (RIAs), Biacore, flow cytometry, Western blotting, and any other suitable quantitative or qualitative antibody-binding assays. Competition ELISA is described in Morris, "Epitope Mapping of Protein Antigens by Competition ELISA", *The Protein Protocols Handbook* (1996), pp 595-600, edited by J. Walker, which is incorporated by reference in its entirety. In certain embodiments, the antibody-binding assay comprises measuring an initial binding of a reference antibody to an ADGRE2, admixing the reference antibody with a test extracellular antigen-binding domain, measuring a second binding of the reference antibody to the ADGRE2 in the presence of the test extracellular antigen-binding domain, and comparing the initial binding with the second binding of the reference antibody, wherein a decreased second binding of the reference antibody to the ADGRE2 in comparison to the initial binding indicates that the test extracellular antigen-binding domain cross-competes with the reference antibody for binding to ADGRE2, e.g., one that recognizes the same or substantially the same epitope, an overlapping epitope, or an adjacent epitope. In certain embodiments, the reference antibody is labeled, e.g., with a fluorochrome, biotin, or peroxidase. In certain embodiments, the ADGRE2 is expressed in cells, e.g., in a flow cytometry test. In certain embodiments, the ADGRE2 is immobilized onto a surface, including a Biacore ship (e.g., in a Biacore test), or other media suitable for surface plasmon resonance analysis. The binding of the reference antibody in the presence of a completely irrelevant antibody (that does not bind to ADGRE2) can serve as the control high value. The control low value can be obtained by incubating a labeled reference antibody with an unlabeled reference antibody, where competition and reduced binding of the labeled reference antibody would occur. In certain embodiments, a test extracellular antigen-binding domain that reduces the binding of the reference antibody to ADGRE2 by at least about 20%, at least about 30%, at least about 40%, at least about 50%, at least about 60%, at least about 70%, at least about 80%, at least about 90%, or at least about 95% is considered to be an extracellular antigen-binding domain that cross-competes with the reference antibody for binding to ADGRE2. In certain embodiments, the assays are performed at room temperature.

In certain embodiments, the antibody-binding assay comprises measuring an initial binding of a test extracellular antigen-binding domain to ADGRE2, admixing the test extracellular antigen-binding domain with a reference antibody, measuring a second binding of the test extracellular antigen-binding domain to ADGRE2 in the presence of the reference antibody, and comparing the initial binding with the second binding of the test extracellular antigen-binding domain, where a decreased second binding of the test extracellular antigen-binding domain to ADGRE2 in comparison to the initial binding indicates that the test extracellular antigen-binding domain cross-competes with the reference antibody for binding to ADGRE2, e.g., one that recognizes the same or substantially the same epitope, an overlapping epitope, or an adjacent epitope. In certain embodiments, the test extracellular antigen-binding domain is labeled, e.g., with a fluorochrome, biotin, or peroxidase. In certain embodiments, the ADGRE2 is expressed in cells, e.g., in a flow cytometry test. In certain embodiments, the ADGRE2 is immobilized onto a surface, including a Biacore ship (e.g., in a Biacore test), or other media suitable for surface plasmon resonance analysis. The binding of the test extracellular antigen-binding domain in the presence of a completely irrelevant antibody (that does not bind to ADGRE2) can serve as the control high value. The control low value can be obtained by incubating a labeled test extracellular antigen-binding domain with an unlabeled test extracellular antigen-binding domain, where competition and reduced binding of the labeled test extracellular antigen-binding domain would occur. In certain embodiments, a test extracellular antigen-binding domain, whose binding to ADGRE2 is decreased by at least about 20%, at least about 30%, at least about 40%, at least about 50%, at least about 60%, at least about 70%, at least about 80%, at least about 90%, or at least about 95% in the presence of a reference antibody, is considered to be an extracellular antigen-binding domain that cross-competes with the reference antibody for binding to ADGRE2. In certain embodiments, the assays are performed at room temperature.

In certain embodiments, the extracellular antigen-binding domain of the presently disclosed ADGRE2-targeted chimeric receptor comprises a linker connecting the heavy chain variable region and light chain variable region of the extracellular antigen-binding domain. In certain embodiments, the linker comprises the amino acid sequence set forth in SEQ ID NO: 1. In certain embodiments, the linker comprises the amino acid sequence set forth in SEQ ID NO: 2. In certain embodiments, the linker comprises the amino acid sequence set forth in SEQ ID NO: 3. In certain embodiments, the linker comprises the amino acid sequence set forth in SEQ ID NO: 4. In certain embodiments, the linker comprises the amino acid sequence set forth in SEQ ID NO: 5. In certain embodiments, the linker comprises the amino acid sequence set forth in SEQ ID NO: 6. In certain embodiments, the linker comprises the amino acid sequence set forth in SEQ ID NO: 149.

In certain embodiments, the variable regions within the extracellular antigen-binding domain of the ADGRE2-targeted chimeric receptor have to be linked one after another such that at the N-terminus of the extracellular antigen-binding domain, a heavy chain variable region ($V_H$) is positioned. In certain embodiments, if the extracellular antigen-binding domain of the ADGRE2-targeted chimeric receptor is an scFv, the variable regions are positioned from the N- to the C-terminus: $V_H$-$V_L$.

In certain embodiments, the variable regions within the extracellular antigen-binding domain of the ADGRE2-targeted chimeric receptor have to be linked one after another such that at the N-terminus of the extracellular antigen-binding domain, a light chain variable region ($V_L$) is positioned. In certain embodiments, if the extracellular antigen-binding domain of the ADGRE2-targeted chimeric receptor is an scFv, the variable regions are positioned from the N- to the C-terminus: $V_L$-$V_H$.

In addition, the ADGRE2-targeted chimeric receptor can comprise a leader or a signal peptide that directs the nascent protein into the endoplasmic reticulum. In certain embodiments, the leader or signal peptide is positioned at (e.g., covalently joined to) the N-terminus of the extracellular antigen-binding domain of the ADGRE2-targeted chimeric receptor. Signal peptide or leader can be essential if the chimeric receptor is to be glycosylated and anchored in the cell membrane. The signal sequence or leader can be a peptide sequence (about 5, about 10, about 15, about 20, about 25, or about 30 amino acids long) present at the N-terminus of newly synthesized proteins that directs their entry to the secretory pathway. Non-limiting examples of signal peptides or leader sequences include an IL-2 signal sequence, a CD8 leader sequence, a kappa leader sequence, an albumin leader sequence, and a prolactin leader sequence. In certain embodiments, the IL-2 signal sequence comprises or consists of the amino acid sequence set forth in SEQ ID NO. 58 or SEQ ID NO: 59. In certain embodiments, the kappa leader sequence comprises or consists of the amino acid sequence set forth in SEQ ID NO. 60 or SEQ ID NO: 61. In certain embodiments, the CD8 signal sequence comprises or consists of the amino acid sequence set forth in SEQ ID NO. 62 or SEQ ID NO: 63. In certain embodiments, the albumin leader sequence comprises or consists of the amino acid sequence set forth in SEQ ID NO: 64. In certain embodiments, the prolactin leader sequence comprises or consists of the amino acid sequence set forth in SEQ ID NO: 65. In certain embodiments, the ADGRE2-targeted chimeric receptor comprises a signal peptide that comprises a CD8 polypeptide. In certain embodiments, the ADGRE2-targeted chimeric receptor comprises a signal peptide that comprises a CD8 polypeptide comprising or consisting of the amino acid sequence set forth in SEQ ID NO: 63.

```
                            [SEQ ID NO: 58]
MYRMQLLSCIALSLALVTNS

[SEQ ID NO: 59]
MYSMQLASCVTLTLVLLVNS

[SEQ ID NO: 60]
METPAQLLFLLLLWLPDTTG

[SEQ ID NO: 61]
METDTLLLWVLLLWVPGSTG
```

```
                            [SEQ ID NO: 62]
MALPVTALLLPLALLLHAARP

[SEQ ID NO: 63]
MALPVTALLLPLALLLHA

[SEQ ID NO: 64]
MKWVTFISLLESSAYS

[SEQ ID NO: 65]
MDSKGSSQKGSRLLLLLVVSNLLLCQGVVS
```

5.4. Exemplified ADGRE2-Targeted Chimeric Receptors

In certain embodiments, the ADGRE2-targeted chimeric receptor is an ADGRE2-targeted CAR. In certain embodiments, the ADGRE2-targeted CAR comprises (a) an extracellular antigen-binding domain comprising (i) a $V_H$ that comprises a CDR1 comprising the amino acid sequence set forth in SEQ ID NO: 33, a CDR2 comprising the amino acid sequence set forth in SEQ ID NO: 34, and a $V_H$ CDR3 comprising the amino acid sequence set forth in SEQ ID NO: 35, and (ii) a $V_L$ that comprises a CDR1 comprising the amino acid sequence set forth in SEQ ID NO: 36, a CDR2 comprising the amino acid sequence set forth in SEQ ID NO: 37, and a CDR3 comprising the amino acid sequence set forth in SEQ ID NO: 38; (b) a hinge/spacer region comprising a CD28 polypeptide, (c) a transmembrane domain comprising a CD28 polypeptide (e.g., a transmembrane domain of human CD28 or a fragment thereof), and (d) an intracellular signaling domain comprising (i) a CD3ζ polypeptide, and (ii) a co-stimulatory signaling region comprising a CD28 polypeptide (e.g., an intracellular domain of human CD28 or a fragment thereof). In certain embodiments, the $V_H$ and $V_L$ are linked via a linker comprising or consisting of the amino acid sequence set forth in SEQ ID NO: 2. In certain embodiments, the $V_H$ and $V_L$ are positioned from the N- to the C-terminus: $V_H$-$V_L$. In certain embodiments, the transmembrane domain comprises a CD28 polypeptide comprising or consisting of the amino acids 153 to 179 of SEQ ID NO: 10. In certain embodiments, the co-stimulatory signaling region comprises a CD28 polypeptide comprising or consisting of the amino acids 180 to 220 of SEQ ID NO: 10. In certain embodiments, the hinge/spacer region comprises a CD28 polypeptide comprising or consisting of the amino acids 114 to 152 of SEQ ID NO: 10. In certain embodiments, the extracellular antigen-binding domain and transmembrane domain are linked via a linker. In certain embodiments, the linker consists of the amino acid sequence set forth in SEQ ID NO: 150. SEQ ID NO: 150 is provided below. In certain embodiments, the ADGRE2-targeted CAR comprises or consists of the amino acid sequence set forth in SEQ ID NO: 66, which is provided below.

```
                                      [SEQ ID NO: 66]
QVQLQQSGAEVAKPGASVKLSCKASGYTFTNYWMQWIKQAPGQGLEWIGA

VYPGDGDTRHTQKFKGKATLTADKSTSTAYMEVSSLRSEDTAVYYCARGF

TAYGMDYWGQGTTVTVSSGGGGSGGGGSGGGGSEIVLTQSPATMSASPGE

RVTMSCSASSSVSYMHWYQQKSGQSPKRWIYDTSKLASGVPARFSGSGSG

TDYTFTISSMEPEDFATYYCQQWSSNPLTFGGGTKLEIKRAAAIEVMYPP
```

-continued
PYLDNEKSNGTIIHVKGKHLCPSPLFPGPSKPFWVLVVVGGVLACYSLLV

TVAFIIEWVRSKRSRLLHSDYMNMTPRRPGPTRKHYQPYAPPRDFAAYRS

RVKFSRSADAPAYQQGQNQLYNELNLGRREEYDVLDKRRGRDPEMGGKPR

RKNPQEGLFNELQKDKMAEAFSEIGMKGERRRGKGHDGLFQGLSTATKDT

FDALHMQALPPR

[SEQ ID NO: 150]
RAAA

An exemplary nucleic acid sequence the amino acid sequence of SEQ ID NO: 66 is set forth in SEQ ID NO: 67, which is provided below.

[SEQ ID NO: 67]
caagttcagctccagcagagcggcgccgaagtggcaaagcctggagcgtc agtcaagctgtcctgcaaagcgagtggctatacgttcacgaactactgga tgcagtggataaagcaggctcccgggcagggtctggagtggattggagcc gtctacccaggggacggcgacacccggcacactcaaaagttcaagggcaa ggccaccctgaccgctgacaagagcacaagcacagcgtacatggaggtgt cctctttgagatccgaagataccgctgtgtattattgtgccggggcttc actgcatacgggatggattactggggacaaggcactaccgtgactgtcag ctccggggtggaggctcaggcggggggttcaggaggggggggatctg aaattgtgctgacacagagccctgccacaatgtctgctagccctggcgag cgcgtgaccatgtcttgtagcgccagcagcagcgtgtcctacatgcattg gtatcaacgaagtccggccagtctcccaagcggtggatctacgataccaa gcaagctggcctccggcgtgcccgccagattttctggcagcggctctgga acagattacaccttcaccatctctagcatggaacctgaggattttgccac ctactattgccagcagtggtccagcaatcccctgacatttggaggaggca ccaagctggaaattaagagagcggccgcaattgaagttatgtatcctcct ccttacctagacaatgagaagagcaatggaaccattatccatgtgaaagg gaaacacctttgtccaagtcccctatttcccggaccttctaagcccttt gggtgctggtggtggttggtggagtcctggcttgctatagcttgctagta acagtggcctttattattttctgggtgaggagtaagaggagcaggctcct gcacagtgactacatgaacatgactccccgccgcccgggcccaccgca agcattaccagccctatgcccaccacgcgacttcgcagcctatcgctcc agagtgaagttcagcaggagcgcagacgccccgcgtaccagcagggca gaaccagctctataacgagctcaatctaggacgaagagaggagtacgatg ttttggacaagagacgtggccgggaccctgagatggggggaaagccgaga aggaagaacctcaggaaggcctgttcaatgaactgcagaaagataagat ggcggaggccttcagtgagattgggatgaaaggcgagcgccggaggggca aggggcacgatggccttttccagggtctcagtacagccaccaaggacacc ttcgacgcccttcacatgcaggccctgccccctcgc In certain embodiments, the ADGRE2-targeted chimeric receptor comprises a signal peptide at the N-terminus of the extracellular antigen-binding domain. In certain embodiments, the signal peptide comprises a CD8 polypeptide comprising or consisting of the amino acid sequence set forth in SEQ ID NO: 63.

5.5. Extracellular Antigen-Binding Domain of CLEC12A-Targeted Chimeric Receptors In certain embodiments, the presently disclosed chimeric receptor targets CLEC12A. In certain embodiments, the presently disclosed chimeric receptor comprises an extracellular antigen-binding domain that binds to CLEC12A.

C-type lectin domain family 12 member A (CLEC12A), also known as CLL-1, CLL1, DCAL-2, MICL, CD371, is a 30 kD C-type lectin transmembrane glycoprotein. It is expressed on monocytes, granulocytes, natural killer (NK) cells, and basophils. CLEC12A is an immunoinhibitory receptor that recruits Src homology phosphatases SHP-1 and SHP-2 to its phosphorylated cytoplasmic immunoreceptor tyrosine-based inhibitory motif (ITIM) (Sancho et al., *Annu Rev. Immunol* (2012); 30:491-529; Yan et al., *Front Immunol* (2015); 6:408; Lahoud et al., *J Immunol* (2011); 187:842). CLEC12A has been implicated as a negative regulatory uric acid crystals (monosodium urate, MSU) receptor that controls autoimmunity and inflammatory disease (Neumann et al., *Immunity* (2014); 40:389-99). CLEC12A is a negative regulator of granulocyte and monocyte function (Marshall et al., *J Biol Chem* (2004); 279(15):14792-802; Pyz et al., *Eur J Immunol* (2008); 38(4):1157-63).

In certain embodiments, the presently disclosed chimeric receptor targets human CLEC12A. In certain embodiments, the presently disclosed chimeric receptor comprises an extracellular antigen-binding domain that binds to human CLEC12A. In certain embodiments, the human CLEC12A comprises or consists of the amino acid sequence with a UniProt Reference No: Q5QGZ9-2 (SEQ ID NO: 68), or a fragment thereof. SEQ ID NO: 68 is provided below:

[SEQ ID NO: 68]
MSEEVTYADLQFQNSSEMEKIPEIGKFGEKAPPAPSHVWRPAALFLTLLC

LLLLIGLGVLASMEHVTLKIEMKKMNKLQNISEELQRNISLQLMSNMNIS

NKIRNLSTTLQTIATKLCRELYSKEQEHKCKPCPRRWIWHKDSCYFLSDD

VQTWQESKMACAAQNASLLKINNKNALEFIKSQSRSYDYWLGLSPEEDST

RGMRVDNIINSSAWVIRNAPDLNNMYCGYINRLYVQYYHCTYKKRMICEK

MANPVQLGSTYFREA

Human CLEC12A comprises a cytoplasmic domain, a transmembrane domain, and an extracellular domain. In certain embodiments, the cytoplasmic domain comprises or consists of amino acids 1 to 43 of SEQ ID NO: 68. In certain embodiments, the transmembrane domain comprises or consists of amino acid 44 to 64 of SEQ ID NO: 68. In certain embodiments, the extracellular domain comprises or consists of amino acid 65 to 265 of SEQ ID NO: 68.

In certain embodiments, the presently disclosed chimeric receptor targets a CLECL12A polypeptide comprising or consisting of an amino acid sequence that is at least about 80%, at least about 85%, at least about 90%, at least about 95%, at least about 96%, at least about 97%, at least about 98%, or at least about 99%, at least about 100% identical to the amino acid sequence set forth in SEQ ID NO: 68 or a fragment thereof.

In certain embodiments, the extracellular antigen-binding domain of a presently disclosed CLEC12A-targeted chimeric receptor binds to the extracellular domain of CLEC12A.

In certain embodiments, the CLEC12A-targeted chimeric receptor is a chimeric antigen receptor (CAR). In certain embodiments, the CLEC12A-targeted CAR has the structure disclosed in Section 5.2.1. In certain embodiments, the CLEC12A-targeted CAR comprises an extracellular antigen-binding domain that binds to CLEC12A, a transmembrane domain, and an intracellular signaling domain.

In certain embodiments, the CLEC12A-targeted chimeric receptor is a Chimeric Co-Stimulatory Receptor (CCR). In certain embodiments, the CLEC12A-targeted CCR has the structure disclosed in Section 5.2.2. In certain embodiments, the CLEC12A-targeted CCR comprises an extracellular antigen-binding domain that binds to CLEC12A, a transmembrane domain, and an intracellular signaling domain that does not provide an activation signal to an immunoresponsive cell, e.g., the intracellular signaling domain does not comprise a CD3ζ polypeptide.

In certain embodiments, the CLEC12A-targeted chimeric receptor is a TCR like Fusion Molecules. In certain embodiments, the CLEC12A-targeted TCR like Fusion Molecules has the structure disclosed in Section 5.2.3.

In certain embodiments, the extracellular antigen-binding domain of the CLEC12A-targeted chimeric receptor (e.g., a CLEC12A-targeted scFv) binds to CLEC12A (e.g., human CLEC12A) with a dissociation constant ($K_D$) of at least about $1\times10^{-6}$ M, at least about $1\times10^{-7}$ M, at least about $1\times10^{-8}$ M, at least about $1\times10^{-9}$ M, or at least about $1\times10^{-10}$ M. In certain embodiments, the extracellular antigen-binding domain of the CLEC12A-targeted chimeric receptor (e.g., a CLEC12A-targeted scFv) binds to CLEC12A (e.g., human CLEC12A) with a dissociation constant ($K_D$) of at least about $2\times10^{-8}$ M. In certain embodiments, the extracellular antigen-binding domain of the CLEC12A-targeted chimeric receptor (e.g., a CLEC12A-targeted scFv) binds to CLEC12A (e.g., human CLEC12A) with a dissociation constant ($K_D$) of between about $2\times10^{-8}$ M and about $8\times10^{-9}$ M.

In certain embodiments, the extracellular antigen-binding domain of the CLEC12A-targeted chimeric receptor (e.g., a CLEC12A-targeted scFv) binds to CLEC12A (e.g., human CLEC12A) with a dissociation constant ($K_D$) between about 1 nM and about 50 nM, between about 5 nM and 30 nM, between about 5 nM and about 25 nM, or between about 8 nM and about 20 nM. In certain embodiments, the extracellular antigen-binding domain of the CLEC12A-targeted chimeric receptor (e.g., a CLEC12A-targeted scFv) binds to CLEC12A (e.g., human CLEC12A) with a dissociation constant ($K_D$) of at least about 50 nM, at least about 40 nM, at least about 35 nM, at least about 30 nM, at least about 25 nM, at least about 20 nM, at least about 19 nM, at least about 18 nM, at least about 17 nM, at least about 16 nM, at least about 15 nM, at least about 14 nM, at least about 13 nM, at least about 12 nM, at least about 11 nM, at least about 10 nM, at least about 9 nM, at least about 8 nM, at least about 7 nM, at least about 6 nM, at least about 5 nM.

In certain embodiments, the extracellular antigen-binding domain of the CLEC12A-targeted chimeric receptor (e.g., a CLEC12A-targeted scFv) comprises a $V_H$ CDR1 comprising the amino acid sequence set forth in SEQ ID NO: 69 or a conservative modification thereof, a $V_H$ CDR2 comprising the amino acid sequence set forth in SEQ ID NO: 70 or a conservative modification thereof, and a $V_H$ CDR3 comprising the amino acid sequence set forth in SEQ ID NO: 71 or a conservative modification thereof. SEQ ID NOs: 69-71 are provided in Table 8.

In certain embodiments, the extracellular antigen-binding domain of the CLEC12A-targeted chimeric receptor (e.g., a CLEC12A-targeted scFv) comprises a $V_L$ CDR1 comprising the amino acid sequence set forth in SEQ ID NO: 72 or a conservative modification thereof, a $V_L$ CDR2 comprising the amino acid sequence set forth in SEQ ID NO: 73 or a conservative modification thereof, and a $V_L$ CDR3 comprising the amino acid sequence set forth in SEQ ID NO: 74 or a conservative modification thereof. SEQ ID NOs: 72-74 are provided in Table 8.

In certain embodiments, the extracellular antigen-binding domain of the CLEC12A-targeted chimeric receptor (e.g., a CLEC12A-targeted scFv) comprises a $V_H$ CDR1 comprising the amino acid sequence set forth in SEQ ID NO: 69 or a conservative modification thereof, a $V_H$ CDR2 comprising the amino acid sequence set forth in SEQ ID NO: 70 or a conservative modification thereof, a $V_H$ CDR3 comprising the amino acid sequence set forth in SEQ ID NO: 71 or a conservative modification thereof, a $V_L$ CDR1 comprising the amino acid sequence set forth in SEQ ID NO: 72 or a conservative modification thereof, a $V_L$ CDR2 comprising the amino acid sequence set forth in SEQ ID NO: 73 or a conservative modification, and a $V_L$ CDR3 comprising the amino acid sequence set forth in SEQ ID NO: 74 or a conservative modification thereof.

In certain embodiments, the extracellular antigen-binding domain of the CLEC12A-targeted chimeric receptor (e.g., a CLEC12A-targeted scFv) comprises a $V_H$ CDR1 comprising the amino acid sequence set forth in SEQ ID NO: 69, a $V_H$ CDR2 comprising the amino acid sequence set forth in SEQ ID NO: 70, a $V_H$ CDR3 comprising the amino acid sequence set forth in SEQ ID NO: 71, a $V_L$ CDR1 comprising the amino acid sequence set forth in SEQ ID NO: 72, a $V_L$ CDR2 comprising the amino acid sequence set forth in SEQ ID NO: 73, and a $V_L$ CDR3 comprising the amino acid sequence set forth in SEQ ID NO: 74.

In certain embodiments, the extracellular antigen-binding domain of the CLEC12A-targeted chimeric receptor (e.g., a CLEC12A-targeted scFv) comprises a $V_H$ comprising an amino acid sequence that is at least about 80% (e.g., at least about 85%, at least about 90%, or at least about 95%) homologous or identical to the amino acid sequence set forth in SEQ ID NO: 75. For example, the extracellular antigen-binding domain of the CLEC12A-targeted chimeric receptor (e.g., a CLEC12A-targeted scFv) comprises a $V_H$ comprising an amino acid sequence that is about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100% homologous or identical to SEQ ID NO: 108. In certain embodiments, the extracellular antigen-binding domain of the CLEC12A-targeted chimeric receptor comprises a $V_H$ Comprising the amino acid sequence set forth in SEQ ID NO: 75. SEQ ID NO: 75 is provided in Table 8 below.

In certain embodiments, the extracellular antigen-binding domain of the CLEC12A-targeted chimeric receptor (e.g., a CLEC12A-targeted scFv) comprises a $V_L$ comprising an amino acid sequence that is at least about 80% (e.g., at least about 85%, at least about 90%, or at least about 95%) homologous or identical to the amino acid sequence set forth in SEQ ID NO: 76. For example, the extracellular antigen-binding domain of the CLEC12A-targeted chimeric receptor (e.g., a CLEC12A-targeted scFv) comprises a $V_L$ comprising an amino acid sequence that is about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100% homologous or identical to SEQ ID NO: 109. In certain embodiments, the extracellular antigen-binding domain of the CLEC12A-targeted chimeric receptor comprises a $V_L$ comprising the amino acid sequence set forth in SEQ ID NO: 76. SEQ ID NO: 76 is provided in Table 8 below.

In certain embodiments, the extracellular antigen-binding domain of the CLEC12A-targeted chimeric receptor (e.g., a CLEC12A-targeted scFv) comprises a $V_H$ comprising the amino acid sequence set forth in SEQ ID NO: 75, and a $V_L$ comprising the amino acid sequence set forth in SEQ ID NO: 76. In certain embodiments, the $V_H$ and $V_L$ are linked via a linker. In certain embodiments, the linker comprises the amino acid sequence set forth in SEQ ID NO: 149. In antigen-binding domain of the CLEC12A-targeted chimeric receptor is an scFv, the variable regions are positioned from the N- to the C-terminus: $V_H$—$V_L$. In certain embodiments, the CLEC12A-targeted scFv comprises or consists of the amino acid sequence set forth in SEQ ID NO: 79. In certain embodiments, the CLEC12A-targeted scFv is designated as "CLEC12A-A". An exemplary nucleotide sequence encoding the amino acid sequence of SEQ ID NO: 79 is set forth in SEQ ID NO: 80. SEQ ID NOs: 79 and 80 are provided in Table 8. The CDRs provided in Table 8 are identified according to the IMGT numbering system.

TABLE 8

| | (CLEC12A-A) | | |
|---|---|---|---|
| CDRs | 1 | 2 | 3 |
| $V_H$ | GGSISSSTYY [SEQ ID NO: 69] | THYRGST [SEQ ID NO: 70] | ARELTGEVFDY [SEQ ID NO: 71] |
| $V_L$ | QSISSY [SEQ ID NO: 72] | AAS [SEQ ID NO: 73] | QQSYSTPFT [SEQ ID NO: 74] |
| Full $V_H$ | QLQLQESGPGLVKPSETLSLTCTVSGGSISSSTYYWGWIRQPPRKGLEWIGSTHYRGST YYNPSLKSRVTISVDTSKNQFSLKVSSVTAADTAVYYCARELTGEVFDYWGQGTLVTVS S [SEQ ID NO: 75] | | |
| Full $V_L$ | DIQMTQSPSSLSASVGDRVTITCRASQSISSYLNWYQQKPGKAPKLLIYAASSLQSGVP SRFSGSGSGTDFTLTISSLQPEDFATYYCQQSYSTPFTFGPGTKVDIK [SEQ ID NO: 76] | | |
| DNA for Full $V_H$ | Cagctccagctccaagagtcagggccaggtctcgtgaaaccgagtgagaccctgtccct gacctgcacagtgagtggtggatcaatctcaagctctacctactattgggggtggattc ggcagccccctagaaaggggcttgagtggattggcagcactcattatcgaggatctacc tattataatccttctctgaaaagcagagttaccatctctgtggatacgtccaaaaatca gttcagtctgaaggtatcatccgtgactgctgccgacacggccgtgtactattgcgcga gggagctgacaggtgaggtctttgactactggggccagggcacactcgtgaccgtgtct tct [SEQ ID NO: 77] | | |
| DNA for Full $V_L$ | Gacatccagatgacgcagtccccttccagcttgtccgcatctgtgggtgatagggtcac gattacatgtagggctagtcagagtatttctagttacctgaattggtaccagcagaaac caggcaaggcaccaaagttgctcatctatgcggcctcctctctgcaatctggcgtgccg tccagatttagtggatcaggctccggaaccgatttcacccttacgatctcctcacttca acccgaggatttcgccacatattactgtcaacaaagctattctacaccgttcaccttcg gaccggggacaaaagtggatattaaa [SEQ ID NO: 78] | | |
| $V_H$-$V_L$ scFv | QLQLQESGPGLVKPSETLSLTCTVSGGSISSSTYYWGWIRQPPRKGLEWIGSTHYRGST YYNPSLKSRVTISVDTSKNQFSLKVSSVTAADTAVYYCARELTGEVFDYWGQGTLVTVS SASTGGGGSGGGGSGGGGSDIQMTQSPSSLSASVGDRVTITCRASQSISSYLNWYQQKP GKAPKLLIYAASSLQSGVPSRFSGSGSGTDFTLTISSLQPEDFATYYCQQSYSTPFTFG PGTKVDIK [SEQ ID NO: 79] | | |
| DNA for $V_H$-$V_L$ scFv | Cagctccagctccaagagtcagggccaggtctcgtgaaaccgagtgagaccctgtccct gacctgcacagtgagtggtggatcaatctcaagctctacctactattgggggtggattc ggcagccccctagaaaggggcttgagtggattggcagcactcattatcgaggatctacc tattataatccttctctgaaaagcagagttaccatctctgtggatacgtccaaaaatca gttcagtctgaaggtatcatccgtgactgctgccgacacggccgtgtactattgcgcga gggagctgacaggtgaggtctttgactactggggccagggcacactcgtgaccgtgtct tctgcctcaacaggagggggtgggagtggaggcggtggatcaggggagggagggagtga catccagatgacgcagtccccttccagcttgtccgcatctgtgggtgatagggtcacga ttacatgtagggctagtcagagtatttctagttacctgaattggtaccagcagaaacca ggcaaggcaccaaagttgctcatctatgcggcctcctctctgcaatctggcgtgccgtc cagatttagtggatcaggctccggaaccgatttcacccttacgatctcctcacttcaac ccgaggatttcgccacatattactgtcaacaaagctattctacaccgttcaccttcgga ccggggacaaaagtggatattaaa [SEQ ID NO: 80] | | | certain embodiments, the linker comprises the amino acid sequence set forth in SEQ ID NO: 2.

In certain embodiments, the variable regions within the extracellular antigen-binding domain of the CLEC12A-targeted chimeric receptor have to be linked one after another such that at the N-terminus of the extracellular antigen-binding domain, a heavy chain variable region ($V_H$) is positioned. In certain embodiments, if the extracellular In certain embodiments, the extracellular antigen-binding domain of the CLEC12A-targeted chimeric receptor (e.g., a CLEC12A-targeted scFv) comprises a $V_H$ CDR1 comprising the amino acid sequence set forth in SEQ ID NO: 81 or a conservative modification thereof, a $V_H$ CDR2 comprising the amino acid sequence set forth in SEQ ID NO: 82 or a conservative modification thereof, and a $V_H$ CDR3 comprising the amino acid sequence set forth in SEQ ID NO: 83 or a conservative modification thereof. SEQ ID NOs: 81-83 are provided in Table 9.

In certain embodiments, the extracellular antigen-binding domain of the CLEC12A-targeted chimeric receptor (e.g., a CLEC12A-targeted scFv) comprises a $V_L$ CDR1 comprising the amino acid sequence set forth in SEQ ID NO: 84 or a conservative modification thereof, a $V_L$ CDR2 comprising the amino acid sequence set forth in SEQ ID NO: 73 or a conservative modification thereof, and a $V_L$ CDR3 comprising the amino acid sequence set forth in SEQ ID NO: 85 or a conservative modification thereof. SEQ ID NOs: 73, 84 and 85 are provided in Table 9.

In certain embodiments, the extracellular antigen-binding domain of the CLEC12A-targeted chimeric receptor (e.g., a CLEC12A-targeted scFv) comprises a $V_H$ CDR1 comprising the amino acid sequence set forth in SEQ ID NO: 81 or a conservative modification thereof, a $V_H$ CDR2 comprising the amino acid sequence set forth in SEQ ID NO: 82 or a conservative modification thereof, a $V_H$ CDR3 comprising the amino acid sequence set forth in SEQ ID NO: 83 or a conservative modification thereof, a $V_L$ CDR1 comprising the amino acid sequence set forth in SEQ ID NO: 84 or a conservative modification thereof, a $V_L$ CDR2 comprising the amino acid sequence set forth in SEQ ID NO: 73 or a conservative modification, and a $V_L$ CDR3 comprising the amino acid sequence set forth in SEQ ID NO: 85 or a conservative modification thereof.

In certain embodiments, the extracellular antigen-binding domain of the CLEC12A-targeted chimeric receptor (e.g., a CLEC12A-targeted scFv) comprises a $V_H$ CDR1 comprising the amino acid sequence set forth in SEQ ID NO: 81, a $V_H$ CDR2 comprising the amino acid sequence set forth in SEQ ID NO: 82, a $V_H$ CDR3 comprising the amino acid sequence set forth in SEQ ID NO: 83, a $V_L$ CDR1 comprising the amino acid sequence set forth in SEQ ID NO: 84, a $V_L$ CDR2 comprising the amino acid sequence set forth in SEQ ID NO: 73, and a $V_L$ CDR3 comprising the amino acid sequence set forth in SEQ ID NO: 85.

In certain embodiments, the extracellular antigen-binding domain of the CLEC12A-targeted chimeric receptor (e.g., a CLEC12A-targeted scFv) comprises a $V_H$ comprising an amino acid sequence that is at least about 80% (e.g., at least about 85%, at least about 90%, or at least about 95%) homologous or identical to the amino acid sequence set forth in SEQ ID NO: 86. For example, the extracellular antigen-binding domain of the CLEC12A-targeted chimeric receptor (e.g., an scFv) comprises a $V_H$ comprising an amino acid sequence that is about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100% homologous or identical to SEQ ID NO: 86. In certain embodiments, the extracellular antigen-binding domain of the CLEC12A-targeted chimeric receptor comprises a $V_H$ comprising the amino acid sequence set forth in SEQ ID NO: 86. SEQ ID NO: 86 is provided in Table 9 below.

In certain embodiments, the extracellular antigen-binding domain of the CLEC12A-targeted chimeric receptor (e.g., a CLEC12A-targeted scFv) comprises a $V_L$ comprising an amino acid sequence that is at least about 80% (e.g., at least about 85%, at least about 90%, or at least about 95%) homologous or identical to the amino acid sequence set forth in SEQ ID NO: 87. For example, the extracellular antigen-binding domain of the CLEC12A-targeted chimeric receptor (e.g., a CLEC12A-targeted scFv) comprises a $V_L$ comprising an amino acid sequence that is about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100% homologous or identical to SEQ ID NO: 87. In certain embodiments, the extracellular antigen-binding domain of the CLEC12A-targeted chimeric receptor comprises a $V_L$ Comprising the amino acid sequence set forth in SEQ ID NO: 87. SEQ ID NO: 87 is provided in Table 9 below.

In certain embodiments, the extracellular antigen-binding domain of the CLEC12A-targeted chimeric receptor (e.g., a CLEC12A-targeted scFv) comprises a $V_H$ comprising the amino acid sequence set forth in SEQ ID NO: 86, and a $V_L$ comprising the amino acid sequence set forth in SEQ ID NO: 87. In certain embodiments, the $V_H$ and $V_L$ are linked via a linker. In certain embodiments, the linker comprises the amino acid sequence set forth in SEQ ID NO: 149. In certain embodiments, the linker comprises the amino acid sequence set forth in SEQ ID NO: 2.

In certain embodiments, the variable regions within the extracellular antigen-binding domain of the CLEC12A-targeted chimeric receptor have to be linked one after another such that at the N-terminus of the extracellular antigen-binding domain, a heavy chain variable region ($V_H$) is positioned. In certain embodiments, if the extracellular antigen-binding domain of the CLEC12A-targeted chimeric receptor is an scFv, the variable regions are positioned from the N- to the C-terminus: $V_H$-$V_L$. In certain embodiments, the CLEC12A-targeted scFv comprises or consists of the amino acid sequence set forth in SEQ ID NO: 88, which is provided in Table 9. In certain embodiments, the CLEC12A-targeted scFv is designated as "CLEC12A-B". The CDRs provided in Table 9 are identified according to the IMGT numbering system.

TABLE 9

| | (CLEC12A-B) | | |
|---|---|---|---|
| CDRs | 1 | 2 | 3 |
| $V_H$ | GGSISTYY [SEQ ID NO: 81] | IYYSGST [SEQ ID NO: 82] | AREDYYGSGSPFDY [SEQ ID NO: 83] |
| $V_L$ | QGIRYD [SEQ ID NO: 84] | AAS [SEQ ID NO: 73] | LQDYNFPRT [SEQ ID NO: 85] |
| Full $V_H$ | QVQLQESGPGLVKPSETLSLTCTVSGGSISTYYWSWIRQPPGKGLEWIGYIYYSGSTKYNPSLKSRVTISVDTSKNLFSLKLSSVTAADTAVYYCAREDYYGSGSPFDYWGQGTLVTVSS [SEQ ID NO: 86] | | |

TABLE 9-continued

(CLEC12A-B)

| CDRs | 1 | 2 | 3 |
|------|---|---|---|

Full $V_L$: AIQMTQSPSSLSASVGDRVTITCRASQGIRYDLGWYQQKPGKAPKLLIYAASSLQSGVP SRFSGSGSGTDFTLTISSLQPEDFATYYCLQDYNFPRTFGQGTKVEIK [SEQ ID NO: 87]

$V_H$-$V_L$ scFv: QVQLQESGPGLVKPSETLSLTCTVSGGSISTYYWSWIRQPPGKGLEWIGYIYYSGSTKY NPSLKSRVTISVDTSKNLFSLKLSSVTAADTAVYYCAREDYYGSGSPFDYWGQGTLVTV SSASTGGGGSGGGGSGGGGSAIQMTQSPSSLSASVGDRVTITCRASQGIRYDLGWYQQK PGKAPKLLIYAASSLQSGVPSRFSGSGSGTDFTLTISSLQPEDFATYYCLQDYNFPRTF GQGTKVEIK [SEQ ID NO: 88]

In certain embodiments, the extracellular antigen-binding domain of the CLEC12A-targeted chimeric receptor (e.g., a CLEC12A-targeted scFv) comprises a $V_H$ CDR1 comprising the amino acid sequence set forth in SEQ ID NO: 89 or a conservative modification thereof, a $V_H$ CDR2 comprising the amino acid sequence set forth in SEQ ID NO: 90 or a conservative modification thereof, and a $V_H$ CDR3 comprising the amino acid sequence set forth in SEQ ID NO: 91 or a conservative modification thereof. SEQ ID NOs: 89-91 are provided in Table 10.

In certain embodiments, the extracellular antigen-binding domain of the CLEC12A-targeted chimeric receptor (e.g., a CLEC12A-targeted scFv) comprises a $V_L$ CDR1 comprising the amino acid sequence set forth in SEQ ID NO: 92 or a conservative modification thereof, a $V_L$ CDR2 comprising the amino acid sequence set forth in SEQ ID NO: 93 or a conservative modification thereof, and a $V_L$ CDR3 comprising the amino acid sequence set forth in SEQ ID NO: 94 or a conservative modification thereof. SEQ ID NOs: 92-94 are provided in Table 10.

In certain embodiments, the extracellular antigen-binding domain of the CLEC12A-targeted chimeric receptor (e.g., an scFv) comprises a $V_H$ CDR1 comprising the amino acid sequence set forth in SEQ ID NO: 89 or a conservative modification thereof, a $V_H$ CDR2 comprising the amino acid sequence set forth in SEQ ID NO: 90 or a conservative modification thereof, a $V_H$ CDR3 comprising the amino acid sequence set forth in SEQ ID NO: 91 or a conservative modification thereof, a $V_L$ CDR1 comprising the amino acid sequence set forth in SEQ ID NO: 92 or a conservative modification thereof, a $V_L$ CDR2 comprising the amino acid sequence set forth in SEQ ID NO: 93 or a conservative modification, and a $V_L$ CDR3 comprising the amino acid sequence set forth in SEQ ID NO: 94 or a conservative modification thereof.

In certain embodiments, the extracellular antigen-binding domain of the CLEC12A-targeted chimeric receptor (e.g., a CLEC12A-targeted scFv) comprises a $V_H$ CDR1 comprising the amino acid sequence set forth in SEQ ID NO: 89, a $V_H$ CDR2 comprising the amino acid sequence set forth in SEQ ID NO: 90, a $V_H$ CDR3 comprising the amino acid sequence set forth in SEQ ID NO: 91, a $V_L$ CDR1 comprising the amino acid sequence set forth in SEQ ID NO: 92, a $V_L$ CDR2 comprising the amino acid sequence set forth in SEQ ID NO: 93, and a $V_L$ CDR3 comprising the amino acid sequence set forth in SEQ ID NO: 94.

In certain embodiments, the extracellular antigen-binding domain of the CLEC12A-targeted chimeric receptor (e.g., a CLEC12A-targeted scFv) comprises a $V_H$ comprising an amino acid sequence that is at least about 80% (e.g., at least about 85%, at least about 90%, or at least about 95%) homologous or identical to the amino acid sequence set forth in SEQ ID NO: 95. For example, the extracellular antigen-binding domain of the CLEC12A-targeted chimeric receptor (e.g., a CLEC12A-targeted scFv) comprises a $V_H$ comprising an amino acid sequence that is about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100% homologous or identical to SEQ ID NO: 95. In certain embodiments, the extracellular antigen-binding domain of the CLEC12A-targeted chimeric receptor comprises a $V_H$ Comprising the amino acid sequence set forth in SEQ ID NO: 95. SEQ ID NO: 95 is provided in Table 10 below.

In certain embodiments, the extracellular antigen-binding domain of the CLEC12A-targeted chimeric receptor (e.g., a CLEC12A-targeted scFv) comprises a $V_L$ comprising an amino acid sequence that is at least about 80% (e.g., at least about 85%, at least about 90%, or at least about 95%) homologous or identical to the amino acid sequence set forth in SEQ ID NO: 96. For example, the extracellular antigen-binding domain of the CLEC12A-targeted chimeric receptor (e.g., a CLEC12A-targeted scFv) comprises a $V_L$ comprising an amino acid sequence that is about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100% homologous or identical to SEQ ID NO: 96. In certain embodiments, the extracellular antigen-binding domain of the CLEC12A-targeted chimeric receptor comprises a $V_L$ Comprising the amino acid sequence set forth in SEQ ID NO: 96. SEQ ID NO: 96 is provided in Table 10 below.

In certain embodiments, the extracellular antigen-binding domain of the CLEC12A-targeted chimeric receptor (e.g., a CLEC12A-targeted scFv) comprises a $V_H$ comprising the amino acid sequence set forth in SEQ ID NO: 96, and a $V_L$ comprising the amino acid sequence set forth in SEQ ID NO: 96. In certain embodiments, the $V_H$ and $V_L$ are linked via a linker. In certain embodiments, the linker comprises the amino acid sequence set forth in SEQ ID NO: 149. In certain embodiments, the linker comprises the amino acid sequence set forth in SEQ ID NO: 2.

In certain embodiments, the variable regions within the extracellular antigen-binding domain of the CLEC12A-targeted chimeric receptor have to be linked one after another such that at the N-terminus of the extracellular antigen-binding domain, a heavy chain variable region ($V_H$) is positioned. In certain embodiments, if the extracellular antigen-binding domain of the CLEC12A-targeted chimeric receptor is an scFv, the variable regions are positioned from the N- to the C-terminus: $V_H$-$V_L$. In certain embodiments, the CLEC12A-targeted scFv comprises the amino acid sequence set forth in SEQ ID NO: 97, which is provided in Table 10. In certain embodiments, the CLEC12A-targeted scFv is designated as "CLEC12A-C". The CDRs provided in Table 10 are identified according to the IMGT numbering system.

TABLE 10

(CLEC12A-C)

| CDRs | 1 | 2 | 3 |
|---|---|---|---|
| $V_H$ | GFTFSSYG [SEQ ID NO: 89] | ISYDGSDK [SEQ ID NO: 90] | ARDKGYYFDY [SEQ ID NO: 91] |
| $V_L$ | QSVGNRY [SEQ ID NO: 92] | GAS [SEQ ID NO: 93] | QQDYNLPLT [SEQ ID NO: 94] |
| Full $V_H$ | QVQLVESGGGWQPGRSLRLSCAASGFTFSSYGMHWVRQAPGKGLEWVAVISYDGSDKY YVDSVKGRFTISRDNSKNTLYLHMNSLRAEDTAVYYCARDKGYYFDYWGQGTLVTVSS [SEQ ID NO: 95] | | |
| Full $V_L$ | EIVMTQSPATLSLSPGERATLSCRASQSVGNRYLSWYQQKPGQAPRLLIYGASTRATGI PARFSGSGSGTDFTLTISSLQPEDFAVYYCQQDYNLPLTFGGGTKVEIK [SEQ ID NO: 96] | | |
| $V_H$-$V_L$ scFv | QVQLVESGGGVVQPGRSLRLSCAASGFTFSSYGMHWVRQAPGKGLEWVAVISYDGSDKY YVDSVKGRFTISRDNSKNTLYLHMNSLRAEDTAVYYCARDKGYYFDYWGQGTLVTVSSA STGGGGSGGGGSGGGGSEIVMTQSPATLSLSPGERATLSCRASQSVGNRYLSWYQQKPG QAPRLLIYGASTRATGIPARFSGSGSGTDFTLTISSLQPEDFAVYYCQQDYNLPLTFGG GTKVEIK [SEQ ID NO: 97] | | |

In certain embodiments, the extracellular antigen-binding domain of the CLEC12A-targeted chimeric receptor (e.g., a CLEC12A-targeted scFv) comprises a $V_H$ CDR1 comprising the amino acid sequence set forth in SEQ ID NO: 89 or a conservative modification thereof, a $V_H$ CDR2 comprising the amino acid sequence set forth in SEQ ID NO: 90 or a conservative modification thereof, and a $V_H$ CDR3 comprising the amino acid sequence set forth in SEQ ID NO: 98 or a conservative modification thereof. SEQ ID NOs: 89, 90, and 98 are provided in Table 11.

In certain embodiments, the extracellular antigen-binding domain of the CLEC12A-targeted chimeric receptor (e.g., a CLEC12A-targeted scFv) comprises a $V_L$ CDR1 comprising the amino acid sequence set forth in SEQ ID NO: 99 or a conservative modification thereof, a $V_L$ CDR2 comprising the amino acid sequence set forth in SEQ ID NO: 93 or a conservative modification thereof, and a $V_L$ CDR3 comprising the amino acid sequence set forth in SEQ ID NO: 151 or a conservative modification thereof. SEQ ID NOs: 93, 99, and 151 are provided in Table 11.

In certain embodiments, the extracellular antigen-binding domain of the CLEC12A-targeted chimeric receptor (e.g., a CLEC12A-targeted scFv) comprises a $V_H$ CDR1 comprising the amino acid sequence set forth in SEQ ID NO: 89 or a conservative modification thereof, a $V_H$ CDR2 comprising the amino acid sequence set forth in SEQ ID NO: 90 or a conservative modification thereof, a $V_H$ CDR3 comprising the amino acid sequence set forth in SEQ ID NO: 98 or a conservative modification thereof, a $V_L$ CDR1 comprising the amino acid sequence set forth in SEQ ID NO: 99 or a conservative modification thereof, a $V_L$ CDR2 comprising the amino acid sequence set forth in SEQ ID NO: 93 or a conservative modification, and a $V_L$ CDR3 comprising the amino acid sequence set forth in SEQ ID NO: 151 or a conservative modification thereof.

In certain embodiments, the extracellular antigen-binding domain of the CLEC12A-targeted chimeric receptor (e.g., a CLEC12A-targeted scFv) comprises a $V_H$ CDR1 comprising the amino acid sequence set forth in SEQ ID NO: 89, a $V_H$ CDR2 comprising the amino acid sequence set forth in SEQ ID NO: 90, a $V_H$ CDR3 comprising the amino acid sequence set forth in SEQ ID NO: 98, a $V_L$ CDR1 comprising the amino acid sequence set forth in SEQ ID NO: 99, a $V_L$ CDR2 comprising the amino acid sequence set forth in SEQ ID NO: 93, and a $V_L$ CDR3 comprising the amino acid sequence set forth in SEQ ID NO: 151.

In certain embodiments, the extracellular antigen-binding domain of the CLEC12A-targeted chimeric receptor (e.g., a CLEC12A-targeted scFv) comprises a $V_H$ comprising an amino acid sequence that is at least about 80% (e.g., at least about 85%, at least about 90%, or at least about 95%) homologous or identical to the amino acid sequence set forth in SEQ ID NO: 100. For example, the extracellular antigen-binding domain of the CLEC12A-targeted chimeric receptor (e.g., a CLEC12A-targeted scFv) comprises a $V_H$ comprising an amino acid sequence that is about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100% homologous or identical to SEQ ID NO: 100. In certain embodiments, the extracellular antigen-binding domain of the CLEC12A-targeted chimeric receptor comprises a $V_H$ Comprising the amino acid sequence set forth in SEQ ID NO: 100. SEQ ID NO: 100 is provided in Table 11 below.

In certain embodiments, the extracellular antigen-binding domain of the CLEC12A-targeted chimeric receptor (e.g., a CLEC12A-targeted scFv) comprises a $V_L$ comprising an amino acid sequence that is at least about 80% (e.g., at least about 85%, at least about 90%, or at least about 95%) homologous or identical to the amino acid sequence set forth in SEQ ID NO: 101. For example, the extracellular antigen-binding domain of the CLEC12A-targeted chimeric receptor (e.g., a CLEC12A-targeted scFv) comprises a $V_L$ comprising an amino acid sequence that is about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100% homologous or identical to SEQ ID NO: 101. In certain embodiments, the extracellular antigen-binding domain of the CLEC12A-targeted chimeric receptor comprises a $V_L$ Comprising the amino acid sequence set forth in SEQ ID NO: 101. SEQ ID NO: 101 is provided in Table 11 below.

In certain embodiments, the extracellular antigen-binding domain of the CLEC12A-targeted chimeric receptor (e.g., a CLEC12A-targeted scFv) comprises a $V_H$ comprising the amino acid sequence set forth in SEQ ID NO: 100, and a $V_L$ comprising the amino acid sequence set forth in SEQ ID NO: 101. In certain embodiments, the $V_H$ and $V_L$ are linked via a linker. In certain embodiments, the linker comprises the amino acid sequence set forth in SEQ ID NO: 149. In certain embodiments, the linker comprises the amino acid sequence set forth in SEQ ID NO: 2.

In certain embodiments, the variable regions within the extracellular antigen-binding domain of the CLEC12A-targeted chimeric receptor have to be linked one after another such that at the N-terminus of the extracellular antigen-binding domain, a heavy chain variable region ($V_H$) is positioned. In certain embodiments, if the extracellular antigen-binding domain of the CLEC12A-targeted chimeric receptor is an scFv, the variable regions are positioned from the N- to the C-terminus: $V_H$-$V_L$. In certain embodiments, the CLEC12A-targeted scFv comprises the amino acid sequence set forth in SEQ ID NO: 102, which is provided in Table 11. In certain embodiments, the CLEC12A-targeted scFv is designated as "CLEC12A-D". The CDRs provided in Table 11 are identified according to the IMGT numbering system.

In certain embodiments, the extracellular antigen-binding domain of the CLEC12A-targeted chimeric receptor (e.g., a CLEC12A-targeted scFv) comprises a $V_H$ CDR1 comprising the amino acid sequence set forth in SEQ ID NO: 81 or a conservative modification thereof, a $V_H$ CDR2 comprising the amino acid sequence set forth in SEQ ID NO: 103 or a conservative modification thereof, and a $V_H$ CDR3 comprising the amino acid sequence set forth in SEQ ID NO: 83 or a conservative modification thereof. SEQ ID NOs: 81, 83, and 103 are provided in Table 12.

In certain embodiments, the extracellular antigen-binding domain of the CLEC12A-targeted chimeric receptor (e.g., a CLEC12A-targeted scFv) comprises a $V_L$ CDR1 comprising the amino acid sequence set forth in SEQ ID NO: 104 or a conservative modification thereof, a $V_L$ CDR2 comprising the amino acid sequence set forth in SEQ ID NO: 73 or a conservative modification thereof, and a $V_L$ CDR3 comprising the amino acid sequence set forth in SEQ ID NO: 105 or a conservative modification thereof. SEQ ID NOs: 73, 104, and 105 are provided in Table 12.

In certain embodiments, the extracellular antigen-binding domain of the CLEC12A-targeted chimeric receptor (e.g., a CLEC12A-targeted scFv) comprises a $V_H$ CDR1 comprising the amino acid sequence set forth in SEQ ID NO: 81 or a conservative modification thereof, a $V_H$ CDR2 comprising the amino acid sequence set forth in SEQ ID NO: 103 or a conservative modification thereof, a $V_H$ CDR3 comprising the amino acid sequence set forth in SEQ ID NO: 83 or a conservative modification thereof, a $V_L$ CDR1 comprising the amino acid sequence set forth in SEQ ID NO: 104 or a conservative modification thereof, a $V_L$ CDR2 comprising the amino acid sequence set forth in SEQ ID NO: 73 or a conservative modification, and a $V_L$ CDR3 comprising the amino acid sequence set forth in SEQ ID NO: 105 or a conservative modification thereof.

In certain embodiments, the extracellular antigen-binding domain of the CLEC12A-targeted chimeric receptor (e.g., a CLEC12A-targeted scFv) comprises a $V_H$ CDR1 comprising the amino acid sequence set forth in SEQ ID NO: 81, a $V_H$ CDR2 comprising the amino acid sequence set forth in SEQ ID NO: 103, a $V_H$ CDR3 comprising the amino acid sequence set forth in SEQ ID NO: 83, a $V_L$ CDR1 comprising the amino acid sequence set forth in SEQ ID NO: 104, a $V_L$ CDR2 comprising the amino acid sequence set forth in SEQ ID NO: 73, and a $V_L$ CDR3 comprising the amino acid sequence set forth in SEQ ID NO: 105.

TABLE 11

(CLEC12A-D)

| CDRs | 1 | 2 | 3 |
|---|---|---|---|
| $V_H$ | GETFSSYG [SEQ ID NO: 89] | ISYDGSDK [SEQ ID NO: 90] | ARDGSRYFDY [SEQ ID NO: 98] |
| $V_L$ | QSVHSKY [SEQ ID NO: 99] | GAS [SEQ ID NO: 93] | QQDYNLPIT [SEQ ID NO: 151] |
| Full $V_H$ | QVQLVESGGGWQPGRSLRLSCAASGFTFSSYGMHWVRQAPGKGLEWVAVISYDGSDKYSADSVKGRFNISRDNSKNTLYLQMNSLRAEDTAVYYCARDGSRYFDYWGQGTLVTVSS [SEQ ID NO: 100] | | |
| Full $V_L$ | EIFMTQSPATLSLSPGERATLSCRASQSVHSKYLSWYQQKPGQAPSLLIYGASTRATGIPARFSGSGSGTDFTLTISSLQPEDFAVYYCQQDYNLPITFGQGTRLEIK [SEQ ID NO: 101] | | |
| $V_H$-$V_L$ scFv | QVQLVESGGGVVQPGRSLRLSCAASGFTFSSYGMHWVRQAPGKGLEWVAVISYDGSDKYSADSVKGRFNISRDNSKNTLYLQMNSLRAEDTAVYYCARDGSRYFDYWGQGTLVTVSSASTGGGGSGGGGSGGGGSEIFMTQSPATLSLSPGERATLSCRASQSVHSKYLSWYQQKPGQAPSLLIYGASTRATGIPARFSGSGSGTDFTLTISSLQPEDFAVYYCQQDYNLPITFGQGTRLEIK [SEQ ID NO: 102] | | |

In certain embodiments, the extracellular antigen-binding domain of the CLEC12A-targeted chimeric receptor (e.g., a CLEC12A-targeted scFv) comprises a $V_H$ comprising an amino acid sequence that is at least about 80% (e.g., at least about 85%, at least about 90%, or at least about 95%) homologous or identical to the amino acid sequence set forth in SEQ ID NO: 106. For example, the extracellular antigen-binding domain of the CLEC12A-targeted chimeric receptor (e.g., a CLEC12A-targeted scFv) comprises a $V_H$ comprising an amino acid sequence that is about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100% homologous or identical to SEQ ID NO: 106. In certain embodiments, the extracellular antigen-binding domain of the CLEC12A-targeted chimeric receptor comprises a $V_H$ Comprising the amino acid sequence set forth in SEQ ID NO: 106. SEQ ID NO: 106 is provided in Table 12 below.

In certain embodiments, the extracellular antigen-binding domain of the CLEC12A-targeted chimeric receptor (e.g., a CLEC12A-targeted scFv) comprises a $V_L$ comprising an amino acid sequence that is at least about 80% (e.g., at least about 85%, at least about 90%, or at least about 95%) homologous or identical to the amino acid sequence set forth in SEQ ID NO: 107. For example, the extracellular antigen-binding domain of the CLEC12A-targeted chimeric receptor (e.g., a CLEC12A-targeted scFv) comprises a $V_L$ comprising an amino acid sequence that is about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100% homologous or identical to SEQ ID NO: 107. In certain embodiments, the extracellular antigen-binding domain of the CLEC12A-targeted chimeric receptor comprises a $V_L$ Comprising the amino acid sequence set forth in SEQ ID NO: 107. SEQ ID NO: 107 is provided in Table 12 below.

In certain embodiments, the extracellular antigen-binding domain of the CLEC12A-targeted chimeric receptor (e.g., a CLEC12A-targeted scFv) comprises a $V_H$ comprising the amino acid sequence set forth in SEQ ID NO: 106, and a $V_L$ comprising the amino acid sequence set forth in SEQ ID NO: 107. In certain embodiments, the $V_H$ and $V_L$ are linked via a linker. In certain embodiments, the linker comprises the amino acid sequence set forth in SEQ ID NO: 149. In certain embodiments, the linker comprises the amino acid sequence set forth in SEQ ID NO: 2.

In certain embodiments, the variable regions within the extracellular antigen-binding domain of the CLEC12A-targeted chimeric receptor have to be linked one after another such that at the N-terminus of the extracellular antigen-binding domain, a heavy chain variable region ($V_H$) is positioned. In certain embodiments, if the extracellular antigen-binding domain of the CLEC12A-targeted chimeric receptor is an scFv, the variable regions are positioned from the N- to the C-terminus: $V_H$-$V_L$. In certain embodiments, the CLEC12A-targeted scFv comprises the amino acid sequence set forth in SEQ ID NO: 108, which is provided in Table 12. In certain embodiments, the CLEC12A-targeted scFv is designated as "CLEC12A-E". The CDRs provided in Table 12 are identified according to the IMGT numbering system.

TABLE 12

| | (CLEC12A-E) | | |
|---|---|---|---|
| CDRs | 1 | 2 | 3 |
| $V_H$ | GGSISTYY [SEQ ID NO: 81] | IYFSGST [SEQ ID NO: 103] | AREDYYGSGSPFDY [SEQ ID NO: 83] |
| $V_L$ | QGIRND [SEQ ID NO: 104] | AAS [SEQ ID NO: 73] | LQDYNYPRT [SEQ ID NO: 105] |
| Full $V_H$ | QVQLQESGPGLVKPSETLSLTCTVSGGSISTYYWSWIRQPPGKGLEWLGYIYFSGSTNY NPSLKSRLTISVAASKSQFSLKLSSVTAADTAVYYCAREDYYGSGSPFDYWGQGTLVTV SS [SEQ ID NO: 106] | | |
| Full $V_L$ | AIQMTQSPSSLSASVGDRVTITCRASQGIRNDLGWFQQKPGKAPKLLIYAASSLQSGVP SRFSGSGSGTYFTLTISSLQPEDSATYYCLQDYNYPRTFGQGTKVEIK [SEQ ID NO: 107] | | |
| $V_H$-$V_L$ scFv | QVQLQESGPGLVKPSETLSLTCTVSGGSISTYYWSWIRQPPGKGLEWLGYIYFSGSTNY NPSLKSRLTISVAASKSQFSLKLSSVTAADTAVYYCAREDYYGSGSPFDYWGQGTLVTV SSASTGGGGSGGGGSGGGGSAIQMTQSPSSLSASVGDRVTITCRASQGIRNDLGWFQQK PGKAPKLLIYAASSLQSGVPSRFSGSGSGTYFTLTISSLQPEDSATYYCLQDYNYPRTF GQGTKVEIK [SEQ ID NO: 108] | | |

In certain embodiments, the extracellular antigen-binding domain of the CLEC12A-targeted chimeric receptor (e.g., a CLEC12A-targeted scFv) comprises a $V_H$ CDR1 comprising the amino acid sequence set forth in SEQ ID NO: 109 or a conservative modification thereof, a $V_H$ CDR2 comprising the amino acid sequence set forth in SEQ ID NO: 103 or a conservative modification thereof, and a $V_H$ CDR3 comprising the amino acid sequence set forth in SEQ ID NO: 83 or a conservative modification thereof. SEQ ID NOs: 83, 103, and 109 are provided in Table 13.

In certain embodiments, the extracellular antigen-binding domain of the CLEC12A-targeted chimeric receptor (e.g., a CLEC12A-targeted scFv) comprises a $V_L$ CDR1 comprising the amino acid sequence set forth in SEQ ID NO: 110 or a conservative modification thereof, a $V_L$ CDR2 comprising the amino acid sequence set forth in SEQ ID NO: 73 or a conservative modification thereof, and a $V_L$ CDR3 comprising the amino acid sequence set forth in SEQ ID NO: 85 or a conservative modification thereof. SEQ ID NOs: 73, 85, and 110 are provided in Table 13.

In certain embodiments, the extracellular antigen-binding domain of the CLEC12A-targeted chimeric receptor (e.g., a CLEC12A-targeted scFv) comprises a $V_H$ CDR1 comprising the amino acid sequence set forth in SEQ ID NO: 109 or a conservative modification thereof, a $V_H$ CDR2 comprising the amino acid sequence set forth in SEQ ID NO: 103 or a conservative modification thereof, a $V_H$ CDR3 comprising the amino acid sequence set forth in SEQ ID NO: 83 or a conservative modification thereof, a $V_L$ CDR1 comprising the amino acid sequence set forth in SEQ ID NO: 110 or a conservative modification thereof, a $V_L$ CDR2 comprising the amino acid sequence set forth in SEQ ID NO: 73 or a conservative modification, and a $V_L$ CDR3 comprising the amino acid sequence set forth in SEQ ID NO: 85 or a conservative modification thereof.

In certain embodiments, the extracellular antigen-binding domain of the CLEC12A-targeted chimeric receptor (e.g., a CLEC12A-targeted scFv) comprises a $V_H$ CDR1 comprising the amino acid sequence set forth in SEQ ID NO: 109, a $V_H$ CDR2 comprising the amino acid sequence set forth in SEQ ID NO: 103, a $V_H$ CDR3 comprising the amino acid sequence set forth in SEQ ID NO: 83, a $V_L$ CDR1 comprising the amino acid sequence set forth in SEQ ID NO: 110, a $V_L$ CDR2 comprising the amino acid sequence set forth in SEQ ID NO: 73, and a $V_L$ CDR3 comprising the amino acid sequence set forth in SEQ ID NO: 85.

In certain embodiments, the extracellular antigen-binding domain of the CLEC12A-targeted chimeric receptor (e.g., a CLEC12A-targeted scFv) comprises a $V_H$ comprising an amino acid sequence that is at least about 80% (e.g., at least about 85%, at least about 90%, or at least about 95%) homologous or identical to the amino acid sequence set forth in SEQ ID NO: 111. For example, the extracellular antigen-binding domain of the CLEC12A-targeted chimeric receptor (e.g., a CLEC12A-targeted scFv) comprises a $V_H$ comprising an amino acid sequence that is about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100% homologous or identical to SEQ ID NO: 111. In certain embodiments, the extracellular antigen-binding domain of the CLEC12A-targeted chimeric receptor comprises a $V_H$ Comprising the amino acid sequence set forth in SEQ ID NO: 111. SEQ ID NO: 111 is provided in Table 13 below.

In certain embodiments, the extracellular antigen-binding domain of the CLEC12A-targeted chimeric receptor (e.g., a CLEC12A-targeted scFv) comprises a $V_L$ comprising an amino acid sequence that is at least about 80% (e.g., at least about 85%, at least about 90%, or at least about 95%) homologous or identical to the amino acid sequence set forth in SEQ ID NO: 112. For example, the extracellular antigen-binding domain of the CLEC12A-targeted chimeric receptor (e.g., a CLEC12A-targeted scFv) comprises a $V_L$ comprising an amino acid sequence that is about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100% homologous or identical to SEQ ID NO: 112. In certain embodiments, the extracellular antigen-binding domain of the CLEC12A-targeted chimeric receptor comprises a $V_L$ Comprising the amino acid sequence set forth in SEQ ID NO: 112. SEQ ID NO: 112 is provided in Table 13 below.

In certain embodiments, the extracellular antigen-binding domain of the CLEC12A-targeted chimeric receptor (e.g., a CLEC12A-targeted scFv) comprises a $V_H$ comprising the amino acid sequence set forth in SEQ ID NO: 111, and a $V_L$ comprising the amino acid sequence set forth in SEQ ID NO: 112. In certain embodiments, the $V_H$ and $V_L$ are linked via a linker. In certain embodiments, the linker comprises the amino acid sequence set forth in SEQ ID NO: 149. In certain embodiments, the linker comprises the amino acid sequence set forth in SEQ ID NO: 2.

In certain embodiments, the variable regions within the extracellular antigen-binding domain of the CLEC12A-targeted chimeric receptor have to be linked one after another such that at the N-terminus of the extracellular antigen-binding domain, a heavy chain variable region ($V_H$) is positioned. In certain embodiments, if the extracellular antigen-binding domain of the CLEC12A-targeted chimeric receptor is an scFv, the variable regions are positioned from the N- to the C-terminus: $V_H$—$V_L$. In certain embodiments, the CLEC12A-targeted scFv comprises the amino acid sequence set forth in SEQ ID NO: 113, which is provided in Table 13. In certain embodiments, the CLEC12A-targeted scFv is designated as "CLEC12A-F". The CDRs provided in Table 13 are identified according to the IMGT numbering system.

TABLE 13

| | (CLEC12A-F) | | |
|---|---|---|---|
| CDRs | 1 | 2 | 3 |
| $V_H$ | GGSISTDY [SEQ ID NO: 109] | IYFSGST [SEQ ID NO: 103] | AREDYYGSGSPFDY [SEQ ID NO: 83] |
| $V_L$ | QDIRND [SEQ ID NO: 110] | AAS [SEQ ID NO: 73] | LQDYNFPRT [SEQ ID NO: 85] |
| Full $V_H$ | QVQLQESGPGLVKPSETLSLTCTVSGGSISTDYWSWIRQPPGKGLEWIGYIYFSGSTKYNPSLKSRVTISVDTSKNQFSLKLSSVTAADTAVYYCAREDYYGSGSPFDYWGQGTLVTVSS [SEQ ID NO: 111] | | |
| Full $V_L$ | AIQMTQSPSSLSASVGDRVTITCRASQDIRNDLGWFQQKPGKAPKLLIYAASSLQSGVPSRFSGSGSGTDFTLTISSLQPEDFATYYCLQDYNFPRTFGQGTKVEIK [SEQ ID NO: 112] | | |
| $V_H$-$V_L$ scFv | QVQLQESGPGLVKPSETLSLTCTVSGGSISTDYWSWIRQPPGKGLEWIGYIYFSGSTKYNPSLKSRVTISVDTSKNQFSLKLSSVTAADTAVYYCAREDYYGSGSPFDYWGQGTLVTVSSASTGGGGSGGGGSGGGGSAIQMTQSPSSLSASVGDRVTITCRASQDIRNDLGWFQQKPGKAPKLLIYAASSLQSGVPSRFSGSGSGTDFTLTISSLQPEDFATYYCLQDYNFPRTFGQGTKVEIK [SEQ ID NO: 113] | | |

In certain embodiments, the extracellular antigen-binding domain of the CLEC12A-targeted chimeric receptor (e.g., a CLEC12A-targeted scFv) comprises a $V_H$ CDR1 comprising the amino acid sequence set forth in SEQ ID NO: 89 or a conservative modification thereof, a $V_H$ CDR2 comprising the amino acid sequence set forth in SEQ ID NO: 90 or a conservative modification thereof, and a $V_H$ CDR3 comprising the amino acid sequence set forth in SEQ ID NO: 114 or a conservative modification thereof. SEQ ID NOs: 89, 90, and 114 are provided in Table 14.

In certain embodiments, the extracellular antigen-binding domain of the CLEC12A-targeted chimeric receptor (e.g., a CLEC12A-targeted scFv) comprises a $V_L$ CDR1 comprising the amino acid sequence set forth in SEQ ID NO: 115 or a conservative modification thereof, a $V_L$ CDR2 comprising the amino acid sequence set forth in SEQ ID NO: 93 or a conservative modification thereof, and a $V_L$ CDR3 comprising the amino acid sequence set forth in SEQ ID NO: 116 or a conservative modification thereof. SEQ ID NOs: 93, 115, and 116 are provided in Table 14.

In certain embodiments, the extracellular antigen-binding domain of the CLEC12A-targeted chimeric receptor (e.g., a CLEC12A-targeted scFv) comprises a $V_H$ CDR1 comprising the amino acid sequence set forth in SEQ ID NO: 89 or a conservative modification thereof, a $V_H$ CDR2 comprising the amino acid sequence set forth in SEQ ID NO: 90 or a conservative modification thereof, a $V_H$ CDR3 comprising the amino acid sequence set forth in SEQ ID NO: 114 or a conservative modification thereof, a $V_L$ CDR1 comprising the amino acid sequence set forth in SEQ ID NO: 115 or a conservative modification thereof, a $V_L$ CDR2 comprising the amino acid sequence set forth in SEQ ID NO: 93 or a conservative modification, and a $V_L$ CDR3 comprising the amino acid sequence set forth in SEQ ID NO: 116 or a conservative modification thereof.

In certain embodiments, the extracellular antigen-binding domain of the CLEC12A-targeted chimeric receptor (e.g., a CLEC12A-targeted scFv) comprises a $V_H$ CDR1 comprising the amino acid sequence set forth in SEQ ID NO: 89, a $V_H$ CDR2 comprising the amino acid sequence set forth in SEQ ID NO: 90, a $V_H$ CDR3 comprising the amino acid sequence set forth in SEQ ID NO: 114, a $V_L$ CDR1 comprising the amino acid sequence set forth in SEQ ID NO: 115, a $V_L$ CDR2 comprising the amino acid sequence set forth in SEQ ID NO: 93, and a $V_L$ CDR3 comprising the amino acid sequence set forth in SEQ ID NO: 116.

In certain embodiments, the extracellular antigen-binding domain of the CLEC12A-targeted chimeric receptor (e.g., a CLEC12A-targeted scFv) comprises a $V_H$ comprising an amino acid sequence that is at least about 80% (e.g., at least about 85%, at least about 90%, or at least about 95%) homologous or identical to the amino acid sequence set forth in SEQ ID NO: 117. For example, the extracellular antigen-binding domain of the CLEC12A-targeted chimeric receptor (e.g., a CLEC12A-targeted scFv) comprises a $V_H$ comprising an amino acid sequence that is about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100% homologous or identical to SEQ ID NO: 117. In certain embodiments, the extracellular antigen-binding domain of the CLEC12A-targeted chimeric receptor comprises a $V_H$ Comprising the amino acid sequence set forth in SEQ ID NO: 117. SEQ ID NO: 117 is provided in Table 14 below.

In certain embodiments, the extracellular antigen-binding domain of the CLEC12A-targeted chimeric receptor (e.g., a CLEC12A-targeted scFv) comprises a $V_L$ comprising an amino acid sequence that is at least about 80% (e.g., at least about 85%, at least about 90%, or at least about 95%) homologous or identical to the amino acid sequence set forth in SEQ ID NO: 118. For example, the extracellular antigen-binding domain of the CLEC12A-targeted chimeric receptor (e.g., a CLEC12A-targeted scFv) comprises a $V_L$ comprising an amino acid sequence that is about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100% homologous or identical to SEQ ID NO: 118. In certain embodiments, the extracellular antigen-binding domain of the CLEC12A-targeted chimeric receptor comprises a $V_L$ Comprising the amino acid sequence set forth in SEQ ID NO: 118. SEQ ID NO: 118 is provided in Table 14 below.

In certain embodiments, the extracellular antigen-binding domain of the CLEC12A-targeted chimeric receptor (e.g., a CLEC12A-targeted scFv) comprises a $V_H$ comprising the amino acid sequence set forth in SEQ ID NO: 117, and a $V_L$ comprising the amino acid sequence set forth in SEQ ID NO: 118. In certain embodiments, the $V_H$ and $V_L$ are linked via a linker. In certain embodiments, the linker comprises the amino acid sequence set forth in SEQ ID NO: 149. In certain embodiments, the linker comprises the amino acid sequence set forth in SEQ ID NO: 2.

In certain embodiments, the variable regions within the extracellular antigen-binding domain of the CLEC12A-targeted chimeric receptor have to be linked one after another such that at the N-terminus of the extracellular antigen-binding domain, a heavy chain variable region ($V_H$) is positioned. In certain embodiments, if the extracellular antigen-binding domain of the CLEC12A-targeted chimeric receptor is an scFv, the variable regions are positioned from the N- to the C-terminus: $V_H$—$V_L$. In certain embodiments, the CLEC12A-targeted scFv comprises the amino acid sequence set forth in SEQ ID NO: 119, which is provided in Table 14. In certain embodiments, the CLEC12A-targeted scFv is designated as "CLEC12A-G". The CDRs provided in Table 14 are identified according to the IMGT numbering system.

TABLE 14

| | (CLEC12A-G) | | |
|---|---|---|---|
| CDRs | 1 | 2 | 3 |
| $V_H$ | GFTFSSYG [SEQ ID NO: 89] | ISYDGSDK [SEQ ID NO: 90] | ARDGQFYFDY [SEQ ID NO: 114] |
| $V_L$ | QSVTSRY [SEQ ID NO: 115] | GAS [SEQ ID NO: 93] | QQDYNLPLT [SEQ ID NO: 116] |
| Full $V_H$ | QVQLVESGGGWQPGRSLRLSCAASGFTFSSYGMHWVRQAPGEGLEWVTVISYDGSDKYYADSVKGRFTISRDNSKSTLFLQMNSLRAEDTAVYYCARDGQFYFDYWGQGTLVTVSS [SEQ ID NO: 117] | | |
| Full $V_L$ | EIVMTQSPATLSLSPGESATLSCRASQSVTSRYLSWYQQKPGQAPRLLMYGASTRPTGIPARFSGSGSGTDFTLTISSLQPEDFAVYYCQQDYNLPLTFGGGTKVEIK [SEQ ID NO: 118] | | |

TABLE 14-continued (CLEC12A-G)

| CDRs | 1 | 2 | 3 |
|---|---|---|---|
| $V_H$-$V_L$ scFv | QVQLVESGGGVVQPGRSLRLSCAASGFTFSSYGMHWVRQAPGEGLEWVTVISYDGSDKY YADSVKGRFTISRDNSKSTLFLQMNSLRAEDTAVYYCARDGQFYFDYWGQGTLVTVSSA STGGGGSGGGGSGGGGSEIVMTQSPATLSLSPGESATLSCRASQSVTSRYLSWYQQKPG QAPRLLMYGASTRPTGIPARFSGSGSGTDFTLTISSLQPEDFAVYYCQQDYNLPLTFGG GTKVEIK [SEQ ID NO: 119] | | |

In certain embodiments, the extracellular antigen-binding domain of the CLEC12A-targeted chimeric receptor (e.g., a CLEC12A-targeted scFv) comprises a $V_H$ CDR1 comprising the amino acid sequence set forth in SEQ ID NO: 120 or a conservative modification thereof, a $V_H$ CDR2 comprising the amino acid sequence set forth in SEQ ID NO: 121 or a conservative modification thereof, and a $V_H$ CDR3 comprising the amino acid sequence set forth in SEQ ID NO: 122 or a conservative modification thereof. SEQ ID NOs: 120-122 are provided in Table 15.

In certain embodiments, the extracellular antigen-binding domain of the CLEC12A-targeted chimeric receptor (e.g., a CLEC12A-targeted scFv) comprises a $V_L$ CDR1 comprising the amino acid sequence set forth in SEQ ID NO: 123 or a conservative modification thereof, a $V_L$ CDR2 comprising the amino acid sequence set forth in SEQ ID NO: 124 or a conservative modification thereof, and a $V_L$ CDR3 comprising the amino acid sequence set forth in SEQ ID NO: 125 or a conservative modification thereof. SEQ ID NOs: 123-125 are provided in Table 15.

In certain embodiments, the extracellular antigen-binding domain of the CLEC12A-targeted chimeric receptor (e.g., a CLEC12A-targeted scFv) comprises a $V_H$ CDR1 comprising the amino acid sequence set forth in SEQ ID NO: 120 or a conservative modification thereof, a $V_H$ CDR2 comprising the amino acid sequence set forth in SEQ ID NO: 121 or a conservative modification thereof, a $V_H$ CDR3 comprising the amino acid sequence set forth in SEQ ID NO: 122 or a conservative modification thereof, a $V_L$ CDR1 comprising the amino acid sequence set forth in SEQ ID NO: 123 or a conservative modification thereof, a $V_L$ CDR2 comprising the amino acid sequence set forth in SEQ ID NO: 124 or a conservative modification, and a $V_L$ CDR3 comprising the amino acid sequence set forth in SEQ ID NO: 125 or a conservative modification thereof.

In certain embodiments, the extracellular antigen-binding domain of the CLEC12A-targeted chimeric receptor (e.g., a CLEC12A-targeted scFv) comprises a $V_H$ CDR1 comprising the amino acid sequence set forth in SEQ ID NO: 120, a $V_H$ CDR2 comprising the amino acid sequence set forth in SEQ ID NO: 121, a $V_H$ CDR3 comprising the amino acid sequence set forth in SEQ ID NO: 122, a $V_L$ CDR1 comprising the amino acid sequence set forth in SEQ ID NO: 123, a $V_L$ CDR2 comprising the amino acid sequence set forth in SEQ ID NO: 124, and a $V_L$ CDR3 comprising the amino acid sequence set forth in SEQ ID NO: 125.

In certain embodiments, the extracellular antigen-binding domain of the chimeric receptor (e.g., an scFv) comprises a $V_H$ comprising an amino acid sequence that is at least about 80% (e.g., at least about 85%, at least about 90%, or at least about 95%) homologous or identical to the amino acid sequence set forth in SEQ ID NO: 126. For example, the extracellular antigen-binding domain of the chimeric receptor (e.g., an scFv) comprises a $V_H$ comprising an amino acid sequence that is about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100% homologous or identical to SEQ ID NO: 126. In certain embodiments, the extracellular antigen-binding domain comprises a $V_H$ comprising the amino acid sequence set forth in SEQ ID NO: 126. SEQ ID NO: 126 is provided in Table 15 below.

In certain embodiments, the extracellular antigen-binding domain of the chimeric receptor (e.g., an scFv) comprises a $V_L$ comprising an amino acid sequence that is at least about 80% (e.g., at least about 85%, at least about 90%, or at least about 95%) homologous or identical to the amino acid sequence set forth in SEQ ID NO: 127. For example, the extracellular antigen-binding domain of the chimeric receptor (e.g., an scFv) comprises a $V_L$ comprising an amino acid sequence that is about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100% homologous or identical to SEQ ID NO: 127. In certain embodiments, the extracellular antigen-binding domain comprises a $V_L$ comprising the amino acid sequence set forth in SEQ ID NO: 127. SEQ ID NO: 127 is provided in Table 15 below.

In certain embodiments, the extracellular antigen-binding domain of the CLEC12A-targeted chimeric receptor (e.g., a CLEC12A-targeted scFv) comprises a $V_H$ comprising the amino acid sequence set forth in SEQ ID NO: 126, and a $V_L$ comprising the amino acid sequence set forth in SEQ ID NO: 127. In certain embodiments, the $V_H$ and $V_L$ are linked via a linker. In certain embodiments, the linker comprises the amino acid sequence set forth in SEQ ID NO: 149. In certain embodiments, the linker comprises the amino acid sequence set forth in SEQ ID NO: 2.

In certain embodiments, the variable regions within the extracellular antigen-binding domain of the CLEC12A-targeted chimeric receptor have to be linked one after another such that at the N-terminus of the extracellular antigen-binding domain, a heavy chain variable region ($V_H$) is positioned. In certain embodiments, if the extracellular antigen-binding domain of the CLEC12A-targeted chimeric receptor is an scFv, the variable regions are positioned from the N- to the C-terminus: $V_H$-$V_L$. In certain embodiments, the CLEC12A-targeted scFv comprises the amino acid sequence set forth in SEQ ID NO: 128, which is provided in Table 15. In certain embodiments, the CLEC12A-targeted scFv is designated as "CLEC12A-H". The CDRs provided in Table 15 are identified according to the IMGT numbering system.

TABLE 15

| | (CLEC12A-H) | | |
|---|---|---|---|
| CDRs | 1 | 2 | 3 |
| $V_H$ | GFTFSNYG [SEQ ID NO: 120] | ISYDGSDK [SEQ ID NO: 121] | ARDSGRYFFDY [SEQ ID NO: 122] |
| $V_L$ | QSVSSRS [SEQ ID NO: 123] | GPS [SEQ ID NO: 124] | HQDYNLPLT [SEQ ID NO: 125] |
| Full $V_H$ | QVQLVESGGGWQPGRSLRLSCAASGFTFSNYGMHWVRQAPGKGLEWVAVISYDGSDKS YKDSVKGRFTIARDNSKNTLYLQMNSLRAEDTAVYYCARDSGRYFFDYWGQGTLVTVSS [SEQ ID NO: 126] | | |
| Full $V_L$ | EIIMTQSPATLSLSPGERATLSCRASQSVSSRSLSWYQHKPGQAPRLLIYGPSTRATGI PARFSGSGSGTDFTLTISSLQPEDFAVYYCHQDYNLPLTFGGGTKVEIK [SEQ ID NO: 127] | | |
| $V_H$-$V_L$ scFv | QVQLVESGGGVVQPGRSLRLSCAASGFTFSNYGMHWVRQAPGKGLEWVAVISYDGSDKS YKDSVKGRFTIARDNSKNTLYLQMNSLRAEDTAVYYCARDSGRYFFDYWGQGTLVTVSS ASTGGGGSGGGGSGGGGSEIIMTQSPATLSLSPGERATLSCRASQSVSSRSLSWYQHKP GQAPRLLIYGPSTRATGIPARFSGSGSGTDFTLTISSLQPEDFAVYYCHQDYNLPLTFG GGTKVEIK [SEQ ID NO: 128] | | |

In certain embodiments, the extracellular antigen-binding domain of the CLEC12A-targeted chimeric receptor (e.g., a CLEC12A-targeted scFv) comprises a $V_H$ CDR1 comprising the amino acid sequence set forth in SEQ ID NO: 129 or a conservative modification thereof, a $V_H$ CDR2 comprising the amino acid sequence set forth in SEQ ID NO: 130 or a conservative modification thereof, and a $V_H$ CDR3 comprising the amino acid sequence set forth in SEQ ID NO: 131 or a conservative modification thereof. SEQ ID NOs: 129-131 are provided in Table 16.

In certain embodiments, the extracellular antigen-binding domain of the CLEC12A-targeted chimeric receptor (e.g., a CLEC12A-targeted scFv) comprises a $V_L$ CDR1 comprising the amino acid sequence set forth in SEQ ID NO: 132 or a conservative modification thereof, a $V_L$ CDR2 comprising the amino acid sequence set forth in SEQ ID NO: 133 or a conservative modification thereof, and a $V_L$ CDR3 comprising the amino acid sequence set forth in SEQ ID NO: 134 or a conservative modification thereof. SEQ ID NOs: 132-134 are provided in Table 16.

In certain embodiments, the extracellular antigen-binding domain of the CLEC12A-targeted chimeric receptor (e.g., a CLEC12A-targeted scFv) comprises a $V_H$ CDR1 comprising the amino acid sequence set forth in SEQ ID NO: 129 or a conservative modification thereof, a $V_H$ CDR2 comprising the amino acid sequence set forth in SEQ ID NO: 130 or a conservative modification thereof, a $V_H$ CDR3 comprising the amino acid sequence set forth in SEQ ID NO: 131 or a conservative modification thereof, a $V_L$ CDR1 comprising the amino acid sequence set forth in SEQ ID NO: 132 or a conservative modification thereof, a $V_L$ CDR2 comprising the amino acid sequence set forth in SEQ ID NO: 133 or a conservative modification, and a $V_L$ CDR3 comprising the amino acid sequence set forth in SEQ ID NO: 134 or a conservative modification thereof.

In certain embodiments, the extracellular antigen-binding domain of the CLEC12A-targeted chimeric receptor (e.g., a CLEC12A-targeted scFv) comprises a $V_H$ CDR1 comprising the amino acid sequence set forth in SEQ ID NO: 129, a $V_H$ CDR2 comprising the amino acid sequence set forth in SEQ ID NO: 130, a $V_H$ CDR3 comprising the amino acid sequence set forth in SEQ ID NO: 131, a $V_L$ CDR1 comprising the amino acid sequence set forth in SEQ ID NO: 132, a $V_L$ CDR2 comprising the amino acid sequence set forth in SEQ ID NO: 133, and a $V_L$ CDR3 comprising the amino acid sequence set forth in SEQ ID NO: 134.

In certain embodiments, the extracellular antigen-binding domain of the CLEC12A-targeted chimeric receptor (e.g., a CLEC12A-targeted scFv) comprises a $V_H$ comprising an amino acid sequence that is at least about 80% (e.g., at least about 85%, at least about 90%, or at least about 95%) homologous or identical to the amino acid sequence set forth in SEQ ID NO: 135. For example, the extracellular antigen-binding domain of the CLEC12A-targeted chimeric receptor (e.g., a CLEC12A-targeted scFv) comprises a $V_H$ comprising an amino acid sequence that is about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100% homologous or identical to SEQ ID NO: 135. In certain embodiments, the extracellular antigen-binding domain of the CLEC12A-targeted chimeric receptor comprises a $V_H$ Comprising the amino acid sequence set forth in SEQ ID NO: 135. SEQ ID NO: 135 is provided in Table 16 below.

In certain embodiments, the extracellular antigen-binding domain of the CLEC12A-targeted chimeric receptor (e.g., a CLEC12A-targeted scFv) comprises a $V_L$ comprising an amino acid sequence that is at least about 80% (e.g., at least about 85%, at least about 90%, or at least about 95%) homologous or identical to the amino acid sequence set forth in SEQ ID NO: 136. For example, the extracellular antigen-binding domain of the CLEC12A-targeted chimeric receptor (e.g., a CLEC12A-targeted scFv) comprises a $V_L$ comprising an amino acid sequence that is about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100% homologous or identical to SEQ ID NO: 136. In certain embodiments, the extracellular antigen-binding domain of the CLEC12A-targeted chimeric receptor comprises a $V_L$ Comprising the amino acid sequence set forth in SEQ ID NO: 136. SEQ ID NO: 136 is provided in Table 16 below.

In certain embodiments, the extracellular antigen-binding domain of the CLEC12A-targeted chimeric receptor (e.g., a CLEC12A-targeted scFv) comprises a $V_H$ comprising the amino acid sequence set forth in SEQ ID NO: 135, and a $V_L$ comprising the amino acid sequence set forth in SEQ ID NO: 136. In certain embodiments, the $V_H$ and $V_L$ are linked via a linker. In certain embodiments, the linker comprises the amino acid sequence set forth in SEQ ID NO: 149. In certain embodiments, the linker comprises the amino acid sequence set forth in SEQ ID NO: 2.

In certain embodiments, the variable regions within the extracellular antigen-binding domain of the CLEC12A-targeted chimeric receptor have to be linked one after another such that at the N-terminus of the extracellular antigen-binding domain, a heavy chain variable region ($V_H$) is positioned. In certain embodiments, if the extracellular antigen-binding domain of the CLEC12A-targeted chimeric receptor is an scFv, the variable regions are positioned from the N- to the C-terminus: $V_H$-$V_L$. In certain embodiments, the scFv comprises the amino acid sequence set forth in SEQ ID NO: 137, which is provided in Table 16. In certain embodiments, the CLEC12A-targeted scFv is designated as "CLEC12A-J". The CDRs provided in Table 16 are identified according to the IMGT numbering system.

TABLE 16

| (CLEC12A-J) | | | |
|---|---|---|---|
| CDRs | 1 | 2 | 3 |
| $V_H$ | GFTFSKYG [SEQ ID NO: 129] | IWYDGSIK [SEQ ID NO: 130] | ARGSLWFGEFYFDY [SEQ ID NO: 131] |
| $V_L$ | QGISSA [SEQ ID NO: 132] | DAS [SEQ ID NO: 133] | QQFNNYPRT [SEQ ID NO: 134] |
| Full $V_H$ | QVKLVESGGGVVQPGRSLRLSCAASGFTFSKYGMHWVRQAPGKGLEWVAFIWYDGSIKN YADSVKGRFTTSRDNSKNTLYLQMNSLRAEDTAVYYCARGSLWFGEFYFDYWGQGTLVT VSS [SEQ ID NO: 135] | | |
| Full $V_L$ | AIQLTQSPSSLSASVGDRVTITCRTSQGISSALAWYQQKPGKTPKLLIYDASSLESGVP SRFSGSGSGTDFTLTISSLQPEDFATYYCQQFNNYPRTFGQGTKVEIK [SEQ ID NO: 136] | | |
| $V_H$-$V_L$ scFv | QVKLVESGGGVVQPGRSLRLSCAASGFTFSKYGMHWVRQAPGKGLEWVAFIWYDGSIKN YADSVKGRFTTSRDNSKNTLYLQMNSLRAEDTAVYYCARGSLWFGEFYFDYWGQGTLVT VSSASTGGGGSGGGGSGGGGSAIQLTQSPSSLSASVGDRVTITCRTSQGISSALAWYQQ KPGKTPKLLIYDASSLESGVPSRFSGSGSGTDFTLTISSLQPEDFATYYCQQFNNYPRT FGQGTKVEIK [SEQ ID NO: 137] | | |

The $V_H$ and/or $V_L$ amino acid sequences having at least about 80%, at least about 80%, at least about 85%, at least about 90%, or at least about 95% (e.g., about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99%) homology or identity to a specific sequence (e.g., SEQ ID NO: 75, SEQ ID NO: 76, SEQ ID NO: 86, SEQ ID NO: 87, SEQ ID NO: 95, SEQ ID NO: 96, SEQ ID NO: 100, SEQ ID NO: 101, SEQ ID NO: 106, SEQ ID NO: 107, SEQ ID NO: 111, SEQ ID NO: 112, SEQ ID NO: 117, SEQ ID NO: 118, SEQ ID NO: 126, SEQ ID NO: 127, SEQ ID NO: 135, or SEQ ID NO: 136) may contain substitutions (e.g., conservative substitutions), insertions, or deletions relative to the specified sequence(s), but retain the ability to bind to a target antigen (e.g., CLEC12A). In certain embodiments, a total of 1 to 10 amino acids are substituted, inserted and/or deleted in a specific sequence (e.g., SEQ ID NO: 75, SEQ ID NO: 76, SEQ ID NO: 86, SEQ ID NO: 87, SEQ ID NO: 95, SEQ ID NO: 96, SEQ ID NO: 100, SEQ ID NO: 101, SEQ ID NO: 106, SEQ ID NO: 107, SEQ ID NO: 111, SEQ ID NO: 112, SEQ ID NO: 117, SEQ ID NO: 118, SEQ ID NO: 126, SEQ ID NO: 127, SEQ ID NO: 135, or SEQ ID NO: 136). In certain embodiments, substitutions, insertions, or deletions occur in regions outside the CDRs (e.g., in the FRs) of the extracellular antigen-binding domain. In certain embodiments, the extracellular antigen-binding domain comprises $V_H$ and/or $V_L$ sequence selected from SEQ ID NO: 75, SEQ ID NO: 76, SEQ ID NO: 86, SEQ ID NO: 87, SEQ ID NO: 95, SEQ ID NO: 96, SEQ ID NO: 100, SEQ ID NO: 101, SEQ ID NO: 106, SEQ ID NO: 107, SEQ ID NO: 111, SEQ ID NO: 112, SEQ ID NO: 117, SEQ ID NO: 118, SEQ ID NO: 126, SEQ ID NO: 127, SEQ ID NO: 135, or SEQ ID NO: 136, including post-translational modifications of that sequence (SEQ ID NO: 75, SEQ ID NO: 76, SEQ ID NO: 86, SEQ ID NO: 87, SEQ ID NO: 95, SEQ ID NO: 96, SEQ ID NO: 100, SEQ ID NO: 101, SEQ ID NO: 106, SEQ ID NO: 107, SEQ ID NO: 111, SEQ ID NO: 112, SEQ ID NO: 117, SEQ ID NO: 118, SEQ ID NO: 126, SEQ ID NO: 127, SEQ ID NO: 135, or SEQ ID NO: 136).

In certain embodiments, the extracellular antigen-binding domain of a presently disclosed CLEC12A-targeted chimeric receptor cross-competes for binding to CLEC12A with a reference antibody or an antigen-binding fragment thereof comprising the $V_H$ CDR1, CDR2, and CDR3 sequences and the $V_L$ CDR1, CDR2, and CDR3 sequences of, for example, any one of the presently disclosed scFvs (e.g., CLEC12A-A, CLEC12A-B, CLEC12A-C, CLEC12A-D, CLEC12A-E, CLEC12A-F, CLEC12A-G, CLEC12A-H, and CLEC12A-J). In certain embodiments, the extracellular antigen-binding domain of a presently disclosed chimeric receptor cross-competes for binding to CLEC12A with a reference antibody or an antigen-binding portion thereof comprising the $V_H$ and $V_L$ sequences of, for example, any one of the presently disclosed scFvs (e.g., CLEC12A-A, CLEC12A-B, CLEC12A-C, CLEC12A-D, CLEC12A-E, CLEC12A-F, CLEC12A-G, CLEC12A-H, and CLEC12A-J).

In certain embodiments, the extracellular antigen-binding domain of a presently disclosed CLEC12A-targeted chimeric receptor cross-competes for binding to CLEC12A with a reference antibody or an antigen-binding portion thereof comprising the $V_H$ CDR1, CDR2, and CDR3 sequences and the $V_L$ CDR1, CDR2, and CDR3 sequences of scFv CLEC12A-A. For example, the extracellular antigen-binding domain of a presently disclosed CLEC12A-targeted chimeric receptor cross-competes for binding to CLEC12A with a reference antibody or an antigen-binding portion thereof comprising a $V_H$ CDR1 comprising the amino acid sequence set forth in SEQ ID NO: 69, a $V_H$ CDR2 comprising the amino acid sequence set forth in SEQ ID NO: 70; a $V_H$ CDR3 comprising the amino acid sequence set forth in SEQ ID NO: 71; a $V_L$ CDR1 comprising the amino acid sequence set forth in SEQ ID NO: 72; a $V_L$ CDR2 comprising amino acids having the sequence set forth in SEQ ID NO: 73; and a $V_L$ CDR3 comprising amino acids having the sequence set forth in SEQ ID NO: 74. In certain embodiments, the extracellular antigen-binding domain of a presently disclosed CLEC12A-targeted chimeric receptor cross-competes for binding to CLEC12A with a reference antibody or an antigen-binding portion thereof comprising the $V_H$ and $V_L$ sequences of scFv CLEC12A-A. For example, the extracellular antigen-binding domain of a presently disclosed CLEC12A-targeted chimeric receptor cross-competes for binding to CLEC12A with a reference antibody or an antigen-binding portion thereof comprising a $V_H$ comprising amino acids having the sequence set forth in SEQ ID NO: 75, and a $V_L$ comprising amino acids having the sequence set forth in SEQ ID NO: 76.

In certain embodiments, the extracellular antigen-binding domain of the presently disclosed CLEC12A-targeted chimeric receptors binds to the same epitope on CLEC12A as the reference antibody or antigen-binding portion thereof. For example, the extracellular antigen-binding domain of a presently disclosed CLEC12A-targeted chimeric receptor binds to the same epitope on CLEC12A as a reference antibody or an antigen-binding portion thereof comprising the $V_H$ CDR1, CDR2, and CDR3 sequences and the $V_L$ CDR1, CDR2, and CDR3 sequences of, for example, any one of the presently disclosed scFvs (e.g., CLEC12A-A, CLEC12A-B, CLEC12A-C, CLEC12A-D, CLEC12A-E, CLEC12A-F, CLEC12A-G, CLEC12A-H, and CLEC12A-J). In certain embodiments, the extracellular antigen-binding domain of a presently disclosed CLEC12A-targeted chimeric receptor binds to the same epitope on CLEC12A as a reference antibody or an antigen-binding portion thereof comprising the $V_H$ and $V_L$ sequences of, for example, any one of the presently disclosed scFvs (e.g., CLEC12A-A, CLEC12A-B, CLEC12A-C, CLEC12A-D, CLEC12A-E, CLEC12A-F, CLEC12A-G, CLEC12A-H, and CLEC12A-J).

In certain embodiments, the extracellular antigen-binding domain of a presently disclosed CLEC12A-targeted chimeric receptor binds to the same epitope on CLEC12A as a reference antibody or an antigen-binding fragment thereof comprising the $V_H$ CDR1, CDR2, and CDR3 sequences and the $V_L$ CDR1, CDR2, and CDR3 sequences of scFv CLEC12A-A. For example, the extracellular antigen-binding domain of a presently disclosed CLEC12A-targeted chimeric receptor binds to the same epitope on CLEC12A as a reference antibody or an antigen-binding fragment thereof comprising a $V_H$ CDR1 comprising the amino acid sequence set forth in SEQ ID NO: 69; a $V_H$ CDR2 comprising the amino acid sequence set forth in SEQ ID NO: 70; a $V_H$ CDR3 comprising the amino acid sequence set forth in SEQ ID NO: 71; a $V_L$ CDR1 comprising the amino acid sequence set forth in SEQ ID NO: 72; a $V_L$ CDR2 comprising the amino acid sequence set forth in SEQ ID NO: 73; and a $V_L$ CDR3 comprising the amino acid sequence set forth in SEQ ID NO: 74. In certain embodiments, the extracellular antigen-binding domain of a presently disclosed CLEC12A-targeted chimeric receptor binds to the same or substantially the same epitope on CLEC12A as a reference antibody or an antigen-binding fragment thereof comprising the $V_H$ and $V_L$ sequences of scFv CLEC12A-A. For example, the extracellular antigen-binding domain of a presently disclosed CLEC12A-targeted chimeric receptor binds to the same epitope on CLEC12A as a reference antibody or an antigen-binding fragment thereof comprising a $V_H$ comprising the amino acid sequence set forth in SEQ ID NO: 75, and a $V_L$ comprising the amino acid sequence set forth in SEQ ID NO: 76.

Extracellular antigen-binding domains of the presently disclosed CLEC12A-targeted chimeric receptors that cross-compete or compete with the reference antibody or antigen-binding portions thereof for binding to CLEC12A can be identified by using routine methods known in the art, e.g., those disclosed in Section 5.3.

In certain embodiments, the extracellular antigen-binding domain of the presently disclosed CLEC12A-targeted chimeric comprises a linker connecting the heavy chain variable region and light chain variable region of the extracellular antigen-binding domain. In certain embodiments, the linker comprises the amino acid sequence set forth in SEQ ID NO: 1. In certain embodiments, the linker comprises the amino acid sequence set forth in SEQ ID NO: 2. In certain embodiments, the linker comprises the amino acid sequence set forth in SEQ ID NO: 3. In certain embodiments, the linker comprises the amino acid sequence set forth in SEQ ID NO: 4. In certain embodiments, the linker comprises the amino acid sequence set forth in SEQ ID NO: 5. In certain embodiments, the linker comprises the amino acid sequence set forth in SEQ ID NO: 6. In certain embodiments, the linker comprises the amino acid sequence set forth in SEQ ID NO: 149.

In certain embodiments, the variable regions within the extracellular antigen-binding domain of the CLEC12A-targeted chimeric receptor have to be linked one after another such that at the N-terminus of the extracellular antigen-binding domain, a heavy chain variable region ($V_H$) is positioned. In certain embodiments, if the extracellular antigen-binding domain of the CLEC12A-targeted chimeric receptor is an scFv, the variable regions are positioned from the N- to the C-terminus: $V_H$-$V_L$.

In certain embodiments, the variable regions within the extracellular antigen-binding domain of the CLEC12A-targeted chimeric receptor have to be linked one after another such that at the N-terminus of the extracellular antigen-binding domain, a light chain variable region ($V_L$) is positioned. In certain embodiments, if the extracellular antigen-binding domain of the CLEC12A-targeted chimeric receptor is an scFv, the variable regions are positioned from the N- to the C-terminus: $V_L$-$V_H$.

In addition, the CLEC12A-targeted chimeric receptor can comprise a leader or a signal peptide that directs the nascent protein into the endoplasmic reticulum. In certain embodiments, the leader or signal peptide is positioned at (e.g., covalently joined to) the N-terminus of the extracellular antigen-binding domain of the CLEC12A-targeted chimeric receptor. In certain embodiments, the CLEC12A-targeted chimeric receptor comprises a leader or signal peptides disclosed in Section 5.3. In certain embodiments, the CLEC12A-targeted chimeric receptor comprises a signal peptide that comprises a CD8 polypeptide. In certain embodiments, the CLEC12A-targeted chimeric receptor comprises a signal peptide that comprises a CD8 polypeptide comprising or consisting of the amino acid sequence set forth in SEQ ID NO: 63.

5.6. Exemplified CLEC12A-Targeted Chimeric Receptor

In certain embodiments, the CLEC12A-targeted chimeric receptor is a CCR. In certain embodiments, the CLEC12A-targeted CCR comprises (a) an extracellular antigen-binding domain comprising (i) a $V_H$ that comprises a CDR1 comprising the amino acid sequence set forth in SEQ ID NO: 69, a CDR2 comprising the amino acid sequence set forth in SEQ ID NO: 70, and a $V_H$ CDR3 comprising the amino acid sequence set forth in SEQ ID NO: 71, and (ii) a $V_L$ that comprises a CDR1 comprising the amino acid sequence set forth in SEQ ID NO: 72, a CDR2 comprising the amino acid sequence set forth in SEQ ID NO: 73, and a $V_L$ CDR3 comprising the amino acid sequence set forth in SEQ ID NO: 74; (b) an intracellular domain comprising a 4-1BB polypeptide (e.g., a human 4-1BB polypeptide, e.g., an intracellular domain of 4-1BB (e.g., human 4-1BB) of a portion thereof). In certain embodiments, the CLEC12A-targeted CCR further comprises a transmembrane domain comprising a CD8 polypeptide (e.g., a human CD8 polypeptide, e.g., a transmembrane domain of CD8 (e.g., human CD8) or a portion thereof). In certain embodiments, the intracellular domain comprises a 4-1BB polypeptide comprising or consisting of the amino acids 214 to 255 of SEQ ID NO: 30. In certain embodiments, the transmembrane domain comprises a CD8 polypeptide comprising or consisting of the amino acids 137 to 207 of SEQ ID NO: 7. In certain embodiments, the $V_H$ and $V_L$ are linked via a linker comprising or consisting of the amino acid sequence set forth in SEQ ID NO: 149. In certain embodiments, the $V_H$ and $V_L$ are positioned from the N- to the C-terminus: $V_H$-$V_L$. In certain embodiments, the extracellular antigen-binding domain and transmembrane domain are linked via a linker. In certain embodiments, the linker consists of the amino acid sequence set forth in SEQ ID NO: 150. In certain embodiments, the CLEC12A-targeted CCR comprises the amino acid sequence set forth in SEQ ID NO: 138, which is provided below.

[SEQ ID NO: 138]
QLQLQESGPGLVKPSETLSLTCTVSGGSISSSTYYWGWIRQPPRKGLEWI

GSTHYRGSTYYNPSLKSRVTISVDTSKNQFSLKVSSVTAADTAVYYCARE

LTGEVFDYWGQGTLVTVSSASTGGGGSGGGGSGGGGSDIQMTQSPSSLSA

SVGDRVTITCRASQSISSYLNWYQQKPGKAPKLLIYAASSLQSGVPSRFS

GSGSGTDFTLTISSLQPEDFATYYCQQSYSTPFTFGPGTKVDIKRAAAPT

TTPAPRPPTPAPTIASQPLSLRPEACRPAAGGAVHTRGLDFACDIYIWAP

LAGTCGVLLLSLVITLYCNKRGRKKLLYIFKQPFMRPVQTTQEEDGCSCR

FPEEEEGGCEL

An exemplary nucleic acid sequence the amino acid sequence of SEQ ID NO: 138 is set forth in SEQ ID NO: 139, which is provided below.

[SEQ ID NO: 139]
cagctccagctccaagagtcagggccaggtctcgtgaaaccgagtgagac cctgtccctgacctgcacagtgagtggtggatcaatctcaagctctacct actattgggggtggattcggcagccccctagaaaggggcttgagtggatt ggcagcactcattatcgaggatctacctattataatccttctctgaaaag cagagttaccatctctgtggatacgtccaaaaatcagttcagtctgaagg tatcatccgtgactgctgccgacacggccgtgtactattgcgcgagggag ctgacaggtgaggtctttgactactggggccagggcacactcgtgaccgt gtcttctgcctcaacaggaggggtgggagtggaggcggtggatcagggg gaggagggagtgacatccagatgacgcagtccccttccagcttgtccgca tctgtgggtgatagggtcacgattacatgtagggctagtcagagtatttc tagttacctgaattggtaccagcagaaaccaggcaaggcaccaaagttgc tcatctatgcggcctcctctctgcaatctggcgtgccgtccagatttagt ggatcaggctccggaaccgatttcaccctttacgatctcctcacttcaacc cgaggatttcgccacatattactgtcaacaaagctattctacaccgttca ccttcggaccggggacaaaagtggatattaaacgggcggccgccccacc acgacgccagcgccgcgaccaccaacccggcgcccacgatcgcgtcgca gcccctgtccctgcgcccagaggcgtgccggccagcggcggggggcgcag tgcacacgaggggggctggacttcgcctgtgatatctacatctgggcgccc ctggccgggacttgtggggtccttctcctgtcactggttatcaccctta ctgcaacaaacggggcagaaagaagctcctgtatatattcaaacaaccat ttatgagaccagtacaaactactcaagaggaagatggctgtagctgccga tttccagaagaagaagaaggaggatgtgaactg In certain embodiments, the CLEC12A-targeted chimeric receptor comprises a signal peptide at the N-terminus of the extracellular antigen-binding domain. In certain embodiments, the signal peptide comprises a CD8 polypeptide comprising or consisting of the amino acid sequence set forth in SEQ ID NO: 63.

5.7. Cells

The presently disclosed subject matter provides cells comprising a presently disclosed ADGRE2-targeted chimeric receptor (e.g., one disclosed in Sections 5.3 and 5.4). In addition, the presently disclosed subject matter provides cells comprising a presently disclosed CLEC12A-targeted chimeric receptor (e.g., one disclosed in Sections 5.5 and 5.6).

In certain embodiments, the cell is selected from the group consisting of cells of lymphoid lineage and cells of myeloid lineage. In certain embodiments, the cell is an immunoresponsive cell. In certain embodiments, the immunoresponsive cell is a cell of lymphoid lineage.

In certain embodiments, the cell is a cell of the lymphoid lineage. Cells of the lymphoid lineage can provide production of antibodies, regulation of cellular immune system, detection of foreign agents in the blood, detection of cells foreign to the host, and the like. Non-limiting examples of cells of the lymphoid lineage include T cells, Natural Killer (NK) cells, B cells, dendritic cells, stem cells from which lymphoid cells may be differentiated. In certain embodiments, the stem cell is a pluripotent stem cell. In certain embodiments, the pluripotent stem cell is an embryonic stem cell (ESC) or an induced pluripotent stem cell (iPSC).

In certain embodiments, the cell is a T cell. T cells can be lymphocytes that mature in the thymus and are chiefly responsible for cell-mediated immunity. T cells are involved in the adaptive immune system. The T cells of the presently disclosed subject matter can be any type of T cells, including, but not limited to, helper T cells, cytotoxic T cells, memory T cells (including central memory T cells, stem-cell-like memory T cells (or stem-like memory T cells), and two types of effector memory T cells: e.g., TEM cells and TEMRA cells, Regulatory T cells (also known as suppressor T cells), tumor-infiltrating lymphocyte (TIL), Natural killer T cells, Mucosal associated invariant T cells, and T6 T cells. Cytotoxic T cells (CTL or killer T cells) are a subset of T lymphocytes capable of inducing the death of infected somatic or tumor cells. A patient's own T cells may be genetically modified to target specific antigens through the introduction of an chimeric receptor, e.g., a CAR or a CCR. In certain embodiments, the immunoresponsive cell is a T cell. The T cell can be a CD4+ T cell or a CD8+ T cell. In certain embodiments, the T cell is a CD4+ T cell. In certain embodiments, the T cell is a CD8+ T cell.

In certain embodiments, the cell is a NK cell. Natural killer (NK) cells can be lymphocytes that are part of cell-mediated immunity and act during the innate immune response. NK cells do not require prior activation in order to perform their cytotoxic effect on target cells. In certain embodiments, the cell is a genetically modified NK cell. In certain embodiments, the cell is an edited NK cell. In certain embodiments, the cell is a NK cell derived from a stem cell. In certain embodiments, the cell is a NK cell derived from a pluripotent stem cell. In certain embodiments, the cell is an induced pluripotent stem cell (iPSC)-derived NK cell.

Types of human lymphocytes of the presently disclosed subject matter include, without limitation, peripheral donor lymphocytes. e.g., those disclosed in Sadelain et al., *Nat Rev Cancer* (2003); 3:35-45 (disclosing peripheral donor lymphocytes genetically modified to express CARs), in Morgan, R. A., et al. 2006 *Science* 314:126-129 (disclosing peripheral donor lymphocytes genetically modified to express a full-length tumor antigen-recognizing T cell receptor complex comprising the a and 3 heterodimer), in Panelli et al., *J Immunol* (2000); 164:495-504; Panelli et al., *J Immunol* (2000); 164:4382-4392 (disclosing lymphocyte cultures derived from tumor infiltrating lymphocytes (TILs) in tumor biopsies), and in Dupont et al., Cancer Res (2005); 65:5417-5427; Papanicolaou et al., *Blood* (2003); 102:2498-2505 (disclosing selectively in vitro-expanded antigen-specific peripheral blood leukocytes employing artificial antigen-presenting cells (AAPCs) or pulsed dendritic cells).

The cells (e.g., T cells or NK cells) can be autologous, non-autologous (e.g., allogeneic), or derived in vitro from engineered progenitor or stem cells.

The cells of the presently disclosed subject matter can be cells of the myeloid lineage. Non-limiting examples of cells of the myeloid lineage include monocytes, macrophages, neutrophils, dendritic cells, basophils, neutrophils, eosinophils, megakaryocytes, mast cell, erythrocyte, thrombocytes, and stem cells from which myeloid cells may be differentiated. In certain embodiments, the stem cell is a pluripotent stem cell (e.g., an embryonic stem cell or an induced pluripotent stem cell).

In certain embodiments, the presently disclosed cells are capable of modulating the tumor microenvironment. Tumors have a microenvironment that is hostile to the host immune response involving a series of mechanisms by malignant cells to protect themselves from immune recognition and elimination. This "hostile tumor microenvironment" comprises a variety of immune suppressive factors including infiltrating regulatory CD4+ T cells (Tregs), myeloid derived suppressor cells (MDSCs), tumor associated macrophages (TAMs), immune suppressive cytokines including TGF-β, and expression of ligands targeted to immune suppressive receptors expressed by activated T cells (CTLA-4 and PD-1). These mechanisms of immune suppression play a role in the maintenance of tolerance and suppressing inappropriate immune responses, however within the tumor microenvironment these mechanisms prevent an effective anti-tumor immune response. Collectively these immune suppressive factors can induce either marked anergy or apoptosis of adoptively transferred modified T cells upon encounter with targeted tumor cells.

In certain embodiments, the cells can be transduced with the presently disclosed ADGRE2-targeted chimeric receptor and/or the presently disclosed CLEC12A-targeted chimeric receptor such that the cells express the chimeric receptor(s).

Furthermore, the presently disclosed subject matter provides cells comprising a presently disclosed ADGRE2-targeted chimeric receptor (e.g., one disclosed in Section 5.3) and a presently disclosed CLEC12A-targeted chimeric receptor (e.g., one disclosed in Section 5.4). In certain embodiments, the ADGRE2-targeted chimeric receptor is a CAR. In certain embodiments, the CLEC12-targeted chimeric receptor is a CCR. Thus, in certain embodiments, the presently disclosed subject matter provides cells comprising a presently disclosed CLEC12A-targeted CAR and a presently disclosed CLEC12A-targeted CCR.

In certain embodiments, the presently disclosed cells exhibit a greater degree of cytolytic activity against cells that are positive for both ADGRE2 and CLEC12A as compared to against cells that are singly positive for ADGRE2. In certain embodiments, the ADGRE2-targeted CAR binds to the ADGRE2 with a low binding affinity or a low binding avidity. In certain embodiments, the ADGRE2-targeted CAR binds to ADGRE2 at an epitope of low accessibility. In certain embodiments, the ADGRE2-targeted CAR binds to ADGRE2 with a binding affinity that is lower compared to the binding affinity with which the CLEC12A-targeted CCR binds to CLEC12A. In certain embodiments, the ADGRE2-targeted CAR binds to ADGRE2 with a binding affinity that is at least 5-fold lower compared to the binding affinity with which the CLEC12A-targeted CCR binds to CLEC12A. In certain embodiments, the ADGRE2-targeted CAR binds to ADGRE2 with a binding affinity that is at least 10 fold, 20 fold, 30 fold, 40 fold, 50 fold, 60 fold, 70 fold, 80 fold, 90 fold, 100 fold, 200 fold, 5000 fold, 1000 fold, 5000 fold, or 10000 fold lower compared to the binding affinity with which the CLEC12A-targeted CCR binds to CLEC12A.

5.5.1. Exemplified Cells

In certain embodiments, the cell comprises an ADGRE2-targeted CAR and a CLEC12A-targeted CCR.

In certain embodiments, the ADGRE2-targeted CAR comprises (a) an extracellular antigen-binding domain comprising (i) a $V_H$ that comprises a CDR1 comprising the amino acid sequence set forth in SEQ ID NO: 33, a CDR2 comprising the amino acid sequence set forth in SEQ ID NO: 34, and a $V_H$ CDR3 comprising the amino acid sequence set forth in SEQ ID NO: 35, and (ii) a $V_L$ that comprises a CDR1 comprising the amino acid sequence set forth in SEQ ID NO: 36, a CDR2 comprising the amino acid sequence set forth in SEQ ID NO: 37, and a CDR3 comprising the amino acid sequence set forth in SEQ ID NO: 38; (b) a hinge/spacer region comprising a CD28 polypeptide, (c) a transmembrane domain comprising a CD28 polypeptide (e.g., a transmembrane domain of human CD28 or a fragment thereof), and (d) an intracellular signaling domain comprising (i) a CD3ζ polypeptide, and (ii) a co-stimulatory signaling region comprising a CD28 polypeptide (e.g., an intracellular domain of human CD28 or a fragment thereof). In certain embodiments, the $V_H$ and $V_L$ are linked via a linker comprising or consisting of the amino acid sequence set forth in SEQ ID NO: 2. In certain embodiments, the $V_H$ and $V_L$ are positioned from the N- to the C-terminus: $V_H$—$V_L$. In certain embodiments, the transmembrane domain comprises a CD28 polypeptide comprising or consisting of the amino acids 153 to 179 of SEQ ID NO: 10. In certain embodiments, the co-stimulatory signaling region comprises a CD28 polypeptide comprising or consisting of the amino acids 180 to 220 of SEQ ID NO: 10. In certain embodiments, the hinge/spacer region comprises a CD28 polypeptide comprising or consisting of the amino acids 114 to 152 of SEQ ID NO: 10. In certain embodiments, the ADGRE2-targeted CAR comprises or consists of the amino acid sequence set forth in SEQ ID NO: 66.

In certain embodiments, the CLEC12A-targeted CCR comprises (a) an extracellular antigen-binding domain comprising (i) a $V_H$ that comprises a CDR1 comprising the amino acid sequence set forth in SEQ ID NO: 69, a CDR2 comprising the amino acid sequence set forth in SEQ ID NO: 70, and a $V_H$ CDR3 comprising the amino acid sequence set forth in SEQ ID NO: 71, and (ii) a $V_L$ that comprises a CDR1 comprising the amino acid sequence set forth in SEQ ID NO: 72, a CDR2 comprising the amino acid sequence set forth in SEQ ID NO: 73, and a $V_L$ CDR3 comprising the amino acid sequence set forth in SEQ ID NO: 74; (b) an intracellular domain comprising a 4-1BB polypeptide (e.g., a human 4-1BB polypeptide, e.g., an intracellular domain of 4-1BB (e.g., human 4-1BB) of a portion thereof). In certain embodiments, the CLEC12A-targeted CCR further comprises a transmembrane domain comprising a CD8 polypeptide (e.g., a human CD8 polypeptide, e.g., a transmembrane domain of CD8 (e.g., human CD8) or a portion thereof). In certain embodiments, the intracellular domain comprises a 4-1BB polypeptide comprising or consisting of the amino acids 214 to 255 of SEQ ID NO: 30. In certain embodiments, the transmembrane domain comprises a CD8 polypeptide comprising or consisting of the amino acids 137 to 207 of SEQ ID NO: 7. In certain embodiments, the $V_H$ and $V_L$ are linked via a linker comprising or consisting of the amino acid sequence set forth in SEQ ID NO: 2. In certain embodiments, the $V_H$ and $V_L$ are positioned from the N- to the C-terminus: $V_H$—$V_L$. In certain embodiments, the CLEC12A-targeted CCR comprises the amino acid sequence set forth in SEQ ID NO: 136.

5.8. Nucleic Acid Molecules, Vector and Genetic Modifications

The presently disclosed subject matter provides nucleic acid molecules encoding the presently disclosed ADGRE2-targeted chimeric receptors (e.g., those disclosed in Sections 5.3 and 5.4). In certain embodiments, the nucleic acid molecule further comprises a promoter that is operably linked to the presently disclosed ADGRE2-targeted CAR. Also provided are cells comprising such nucleic acid molecules.

In addition, the presently disclosed subject matter provides nucleic acid molecules encoding the presently disclosed CLEC12A-targeted chimeric receptors (e.g., those disclosed in Sections 5.5 and 5.6). In certain embodiments, the nucleic acid molecule further comprises a promoter that is operably linked to the presently disclosed CLEC12A-targeted CAR. Also provided are cells comprising such nucleic acid molecules.

Furthermore, the presently disclosed subject matter provides nucleic acid compositions comprising a nucleic acid molecule encoding an ADGRE2-targeted chimeric receptor and a nucleic acid molecule encoding a CLEC12A-targeted chimeric receptor. Also provided are cells comprising such nucleic acid compositions.

In certain embodiments, the promoter is endogenous or exogenous. In certain embodiments, the exogenous promoter is selected from the group consisting of an elongation factor (EF)-1 promoter, a cytomegalovirus immediate-early promoter (CMV) promoter, a simian virus 40 early promoter (SV40) promoter, a phosphoglycerate kinase (PGK) promoter, a metallothionein promoter, and Ubiquitin C promoter. In certain embodiments, the endogenous promoter is selected from a TCR alpha promoter, a TCR beta promoter, and a beta 2-microglobulin promoter. In certain embodiments, the promoter is an inducible promoter. In certain embodiment, the inducible promoter is selected from the group consisting of a NFAT transcriptional response element (TRE) promoter, a CD69 promoter, a CD25 promoter, an IL-2 promoter, a 4-1BB promoter, a PD1 promoter, and a LAG3 promoter.

The presently disclosed subject matter also provides vectors comprising the presently disclosed nucleic acid molecules. In certain embodiments, the vector is a viral vector. In certain embodiments, the viral vector is a retroviral vector. In certain embodiments, the retroviral vector is a gamma retroviral vector or lentiviral vector.

In certain embodiments, the vector comprises a nucleic acid molecule encoding a presently disclosed ADGRE2-targeted CAR and a presently disclosed CLEC12A-targeted CCR. In certain embodiments, the nucleic acid molecule encodes a polypeptide comprising the amino acid sequence set forth in SEQ ID NO: 140. In certain embodiments, the nucleic acid molecule comprises the nucleotide sequence set forth in SEQ ID NO: 141. SEQ ID NOs: 140 and 141 are provided below.

[SEQ ID NO: 140]

MALPVTALLLPLALLLHAQVQLQQSGAEVAKPGASVKLSCKASGYTETNYWMQWIKQAPGQGLEWIGAVYPGDGDTR

HTQKFKGKATLTADKSTSTAYMEVSSLRSEDTAVYYCARGFTAYGMDYWGQGTTVTVSSGGGGSGGGGSGGGGSEIV

LTQSPATMSASPGERVTMSCSASSSVSYMHWYQQKSGQSPKRWIYDTSKLASGVPARFSGSGSGTDYTFTISSMEPE

DFATYYCQQWSSNPLTFGGGTKLEIKRAAAIEVMYPPPYLDNEKSNGTIIHVKGKHLCPSPLFPGPSKPFWVLVVVG

GVLACYSLLVTVAFIIFWVRSKRSRLLHSDYMNMTPRRPGPTRKHYQPYAPPRDFAAYRSRVKFSRSADAPAYQQGQ

NQLYNELNLGRREEYDVLDKRRGRDPEMGGKPRRKNPQEGLFNELQKDKMAEAFSEIGMKGERRRGKGHDGLFQGLS

TATKDTFDALHMQALPPRGSGATNFSLLKQAGDVEENPGPMALPVTALLLPLALLLHAQLQLQESGPGLVKPSETLS

LTCTVSGGSISSSTYYWGWIRQPPRKGLEWIGSTHYRGSTYYNPSLKSRVTISVDTSKNQFSLKVSSVTAADTAVYY
CARELTGEVFDYWGQGTLVTVSSASTGGGGSGGGGSGGGGSDIQMTQSPSSLSASVGDRVTITCRASQSISSYLNWY
QQKPGKAPKLLIYAASSLQSGVPSRFSGSGSGTDFTLTISSLQPEDFATYYCQQSYSTPFTFGPGTKVDIKRAAAPT
TTPAPRPPTPAPTIASQPLSLRPEACRPAAGGAVHTRGLDFACDIYIWAPLAGTCGVLLLSLVITLYCNKRGRKKLL
YIFKQPFMRPVQTTQEEDGCSCRFPEEEEGGCEL

[SEQ ID NO: 141]
GGATTAGTCCAATTTGTTAAAGACAGGATATCAGTGGTCCAGGCTCTAGTTTTGACTCAACAATATCACCAGCTGAA
GCCTATAGAGTACGAGCCATAGATAAAATAAAAGATTTTATTTAGTCTCCAGAAAAGGGGGAATGAAAGACCCCA
CCTGTAGGTTTGGCAAGCTAGCTTAAGTAACGCCATTTTGCAAGGCATGGAAAAATACATAACTGAGAATAGAGAAG
TTCAGATCAAGGTCAGGAACAGATGGAACAGCTGAATATGGGCCAAACAGGATATCTGTGGTAAGCAGTTCCTGCCC
CGGCTCAGGGCCAAGAACAGATGGAACAGCTGAATATGGGCCAAACAGGATATCTGTGGTAAGCAGTTCCTGCCCCG
GCTCAGGGCCAAGAACAGATGGTCCCCAGATGCGGTCCAGCCCTCAGCAGTTTCTAGAGAACCATCAGATGTTTCCA
GGGTGCCCCAAGGACCTGAAATGACCCTGTGCCTTATTTGAACTAACCAATCAGTTCGCTTCTCGCTTCTGTTCGCG
CGCTTCTGCTCCCCGAGCTCAATAAAAGAGCCCACAACCCCTCACTCGGGGCGCCAGTCCTCCGATTGACTGAGTCG
CCCGGGTACCCGTGTATCCAATAAACCCTCTTGCAGTTGCATCCGACTTGTGGTCTCGCTGTTCCTTGGGAGGGTCT
CCTCTGAGTGATTGACTACCCGTCAGCGGGGGTCTTTCACATGCAGCATGTATCAAAATTAATTTGGTTTTTTTTCT
TAAGTATTTACATTAAATGGCCATAGTACTTAAAGTTACATTGGCTTCCTTGAAATAAACATGGAGTATTCAGAATG
TGTCATAAATATTTCTAATTTTAAGATAGTATCTCCATTGGCTTTCTACTTTTTCTTTTATTTTTTTTGTCCTCTG
TCTTCCATTTGTTGTTGTTGTTGTTTGTTTGTTTGTTGGTTGGTTGGTTAATTTTTTTTAAAGATCCTACAC
TATAGTTCAAGCTAGACTATTAGCTACTCTGTAACCCAGGGTGACCTTGAAGTCATGGGTAGCCTGCTGTTTTAGCC
TTCCCACATCTAAGATTACAGGTATGAGCTATCATTTTTGGTATATTGATTGATTGATTGATTGATGTGTGTGTGTG
TGATTGTGTTTGTGTGTGATTGTGTATATGTGTGTATGGTTGTGTGTGATTGTGTGTATGTATGTTTGTGTGTGA
TTGTGTGTGTGTGATTGTGCATGTGTGTGTGTGATTGTGTTTATGTGTATGATTGTGTGTGTGTGTGTGTGTGTG
TGTGTGTGTGTGTGTGTGTGTGTTGTGTATATATATTTATGGTAGTGAGAGGCAACGCTCCGGCTCAGGTGTCAG
GTTGGTTTTTGAGACAGAGTCTTTCACTTAGCTTGGAATTCACTGGCCGTCGTTTTACAACGTCGTGACTGGGAAAA
CCCTGGCGTTACCCAACTTAATCGCCTTGCAGCACATCCCCCTTTCGCCAGCTGGCGTAATAGCGAAGAGGCCCGCA
CCGATCGCCCTTCCCAACAGTTGCGCAGCCTGAATGGCGAATGGCGCCTGATGCGGTATTTTCTCCTTACGCATCTG
TGCGGTATTTCACACCGCATATGGTGCACTCTCAGTACAATCTGCTCTGATGCCGCATAGTTAAGCCAGCCCCGACA
CCCGCCAACACCCGCTGACGCGCCCTGACGGGCTTGTCTGCTCCCGGCATCCGCTTACAGACAAGCTGTGACCGTCT
CCGGGAGCTGCATGTGTCAGAGGTTTTCACCGTCATCACCGAAACGCGCGAGACGAAAGGGCCTCGTGATACGCCTA
TTTTTATAGGTTAATGTCATGATAATAATGGTTTCTTAGACGTCAGGTGGCACTTTTCGGGGAAATGTGCGCGGAAC
CCCTATTTGTTTATTTTTTAAATACATTCAAATATGTATCCGCTCATGAGACAATAACCCTGATAAATGCTTCAAT
AATATTGAAAAAGGAAGAGTATGAGCCATATTCAACGGGAAACGTCGAGGCCGCGATTAAATTCCAACATGGATGCT
GATTTATATGGGTATAAATGGGCTCGCGATAATGTCGGGCAATCAGGTGCGACAATCTATCGCTTGTATGGGAAGCC
CGATGCGCCAGAGTTGTTTCTGAAACATGGCAAAGGTAGCGTTGCCAATGATGTTACAGATGAGATGGTCAGACTAA
ACTGGCTGACGGAATTTATGCCTCTTCCGACCATCAAGCATTTTATCCGTACTCCTGATGATGCATGGTTACTCACC
ACTGCGATCCCCGGAAAAACAGCATTCCAGGTATTAGAAGAATATCCTGATTCAGGTGAAAATATTGTTGATGCGCT
GGCAGTGTTCCTGCGCCGGTTGCATTCGATTCCTGTTTGTAATTGTCCTTTTAACAGCGATCGCGTATTTCGTCTCG
CTCAGGCGCAATCACGAATGAATAACGGTTTGGTTGATGCGAGTGATTTTGATGACGAGCGTAATGGCTGGCCTGTT
GAACAAGTCTGGAAAGAAATGCATAAACTTTTGCCATTCTCACCGGATTCAGTCGTCACTCATGGTGATTTCTCACT
TGATAACCTTATTTTTGACGAGGGGAAATTAATAGGTTGTATTGATGTTGGACGAGTCGGAATCGCAGACCGATACC

-continued

```
AGGATCTTGCCATCCTATGGAACTGCCTCGGTGAGTTTTCTCCTTCATTACAGAAACGGCTTTTTCAAAAATATGGT
ATTGATAATCCTGATATGAATAAATTGCAGTTTCATTTGATGCTCGATGAGTTTTTCTAACTGTCAGACCAAGTTTA
CTCATATATACTTTAGATTGATTTAAAACTTCATTTTTAATTTAAAAGGATCTAGGTGAAGATCCTTTTTGATAATC
TCATGACCAAAATCCCTTAACGTGAGTTTTCGTTCCACTGAGCGTCAGACCCCGTAGAAAAGATCAAAGGATCTTCT
TGAGATCCTTTTTTTCTGCGCGTAATCTGCTGCTTGCAAACAAAAAAACCACCGCTACCAGCGGTGGTTTGTTTGCC
GGATCAAGAGCTACCAACTCTTTTTCCGAAGGTAACTGGCTTCAGCAGAGCGCAGATACCAAATACTGTTCTTCTAG
TGTAGCCGTAGTTAGGCCACCACTTCAAGAACTCTGTAGCACCGCCTACATACCTCGCTCTGCTAATCCTGTTACCA
GTGGCTGCTGCCAGTGGCGATAAGTCGTGTCTTACCGGGTTGGACTCAAGACGATAGTTACCGGATAAGGCGCAGCG
GTCGGGCTGAACGGGGGGTTCGTGCACACAGCCCAGCTTGGAGCGAACGACCTACACCGAACTGAGATACCTACAGC
GTGAGCTATGAGAAAGCGCCACGCTTCCCGAAGGGAGAAAGGCGGACAGGTATCCGGTAAGCGGCAGGGTCGGAACA
GGAGAGCGCACGAGGGAGCTTCCAGGGGGAAACGCCTGGTATCTTTATAGTCCTGTCGGGTTTCGCCACCTCTGACT
TGAGCGTCGATTTTTGTGATGCTCGTCAGGGGGGCGGAGCCTATGGAAAAACGCCAGCAACGCGGCCTTTTTACGGT
TCCTGGCCTTTTGCTGGCCTTTTGCTCACATGTTCTTTCCTGCGTTATCCCCTGATTCTGTGGATAACCGTATTACC
GCCTTTGAGTGAGCTGATACCGCTCGCCGCAGCCGAACGACCGAGCGCAGCGAGTCAGTGAGCGAGGAAGCGGAAGA
GCGCCCAATACGCAAACCGCCTCTCCCCGCGCGTTGGCCGATTCATTAATGCAGCTGGCACGACAGGTTTCCCGACT
GGAAAGCGGGCAGTGAGCGCAACGCAATTAATGTGAGTTAGCTCACTCATTAGGCACCCCAGGCTTTACACTTTATG
CTTCCGGCTCGTATGTTGTGTGGAATTGTGAGCGGATAACAATTTCACACAGGAAACAGCTATGACCATGATTACGC
CAAGCTTTGCTCTTAGGAGTTTCCTAATACATCCCAAACTCAAATATATAAAGCATTTGACTTGTTCTATGCCCTAG
GGGGCGGGGGGAAGCTAAGCCAGCTTTTTTTAACATTTAAAATGTTAATTCCATTTTAAATGCACAGATGTTTTTAT
TTCATAAGGGTTTCAATGTGCATGAATGCTGCAATATTCCTGTTACCAAAGCTAGTATAAATAAAAATAGATAAACG
TGGAAATTACTTAGAGTTTCTGTCATTAACGTTTCCTTCCTCAGTTGACAACATAAATGCGCTGCTGAGAAGCCAGT
TTGCATCTGTCAGGATCAATTTCCCATTATGCCAGTCATATTAATTACTAGTCAATTAGTTGATTTTTATTTTTGAC
ATATACATGTGAAAGACCCCACCTGTAGGTTTGGCAAGCTAGCTTAAGTAACGCCATTTTGCAAGGCATGGAAAAAT
ACATAACTGAGAATAGAAAAGTTCAGATCAAGGTCAGGAACAGATGGAACAGCTGAATATGGGCCAAACAGGATATC
TGTGGTAAGCAGTTCCTGCCCCGGCTCAGGGCCAAGAACAGATGGAACAGCTGAATATGGGCCAAACAGGATATCTG
TGGTAAGCAGTTCCTGCCCCGGCTCAGGGCCAAGAACAGATGGTCCCCAGATGCGGTCCAGCCCTCAGCAGTTTCTA
GAGAACCATCAGATGTTTCCAGGGTGCCCCAAGGACCTGAAATGACCCTGTGCCTTATTTGAACTAACCAATCAGTT
CGCTTCTCGCTTCTGTTCGCGCGCTTCTGCTCCCCGAGCTCAATAAAAGAGCCCACAACCCCTCACTCGGCGCGCCA
GTCCTCCGATTGACTGAGTCGCCCGGGTACCCGTGTATCCAATAAACCCTCTTGCAGTTGCATCCGACTTGTGGTCT
CGCTGTTCCTTGGGAGGGTCTCCTCTGAGTGATTGACTACCCGTCAGCGGGGGTCTTTCATTTGGGGGCTCGTCCGG
GATCGGGAGACCCCTGCCCAGGGACCACCGACCCACCACCGGGAGGTAAGCTGGCCAGCAACTTATCTGTGTCTGTC
CGATTGTCTAGTGTCTATGACTGATTTTATGCGCCTGCGTCGGTACTAGTTAGCTAACTAGCTCTGTATCTGGCGGA
CCCGTGGTGGAACTGACGAGTTCGGAACACCCGGCCGCAACCCTGGGAGACGTCCCAGGGACTTCGGGGCCGTTTT
TGTGGCCCGACCTGAGTCCTAAAATCCCGATCGTTTAGGACTCTTTGGTGCACCCCCCTTAGAGGAGGGATATGTGG
TTCTGGTAGGAGACGAGAACCTAAAACAGTTCCCGCCTCCGTCTGAATTTTTGCTTTCGGTTTGGGACCGAAGCCGC
GCCGCGCGTCTTGTCTGCTGCAGCATCGTTCTGTGTTGTCTCTGTCTGACTGTGTTTCTGTATTTGTCTGAAAATAT
GGGCCCGGGCTAGACTGTTACCACTCCCTTAAGTTTGACCTTAGGTCACTGGAAAGATGTCGAGCGGATCGCTCACA
ACCAGTCGGTAGATGTCAAGAAGAGACGTTGGGTTACCTTCTGCTCTGCAGAATGGCCAACCTTTAACGTCGGATGG
CCGCGAGACGGCACCTTTAACCGAGACCTCATCACCCAGGTTAAGATCAAGGTCTTTTCACCTGGCCCGCATGGACA
CCCAGACCAGGTCCCCTACATCGTGACCTGGGAAGCCTTGGCTTTTGACCCCCCTCCCTGGGTCAAGCCCTTTGTAC
ACCCTAAGCCTCCGCCTCCTCTTCCTCCATCCGCCCCGTCTCTCCCCCTTGAACCTCCTCGTTCGACCCCGCCTCGA
```

-continued

```
TCCTCCCTTTATCCAGCCCTCACTCCTTCTCTAGGCGCCCCCATATGGCCATATGAGATCTTATATGGGGCACCCCC
GCCCCTTGTAAACTTCCCTGACCCTGACATGACAAGAGTTACTAACAGCCCCTCTCTCCAAGCTCACTTACAGGCTC
TCTACTTAGTCCAGCACGAAGTCTGGAGACCTCTGGCGGCAGCCTACCAAGAACAACTGGACCGACCGGTGGTACCT
CACCCTTACCGAGTCGGCGACACAGTGTGGGTCCGCCGACACCGACTAAGAACCTAGAACCTCGCTGGAAAGGACC
TTACACAGTCCTGCTGACCACCCCACCGCCCTCAAAGTAGACGGCATCGCAGCTTGGATACACGCCGCCCACGTGA
AGGCTGCCGACCCCGGGGGTGGACCATCCTCTAGACTGCCatggctctcccagtgactgccctactgcttcccctag
cgcttctcctgcatgcacaagttcagctccagcagagcggcgccgaagtggcaaagcctggagcgtcagtcaagctg
tcctgcaaagcgagtggctatacgttcacgaactactggatgcagtggataaagcaggctcccgggcagggtctgga
gtggattggagccgtctacccaggggacggcgacacccggcacactcaaaagttcaagggcaaggccaccctgaccg
ctgacaagagcacaagcacagcgtacatggaggtgtcctctttgagatccgaagataccgctgtgtattattgtgcc
cggggcttcactgcatacgggatggattactggggacaaggcactaccgtgactgtcagctccgggggtggaggctc
aggcggggggggttcaggagggggggatctgaaattgtgctgacacagagccctgccacaatgtctgctagccctg
gcgagcgcgtgaccatgtcttgtagcgccagcagcagcgtgtcctacatgcattggtatcaacagaagtccggccag
tctcccaagcggtggatctacgatacaagcaagctggcctccggcgtgcccgccagattttctggcagcggctctgg
aacagattacaccttcaccatctctagcatggaacctgaggattttgccacctactattgccagcagtggtccagca
atcccctgacatttggaggaggcaccaagctggaaattaagagagcggccgcaattgaagttatgtatcctcctcct
tacctagacaatgagaagagcaatggaaccattatccatgtgaaaggaaacacctttgtccaagtcccctatttcc
cggaccttctaagcccttttgggtgctggtggtggttggtggagtcctggcttgctatagcttgctagtaacagtgg
cctttattattttctgggtgaggagtaagaggagcaggctcctgcacagtgactacatgaacatgactcccgccgc
cccgggcccacccgcaagcattaccagccctatgccccaccacgcgacttcgcagcctatcgctccagagtgaagtt
cagcaggagcgcagacgcccccgcgtaccagcagggccagaaccagctctataacgagctcaatctaggacgaagag
aggagtacgatgttttggacaagagacgtggccgggaccctgagatgggggaaagccgagaaggaagaaccctcag
gaaggcctgttcaatgaactgcagaaagataagatggcggaggccttcagtgagattgggatgaaaggcgagcgccg
gaggggcaaggggcacgatggcctttccagggtctcagtacagccaccaaggacaccttcgacgcccttcacatgc
aggccctgccccctcgcggaagcggagctactaacttcagcctgctgaagcaggctggagacgtggaggagaaccct
ggacccatggccctgccgtcaccgctttgcttctgccactggccttgctgctccacgctcagctccagctccaaga
gtcagggccaggtctcgtgaaaccgagtgagaccctgtccctgacctgcacagtgagtggtggatcaatctcaagct
ctacctactattgggggtggattcggcagccccctagaaaggggcttgagtggattggcagcactcattatcgagga
tctacctattataatccttctctgaaaagcagagttaccatctctgtggatacgtccaaaaatcagttcagtctgaa
ggtatcatccgtgactgctgccgacacggccgtgtactattgcgcgagggagctgacaggtgaggtctttgactact
ggggccagggcacactcgtgaccgtgtcttctgcctcaacaggagggggtgggagtggaggcggtggatcagggga
ggagggagtgacatccagatgacgcagtcccttccagcttgtccgcatctgtgggtgatagggtcacgattacatg
tagggctagtcagagtatttctagttacctgaattggtaccagcagaaaccaggcaaggcaccaaagttgctcatct
atgcggcctcctctctgcaatctggcgtgccgtccagatttagtggatcaggctccggaaccgatttcaccccttacg
atctcctcacttcaacccgaggatttcgccacatattactgtcaacaaagctattctacaccgttcaccttcggacc
ggggacaaaagtggatattaaacgggcggccgccccaccacgacgccagcgccgcgaccaccaaccccggcgccca
cgatcgcgtcgcagcccctgtcctgcgcccagaggcgtgccggccagcggcggggggcgcagtgcacacgaggggg
ctggacttcgcctgtgatatctacatctgggcgccctggccgggacttgtggggtccttctcctgtcactggttat
cacccctttactgcaacaaacggggcagaaagaagctcctgtatatattcaaacaaccatttatgagaccagtacaaa
```

```
ctactcaagaggaagatggctgtagctgccgatttccagaagaagaagaaggaggatgtgaactgtaaCAGCCACTC

GAGGATCC
```

The nucleic acid molecules can be delivered into cells by art-known methods or as described herein. Genetic modification of a cell can be accomplished by transducing a substantially homogeneous cell composition with a recombinant DNA construct. In certain embodiments, a retroviral vector (e.g., gammaretroviral vector or lentiviral vector) is employed for the introduction of the DNA construct into the cell. For example, a polynucleotide encoding a presently disclosed chimeric receptor can be cloned into a retroviral vector and expression can be driven from its endogenous promoter, from the retroviral long terminal repeat, or from a promoter specific for a target cell type of interest. Non-viral vectors may be used as well.

For initial genetic modification of a cell to include at least one presently disclosed chimeric receptor (e.g., two presently disclosed chimeric receptors, e.g., a presently disclosed ADGRE2-targeted chimeric receptor and a presently disclosed CLEC12A-targeted chimeric receptor), a retroviral vector can be employed for transduction, however any other suitable viral vector or non-viral delivery system can be used. The chimeric receptor(s) can be constructed in a single, multicistronic expression cassette, in multiple expression cassettes of a single vector, or in multiple vectors. Examples of elements that create polycistronic expression cassette include, but is not limited to, various viral and non-viral Internal Ribosome Entry Sites (IRES, e.g., FGF-1 IRES, FGF-2 IRES, VEGF IRES, IGF-II IRES, NF-κB IRES, RUNX1 IRES, p53 IRES, hepatitis A IRES, hepatitis C IRES, pestivirus IRES, aphthovirus IRES, picornavirus IRES, poliovirus IRES and encephalomyocarditis virus IRES) and cleavable linkers (e.g., 2A peptides, e.g., P2A, T2A, E2A and F2A peptides). In certain embodiments, the P2A peptide comprises or consists of the amino acid sequence set forth in SEQ ID NO: 142, which is provided below:

[SEQ ID NO: 142]
GSGATNFSLLKQAGDVEENPGP

An exemplary nucleotide sequence encoding the amino acid sequence of SEQ ID NO: 142 is set forth in 143, which is provided below:

[SEQ ID NO: 143]
ggaagcggagctactaacttcagcctgctgaagcaggctggagacgtgga ggagaaccctggaccc Combinations of retroviral vector and an appropriate packaging line are also suitable, where the capsid proteins will be functional for infecting human cells. Various amphotropic virus-producing cell lines are known, including, but not limited to, PA12 (Miller et al., (1985) *Mol Cell Biol* (1985); 5:431-437); PA317 (Miller., et al., *Mol Cell Biol* (1986); 6:2895-2902); and CRIP (Danos et al., *Proc Natl Acad Sci* USA (1988); 85:6460-6464). Non-amphotropic particles are suitable too, e.g., particles pseudotyped with VSVG, RD114 or GALV envelope and any other known in the art.

Possible methods of transduction also include direct co-culture of the cells with producer cells (Bregni et al., *Blood* (1992); 80:1418-1422), or culturing with viral supernatant alone or concentrated vector stocks with or without appropriate growth factors and polycations(Xu et al., *Exp Hemat* (1994); 22:223-230; and Hughes et al. *J Clin Invest* (1992); 89:1817).

Other transducing viral vectors can be used to modify a cell. In certain embodiments, the chosen vector exhibits high efficiency of infection and stable integration and expression (see, e.g., Cayouette et al., Human Gene Therapy 8:423-430, 1997; Kido et al., Current Eye Research 15:833-844, 1996; Bloomer et al., Journal of Virology 71:6641-6649, 1997; Naldini et al., Science 272:263-267, 1996; and Miyoshi et al., Proc. Natl. Acad. Sci. U.S.A. 94:10319, 1997). Other viral vectors that can be used include, for example, adenoviral, lentiviral, and adena-associated viral vectors, vaccinia virus, a bovine papilloma virus, or a herpes virus, such as Epstein-Barr Virus (also see, for example, the vectors of Miller, *Human Gene Thera* (1990); 15-14; Friedman, *Science* 244:1275-1281, 1989; Eglitis et al., *BioTechniques* (1988); 6:608-614; Tolstoshev et al., *Cur Opin Biotechnol* (1990); 1:55-61; Sharp, *The Lancet* (1991); 337:1277-78; Cornetta et al., Nucleic Acid Research and Molecular Biology 36:311-22, 1987; Anderson, Science (1984); 226:401-409; Moen, Blood Cells 17:407-16, 1991; Miller et al., *Biotechnol* (1989); 7:980-90; LeGal La Salle et al., *Science* (1993); 259:988-90; and Johnson, Chest (1995)107:775-83S). Retroviral vectors are particularly well developed and have been used in clinical settings (Rosenberg et al., *N Engl J Med* (1990); 323:370, 1990; Anderson et al., U.S. Pat. No. 5,399,346).

Non-viral approaches can also be employed for genetic modification of a cell. For example, a nucleic acid molecule can be introduced into a cell by administering the nucleic acid in the presence of lipofection (Feigner et al., *Proc Natl Acad Sci U.S.A.* (1987); 84:7413; Ono et al., *Neurosci Lett* (1990); 17:259; Brigham et al., *Am J Med Sci* (1989); 298:278; Staubinger et al., *Methods in Enzymol* (1983); 101:512, Wu et al., *J Biol Chem* (1988); 263:14621; Wu et al., *J Biol Chem* (1989); 264:16985), or by micro-injection under surgical conditions (Wolff et al., *Science* (1990); 247:1465). Other non-viral means for gene transfer include transfection in vitro using calcium phosphate, DEAE dextran, electroporation, and protoplast fusion. Liposomes can also be potentially beneficial for delivery of DNA into a cell. Transplantation of normal genes into the affected tissues of a subject can also be accomplished by transferring a normal nucleic acid into a cultivatable cell type ex vivo (e.g., an autologous or heterologous primary cell or progeny thereof), after which the cell (or its descendants) are injected into a targeted tissue or are injected systemically. Recombinant receptors can also be derived or obtained using transposases or targeted nucleases (e.g. Zinc finger nucleases, meganucleases, or TALEN, CRISPR). Transient expression may be obtained by RNA electroporation.

Any targeted genome editing methods can also be used to deliver at least one presently disclosed chimeric receptor (e.g., two presently disclosed chimeric receptors, e.g., a presently disclosed ADGRE2-targeted chimeric receptor and a presently disclosed CLEC12A-targeted chimeric receptor) to a cell. In certain embodiments, a CRISPR system is used to deliver at least one presently disclosed chimeric receptor (e.g., two presently disclosed chimeric receptors, e.g., a presently disclosed ADGRE2-targeted chimeric receptor and a presently disclosed CLEC12A-targeted chimeric receptor). In certain embodiments, zinc-finger nucleases are used to deliver at least one presently disclosed chimeric receptor (e.g., two presently disclosed chimeric receptors, e.g., a presently disclosed ADGRE2-targeted chimeric receptor and a presently disclosed CLEC12A-targeted chimeric receptor). In certain embodiments, a TALEN system is used to deliver at least one presently disclosed chimeric receptor (e.g., two presently disclosed chimeric receptors, e.g., a presently disclosed ADGRE2-targeted chimeric receptor and a presently disclosed CLEC12A-targeted chimeric receptor).

Clustered regularly-interspaced short palindromic repeats (CRISPR) system is a genome editing tool discovered in prokaryotic cells. When utilized for genome editing, the system includes Cas9 (a protein able to modify DNA utilizing crRNA as its guide), CRISPR RNA (crRNA, contains the RNA used by Cas9 to guide it to the correct section of host DNA along with a region that binds to tracrRNA (generally in a hairpin loop form) forming an active complex with Cas9), trans-activating crRNA (tracrRNA, binds to crRNA and forms an active complex with Cas9), and an optional section of DNA repair template (DNA that guides the cellular repair process allowing insertion of a specific DNA sequence). CRISPR/Cas9 often employs a plasmid to transfect the target cells. The crRNA needs to be designed for each application as this is the sequence that Cas9 uses to identify and directly bind to the target DNA in a cell. The repair template carrying CAR expression cassette need also be designed for each application, as it must overlap with the sequences on either side of the cut and code for the insertion sequence. Multiple crRNA's and the tracrRNA can be packaged together to form a single-guide RNA (sgRNA). This sgRNA can be joined together with the Cas9 gene and made into a plasmid in order to be transfected into cells.

A zinc-finger nuclease (ZFN) is an artificial restriction enzyme, which is generated by combining a zinc finger DNA-binding domain with a DNA-cleavage domain. A zinc finger domain can be engineered to target specific DNA sequences which allows a zinc-finger nuclease to target desired sequences within genomes. The DNA-binding domains of individual ZFNs typically contain a plurality of individual zinc finger repeats and can each recognize a plurality of base pairs. The most common method to generate new zinc-finger domain is to combine smaller zinc-finger "modules" of known specificity. The most common cleavage domain in ZFNs is the non-specific cleavage domain from the type IIs restriction endonuclease FokI. Using the endogenous homologous recombination (HR) machinery and a homologous DNA template carrying CAR expression cassette, ZFNs can be used to insert the CAR expression cassette into genome. When the targeted sequence is cleaved by ZFNs, the HR machinery searches for homology between the damaged chromosome and the homologous DNA template, and then copies the sequence of the template between the two broken ends of the chromosome, whereby the homologous DNA template is integrated into the genome.

Transcription activator-like effector nucleases (TALEN) are restriction enzymes that can be engineered to cut specific sequences of DNA. TALEN system operates on almost the same principle as ZFNs. They are generated by combining a transcription activator-like effectors DNA-binding domain with a DNA cleavage domain. Transcription activator-like effectors (TALEs) are composed of 33-34 amino acid repeating motifs with two variable positions that have a strong recognition for specific nucleotides. By assembling arrays of these TALEs, the TALE DNA-binding domain can be engineered to bind desired DNA sequence, and thereby guide the nuclease to cut at specific locations in genome. cDNA expression for use in polynucleotide therapy methods can be directed from any suitable promoter (e.g., the human cytomegalovirus (CMV), simian virus 40 (SV40), metallothionein promoters, or Ubiquitin C promoter), and regulated by any appropriate mammalian regulatory element or intron (e.g. the elongation factor 1a enhancer/promoter/intron structure). For example, if desired, enhancers known to preferentially direct gene expression in specific cell types can be used to direct the expression of a nucleic acid. The enhancers used can include, without limitation, those that are characterized as tissue- or cell-specific enhancers. Alternatively, if a genomic clone is used as a therapeutic construct, regulation can be mediated by the cognate regulatory sequences or, if desired, by regulatory sequences derived from a heterologous source, including any of the promoters or regulatory elements described above.

Methods for delivering the genome editing agents/systems can vary depending on the need. In certain embodiments, the components of a selected genome editing method are delivered as DNA constructs in one or more plasmids. In certain embodiments, the components are delivered via viral vectors. Common delivery methods include but is not limited to, electroporation, microinjection, gene gun, impalefection, hydrostatic pressure, continuous infusion, sonication, magnetofection, adeno-associated viruses, envelope protein pseudotyping of viral vectors, replication-competent vectors cis and trans-acting elements, herpes simplex virus, and chemical vehicles (e.g., oligonucleotides, lipoplexes, polymersomes, polyplexes, dendrimers, inorganic Nanoparticles, and cell-penetrating peptides).

5.9. Formulations and Administration

The presently disclosed subject matter also provides compositions comprising the presently disclosed cells (e.g., those disclosed in Section 5.5). In certain embodiments, the composition is a pharmaceutical composition that further comprises a pharmaceutically acceptable carrier.

Compositions comprising the presently disclosed cells can be conveniently provided as sterile liquid preparations, e.g., isotonic aqueous solutions, suspensions, emulsions, dispersions, or viscous compositions, which may be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues. Liquid or viscous compositions can comprise carriers, which can be a solvent or dispersing medium containing, for example, water, saline, phosphate buffered saline, polyol (for example, glycerol, propylene glycol, liquid polyethylene glycol, and the like) and suitable mixtures thereof.

Compositions comprising the presently disclosed cells can be provided systemically or directly to a subject for inducing and/or enhancing an immune response to an antigen and/or treating and/or preventing a neoplasm. In certain embodiments, the presently disclosed cells or compositions comprising thereof are directly injected into an organ of interest (e.g., an organ affected by a neoplasm). Alternatively, the presently disclosed cells or compositions comprising thereof are provided indirectly to the organ of interest, for example, by administration into the circulatory system (e.g., the tumor vasculature). Expansion and differentiation agents can be provided prior to, during or after administration of the cells or compositions to increase production of cells in vitro or in vivo.

The quantity of cells to be administered can vary for the subject being treated. In certain embodiments, between about $10^4$ and about $10^{10}$, between about $10^4$ and about $10^7$, between about $10^5$ and about $10^7$, between about $10^5$ and about $10^9$, or between about $10^6$ and about $10^8$ of the presently disclosed cells are administered to a subject. In certain embodiments, between about $10 \times 10^6$ and about $150 \times 10^6$ of the presently disclosed cells are administered to a subject. In certain embodiments, between about $25 \times 10^6$ and about $150 \times 10^6$ of the presently disclosed cells are administered to a subject. In certain embodiments, between about $25 \times 10^6$ and about $50 \times 10^6$ of the presently disclosed cells are administered to a subject. In certain embodiments, at least about $10 \times 10^6$, about $25 \times 10^6$, about $50 \times 10^6$, about $100 \times 10^6$, or about $150 \times 10^6$ of the presently disclosed cells are administered to a subject. In certain embodiments, about $25 \times 10^6$ of the presently disclosed cells are administered to a subject. The precise determination of what would be considered an effective dose can be based on factors individual to each subject, including their size, age, sex, weight, and condition of the particular subject. Dosages can be readily ascertained by those skilled in the art from this disclosure and the knowledge in the art.

The presently disclosed cells and compositions can be administered by any method known in the art including, but not limited to, intravenous administration, subcutaneous administration, intranodal administration, intratumoral administration, intrathecal administration, intrapleural administration, intraosseous administration, intraperitoneal administration, pleural administration, and direct administration to the subject. The presently disclosed cells can be administered in any physiologically acceptable vehicle, normally intravascularly, although they may also be introduced into bone or other convenient site where the cells may find an appropriate site for regeneration and differentiation (e.g., thymus).

5.10. Methods of Treatment

The presently disclosed subject matter provides various methods of using the presently disclosed cells or compositions comprising thereof. The presently disclosed cells and compositions comprising thereof can be used in a therapy or medicament. For example, the presently disclosed subject matter provides methods for inducing and/or increasing an immune response in a subject in need thereof. The presently disclosed cells and compositions comprising thereof can be used for reducing tumor burden in a subject. The presently disclosed cells and compositions comprising thereof can reduce the number of tumor cells, reduce tumor size, and/or eradicate the tumor in the subject. The presently disclosed cells and compositions comprising thereof can be used for treating and/or preventing a tumor in a subject. The presently disclosed cells and compositions comprising thereof can be used for prolonging the survival of a subject suffering from a tumor. In certain embodiments, each of the above-noted method comprises administering the presently disclosed cells or a composition (e.g., a pharmaceutical composition) comprising thereof to achieve the desired effect, e.g., palliation of an existing condition or prevention of recurrence. For treatment, the amount administered is an amount effective in producing the desired effect. An effective amount can be provided in one or a series of administrations. An effective amount can be provided in a bolus or by continuous perfusion.

In certain embodiments, the tumor is associated with ADGRE2 and/or CLEC12A. In certain embodiments, the tumor cell expresses both ADGRE2 and CLEC12A. In certain embodiments, the tumor cell overexpresses both ADGRE2 and CLEC12A.

In certain embodiments, the tumor is a cancer. In certain embodiments, the tumor is blood cancer. In certain embodiments, the tumor is selected from the group consisting of multiple myeloma, leukemia, lymphomas, and myeloid malignancies. Non-limiting examples of leukemia include acute myeloid leukemia (AML), chronic myeloid leukemia (CML), acute lymphocytic leukemia (ALL), chronic lymphocytic leukemia (CLL), acute promyelocytic leukemia (APL), mixed-phenotype acute leukemia (MLL), hairy cell leukemia, and B cell prolymphocytic leukemia. Non-limiting examples of lymphoma include AIDS-related lymphoma, ALK-positive large B-cell lymphoma, Burkitt's lymphoma, Diffuse large B-cell lymphoma (DLBCL), Follicular lymphoma, Intravascular large B-cell lymphoma, Large B-cell lymphoma arising in HHV8-associated multicentric Castleman's disease, Lymphomatoid granulomatosis, Lymphoplasmacytic lymphoma, Mantle cell lymphoma (MCL), Marginal zone B-cell lymphoma (MZL), Mucosa-Associated Lymphatic Tissue lymphoma (MALT), Nodal marginal zone B cell lymphoma (NMZL), Nodular lymphocyte predominant Hodgkin's lymphoma, Non-Hodgkin's lymphoma, Plasmablastic lymphoma, Primary central nervous system lymphoma, Primary effusion lymphoma, Splenic marginal zone lymphoma (SMZL), and Waldenstrom's macroglobulinemia. The lymphoma can be Hodgkin's lymphoma or non-Hodgkin's lymphoma. Non-limiting examples of myeloid malignancies include myelodysplastic syndromes (MDS), myeloproliferative neoplasms (MPN), myeloid/lymphoid neoplasms (e.g., myeloid/lymphoid neoplasms with eosinophilia and rearrangement of Platelet Derived Growth Factor Receptor Alpha (PDGFRA), Platelet Derived Growth Factor Receptor Beta (PDGFRB), or Fibroblast Growth Factor Receptor 1 (FGFR1), or with PCM1-JAK2), acute myeloid leukemia (AML), blastic plasmacytoid dendritic cell neoplasm, B-lymphoblastic leukemia/lymphoma, and T-lymphoblastic leukemia/lymphoma. In certain embodiments, the myeloid malignancies comprise myelodysplastic syndromes.

In certain embodiments, the tumor is acute myeloid leukemia (AML). In certain embodiments, the tumor is relapsed/refractory acute myeloid leukemia (R/R AML).

In certain embodiments, the subject is a human subject. The subjects can have an advanced form of disease, in which case the treatment objective can include mitigation or reversal of disease progression, and/or amelioration of side effects. The subjects can have a history of the condition, for which they have already been treated, in which case the therapeutic objective will typically include a decrease or delay in the risk of recurrence. As a consequence of surface expression of at least one presently disclosed chimeric receptor (e.g., two presently disclosed chimeric receptors, e.g., a presently disclosed ADGRE2-targeted CAR and a presently disclosed CLEC12A-targeted CCR), adoptively transferred cells are endowed with augmented and selective cytolytic activity at the tumor site. Furthermore, subsequent to their localization to tumor and their proliferation, the cells turn the tumor site into a highly conductive environment for a wide range of cells involved in the physiological antitumor response.

Further modification can be introduced to the presently disclosed cells to avert or minimize the risks of immunological complications (known as "malignant T-cell transformation"), e.g., graft versus-host disease (GvHD), or when healthy tissues express the same target antigens as the tumor cells, leading to outcomes similar to GvHD. A potential solution to this problem is engineering a suicide gene into the presently disclosed cells. Suitable suicide genes include, but are not limited to, Herpes simplex virus thymidine kinase (hsv-tk), inducible Caspase 9 Suicide gene (iCasp-9), and a truncated human epidermal growth factor receptor (EGFRt) polypeptide. In certain embodiments, the suicide gene is an EGFRt polypeptide. The EGFRt polypeptide can enable T-cell elimination by administering anti-EGFR monoclonal antibody (e.g., cetuximab). EGFRt can be covalently joined to the upstream of the presently disclosed chimeric receptor(s). The suicide gene can be included within the vector comprising a nucleic acid encoding a presently disclosed chimeric receptor. In this way, administration of a prodrug designed to activate the suicide gene (e.g., a prodrug (e.g., AP1903 that can activate iCasp-9) during malignant T-cell transformation (e.g., GVHD) triggers apoptosis in the suicide gene-activated cells expressing the presently disclosed chimeric receptor. The incorporation of a suicide gene into the a presently disclosed chimeric receptor gives an added level of safety with the ability to eliminate the majority of receptor-expressing cells within a very short time period. A presently disclosed cell incorporated with a suicide gene can be pre-emptively eliminated at a given timepoint post the cell infusion, or eradicated at the earliest signs of toxicity.

6. EXAMPLES

The practice of the present disclosure employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides disclosed herein, and, as such, may be considered in making and practicing the presently disclosed subject matter. Particularly useful techniques for particular embodiments will be discussed in the sections that follow.

The following examples are put forth so as to provide those of ordinary skill in the art with a complete disclosure and description of how to make and use the presently disclosed cells and compositions, and are not intended to limit the scope of what the inventors regard as their invention.

Example 1—Targeting ADGRE2 and CLEC12A

The presently disclosed subject matter evaluates a novel combinatorial CAR format for R/R AML that has the potential to provide improved safety and efficacy relative to alternative CAR therapies currently under clinical investigation.

Application of CAR therapy in AML is challenged by its intra- and interindividual phenotypic heterogeneity, and the ideal CAR target needs to be validated. To identify potential CAR targets, the available transcriptomics and proteomics datasets from malignant and normal tissues were analyzed and flow cytometric analysis of primary AML patient samples, healthy bone marrow hematopoietic stem/progenitor cells (HSPCs), and healthy primary T cells were carried out (Perna et al., *Cancer Cell* 2(4):506-519.e5. (2017)). None of the targets showed a surface expression profile comparable with that of CD19, which was expressed at high levels in virtually all B cell leukemia cells, completely absent from HSPCs and T cells, and undetectable systematically outside B cell areas. However, the analysis identified the adhesion G protein-coupled receptor E2 (ADGRE2), a novel potential CAR target for AML. Pair-wise analyses of the potential CAR targets suggested that, consistent with AML clonal heterogeneity, a combinatorial CAR targeting approach can be potentially efficacious in eradicating AML tumors while minimizing toxicity.

ADGRE2 (EMR2) is a member of the epidermal growth factor (EGF)-TM7 family of proteins (Lin et al., *Genomics* 41.3 (1997): 301-308). Its expression is restricted to monocytes/macrophages and is not upregulated in activated T and B cells (Lin et al., *Genomics* 67.2 (2000): 188-200). Flow cytometric analyses revealed ADGRE2 positivity on >90% of AML cells in the majority of the analyzed R/R AML patient population (FIG. 1). ADGRE2 was found to be positive both in the total AML bulk population and, most importantly, in the therapeutically relevant fraction of leukemic stem cells (LSC). Other candidate targets such as CD33 and CD123 were also found to be positive in the majority of patients, however not as consistently as ADGRE2, especially in LSCs. Therefore, ADGRE2 was selected as the CAR target as it can offer a higher chance for achieving complete remission in R/R AML patients.

C-type lectin domain family 12 member A (CLEC12A/CD371) is a well-described candidate target in AML, and it is expressed in the majority of AML patients (Perna et al., *Cancer cell* 32.4 (2017): 506-519; Haubner et al., *Leukemia* 33.1 (2019): 64-74; Bakker et al., *Cancer research* 64.22 (2004): 8443-8450). Other groups are already pursuing it as a CAR target in ongoing Phase 1 clinical trials in the US (Tashiro et al., *Molecular Therapy* 25.9 (2017): 2202-2213).

Figure 2:
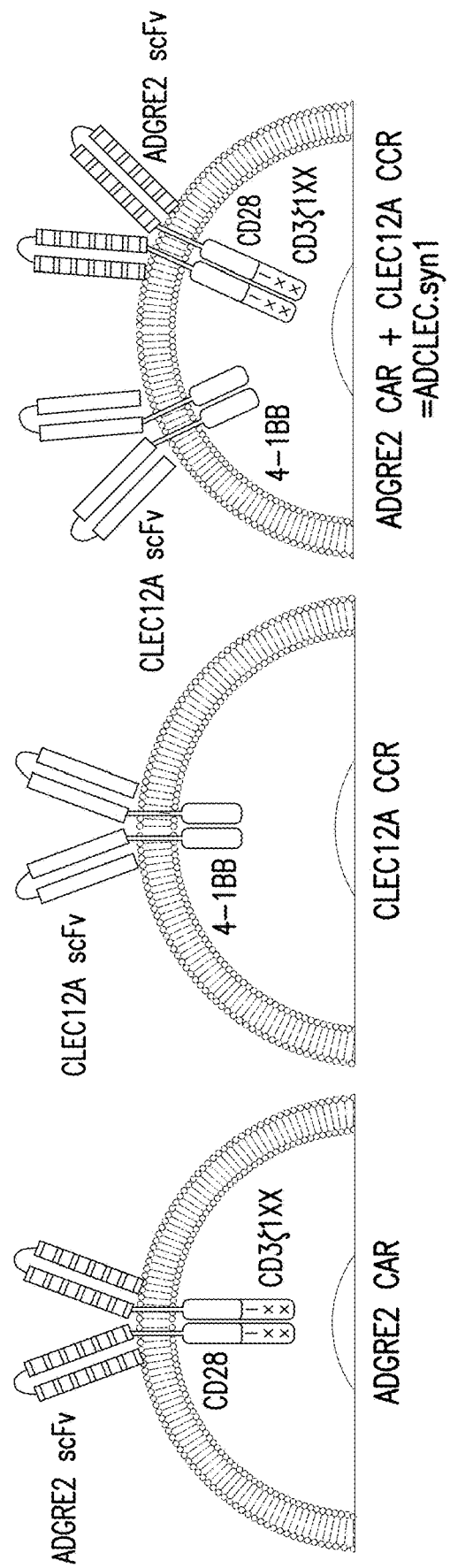

The presently disclosed subject matter proposes using a combinatorial CAR-CCR vector, termed ADCLEC.syn1 (FIG. 2), which encodes a CAR specific for ADGRE2 and a CCR specific for CLEC12A to treat R/R AML. The CAR comprises a CD28 costimulatory domain and an attenuated CD3ζ1XX activation domain. It was previously demonstrated that genetic modification of the ITAM motifs of the CD3ζ signaling domain provided an enhanced therapeutic benefit by achieving a favorable balance of effector and memory signatures, thereby enhancing the persistence of functional CAR T cells in a pre-B acute lymphoblastic leukemia NALM6 mouse model (Feucht et al., *Nature medicine* 25.1 (2019): 82-88). The CCR provides 4-1BB co-stimulation to enhance T cell persistence and prevents antigen-low AML escape; it does not comprise a CD3ζ domain and thus does not mediate cell killing like a CAR.

ADGRE2 expression is commonly upregulated in AML cells as compared to non-malignant cells. Considering the ADGRE2 expression in some normal cell types, including HSCs, a targeting strategy that would preferentially target AML cells was designed. In this approach, a first step was decreasing the affinity and activation potential of the ADGRE2 CAR to improve the safety of the CAR therapy, and a second step was rescuing ADGRE2 CAR engagement against LSCs by co-targeting CLEC12A (CD371), a second molecule expressed on LSCs but not HSCs, to prevent AML escape. CLEC12A was targeted through a chimeric costimulatory receptor (CCR), which provides increased avidity and co-stimulation but does not initiate cytolytic activity. Thus, the CCR assists the CAR to detect ADGRE2 in AML cells.

Figure 3:
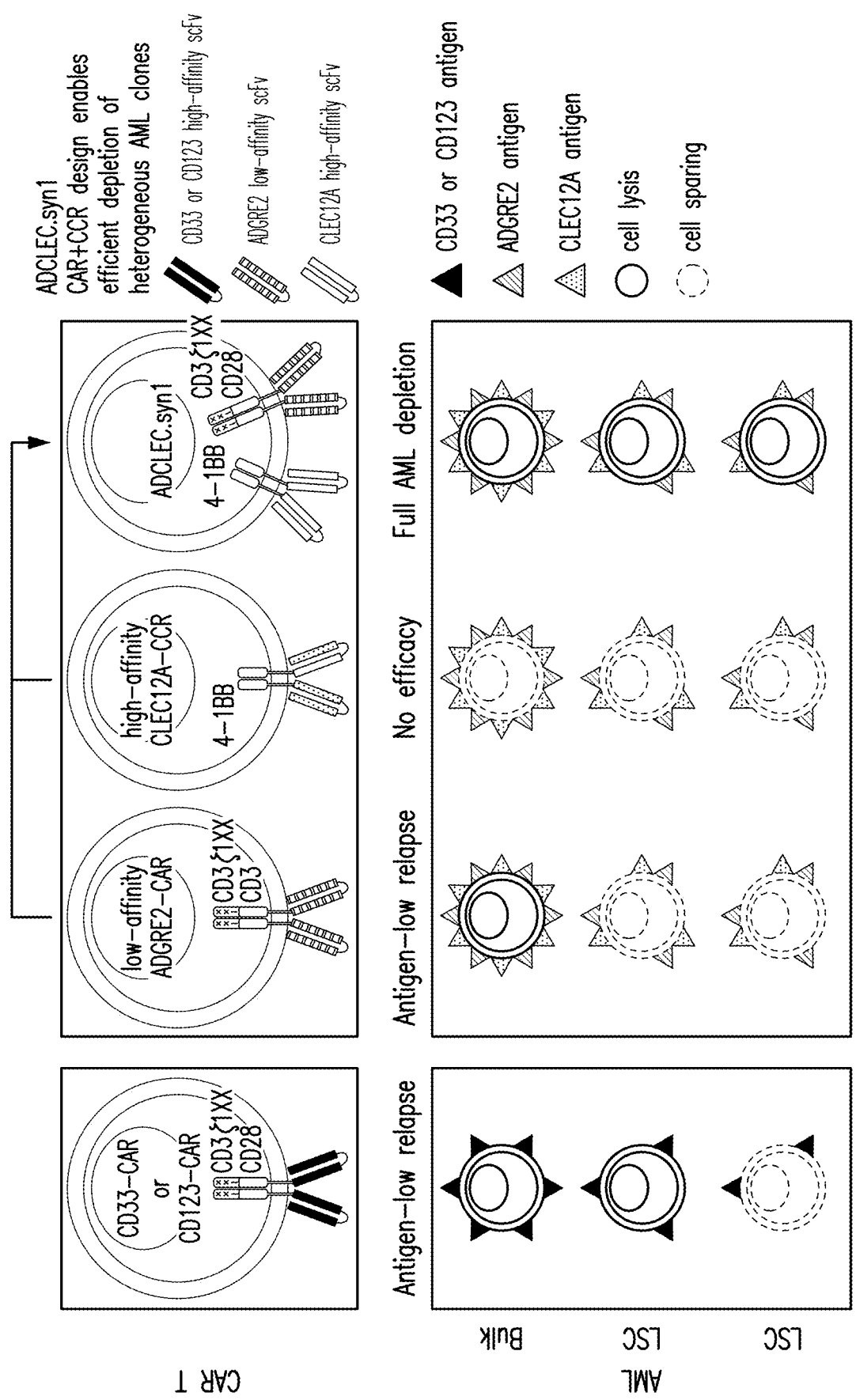

CAR signaling is triggered upon target engagement of the scFv portion of the CAR, which depends on CAR scFv affinity and CAR target antigen density. The ADGRE2 CAR scFv affinity were optimized so that healthy cells, which have lower ADGRE2 antigen levels than AML tumor cells, did not trigger CAR activation and were therefore spared, adding an important safety feature but at the same time increasing the risk of AML escape via downregulation of ADGRE2 antigen levels (FIG. 3). To mitigate the risk of ADGRE2-low AML escape, the addition of the CLEC12A CCR increased the overall avidity to AML cells and thereby "compensated" for the lower-affinity ADGRE2 CAR, while it does not initiate the elimination of ADGRE2-negative/CLEC12a-positive cells. As the CLEC12A CCR lacks a CD3ζ domain, it did not function as a CAR. Isolated CCR activation in the absence of simultaneous CAR activation did not trigger T cell activation or cytotoxicity (FIG. 3).

Figure 4C:
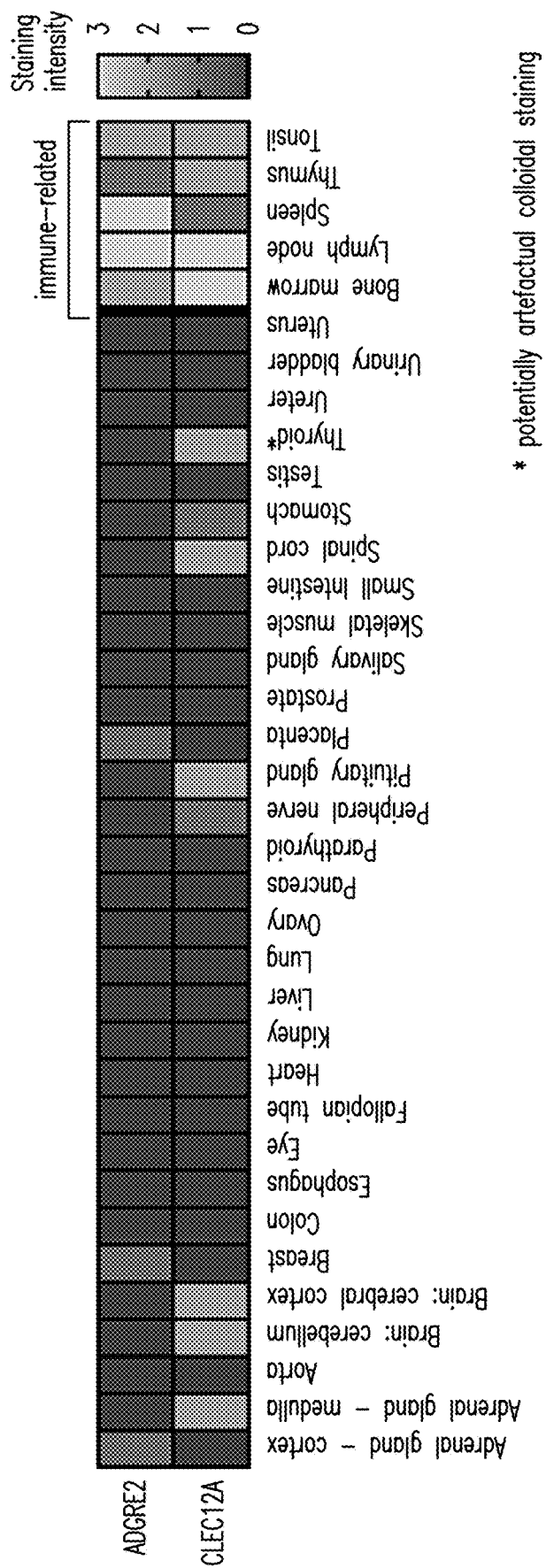
Figure 5:
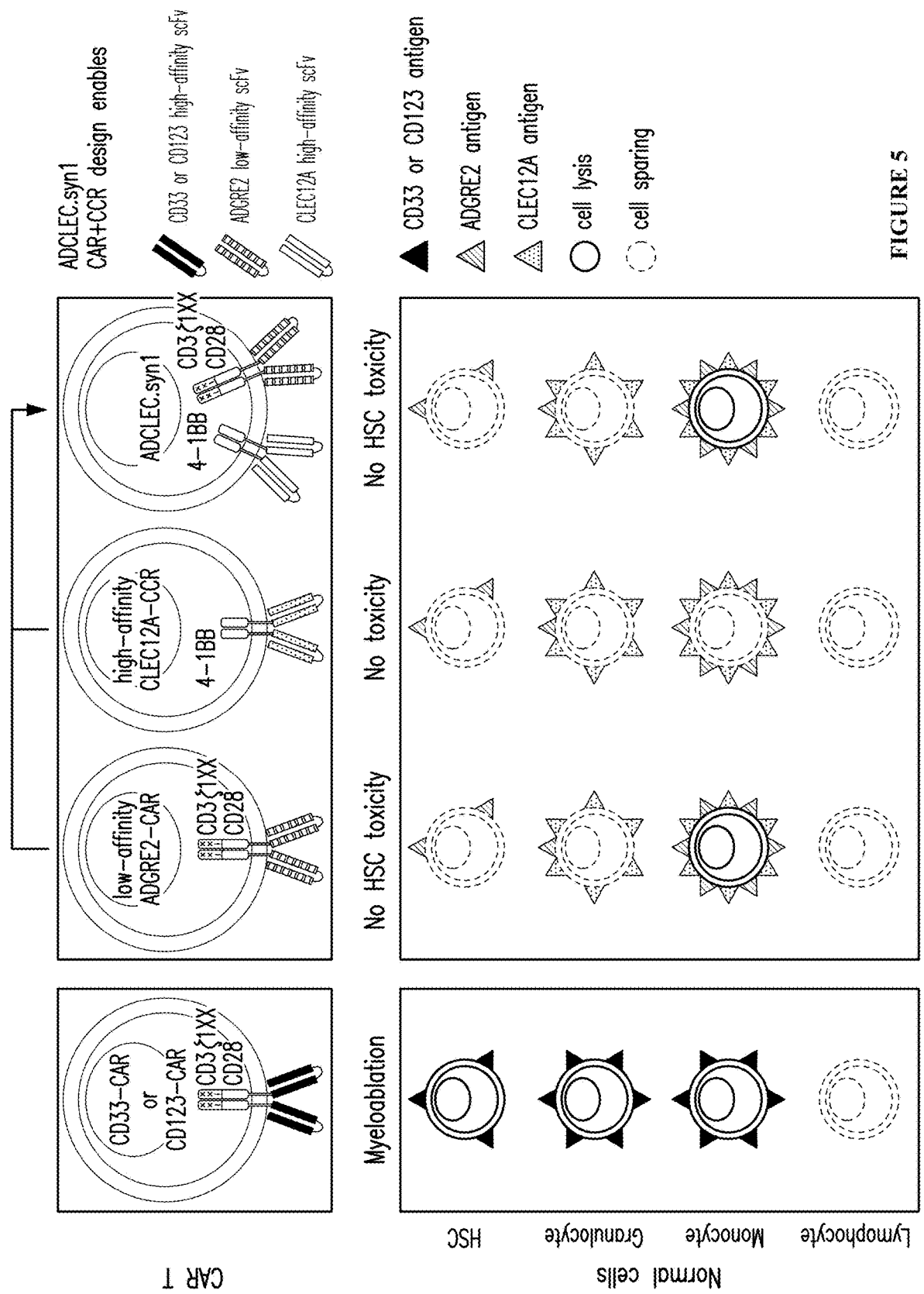

The choice of targets and chimeric receptor design was made under consideration of safety features linked to the target expression in normal tissues and normal hematopoiesis. Co-expression of ADGRE2 and CLEC12A was limited to the monocyte subset, while all other major lineages had either a low or undetectable expression of ADGRE2 by flow cytometry (FIG. 4A) suggesting that ADCLEC.syn1 would display diminished activity against HSCs and granulocytes (FIG. 5). In comparison, the alternative targets CD33 and CD123, which were co-expressed in HSCs, led to greater CAR-mediated hematologic toxicity (FIGS. 4B and 5). Using commercially available antibodies for ADGRE2 and CLEC12A for IHC, the presently disclosed subject matter demonstrated that non-hematopoietic tissues had a largely non-overlapping expression profile with the majority of the detected signal associated with tissue-resident myeloid-derived cells such as macrophages (FIG. 4C). Taken together, these target expression data indicate that combinatorial targeting of ADGRE2 with a CAR and CLEC12A with a CCR via ADCLEC.syn1 vector can minimize the toxicity of the CAR-CCR T cells to normal hematopoietic and non-hematopoietic tissues relative to ADGRE2 targeting alone and provides a higher chance of sparing HSC compared to CD33 or CD123 CAR T cells.

In summary, the ADGRE2 CAR and CLEC12A CCR combined in the ADCLEC.syn1 vector mitigated the risk of ADGRE2 antigen escape and enhanced overall CAR T cell efficacy via optimized delivery of CD28 and 4-1BB costimulatory signaling in the context of fine-tuned CD3ζ1XX CAR signaling, but without cumulating potential on-target/off-tumor toxicity as would arise by combining two CARs. This rational combinatorial choice of target and chimeric receptor design can reduce the risk of unwanted toxicity while enhancing the targeting of R/R AML, including LSCs.

Example 2—ADGRE2 scFv

Figure 6:
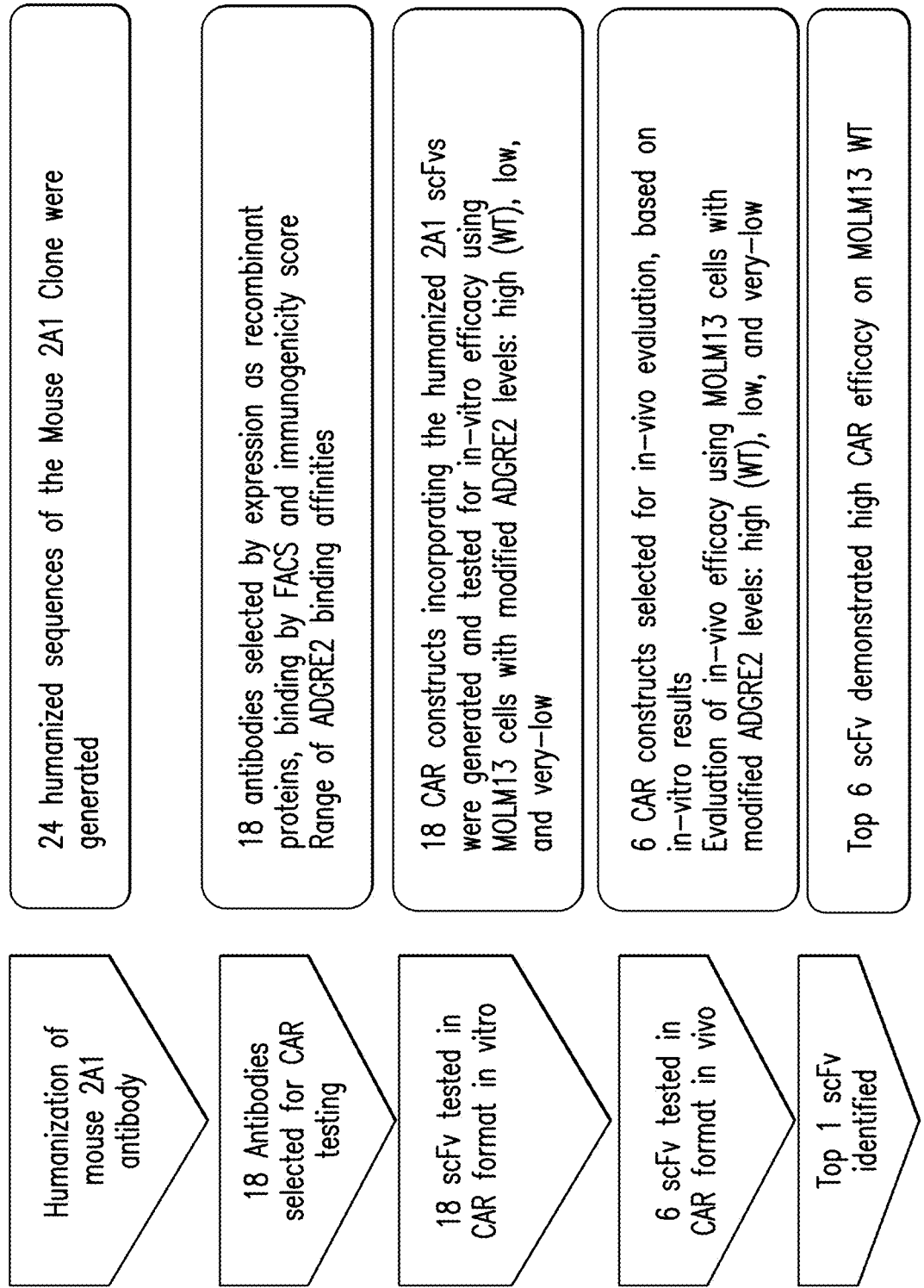

The ADGRE2 single-chain fragment variable (scFv) in the ADCLEC.syn1 vector was selected from 24 versions of the humanized recombinant antibodies generated using the peptide sequence of the monoclonal anti-human ADGRE2 clone 2A1 antibody. The binder selection scheme is present in FIG. 6. The mouse monoclonal anti-human ADGRE2 clone 2A1 is a widely used antibody to detect ADGRE2 expression in human samples (Boyden et al., N Engl J Med. 374(7):656-63. (2016)). Based on (1) the expression of the humanized 2A1 antibody variants, (2) the binding of the recombinant antibodies to ADGRE2-overexpressing murine lymphoma EL4 cells as measured by flow cytometry, and (3) the immunogenicity score, 18 humanized recombinant antibodies were selected from the pool of candidates. Next, VH and VL domains were identified to generate 18 scFv candidates that were subsequently integrated into the SFG based gammaretroviral CAR vectors and tested in functional CAR assays (FIGS. 7A-7C and 8).

ADGRE2-specific CAR T cells were produced by transducing T cells with the SFG-gammaretroviral vector expressing each of the humanized 2A1 scFv in the CAR cassette, and CAR T cell cytotoxicity was measured using the AML cell line MOLM13. Cognizant of ADGRE2 expression in some normal cell types, including HSCs, which express lower levels of ADGRE2 than AML cells, MOLM13 cell lines were genetically modified for high (WT), low, or very low levels of ADGRE2 expression, with coexpression of low (WT) or high levels of CLEC12A (see Table 17 below).

TABLE 17

MOLM13 cell lines for CAR studies used for identification of lead ADGRE2 and CLEC12A scFvs

| Target cell line | ADGRE2 level (MFI relative to WT) | CLEC12A level (MFI relative to WT) |
| --- | --- | --- |
| MOLM13-WT | high (1x) | low (1x) |
| MOLM13_ADGRE2-1E8 | low (0.2x) | low (1x) |
| MOLM13_ADGRE2-9D6 | very-low (0.1x) | low (1x) |
| MOLM13_ADGRE2-E6_CLEC12A-C6 | low (0.2x) | high (25.9x) |
| MOLM13_ADGRE2-9D6_CLEC12A-B6 | very-low (0.1x) | high (15.7x) |

Figure 7A:
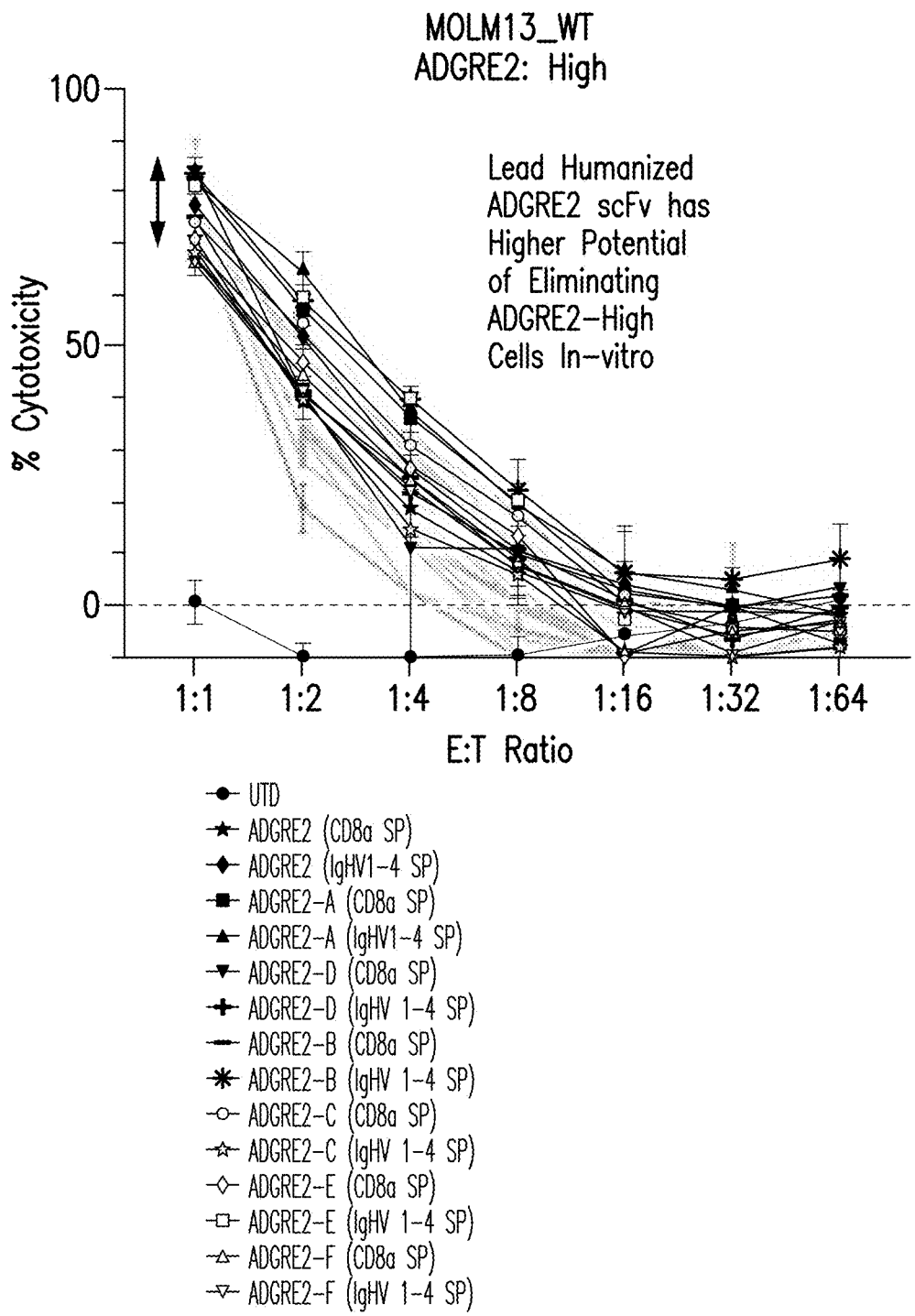
Figure 7B:
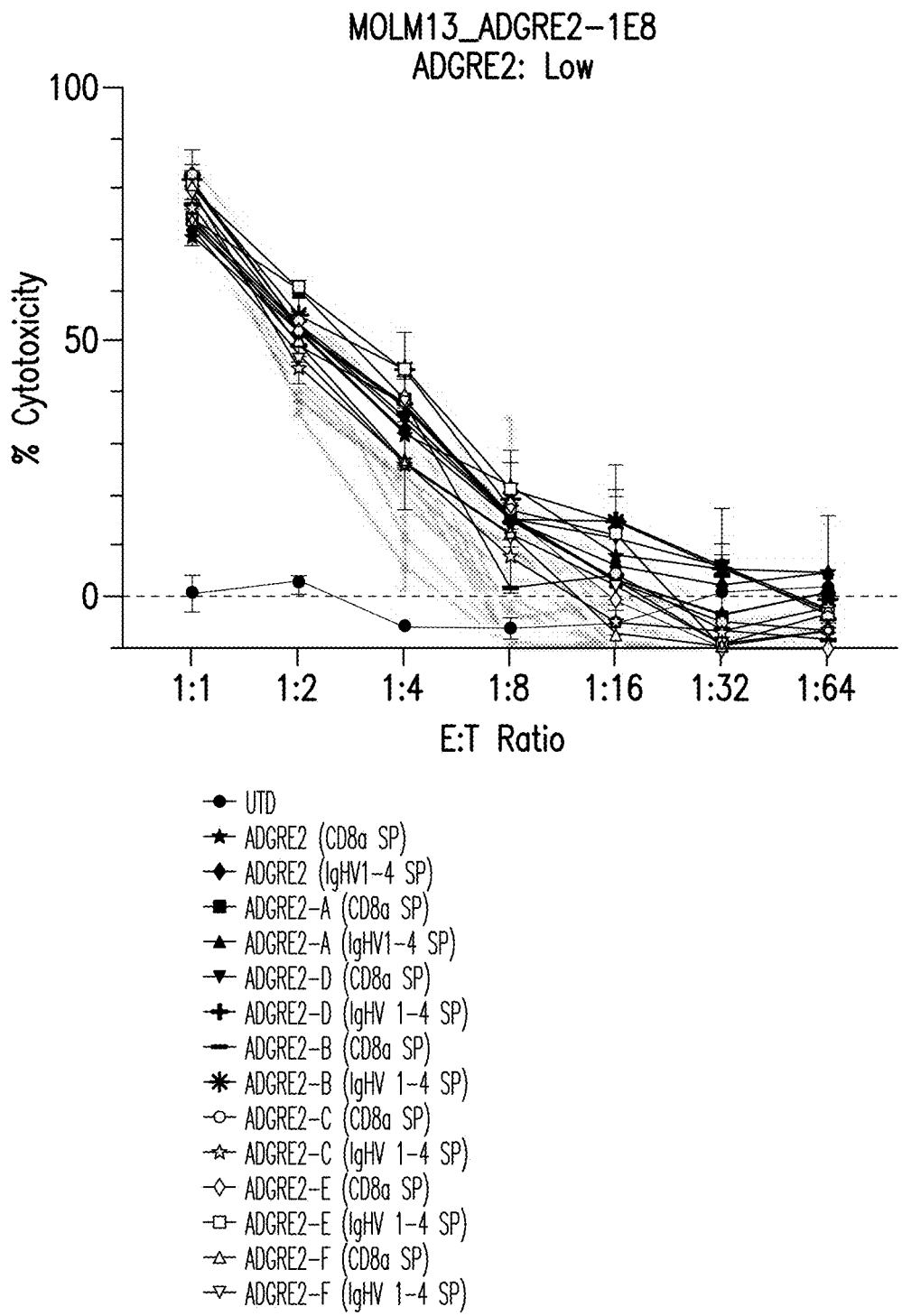
Figure 7C:
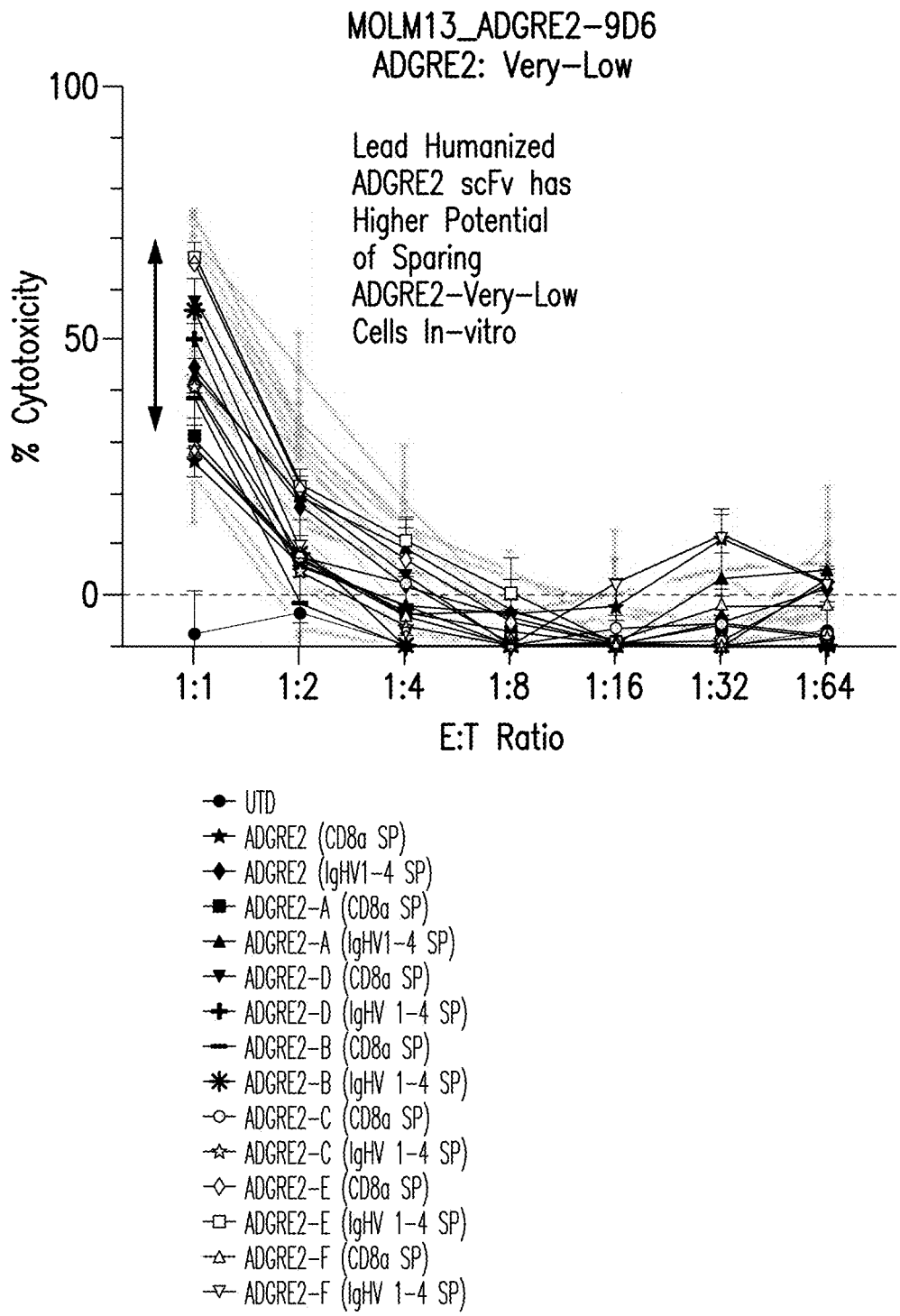
Figure 8:
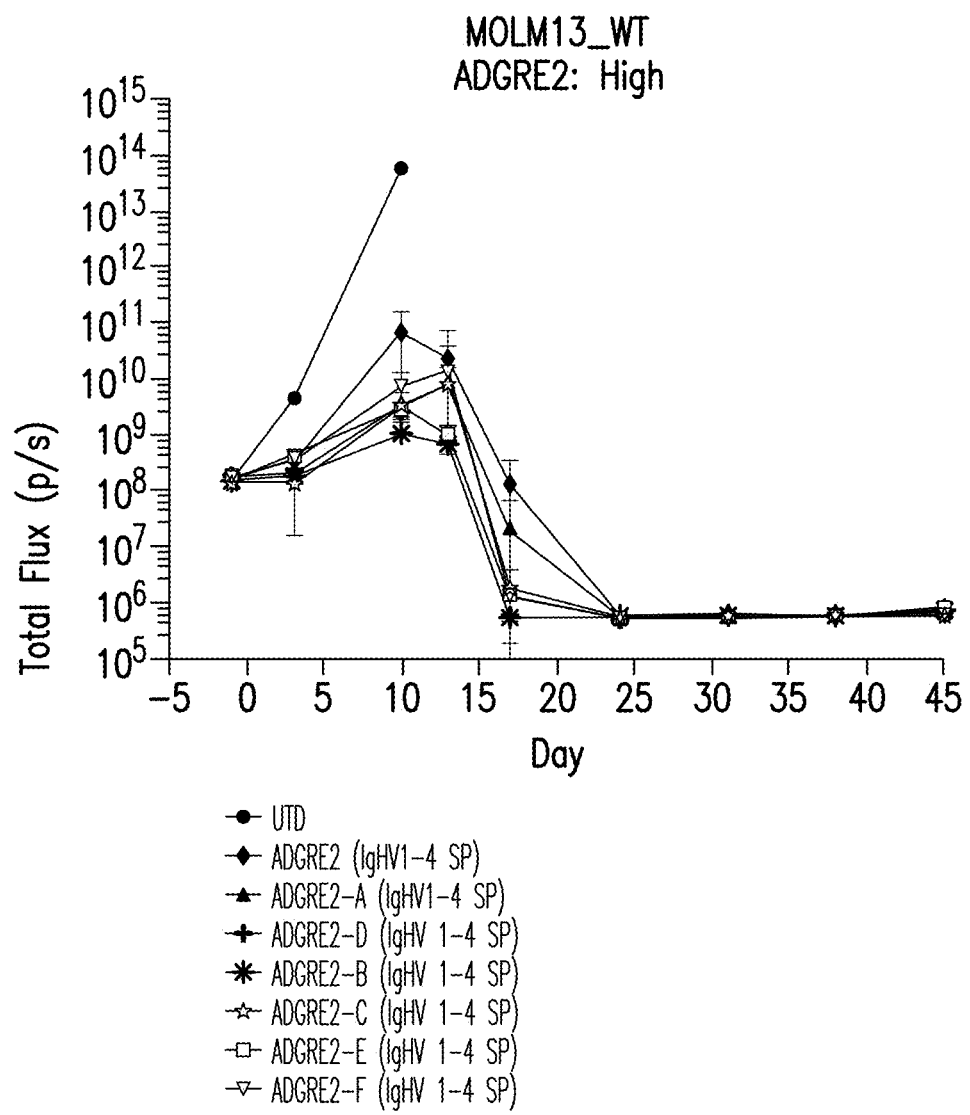
Figure 8:
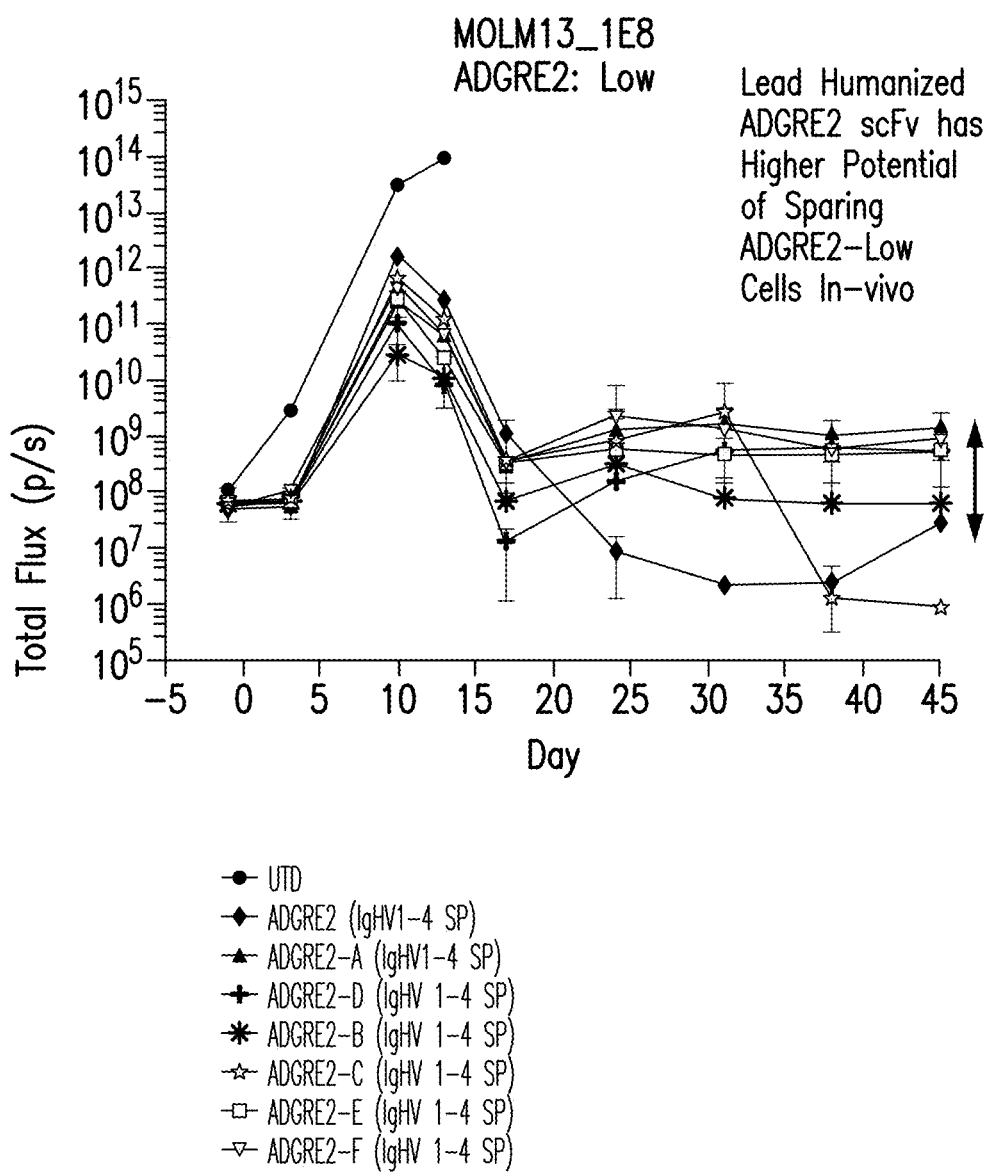
Figure 8:
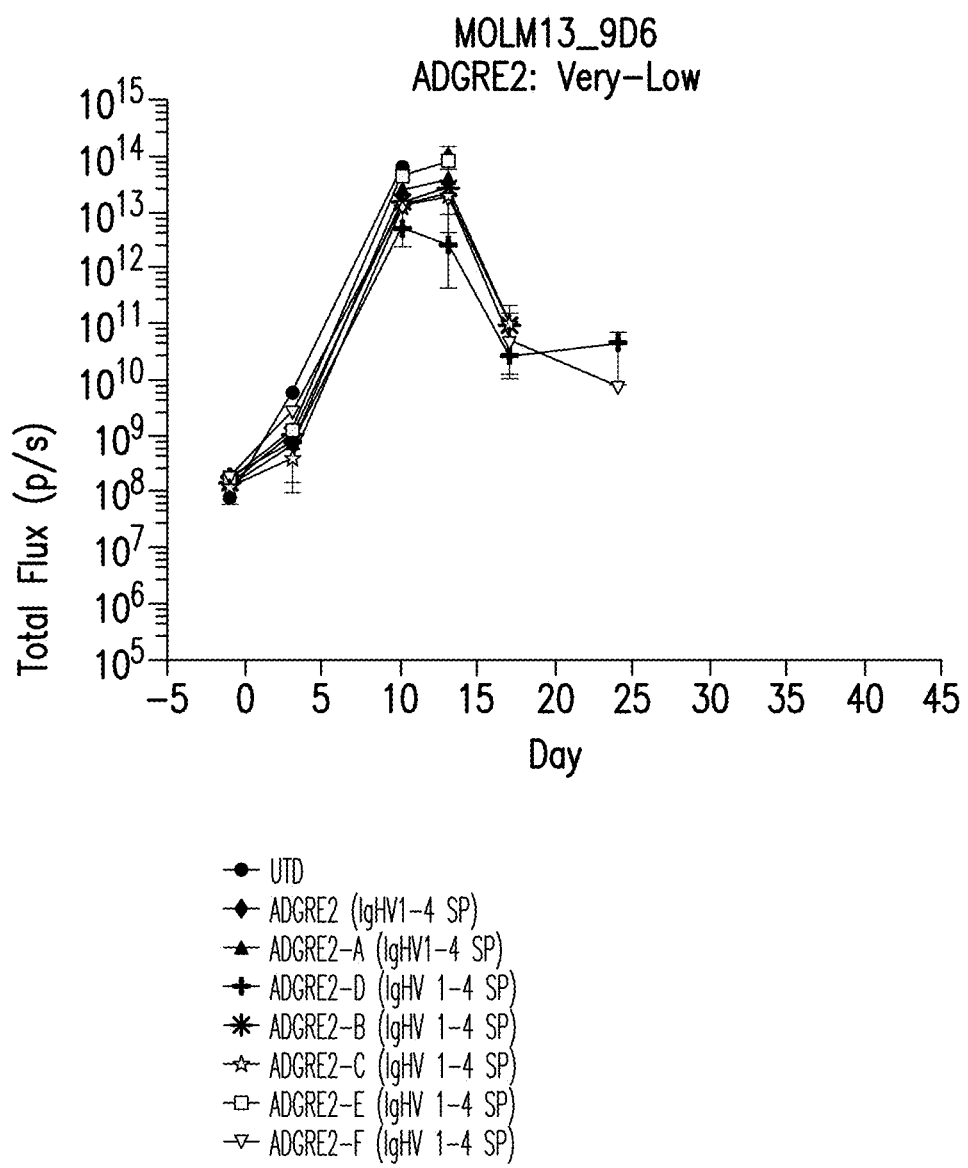

These modified MOLM13 cell lines allowed the identification of the humanized ADGRE2 scFv with the highest potential of efficiently depleting ADGRE2-high AML cells while sparing ADGRE2-low normal cells and thereby maintaining a favorable safety profile (FIGS. 7A-7C and 8). The in vitro CAR screening included 18 different ADGRE2 scFv candidates in the context of two different signal peptides (CD8a or IgHV1-4). A set of 6 scFvs that mediated the most suitable pattern of in vitro target cell lysis (maximum lysis of ADGRE2-high cells and minimum lysis of ADGRE2-very-low cells) were identified with a high similarity between the two tested signal peptides (FIGS. 7A-7C). Then, these 6 scFvs were tested in in vivo model using the same AML cell line MOLM13 with high (WT), low or very low levels of ADGRE2. Here, the ADGRE2 scFv ADGRE2-A showed the most suitable in vivo response pattern, with maximum efficacy against target cells with high ADGRE2 levels and reduced/absent efficacy against target cells with low/very-low ADGRE2 levels, respectively. Therefore, ADGRE2-A was selected as ADGRE2 scFv and with the CD8a signal peptide.

Example 3—CLEC12A scFv

Figure 9:
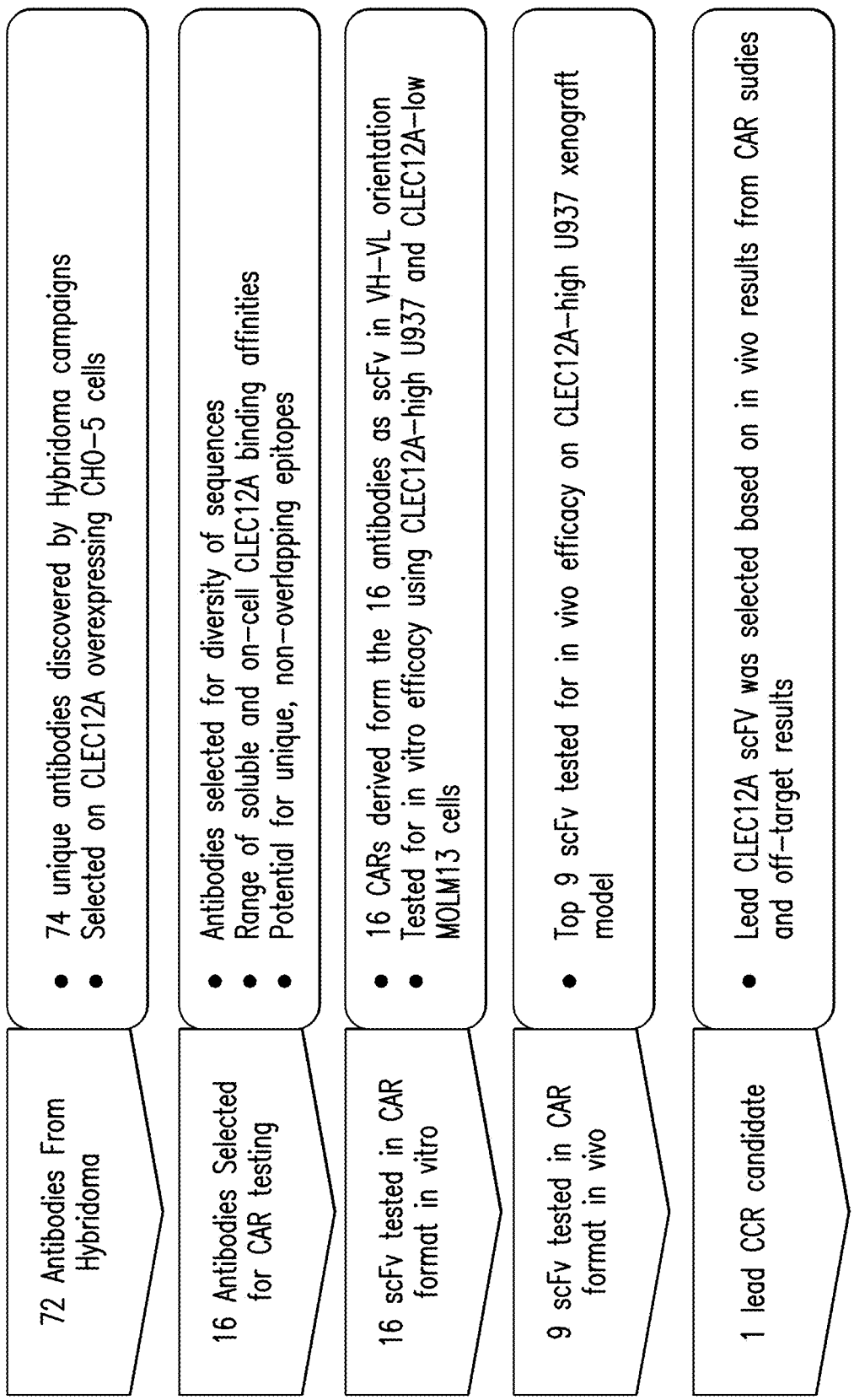

The human CLEC12A scFv was selected from 74 unique human antibodies produced by hybridomas generated by fusing P3X63Ag8U.1 cell with lymphocytes isolated from mice immunized with recombinant human CLEC12A protein. Positive clones were selected by using on-cell binding to CLEC12A-expressing CHO-S cells and surface plasmon resonance assay. The selection scheme of the scFv selection is shown in FIG. 9.

Figure 10A:
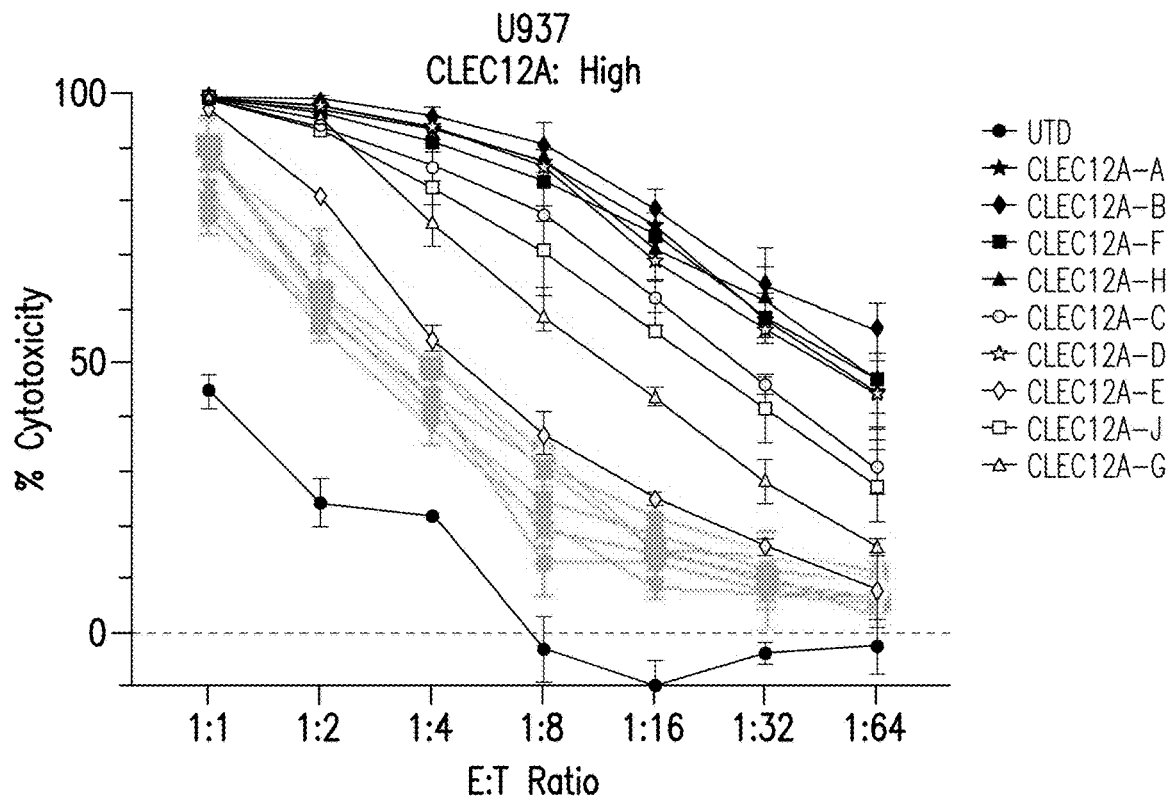
Figure 10B:
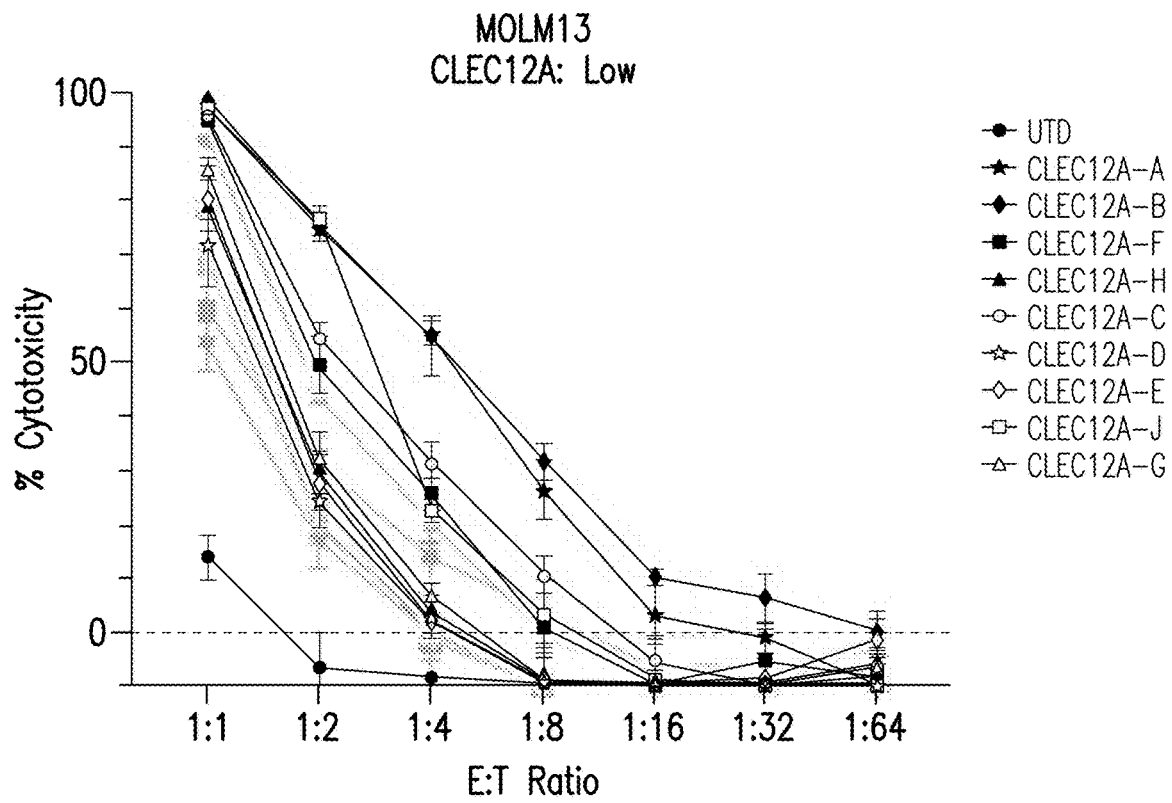
Figure 11:
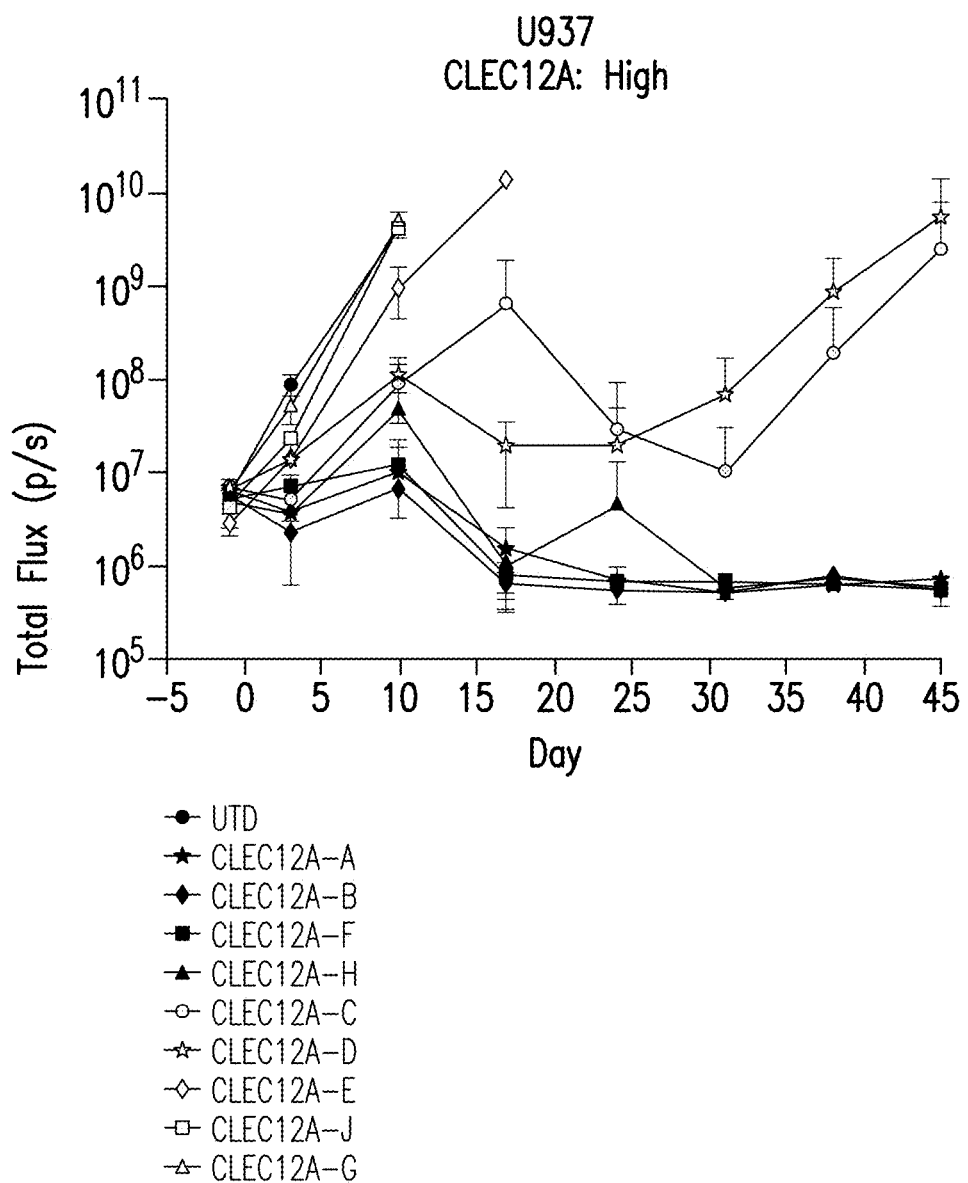

16 different human CLEC12A scFv candidates were tested in a 28z1XX TRAC-CAR format using in vitro 18 h CAR cytotoxicity assays and in vivo xenograft models. Different from the strategy for ADGRE2 scFv identification, here the efficacious scFv were prioritized in the context of both high and low target antigen levels, considering that the eventual application of the scFv would be in a CCR, not CAR, and high target sensitivity of the CLEC12A scFv would therefore not be associated with increased toxicity. In vitro screening of 16 scFvs in the context of U937 (CLEC12A-high) and MOLM13 (CLEC12A-low) cell lines identified 9 highly potent CLEC12A scFvs (FIGS. 10A and 10B). Subsequent in vivo screening of these 9 scFvs identified the lead CLEC12A scFv (CLEC12A-A) (FIG. 11).

Example 4—Off-Target Binding of ADGRE2 scFv and CLEC12A scFv

The off-target binding interactions of ADGRE2 scFv (ADGRE2-A) and CLEC12A scFv (CLEC12A-A) to human plasma membrane proteins were carried out in a 4-phase approach: (1) pre-screening to determine the optimal concentrations of purified recombinant ADGRE2 scFv-Fc and CLEC12A scFv-Fc test proteins for the screening; (2) screening for binding of the test proteins against fixed HEK293 cells overexpressing 5,474 full-length human plasma membrane proteins and cell surface tethered human secreted proteins and 371 human cell surface heterodimers, which identified library hits; (3) confirmatory/specific screens using fixed-cell and live-cell microarrays; (4) flow cytometry-based follow-on study to investigate further identified test protein-specific interactions on live cells; and (5) cell-to-cell binding assays to confirm positive hits. The table below summarizes the off-binding data for ADGRE2 scFv and CLEC12A scFv.

live-cell microarrays and with RTN3R in live-cell microarray only. Follow-on studies using dose titration and flow cytometry experiments using purified CLEC12A scFv-Fc demonstrated that CLEC12A scFv EC50s against SECTM1 and RTN4R were 800-fold and >3,700-fold greater than against the primary target CLEC12A, respectively. Furthermore, although the CLEC12A CCR-expressing Jurkat cells bound CLEC12A-overexpressing HEK293 cells, CLEC12A CCR-expressing Jurkat cells had very weak to weak binding to SECTM1-overexpressing HEK293 cells. Together, these data suggest that the binding of CLEC12A scFv-Fc to SECTM1 and RTN4R may not be physiologically relevant. Any potential off-target binding of the CLEC12A CCR does not lead to cytotoxicity without simultaneous ADGRE2 CAR activation, adding another safety layer (FIG. 12).

Example 5—Validation of Combinatorial CAR+CCR Targeting Concept of ADCLEC.Syn1

As outlined in the schematics depicted in FIGS. 3 and 5, the presently disclosed subject matter hypothesized that the combinatorial CAR+CCR design of ADCLEC.syn1 would allow efficient elimination of AML while sparing normal cells with low CAR target levels. Importantly, the CCR alone should assist and enhance CAR-mediated cytolysis, however, not trigger cytolysis independently. This approach was validated in in vitro and in vivo models (FIG. 12). First, an in vitro model was established with a target cell line expressing either no target (ADGRE2−/CLEC12A−), CAR target alone (ADGRE2+/CLEC12A−), CCR target alone (ADGRE2−/CLEC12A+), or both CAR and CCR targets (ADGRE2+/CLEC12A+). The CCR target alone did not trigger in vitro killing, however, the CAR target alone triggered killing, which was further enhanced when the CCR target was co-expressed on the target cell line (FIG. 12A). Next, it was demonstrated in vivo that ADGRE2 CAR signaling alone was not sufficient to fully eradicate ADGRE2-low cells (modeling normal cells), however, combined ADGRE2 CAR and CLEC12A CCR signaling allowed for complete and durable AML remission (FIGS. 12B and 12C). Overall, these results indicate the potential of

TABLE 18

Binding of ADGRE2 scFv and CLEC12A scFv to proteins identified in the fixed and live-cell screenings

| Test Article | Interacting Proteins identified from the screens | Protein Name | Flow Cytometry EC50 | Cell-to-Cell Binding |
|---|---|---|---|---|
| ADGRE2 scFv-Fc | ADGRE2 | Adhesion G protein-coupled receptor E2 | Not tested | Not tested |
| CLEC12A scFv-Fc | CLEC12A | C-type lectin domain family 12 member A | 0.081 µg/mL | medium to strong |
| | SECTM1 | Secreted and transmembrane protein 1 | 799.5 µg/mL | weak to very weak |
| | RTN4R | Reticulon-4 receptor | >300 µg/mL | Not tested |

From the 5,845 plasma membrane proteins tested, the purified ADGRE2-scFv-Fc protein bound only its primary target cell surface protein, ADGRE2, both in fixed-cell and live-cell microarrays. In addition, ADGRE2-scFv-Fc did not bind to other ADGRE proteins ADGRE1, ADGRE3, and ADGRE5.

CLEC12A scFv-Fc showed a strong specific interaction with its primary target, CLEC12A. It also had a low but detectable interaction with SECTM1 in both fixed-cell and ADCLEC.syn1 to spare normal cells with low levels of CAR target while efficiently eradicating AML.

Example 6—SFG-ADCLEC.syn1 Retroviral Vector

Figure 13:
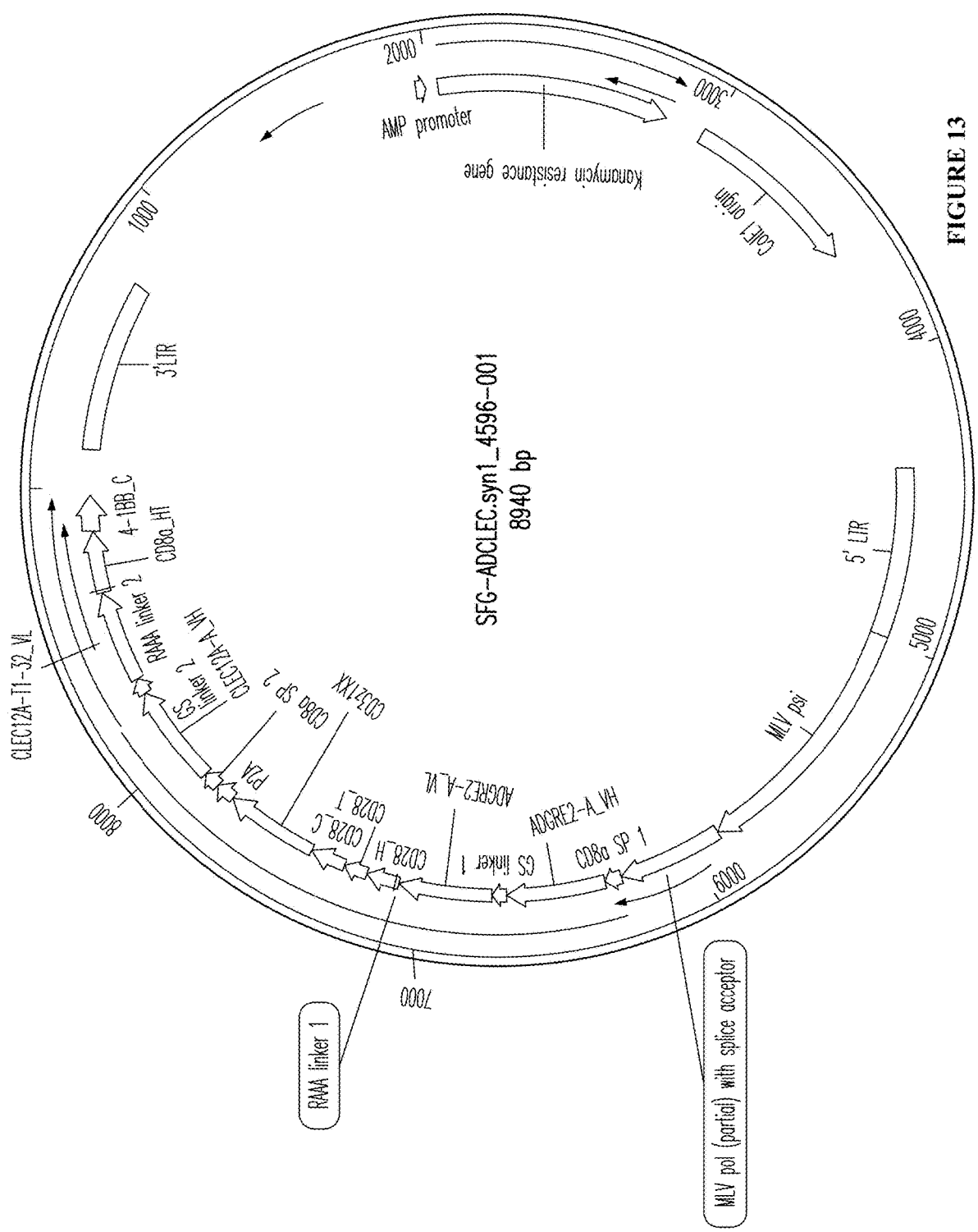
FIG. 13 illustrates a pSFG-ADCLEC.syn1 restriction map (8940 bp).
Figure 14:
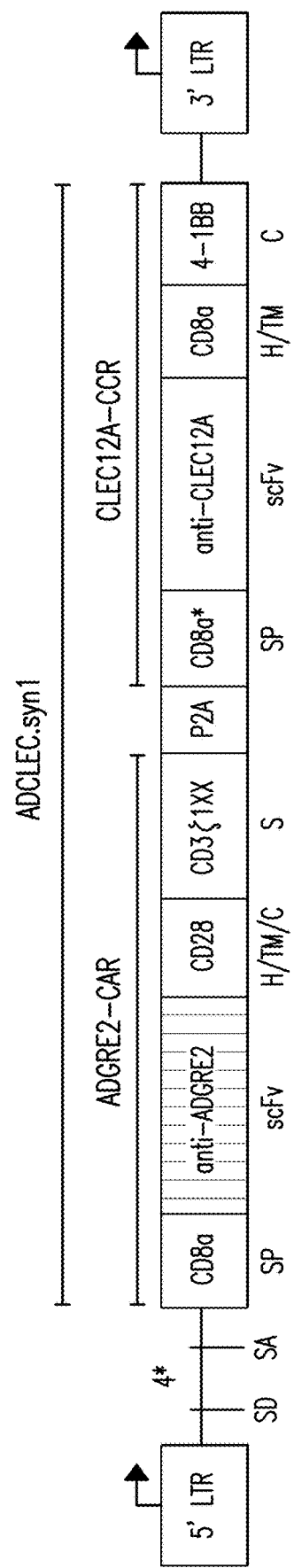
FIG. 14 illustrates the gammaretroviral vector design for ADCLEC.syn1 bicistronic construct including ADGRE2ADGRE2-A-CAR and CLEC12ACLEC12A-A-CCR. Abbreviations: LTR=long terminal repeat, SD=splice donor site, SA=splice acceptor site, SP=signal peptide, scFv=single-chain variable fragment, H=hinge, TM=transmembrane, C=costimulatory domain, S=stimulatory domain.

The gammaretroviral plasmid SFG-ADCLEC.syn1 (FIG. 13) was constructed and the identity of the plasmid was verified by Sanger sequencing analysis. The gammaretroviral vector SFG-ADCLEC.syn1 expresses both the ADGRE2-specific CAR and CLEC12A-specific CCR linked through a P2A element, as shown in FIG. 14.

The SFG plasmid is used to transiently transfect 293Vec-RD114 cells, a HEK 293-based packaging cell line that produces retroviral vectors pseudotyped with feline RD114 envelope. The vector supernatant that is harvested from the 293Vec-RD114™ packaging cells is subsequently used to transduce the 293Vec-GalV™, a second HEK 293-based packaging cell line pseudotyped with the gibbon ape leukemia virus envelope protein, to generate a stable producer cell population expressing the 293Vec-GalV-SFG-AD-CLEC.syn1. Single clones are isolated from the 293Vec-GalV™ SFG-ADCLEC.syn1 vector producer population, and several seed banks are generated and best titer clones are characterized. The best producer cell line, the lead clone, is used to generate the Master Cell Bank (MCB) from the seed banks. Retroviral Vector stock (VS) is manufactured from one vial of the MCB.

Example 7—Ex Vivo Transduction of Autologous T Cells with SFG-ADCLEC.Syn1

Activated, autologous patient-derived peripheral blood T cells are transduced ex vivo with GaLV pseudotyped SFG-ADCLEC.syn1 retroviral vector stocks. CD8+ and CD4+ T cells are positively isolated using CD8 and CD4 Microbeads using the Prodigy CliniMACS plus instrument (Miltenyi Biotec) and activated with Dynabeads (ThermoFisher). The initial positive selection of CD8+ and CD4+ T cells mainly minimizes the number of B lymphocytes, plasma cells, and monocytes in the transduced T cell product. Fluorescence-activated cell sorting (FACS) assays using dye-labeled purified ADGRE2 or CLEC12A polypeptides are carried out to measure the expression of the ADGRE2 CAR and CLEC12A CCR to determine transduction efficiency. Products for patient administration have transduction efficiency greater than or equal to 4%.

Example 8—Dosage Form, Route of Administration, and Dosing Regimen (Frequency and Duration)

ADCLEC.syn1 CAR T cells are provided in a cryopreserved bag, thawed at the facility, e.g., hospital facility, and administered as an intravenous (IV) infusion via gravity. The planned dose levels to be evaluated during dose escalation are described in Table 19 below.

TABLE 19

Planned ADCLEC.syn1 CAR T cells Dose Levels

| Dose Level (DL) | ADCLEC.syn1 CAR T cell dose (flat) |
|---|---|
| −1 | $10 \times 10^6$ |
| 1 | $25 \times 10^6$ |
| 2 | $50 \times 10^6$ |
| 3 | $100 \times 10^6$ |
| 4 | $150 \times 10^6$ |

The starting dose for ADCLEC.syn1 CAR T cells is $25 \times 10^6$ CAR T cells. This dose is significantly lower than the approved dosing of CD19 CARs ($2 \times 10^6$ CAR T cells/kg for axicabtagene and $6\text{-}60 \times 10^7$ CAR T cells for tisagenlecleucel), and also lower than the doses of BCMA CARs currently being investigated in multiple myeloma ($50\text{-}800 \times 10^6$ CAR T cells). Dose escalation follows a standard 3+3 design. Following identification of the RP2D, the RP2D dose cohort can be expanded.

Example 9—Clinical Study

The present example is a phase 1, open-label, dose-escalation study to evaluate safety and activity of ADCLEC.syn1 CAR T cells disclosed herein in adult patients with R/R AML. A standard 3+3 dose escalation scheme is used to determine the maximum tolerated dose (MTD) or maximal administered dose (MAD) if the MTD is not reached. Once the MTD or MAD is identified, the cohort is expanded to include additional patients to further evaluate the safety and activity of ADCLEC.syn1 CAR T cells.

Cohorts of 3-6 patients are infused with escalating doses of ADCLEC.syn1 CAR T cells to establish the MTD. There are 4 planned dose levels: $25 \times 10^6$, $50 \times 10^6$, $100 \times 10^6$, $150 \times 10^6$ CAR T cells. A standard 3+3 dose escalation design is implemented starting from dose $25 \times 10^6$. 3-6 patients are treated in each cohort and dose escalation proceeds to the next cohort if less than 33% of patients in a cohort experience unanticipated dose-limiting toxicity (DLT). If unacceptable toxicity is seen in 1 of 3 patients in any given cohort, up to 6 patients are treated in that cohort using a conventional dose escalation scheme. If 2 of 6 patients in any given cohort experience unacceptable toxicity, the MTD of T cells has been exceeded, and established at the previous cohort dose level. If the first dose level exceeds the MTD, a subsequent cohort of 3-6 patients is treated at the −1 dose level of $10 \times 10^6$ ADCLEC.syn1 CAR T cells.

Conditioning or lymphodepleting chemotherapy. Patients receive conditioning chemotherapy consisting of fludarabine 25 mg/m$^2$ on days −4, −3, −2, and cyclophosphamide 500 mg/m$^2$ on days −3, −2, followed by CAR T cell infusion on day 0.

Bridging therapy. At the discretion of the treating physician, bridging therapy may be considered. Bridging therapy may be administered after leukapheresis and must be discontinued at least 1 week prior to administration of conditioning chemotherapy, with the exception of hydroxyurea which can be continued until at least 24 hours prior to the start of conditioning chemotherapy. Subjects should be restaged after the end of the bridging therapy and prior to start of conditioning chemotherapy or within 48 hours prior to administration of conditioning chemotherapy.

Disease response assessment. Bone marrow biopsy is obtained at day 28-35 of CAR T cell infusion for response assessment and is assessed by the ELN criteria.

Figure 16:
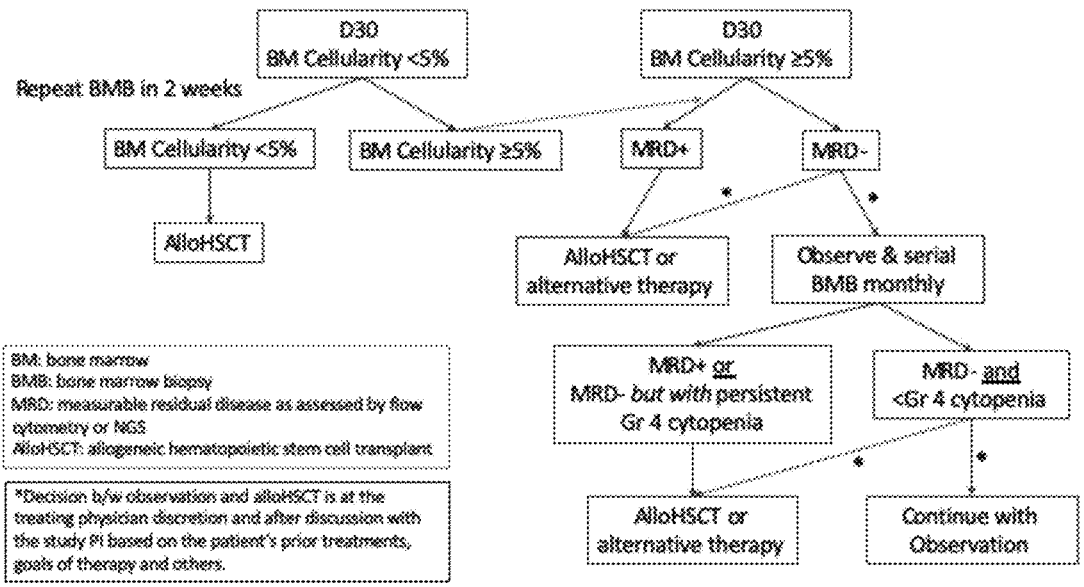
FIG. 16 illustrates an algorithm to guide treatment course following D30 disease assessment.

Treatment course following D28-35 disease response assessment. Following the disease response assessment, subsequent care is guided per the suggested algorithm as shown in FIG. 16.

Toxicity assessment. At each study visit, toxicities are graded according to the National Cancer Institute (NCI) Common Terminology Criteria for Adverse Events (CT-CAE) Version 5.0 and ASTCT consensus grading for cytokine release syndrome (CRS) and immune effector cell-associated neurotoxicity syndrome (ICANS).

Pharmacokinetic assessment. Blood tests for pharmacokinetic measurements are performed prior to dosing, on day 1, 3, 5, 7, 14, 21, and 28-30. Subsequent blood samples are collected on months 2, 3, 6, 9, 12 and 24 months.

ADCLEC.syn1 CAR T cell Dose Levels. The starting dose for ADCLEC.syn1 CAR T cells is $25 \times 10^6$ CAR T cells. This dose is significantly lower than the approved dosing of CD19 CARs ($2 \times 10^6$ CAR T cells/kg for axicabtagene and $6\text{-}60 \times 10^7$ CAR T cells for tisagenlecleucel), and also lower than the doses of BCMA CARs currently being investigated in multiple myeloma (50-800×10⁶ CAR T cells). Assuming a body weight of 70 kg, the proposed starting dose translates to $2 \times 10^5$ CAR T cells/kg and is comparable (or slightly lower) compared to other autologous AML CAR starting doses.

Dose Limiting Toxicity (DLT). A DLT is defined as any of the following adverse event (AE) that occurs within 28 days of the ADCLEC.syn1 CAR T cell infusion, based on Common Terminology Criteria for Adverse Events (CTCAE) v5.0, or the ASTCT Consensus Grading guidelines for Cytokine Release Syndrome (CRS) and Immune Effector Cell Associated Neurotoxicity Syndrome (ICANS): (a) any Grade ≥3 non-hematologic AE to vital organs (excluding CRS and ICANS) which fail to resolve to grade 2 or below within 7 days; (b) Grade 4 neutropenia or thrombocytopenia and day 28 bone marrow cellularity of <5% in the absence of persistent AML. Persistent cytopenias that were present at baseline (pre-conditioning chemotherapy and T cell infusion) that persist until day 30 in the absence of active disease is not considered a DLT; (c) ≥Grade 3 infusion reaction; (d) Grade 3 or 4 ICANS of any duration; (e) Grade 4 CRS of any duration; (f) Grade 4 tumor lysis syndrome; (g) Grade 4 capillary leak syndrome; and (h) any Grade 5 event related to ADCLEC.syn1 CAR T cells.

Dose Escalation. The objective of Dose Escalation is to determine the MTD/MAD of ADCLEC.syn1 CAR T cells. Dose escalation follows 3+3 dose escalation rules as follows: (a) subjects are enrolled in cohorts of three subjects per dose level with a minimum of 10 days between ADCLEC.syn1 CAR T cells dosing of the first and the second subject within a cohort; (b) if no DLT is reported in the initial cohort of three subjects, dose escalation can proceed to the next higher dose level; (c) if one subject has a DLT, the cohort is expanded up to six subjects. If no additional DLTs are observed, that dose level is considered tolerable and dose escalation can proceed to the next higher dose level; (d) a subject who discontinues study treatment or withdraws from the study prior to the end of the DLT observation period for reasons other than DLT is considered unevaluable for DLT and is replaced; (e) if more than one subject out of six enrolled subjects enrolled at the same dose level cohort has a DLT, the MTD has been exceeded. Further enrollment in that dose cohort stops; six subjects at a lower dose level are enrolled to determine the MTD per 3+3 dose escalation rules; (f) if the dose level that exceeded the MTD is ≥2 times higher than the previously highest tolerable dose level, another dose level approximately midway between these two levels can be enrolled to determine the MTD per 3+3 dose escalation rules; (g) the MTD is the highest dose level cohort with at most one DLT in six evaluable subjects.

Dose Expansion. The objectives of Dose Expansion are to further assess safety and tolerability and to identify activity signals to guide and support future development. The dose of ADCLEC.syn1 CAR T cells in the Dose Expansion is the MTD/MAD that was established during Dose Escalation. During the Dose Expansion phase, subjects with R/R AML are treated in the same manner as in the Dose Escalation phase and includes up to approximal 12 subjects.

Investigational Medicinal Product. ADCLEC.syn1 CAR T cells are provided as a cryopreserved bag, thawed at the facility, and administered as an intravenous (IV) infusion via gravity. The planned dose levels is evaluated during dose escalation described herein. ADCLEC.syn1 CAR T cells are administered on Day 0.

Non-Investigational Medicinal Products. Conditioning chemotherapy includes (a) cyclophosphamide (CY), 500 mg/m2 IV on Days −3 and −2 of each treatment cycle; and (b) fludarabine (FLU), 25 mg/m2 IV on Days −4, −3 and −2 of each treatment cycle. The dose and schedule of CY and FLU may be modified based on cytopenia and medical comorbidities.

Study Endpoints. Primary endpoints include the incidence and nature of DLTs when ADCLEC.syn1 CAR T cells are administered in patients with R/R AML. Secondary endpoints include (a) incidence, nature and severity of adverse events of ADCLEC.syn1 CAR T cells; (b) investigator-assessed objective-response rate (ORR), defined as the proportion of subjects who achieve a Complete Response (CR), CR with incomplete hematologic recovery (CRi), morphologic leukemia free state (MLFS) and partial response (PR), as per the ELN response criteria; (c) progression-free survival (PFS), defined as the duration from first dose of ADCLEC.syn1 CAR T cells (Day 0) to progressive disease (PD), or to the day of death for any reason, whichever occurs earlier; (d) one-year overall survival (OS), defined as the percentage of subjects who are alive at one year from initiation of study treatment; and (e) cellular kinetics of ADCLEC.syn1 CAR T cell, peak expansion and persistence defined as duration from Day 1 to the last assessment of detectable levels of ADCLEC.syn1 CAR T cells, as assessed by PCR and flow cytometry. Exploratory endpoints include (a) association of ORR and/or PFS with expansion and duration of ADCLEC.syn1 CAR T cells, with ADGRE2 and CLEC12A antigen expression, and CAR T cell phenotypes; (b) MRD assessment in those patients who achieve CR or CRi as assessed by multiparameter flow cytometry and/or NGS; (c) analysis of serum cytokines following CAR T cell infusion; (d) analysis for immunogenicity towards the CAR-CCR construct; and (e) association of relapse with ADGRE2 and CLEC12A expression levels, ADCLEC.syn1 CAR T cell persistence and phenotype and changes in tumor microenvironment.

Tumor Response Assessment Criteria. Antitumor responses is assessed according to the ELN response criteria in AML. Eligibility/Inclusion criteria include (a) being ≥18 years of age at the time of signing the ICF; (b) have been refractory or relapsed AML who have exhausted or are not eligible or intolerant to, standard therapeutic options (the following disease status is eligible for the study: (1) primary refractory disease after two courses of induction chemotherapy or after one course of hypomethylating agent or low dose cytarabine in combination with venetoclax that has not achieved CR/CRi or MLFS by the ELN criteria; or (2) recurrent AML at any time after achieving a response (CR or CRi) during or after the course of treatment, including HSCT); (c) any degree of detectable disease is eligible; (d) ECOG performance status 0 or 1; (e) having a suitable stem cell donor identified who may donate cells in the event that the subject needs to undergo an allogeneic HSCT for rescue from prolonged marrow aplasia (donor can be from related or unrelated matched source, haplo or cord, and must be found to be suitable according to standard criteria); and (f) having adequate organ function defined as serum creatinine <2.0 mg/100 ml, direct bilirubin <2.0 mg/100 ml, AST and/or ALT ≤5×ULN, unless considered due to leukemic organ involvement. Exclusion Criteria include (a) diagnosis of acute promyelocytic leukemia; (b) radiologically-detected or symptomatic CNS disease or CNS 3 disease, i.e., presence of ≥5/ul WBCs in CSF (subjects with adequately treated CNS leukemia are eligible); (c) oxygen saturation <90% on room air; (d) prior allogeneic HSCT within 3 months of signing ICF or with ongoing requirement for systemic graft-versus-host therapy; (e) clinically significant cardiovascular disease, including stroke or myocardial infarction within 6 months prior to first study medication; or the presence of unstable angina or congestive heart failure of New York Heart Association grade 2 or higher, or cardiac ejection fraction <40%; (f) uncontrolled clinically significant infections; (g) positive serologic test results for HIV; (h) acute or chronic HBV or HCV infection as assessed by serologic (HBVsAg or HCV ab) or PCR results; and (i) active second malignancy that requires systemic treatments, with the exception of malignancy treated with curative intent and without evidence of disease for >2 years before screening. Stopping Rules include (a) for Dose Escalation, the stopping rules are as per the dose escalation rules; (b) for Dose Expansion, a temporary halt to enrollment in the study occurs when any patient death deemed probably or possibly related to ADCLEC.syn1 CAR T cells, or ≥30% subjects in an expansion cohort, where at least 6 subjects have been enrolled, experience an ADCLEC.syn1 CAR T cell treatment-related toxicity at any time on study that would have otherwise qualified as a DLT.

Statistical Methods. In general, clinical data are summarized by cohort, separately by each regimen, using descriptive statistics (n, mean, standard deviation, standard error, median, first quartile (Q1), third quartile (Q3), minimum, and maximum for continuous variables, and frequencies and percentages for categorical variables). When categorical data are presented, the percentages are suppressed when the frequency count is zero. Non-zero percentages are rounded to one decimal place, except 100% is displayed without any decimal places. For selected assessments, confidence intervals (CIs) is displayed. Time-to-event variables are summarized using Kaplan-Meier methods.

Example 10—Identification and Characterization of Anti-ADGRE2 Antibodies and scFvs The present example demonstrates derivation and characterization of binding affinities of anti-ADGRE2 antibodies and scFvs. Antibodies were developed using hybridoma technology, comprising 24 humanized sequences of the mouse Reference 1 Clone. Antibodies were selected based on expression as recombinant protein variants, binding to ADGRE2-overexpressing murine lymphoma EL4 cells as measured by FACS, and immunogenicity score, 18 humanized recombinant antibodies were selected representing a range of ADGRE2 binding affinities. The amino acid sequence of the Reference 1 anti-ADGRE2 antibody was determined by endoprotease digestion and subsequent analysis of peptide pools by LC-MS/MS. Briefly, the heavy and light chains of the antibody were separated by SDS-PAGE under reducing conditions. After staining with Coomassie Blue, respective bands were cut from the gel and digested with Asp N, chymotrypsin, trypsin and elastase endopeptidases. In addition, antibody was digested in solution by pepsin. The pool of peptides generated from digestion was analyzed on an Orbitrap analyzer (LC-MS/MS Q-Exactive, ThermoFisher). LC-MS/MS data was processed using the PEAKS AB antibody sequencing software. The Reference 1 anti-ADGRE2 VH and VL coding sequences were derived from the respective antibody chain sequences, and cloned with an IgG2 constant region. Recombinant Reference 1 antibody was expressed in HEK293 cells, and purified antibody was compared with commercially available Reference 1 antibody by surface plasmon resonance (SPR) $K_D$ analysis using a recombinantly produced protein comprising the extracellular domain of ADGRE2 as well as EC50 determination was carried out for binding to cells expressing ADGRE2. For subsequent antibody screening work, purified recombinant Reference 1 antibody was used as a reference antibody.

Example 11—On-Cell Binding of Anti-ADGRE2 scFvs

This example illustrates the on-cell binding for the anti-ADGRE2 scFvs as measured by flow cytometry. The on-cell binding for the anti-ADGRE2 scFvs was assessed by flow cytometry on the E4 cells overexpressing ADGRE2. Each of the scFvs were tested for binding to ADGRE2 and compared to the Reference 1 mAb. Briefly, 100,000 cells per well, were plated in 96 well V bottom plate, scFvs were diluted to 200 nMscFv then 1:4 serially down to 0.01 nM. A dose dependent titration of the scFvs validated recombinant scFvs folding and binding to ADGRE2. $EC_{50}$ affinities were compared in order to better interpret any differences seen in-vivo that might be caused by variations in affinities resulting from the humanization process Data was analyzed using Prism software, using a four parameter regression. The approximate $EC_{50}$ values were determined using equation: Y=Bottom+(Top−Bottom)/(1+10^((LogEC_{50}−X)*Hill-Slope)) where the fitted parameters are defined as follows: Bottom, the lower plateau describing minimum binding achievable; Top, the upper plateau describing the maximum binding achievable; LogEC50, the inflection point of the dose response curve also known as the concentration producing a half-maximal response; and Hill-Slope, the slope of the dose response curve.

TABLE 20

Binding Affinity of anti-ADGRE2 scFv

| scFv | Affinity ($EC_{50}$ nm) |
|---|---|
| ADGRE2-D | 16.4 |
| ADGRE2-B | 55.3 |
| ADGRE2-E | 10.6 |
| ADGRE2-A | 93.8 |
| ADGRE2-F | 16.4 |
| ADGRE2-C | 53.2 |
| Reference 1 | 10.1 |

As shown in Table 20, the $EC_{50}$ values calculated from the curves show that each of the antibodies binds cells at affinities from 10.2 to 93.8. Overall, the results showed that the tested humanized scFvs had $EC_{50}$ values comparable to the Reference 1 standard.

Example 12—in Silico Immunogenicity Analysis of Anti-ADGRE2 scFv

This example illustrates in silico immunogenicity analysis. Briefly, mouse Reference 1 scFv sequences was analyzed with the humanized scFvs by a human MHCI and MHCII presentation prediction software, based on various prediction databases IEDB, SMN-Align, NN-Align.

TABLE 21

Immunogenicity of anti-ADGRE2 scFvs

| | Immunogenicity | | |
|---|---|---|---|
| scFv | MHC I | MHC II | MHC I + MHC II |
| ADGRE2-D | 533 | 645 | 1178 |
| ADGRE2-B | 686 | 876 | 1562 |

TABLE 21-continued

Immunogenicity of anti-ADGRE2 scFvs

| scFv | Immunogenicity | | |
|---|---|---|---|
| | MHC I | MHC II | MHC I + MHC II |
| ADGRE2-E | 500 | 685 | 1185 |
| ADGRE2-A | 647 | 995 | 1642 |
| ADGRE2-F | 628 | 844 | 1472 |
| ADGRE2-C | 643 | 941 | 1584 |
| Reference 1 | 886 | 1183 | 2069 |

As shown in Table 21, the immunogenicity of the antibody was characterized based on MHC I or MHC II binding or binding to both MHC I and MHC II. Overall, the data predict low immunogenicity for all tested humanized antibodies.

Example 13—Off-Target Screening Panel Assay of Anti-ADGRE2 scFv

This example illustrates the specificity of anti-ADGRE2 scFvs in an off-target binding assay. Briefly, humanized scFv variants were tested for off-target binding. Three exemplary ADGRE2 scFv clones were run in the "Cut-down Assay" to screen for binding of to over 3000 human receptors. In the cut-down assay, the higher the binding, the higher the likelihood of the interaction being real. Generally, hits labelled "V. weak" are unlikely to be real interactions. The results showed that all the clones tested did not show any off-target binding. Thus, these clones were found to be highly specific for ADGRE2.

Example 14—Characterization of Clec12A Binding of Anti-CLEC12A scFv

The present example demonstrates derivation and characterization of binding affinities of anti-CLEC12A antibodies. In order to select and screen for Clec12A antibodies, hybridoma technology was used. Selections were carried out on Clec12A overexpressing CHO-S cells. Antibodies were selected for a diversity of sequences. 16 antibodies were selected out of 74 antibodies for a range of soluble and on-cell Clec12A binding affinities. The binding affinities of Clec12A antibodies were determined by Biacore analysis.

Figure 17A:
FIGS. 17A and 17B illustrate solubilized membrane protein (SMP) assays.

Further, the present example evaluates non-specific binding of the anti-CLEC12A antibodies. To assess the potential for the anti-CLEC12A antibodies to bind non-specific membrane proteins, scFvs derived from the 4 lead antibodies were evaluated in a surface membrane protein (SMP) assay (FIG. 17A). The SMP assay used was an ELISA based assay with human HEK-293 or insect SF9 cell membranes coated on the plate to test for non-specific binding to these membranes by the test antibodies. Internal control high and low non-specific binding antibodies were included. The high non-specific binding control, sc209, used was an antibody that has off target tox in clinic while the low non-specific binding control, 5f9, has not demonstrated off target tox in clinic (FIG. 17B).

Figure 17B:
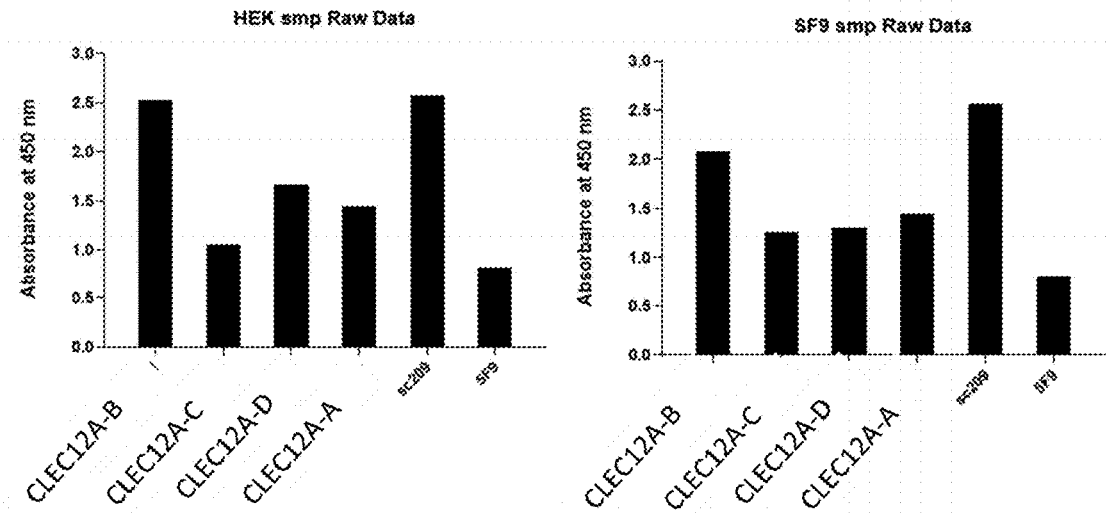

Overall, the results showed low non-specific binding by anti-CLEC12A antibodies CLEC12-C, CLEC12-D, and CLEC12A (FIG. 17B)

Example 15—Off-Target Screening Panel Assay of Anti-CLEC12A scFvs

This example illustrates the specificity of anti-CLEC12A scFvs in an off-target binding assay. Briefly, to test anti-CLEC12A scFvs for specificity to Clec12A as well as other membrane proteins, an off-target binding assay was conducted. Two selected Clec12A scFv clones were run in a "cut-down assay" to screen for binding of over 3000 human receptors. In the cut-down assay, the higher the binding, the higher the likelihood of the interaction being real. Generally, hits labelled "V. weak" are unlikely to be real interactions. scFvCLEC12A-A did not show any non-specific interactions to any receptor other than Clec12A or the receptors which come up as artifacts in this assay. The cut-down assay was used to screen clones for off-target assays. Selected scFv-Fc clones are being tested more comprehensively in additional screening and confirmation assays.

Example 16—Preclinical Study

CAR T cell therapy provides a potent therapeutic option in various B cell-related hematologic malignancies. One of the major efficacy challenges is escape of tumor cells with low antigen density, which has been clinically observed in several malignancies treated with CAR therapy. Novel concepts of CAR design are needed to address phenotypic heterogeneity including clonal variability of target antigen expression. FIG. 18A illustrates previously reported combinatorial CAR concepts including Boolean-logic OR- and AND-gate concepts as well as IF-THEN-gated CAR expression.

The inventors developed a combinatorial CAR concept that can overcome AML resistance due to target heterogeneity and antigen-low escape. Antigen-low relapse can be prevented via a novel chimeric receptor design with combinatorial signaling that is synergistic and adjusted to the respective target choice.

Flow cytometric antigen expression profiling in AML versus normal hematopoiesis was performed for several previously discovered CAR target candidates in AML. To provide a platform for identification of the ideal combinatorial CAR design, in-vitro and in-vivo models based on human AML cell lines with up- or down-regulated antigen levels of ADGRE2 and CLEC12A were established to mimic AML target heterogeneity and antigen-low escape. Using a bicistronic 7-retroviral vector, different combinatorial CAR formats targeting ADGRE2 and CLEC12A were screened.

ADGRE2 was selected as a CAR target due to its high rate of positivity on AML bulk and leukemic stem cells (LSC) in a molecularly heterogeneous AML patient population (FIGS. 1A and 1B). The affinity of an ADGRE2-targeted CAR comprising an extracellular antigen-binding domain comprising the ADGRE2-A scFv was measured and CD3zeta signaling was fine-tuned to achieve an ideal killing threshold that would allow for sparing of ADGRE2-low normal cells. Next, the inventors investigated the potential of co-targeting of a second AML-related antigen to mitigate potential CAR target antigen-low AML escape. CLEC12A was identified as a suitable co-target due to its non-overlapping expression profiles in normal hematopoiesis and other vital tissues (FIGS. 4A-4C).

ADCLEC.syn1, a novel combinatorial CAR construct including an ADGRE2-targeted 28z1XX-CAR that comprises an extracellular antigen-binding domain comprising the ADGRE2-A scFv and a CLEC12A-targeted chimeric costimulatory receptor (CCR) that comprises an extracellular antigen-binding domain comprising the CLEC12A-A scFv was developed. In addition, a construct including an ADGRE2-targeted 28z1XX-CAR that comprises an extracellular antigen-binding domain comprising the ADGRE2-A scFv and a CLEC12A-targeted BBz-CAR that comprises an extracellular antigen-binding domain comprising the CLEC12A-A scFv was also developed.

ADCLEC.syn1 operates based on a gating strategy described as "IF-BETTER" (FIG. 18B): high CAR target expression alone triggers killing, whereas low CAR target expression does not, unless a CCR target is present. Additional CCR interaction lowers the threshold for CAR-mediated killing through increased avidity and co-stimulation, allowing for higher CAR sensitivity that is purposefully limited to target cells expressing both antigens.

In the context of ADCLEC.syn1, ADGRE2-positive/ CLEC12A-negative and ADGRE2-positive/CLEC12A-positive cells triggered cell lysis while ADGRE2-negative/ CLEC12A-positive cells and ADGRE2-negative/ CLEC12A-negative cells were spared. Importantly, ADCLEC.syn1 mediated more efficient killing of ADGRE2-positive/CLEC12A-positive cells as compared to ADGRE2-positive/CLEC12A-negative cells (FIG. 19A).

Using AML cell lines with varying levels of ADGRE2 to model antigen escape, ADCLEC.syn1 had superior killing capacity against ADGRE2-low/CLEC12A-low and ADGRE2-very-low/CLEC12A-low AML target cells as compared to ADGRE2-CAR (FIG. 19B).

Using NSG in-vivo xenograft models of engineered MOLM13 AML cell line variants with low levels of ADGRE2 to model antigen escape, it was found that ADCLEC.syn1 outperformed an ADGRE2-targeted CAR comprising an extracellular antigen-binding domain comprising the ADGRE2-A scFv alone without a CLEC12A-targeted CCR lacking assistance via CLEC12A-CCR. Importantly, ADCLEC.syn1 also outperformed an otherwise identical alternative dual-CAR version (OR-gated ADGRE2-CAR+CLEC12A-CAR) in the setting of ADGRE2-low MOLM13, further underlining the importance of fine-tuned overall signaling (FIG. 20). High in-vivo potency was also confirmed against diverse AML cell lines with a wide range of ADGRE2 and CLEC12A levels reflecting population-wide AML heterogeneity (FIG. 20).

At clinically relevant CAR T cell doses, ADCLEC.syn1 induced complete and durable remissions in xenograft models of MOLM13 (ADGRE2-high/CLEC12A-low) and U937 (ADGRE2-low/CLEC12A-high). Specifically, in NSG xenograft models using a MOLM13 AML cell line variant with ADGRE2-high(WT) and CLEC12A-high antigen levels, ADCLEC.syn1 CAR T cells were titrated to low doses, establishing $1 \times 10^5$ ADCLEC.syn1 T cells as minimum efficacious dose to induce complete and durable remission (FIG. 20). ADCLEC.syn1 CAR T cells were found to be functionally persistent for >70 days, with a single CAR T cell dose potently averting relapse modeled via AML re-challenges (FIG. 21).

In summary, these data provide pre-clinical evidence that an "IF-BETTER"-gated CAR+CCR T cell (ADCLEC.syn1) can outperform a single-CAR T cell (ADGRE2-CAR) and a dual-CAR T cell (ADGRE2-CAR+CLEC12A-CAR). ADCLEC.syn1 enhanced antileukemic efficacy and prevented antigen-low AML escape via detection of a rationally selected combinatorial target antigen signature that is commonly found in AML but limited in vital normal cells. Using phenotypically representative AML xenograft models and clinically relevant T cell doses, it was demonstrated the high therapeutic potential of ADCLEC.syn1 CAR T cells, further supporting clinical translation of an "IF-BETTER"-gated CAR concept into a phase 1 trial.

Although the presently disclosed subject matter and certain of its advantages have been described in detail, it should be understood that various changes, substitutions and alterations can be made herein without departing from the spirit and scope of the disclosure. Moreover, the scope of the present application is not intended to be limited to the particular embodiments of the process, machine, manufacture, and composition of matter, and methods described in the specification. As one of ordinary skill in the art will readily appreciate from the disclosure of the presently disclosed subject matter, processes, machines, manufacture, compositions of matter, or methods, presently existing or later to be developed that perform substantially the same function or achieve substantially the same result as the corresponding embodiments described herein may be utilized according to the presently disclosed subject matter. Accordingly, the appended claims are intended to include within their scope such processes, machines, manufacture, compositions of matter, or methods.

Various patents, patent applications, publications, product descriptions, protocols, and sequence accession numbers are cited throughout this application, the disclosure of which are incorporated herein by reference in their entireties for all purposes.

What is claimed is:

1. A cell comprising a chimeric antigen receptor (CAR) and a chimeric co-stimulatory receptor (CCR), wherein
   a) the CAR comprises an extracellular antigen-binding domain that binds to ADGRE2, a transmembrane domain, and an intracellular domain, wherein the extracellular antigen-binding domain comprises a heavy chain variable region comprising a CDR1 comprising the amino acid sequence set forth in SEQ ID NO: 33, a CDR2 comprising the amino acid sequence set forth in SEQ ID NO: 34, and a CDR3 comprising the amino acid sequence set forth in SEQ ID NO: 35; and a light chain variable region comprising a CDR1 comprising the amino acid sequence set forth in SEQ ID NO: 36, a CDR2 comprising the amino acid sequence set forth in SEQ ID NO: 37, and a CDR3 comprising the amino acid sequence set forth in SEQ ID NO: 38; and
   b) the CCR comprises an extracellular antigen-binding domain that binds to CLEC12A, a transmembrane domain, and an intracellular domain, wherein the extracellular antigen-binding domain comprises:
      i) a heavy chain variable region comprising a CDR1 comprising the amino acid sequence set forth in SEQ ID NO: 69, a CDR2 comprising the amino acid sequence set forth in SEQ ID NO: 70, and a CDR3 comprising the amino acid sequence set forth in SEQ ID NO: 71; and a light chain variable region comprising a CDR1 comprising the amino acid sequence set forth in SEQ ID NO: 72, a CDR2 comprising the amino acid sequence set forth in SEQ ID NO: 73, and a CDR3 comprising the amino acid sequence set forth in SEQ ID NO: 74;
      ii) a heavy chain variable region comprising a CDR1 comprising the amino acid sequence set forth in SEQ ID NO: 81, a CDR2 comprising the amino acid sequence set forth in SEQ ID NO: 82, and a CDR3 comprising the amino acid sequence set forth in SEQ ID NO: 83; and a light chain variable region comprising a CDR1 comprising the amino acid sequence set forth in SEQ ID NO: 84, a CDR2 comprising the amino acid sequence set forth in SEQ ID NO: 73, and a CDR3 comprising the amino acid sequence set forth in SEQ ID NO: 85;
      iii) a heavy chain variable region comprising a CDR1 comprising the amino acid sequence set forth in SEQ ID NO: 89, a CDR2 comprising the amino acid sequence set forth in SEQ ID NO: 90, and a CDR3 comprising the amino acid sequence set forth in SEQ ID NO: 91; and a light chain variable region comprising a CDR1 comprising the amino acid sequence set forth in SEQ ID NO: 92, a CDR2 comprising the amino acid sequence set forth in SEQ ID NO: 93, and a CDR3 comprising the amino acid sequence set forth in SEQ ID NO: 94;
      iv) a heavy chain variable region comprising a CDR1 comprising the amino acid sequence set forth in SEQ ID NO: 89, a CDR2 comprising the amino acid sequence set forth in SEQ ID NO: 90, and a CDR3 comprising the amino acid sequence set forth in SEQ ID NO: 98; and a light chain variable region comprising a CDR1 comprising the amino acid sequence set forth in SEQ ID NO: 99, a CDR2 comprising the amino acid sequence set forth in SEQ ID NO: 93, and a CDR3 comprising the amino acid sequence set forth in SEQ ID NO: 94;
      v) a heavy chain variable region comprising a CDR1 comprising the amino acid sequence set forth in SEQ ID NO: 81, a CDR2 comprising the amino acid sequence set forth in SEQ ID NO: 103, and a CDR3 comprising the amino acid sequence set forth in SEQ ID NO: 83; and a light chain variable region comprising a CDR1 comprising the amino acid sequence set forth in SEQ ID NO: 104, a CDR2 comprising the amino acid sequence set forth in SEQ ID NO: 73, and a CDR3 comprising the amino acid sequence set forth in SEQ ID NO: 105;
      vi) a heavy chain variable region comprising a CDR1 comprising the amino acid sequence set forth in SEQ ID NO: 109, a CDR2 comprising the amino acid sequence set forth in SEQ ID NO: 103, and a CDR3 comprising the amino acid sequence set forth in SEQ ID NO: 83; and a light chain variable region comprising a CDR1 comprising the amino acid sequence set forth in SEQ ID NO: 110, a CDR2 comprising the amino acid sequence set forth in SEQ ID NO: 73, and a CDR3 comprising the amino acid sequence set forth in SEQ ID NO: 85;

vii) a heavy chain variable region comprising a CDR1 comprising the amino acid sequence set forth in SEQ ID NO: 89, a CDR2 comprising the amino acid sequence set forth in SEQ ID NO: 90, and a CDR3 comprising the amino acid sequence set forth in SEQ ID NO: 114; and a light chain variable region comprising a CDR1 comprising the amino acid sequence set forth in SEQ ID NO: 115, a CDR2 comprising the amino acid sequence set forth in SEQ ID NO: 93, and a CDR3 comprising the amino acid sequence set forth in SEQ ID NO: 116; or viii) a heavy chain variable region comprising a CDR1 comprising the amino acid sequence set forth in SEQ ID NO: 120, a CDR2 comprising the amino acid sequence set forth in SEQ ID NO: 121, and a CDR3 comprising the amino acid sequence set forth in SEQ ID NO: 122; and a light chain variable region comprising a CDR1 comprising the amino acid sequence set forth in SEQ ID NO: 123, a CDR2 comprising the amino acid sequence set forth in SEQ ID NO: 124, and a CDR3 comprising the amino acid sequence set forth in SEQ ID NO: 125.

2. The cell of claim 1, wherein the CAR comprises a heavy chain variable region comprising an amino acid sequence that is at least 80% identical to the amino acid sequence set forth in SEQ ID NO: 39, SEQ ID NO:43, SEQ ID NO:46, SEQ ID NO:49, SEQ ID NO: 52, SEQ ID NO: 55, or SEQ ID NO: 146; and a light chain variable region comprising an amino acid sequence that is at least 80% identical to the amino acid sequence set forth in SEQ ID NO: 40, SEQ ID NO: 44, SEQ ID NO: 47, SEQ ID NO: 50, SEQ ID NO: 53, SEQ ID NO: 56, or SEQ ID NO: 147.

3. The cell of claim 2, wherein the CAR comprises a heavy chain variable region comprising the amino acid sequence set forth in SEQ ID NO: 39, SEQ ID NO:43, SEQ ID NO:46, SEQ ID NO:49, SEQ ID NO: 52, SEQ ID NO: 55, or SEQ ID NO: 146; and a light chain variable region comprising the amino acid sequence set forth in SEQ ID NO: 40, SEQ ID NO: 44, SEQ ID NO: 47, SEQ ID NO: 50, SEQ ID NO: 53, SEQ ID NO: 56, or SEQ ID NO: 147.

4. The cell of claim 3, wherein the CAR comprises a heavy chain variable region comprising the amino acid sequence set forth in SEQ ID NO: 39; and a light chain variable region comprising the amino acid sequence set forth in SEQ ID NO: 40.

5. The cell of claim 1, wherein the CCR comprises a heavy chain variable region comprising an amino acid sequence that is at least 80% identical to the amino acid sequence set forth in SEQ ID NO: 75, SEQ ID NO: 86, SEQ ID NO: 95, SEQ ID NO: 100, SEQ ID NO: 106, SEQ ID NO: 111, SEQ ID NO: 117, or SEQ ID NO: 126; and a light chain variable region comprising an amino acid sequence that is at least 80% identical to the amino acid sequence set forth in SEQ ID NO: 76, SEQ ID NO: 87, SEQ ID NO: 96, SEQ ID NO: 101, SEQ ID NO: 107, SEQ ID NO: 112, SEQ ID NO: 118, or SEQ ID NO: 127.

6. The cell of claim 1, wherein the cell is transduced with the CAR and the CCR.

7. The cell of claim 1, wherein the CAR and/or the CCR is constitutively expressed on the surface of the cell.

8. The cell of claim 1, wherein the cell is selected from the group consisting of a T cell, a Natural Killer (NK) cell, a stem cell from which a lymphoid cell may be differentiated, and a stem cell from which a myeloid cell may be differentiated.

9. The cell of claim 8, wherein the stem cell is a pluripotent stem cell.

10. The cell of claim 1, wherein the cell is a T cell.

11. The cell of claim 10, wherein the T cell is selected from the group consisting of helper T cells, cytotoxic T cells, memory T cells, regulatory T cells, tumor-infiltrating lymphocyte (TIL), Natural Killer T cells, mucosal associated invariant T cells, and γδ T cells.

12. The cell of claim 1, wherein the cell is a Natural Killer (NK) cell.

13. A composition comprising the cell of claim 1 and a pharmaceutically acceptable carrier.

14. The composition of claim 13, comprising between $25 \times 10^6$ and $150 \times 10^6$ cells.

15. The composition of claim 13, comprising between $25 \times 10^6$ and $50 \times 10^6$ cells.

16. The composition of claim 13, comprising between $2.5 \times 10^6$ cells.

17. A method of reducing tumor burden, increasing or lengthening survival of a subject having a tumor, and/or treating and/or preventing a tumor in a subject, comprising administering to the subject the cell of claim 1.

18. The method of claim 17, wherein the tumor is cancerous.

19. The method of claim 18, wherein the subject is a human subject.

20. The method of claim 18, wherein the tumor is blood cancer.

21. The method of claim 17, wherein the tumor is selected from the group consisting of multiple myeloma, leukemia, lymphomas, and myeloid malignancies.

22. The method of claim 21, wherein the leukemia is selected from the group consisting of acute myeloid leukemia (AML), chronic myeloid leukemia (CML), acute lymphocytic leukemia (ALL), chronic lymphocytic leukemia (CLL), acute promyelocytic leukemia (APL), mixed-phenotype acute leukemia (MLL), hairy cell leukemia, and B cell prolymphocytic leukemia.

23. The method of claim 22, wherein the leukemia is acute myeloid leukemia (AML).

24. The method of claim 23, wherein the AML is relapsed/refractory acute myeloid leukemia (R/R AML).

25. The method of claim 21, wherein the myeloid malignancies are selected from the group consisting of myelodysplastic syndromes (MDS), myeloproliferative neoplasms (MPN), myeloid/lymphoid neoplasms, acute myeloid leukemia (AML), blastic plasmacytoid dendritic cell neoplasm, B-lymphoblastic leukemia/lymphoma, and T-lymphoblastic leukemia/lymphoma.

26. The method of claim 25, wherein the myeloid malignancies comprise myelodysplastic syndromes (MDS).

27. The cell of claim 1, wherein the extracellular antigen-binding domain of the CAR comprises a single-chain variable fragment (scFv), a Fab, or a F(ab)2.

28. The cell of claim 27, wherein the extracellular antigen-binding domain comprises a single chain variable fragment (scFv).

29. The cell of claim 28, wherein the scFv is a humanized scFv.

30. The cell of claim 1, wherein the heavy chain variable region and the light chain variable region of the CAR are positioned from the N- to the C-terminus: VH-VL.

31. The cell of claim 1, wherein the extracellular antigen-binding domain of the CAR comprises or is an scFv, which comprises the amino acid sequence set forth in SEQ ID NO: 41, SEQ ID NO: 45, SEQ ID NO: 48, SEQ ID NO: 51, SEQ ID NO: 54, SEQ ID NO: 57, or SEQ ID NO: 148.

32. The cell of claim 31, wherein the extracellular antigen-binding domain comprises or is an scFv, which comprises the amino acid sequence set forth in SEQ ID NO: 41, SEQ ID NO: 45, SEQ ID NO: 48, or SEQ ID NO: 51.

33. The cell of claim 32, wherein the extracellular antigen-binding domain comprises or is an scFv, which comprises the amino acid sequence set forth in SEQ ID NO: 41.

34. The cell of claim 1, wherein the transmembrane domain of the CAR comprises a CD8 polypeptide, a CD28 polypeptide, a CD3ζ polypeptide, a CD4 polypeptide, a 4-1BB polypeptide, an OX40 polypeptide, an ICOS polypeptide, a CTLA-4 polypeptide, a PD-1 polypeptide, a LAG-3 polypeptide, a 2B4 polypeptide, or a BTLA polypeptide.

35. The cell of claim 34, wherein the transmembrane domain comprises a CD28 polypeptide.

36. The cell of claim 1, wherein the intracellular domain of the CAR comprises a CD3ζ polypeptide.

37. The cell of claim 36, wherein the CD3ζ polypeptide is a modified CD3ζ polypeptide.

38. The cell of claim 37, wherein the modified CD3ζ polypeptide comprises a native ITAM1, an ITAM2 variant consisting of two loss-of-function mutations, and an ITAM3 variant consisting of two loss-of-function mutations.

39. The cell of claim 38, wherein the native ITAM1 consists of the amino acid sequence set forth in SEQ ID NO: 15.

40. The cell of claim 38, wherein the ITAM2 variant consists of the amino acid sequence set forth in SEQ ID NO: 21.

41. The cell of claim 38, wherein the ITAM3 variant consists of the amino acid sequence set forth in SEQ ID NO: 25.

42. The cell of claim 38, wherein the modified CD3ζ polypeptide comprises or consists of the amino acid sequence set forth in SEQ ID NO: 27.

43. The cell of claim 36, wherein the intracellular domain of the CAR further comprises at least one co-stimulatory signaling region.

44. The cell of claim 43, wherein the at least one co-stimulatory signaling region comprises a CD28 polypeptide, a 4-1BB polypeptide, an OX40 polypeptide, an ICOS polypeptide, a DAP-10 polypeptide, or a combination thereof.

45. The cell of claim 44, wherein the at least one co-stimulatory signaling region comprises a CD28 polypeptide.

46. The cell of claim 1, wherein the CCR comprises:
i) a heavy chain variable region comprising a CDR1 comprising the amino acid sequence set forth in SEQ ID NO: 69, a CDR2 comprising the amino acid sequence set forth in SEQ ID NO: 70, and a CDR3 comprising the amino acid sequence set forth in SEQ ID NO: 71; and a light chain variable region comprising a CDR1 comprising the amino acid sequence set forth in SEQ ID NO: 72, a CDR2 comprising the amino acid sequence set forth in SEQ ID NO: 73, and a CDR3 comprising the amino acid sequence set forth in SEQ ID NO: 74; or
ii) a heavy chain variable region comprising a CDR1 comprising the amino acid sequence set forth in SEQ ID NO: 81, a CDR2 comprising the amino acid sequence set forth in SEQ ID NO: 82, and a CDR3 comprising the amino acid sequence set forth in SEQ ID NO: 83; and a light chain variable region comprising a CDR1 comprising the amino acid sequence set forth in SEQ ID NO: 84, a CDR2 comprising the amino acid sequence set forth in SEQ ID NO: 73, and a CDR3 comprising the amino acid sequence set forth in SEQ ID NO: 85.

47. The cell of claim 46, wherein the CCR comprises a heavy chain variable region comprising a CDR1 comprising the amino acid sequence set forth in SEQ ID NO: 69, a CDR2 comprising the amino acid sequence set forth in SEQ ID NO: 70, and a CDR3 comprising the amino acid sequence set forth in SEQ ID NO: 71; and a light chain variable region comprising a CDR1 comprising the amino acid sequence set forth in SEQ ID NO: 72, a CDR2 comprising the amino acid sequence set forth in SEQ ID NO: 73, and a CDR3 comprising the amino acid sequence set forth in SEQ ID NO: 74.

48. The cell of claim 1, wherein the CCR comprises a heavy chain variable region comprising the amino acid sequence set forth in SEQ ID NO: 75, SEQ ID NO: 86, SEQ ID NO: 95, SEQ ID NO: 100, SEQ ID NO: 106, SEQ ID NO: 111, SEQ ID NO: 117, or SEQ ID NO: 126; and a light chain variable region comprising the amino acid sequence set forth in SEQ ID NO: 76, SEQ ID NO: 87, SEQ ID NO: 96, SEQ ID NO: 101, SEQ ID NO: 107, SEQ ID NO: 112, SEQ ID NO: 118, or SEQ ID NO: 127.

49. The cell of claim 48, wherein the CCR comprises a heavy chain variable region comprising the amino acid sequence set forth in SEQ ID NO: 75; and a light chain variable region comprising the amino acid sequence set forth in SEQ ID NO: 76.

50. The cell of claim 1, wherein the extracellular antigen-binding domain of the CCR comprises a single-chain variable fragment (scFv), a Fab, or a F(ab)$_2$.

51. The cell of claim 50, wherein the extracellular antigen-binding domain comprises a single chain variable fragment (scFv).

52. The cell of claim 51, wherein the scFv is a human scFv.

53. The cell of claim 1, wherein the extracellular antigen-binding domain of the CCR comprises a linker between the heavy chain variable region and the light chain variable region.

54. The cell of claim 1, wherein the heavy chain variable region and the light chain variable region of the CCR are positioned from the N- to the C-terminus: VH-VL.

55. The cell of claim 1, wherein the extracellular antigen-binding domain of the CCR comprises or is an scFv, which comprises the amino acid sequence set forth in SEQ ID NO: 79, SEQ ID NO: 88, SEQ ID NO: 97, SEQ ID NO: 102, SEQ ID NO: 108, SEQ ID NO: 113, SEQ ID NO: 119, or SEQ ID NO: 128.

56. The cell of claim 55, wherein the extracellular antigen-binding domain comprises or is an scFv, which comprises the amino acid sequence set forth in SEQ ID NO: 79, SEQ ID NO: 88, SEQ ID NO: 97, or SEQ ID NO: 102.

57. The cell of claim 56, wherein the extracellular antigen-binding domain comprises or is an scFv, which comprises the amino acid sequence set forth in SEQ ID NO: 79.

58. The cell of claim 1, wherein the transmembrane domain of the CCR comprises a CD8 polypeptide, a CD28 polypeptide, a CD3ζ polypeptide, a CD4 polypeptide, a 4-1BB polypeptide, an OX40 polypeptide, an ICOS polypeptide, a CTLA-4 polypeptide, a PD-1 polypeptide, a LAG-3 polypeptide, a 2B4 polypeptide, or a BTLA polypeptide.

59. The cell of claim 58, wherein the transmembrane domain comprises a CD8 polypeptide.

60. The cell of claim 1, wherein the intracellular domain of the CCR does not comprise a CD3ζ polypeptide.

61. The cell of claim 1, wherein the intracellular domain of the CCR comprises at least one co-stimulatory signaling region.

62. The cell of claim 61, wherein the at least one co-stimulatory signaling region comprises a CD28 polypeptide, a 4-1BB polypeptide, an OX40 polypeptide, an ICOS polypeptide, a DAP-10 polypeptide, or a combination thereof.

63. The cell of claim 62, wherein the at least one co-stimulatory signaling region comprises a 4-1BB polypeptide.

64. The cell of claim 1, wherein the cell is an immunoresponsive cell.

65. The cell of claim 1, wherein the cell is a cell of the lymphoid lineage or a cell of the myeloid lineage.

66. The cell of claim 1, wherein the extracellular antigen-binding domain of the CAR comprises a linker between the heavy chain variable region and the light chain variable region.

* * * * *